(12) United States Patent
Tominaga et al.

(10) Patent No.: US 10,087,457 B2
(45) Date of Patent: Oct. 2, 2018

(54) PLANT WITH ENHANCED GROWTH AND METHOD FOR PRODUCING THE SAME

(75) Inventors: Motoki Tominaga, Wako (JP); Kohji Ito, Chiba (JP)

(73) Assignee: RIKEN, Wako-Shi (JP)

( * ) Notice: Subject to any disclaimer, the term of this patent is extended or adjusted under 35 U.S.C. 154(b) by 995 days.

(21) Appl. No.: 13/344,574

(22) Filed: Jan. 5, 2012

(65) Prior Publication Data

US 2013/0007915 A1    Jan. 3, 2013

Related U.S. Application Data

(60) Provisional application No. 61/502,764, filed on Jun. 29, 2011.

(51) Int. Cl.
*C12N 15/82* (2006.01)
*C07K 14/47* (2006.01)

(52) U.S. Cl.
CPC ...... *C12N 15/8261* (2013.01); *C07K 14/4716* (2013.01); *Y02A 40/146* (2018.01)

(58) Field of Classification Search
None
See application file for complete search history.

(56) References Cited

U.S. PATENT DOCUMENTS 6,372,966 B1 *    4/2002    Rose-Fricker et al. ....... 800/298

OTHER PUBLICATIONS

Peremyslov et al. Two class XI myosins function in organelle trafficking and root hair development in *Arabidopsis*. Plant Physiol. Mar. 2008;146(3):1109-16. Epub Jan. 4, 2008.*
Walsh et al. Cardiomyopathy: a systematic review of disease-causing mutations in myosin heavy chain 7 and their phenotypic manifestations. Cardiology. 2010;115(1):49-60. Epub Oct. 27, 2009.*
Avisar et al. A comparative study of the involvement of 17 *Arabidopsis* myosin family members on the motility of Golgi and other organelles. Plant Physiol. Jun. 2009;150(2):700-9. Epub Apr. 15, 2009.*
Fujita et al. Characterization of mutant myosins of Dictyostelium discoideum equivalent to human familial hypertrophic cardiomyopathy mutants. Molecular force level of mutant myosins may have a prognostic implication. J. Clin. Invest. Mar. 1, 1997;99(5):1010-5.*
Miyagawa, Y., et al., "Overexpression of a cyanobacterial fructose-1,6-/sedoheptulose-1,7-bisphosphatase in tobacco enhances photosynthesis and growth," Nature Biotech. vol. 19, pp. 965-969 (2001).
Chida, H., et al., "Expression of the Algal Cytochrome $c_6$ Gene in *Arabidopsis* Enhances Photosynthesis and Growth," Plant Cell Physiol., vol. 48, No. 7, pp. 948-957 (2007).
Peremyslov, V. V., et al., "Class XI Myosins Are Required for Development, Cell Expansion, and F-Actin Organization in *Arabidopsis*," The Plant Cell, vol. 22, pp. 1883-1897 (2010).
Peremyslov, V. V., et al., "Two Class XI Myosins Function in Organelle Trafficking and Root Hair Development in *Arabidopsis*," Plant Physiol., vol. 146, pp. 1109-1116 (2008).
Prokhnevsky, A. I., et al., "Overlapping functions of the four class XI myosins in *Arabidopsis* growth, root hair elongation, and organelle motility," PNAS, vol. 105, No. 50, pp. 19744-19749 (2008).
Ueda, H., et al., "Myosin-dependent endoplasmic reticulum motility and F-actin organization in plant cells," PNAS, vol. 107, No. 15, pp. 6894-6899 (2010).
Sparkes, I. A., "Truncated myosin XI tail fusions inhibit peroxisome, Golgi, and mitochondrial movement in tobacco leaf epidermal cells: a genetic tool for the next generation," J. Experimental Botany, vol. 59, No. 9, pp. 2499-2512 (2008).
Avisar, D., et al., "Myosin XI-K Is Required for Rapid Trafficking of Golgi Stacks, Peroxisomes, and Mitochondria in Leaf Cells of *Nicotiana benthamiana*," Plant Physiol., vol. 146, pp. 1098-1108 (2008).
Vidali, L., et al., "Myosin XI Is Essential for Tip Growth in *Physcomitrella patens*," The Plant Cell, vol. 22, pp. 1868-1882 (2010).

* cited by examiner

*Primary Examiner* — Cynthia E Collins
(74) *Attorney, Agent, or Firm* — Birch, Stewart, Kolasch & Birch, LLP

(57) ABSTRACT

A method for producing a plant with enhanced growth is provided including a step of introducing a gene encoding a chimeric myosin XI protein into a host plant so as to transform the host plant. The chimeric myosin XI protein comprises a neck domain, a coiled-coil domain, and a globular tail domain from a myosin XI protein involved in cytoplasmic streaming of a donor plant. The motor domain from a myosin XI protein of a plant belongs to the genus *Chara*. The motor domain comprises an amino acid sequence specified in the following (a) or (b): (a) the amino acid sequence shown in SEQ ID NO: 1; or (b) an amino acid sequence having 90% or more identity with the amino acid sequence shown in SEQ ID NO: 1. The host plant belongs to the same family as the donor plant.

8 Claims, 13 Drawing Sheets
Specification includes a Sequence Listing.

(Trans gene)     *A. thaliana* MYA2 WT     *Chara- Arabidopsis* chimeric myosin XI (Strain)     *A. thaliana* MYA2-KO Fig. 9
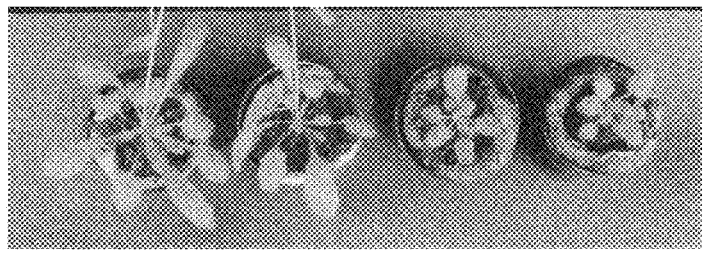
(Strain)     *A. thaliana* columbia     *A. thaliana* MYA2-KO
(Trans gene)     -     *Human-Arabidopsis* Chimeric myosin XI

SEQUENCE LISTING

```
<160> NUMBER OF SEQ ID NOS: 38

<210> SEQ ID NO 1
<211> LENGTH: 660
<212> TYPE: PRT
<213> ORGANISM: C. coralline
<220> FEATURE:
<223> OTHER INFORMATION: myosin XI motor domain

<400> SEQUENCE: 1
```

Val Asp Asp Met Thr Lys Leu Ser Tyr Leu His Glu Pro Gly Val Leu
1               5                   10                  15

His Asn Leu Tyr Thr Arg Phe Lys His Asp Glu Ile Tyr Thr Phe Thr
            20                  25                  30

Gly Asn Ile Leu Ile Ala Val Asn Pro Phe Thr Arg Leu Pro His Leu
        35                  40                  45

Phe Asn Thr Tyr Met Met Lys Gln Tyr Gln Asp Ala Gln Pro Gly Asp
    50                  55                  60

Leu Asn Pro His Val Tyr Ser Val Ala Asp Ala Ala Tyr Lys Ala Met
65                  70                  75                  80

Met Glu Glu Met Lys Ser Gln Ala Ile Leu Val Ser Gly Glu Ser Gly
                85                  90                  95

Ala Gly Lys Thr Glu Thr Thr Lys Gln Ile Met Gln Tyr Leu Ala Phe
            100                 105                 110

Val Gly Gly Arg Thr Val Gly Asp Glu Arg Ser Val Glu Gln Gln Val
        115                 120                 125

```
Leu Gln Ser Asn Pro Leu Leu Glu Ala Phe Gly Asn Ala Lys Thr Val
    130                 135                 140

Arg Asn Asn Ser Ser Arg Phe Gly Lys Phe Val Glu Ile Gln Phe
145                 150                 155                 160

Asn Asn Gly Lys Ile Ser Gly Ala Ala Val Arg Thr Tyr Leu Leu Glu
                165                 170                 175

Arg Ser Arg Val Thr Gln Ile Ser Ser Pro Glu Arg Asn Tyr His Cys
            180                 185                 190

Phe Tyr Gln Leu Val Ala Gly Ala Ser Pro Glu Asp Ala Glu Arg Leu
        195                 200                 205

Lys Leu Gly Pro Pro Asp Ser Phe His Tyr Leu Asn Gln Ser Lys Cys
210                 215                 220

Val Glu Val Gly Ala Ile Asp Asp Cys Lys Glu Tyr Gln Leu Thr Arg
225                 230                 235                 240

Glu Ala Met Asp Ile Val Gly Ile Thr Thr Glu Gln Glu Ala Ile
                245                 250                 255

Phe Arg Thr Ile Ala Ala Val Leu His Leu Gly Asn Ile Glu Phe Asp
            260                 265                 270

Ser Gly Glu Ser Asp Ala Ser Glu Val Ser Thr Glu Lys Ser Lys Phe
    275                 280                 285

His Leu Lys Ala Ala Glu Met Leu Met Cys Asp Glu Gln Met Leu
290                 295                 300

Glu Lys Ser Leu Thr Thr Arg Ile Met Lys Ala Thr Arg Thr Glu Ser
305                 310                 315                 320

Ile Thr Lys Ile Leu Asn Lys Ser Gln Ala Thr Asp Asn Arg Asp Ser
                325                 330                 335

Ile Ala Lys Thr Ile Tyr Ala Lys Leu Phe Asp Trp Leu Val Asn Lys
            340                 345                 350

Val Asn Lys Ser Ile Gly Gln Asp Pro His Ser Thr Val Leu Ile Gly
        355                 360                 365

Val Leu Asp Ile Tyr Gly Phe Glu Ser Phe Glu Ile Asn Ser Phe Glu
        370                 375                 380

Gln Phe Cys Ile Asn Leu Thr Asn Glu Lys Leu Gln Gln His Phe Asn
385                 390                 395                 400

Thr His Val Phe Lys Met Glu Gln Ala Glu Tyr Arg Lys Glu Glu Ile
                405                 410                 415

Asn Trp Asp Asn Ile Asp Phe Val Asp Asn Ile Asp Val Leu Asp Leu
            420                 425                 430

Ile Glu Lys Lys Pro Leu Gly Ile Ile Ala Leu Leu Asp Glu Ala Cys
        435                 440                 445

Met Leu Pro Arg Ser Thr Ala Glu Ser Phe Ala Arg Lys Leu Gly Asp
450                 455                 460

Thr Phe Asn Asn His Arg Arg Phe Ser Lys His Lys Phe Lys Arg Thr
465                 470                 475                 480

Ala Phe Thr Ile Asp His Tyr Ala Gly Gln Val Glu Tyr Arg Ala Asp
                485                 490                 495

Leu Phe Leu Glu Lys Asn Lys Asp Phe Val Val Pro Glu His Gln Gln
            500                 505                 510

Leu Leu His Ala Ser Arg Cys Ala Phe Val Ser Gly Leu Phe Pro Ala
        515                 520                 525

Asp Glu Gly Thr Lys Ala Pro Ser Lys Phe Met Ser Ile Gly Ser Gln
    530                 535                 540

Phe Lys Leu Gln Leu Ala Ala Leu Met Glu Thr Leu Lys Leu Thr Ala
```

```
545                 550                 555                 560
Pro His Tyr Ile Arg Cys Val Lys Pro Asn Met Gln Leu Lys Pro Gln
                565                 570                 575

Ile Phe Glu Asn Lys Asn Val Leu Gln Gln Leu Arg Cys Ser Gly Val
                580                 585                 590

Leu Glu Ala Val Arg Ile Ser Cys Ala Gly Phe Pro Thr Arg Arg Thr
                595                 600                 605

Phe Glu Glu Phe Leu Asp Arg Phe Gly Leu Leu His Pro Glu Val Leu
                610                 615                 620

Ile Glu Ser Ala Glu Ser Ala Asp Glu Lys Val Ala Cys Gln Asn
625                 630                 635                 640

Leu Leu Glu Lys Cys Asn Leu Lys Gly Tyr Gln Ile Gly Lys Thr Lys
                645                 650                 655

Val Phe Leu Arg
                660

<210> SEQ ID NO 2
<211> LENGTH: 2182
<212> TYPE: PRT
<213> ORGANISM: C. coralline
<220> FEATURE:
<223> OTHER INFORMATION: myosin XI full length

<400> SEQUENCE: 2

Met Gly Leu Glu Lys Ala Arg Ser Ser Ala Leu Gly Ile Gly Ser Pro
1               5                   10                  15

Ala Trp Val Glu Asp Val Glu Thr Val Trp Ile Glu Ala Thr Val Val
                20                  25                  30

Lys Leu Asp Gly Asp Ala Ile Thr Ala Arg Thr Val Asn Gly Asp Leu
                35                  40                  45

Val Glu Thr Thr Met Ala Asn Ala Leu Pro Arg Asp Glu Asp Val Thr
                50                  55                  60

Met Arg Gly Val Asp Asp Met Thr Lys Leu Ser Tyr Leu His Glu Pro
65                  70                  75                  80

Gly Val Leu His Asn Leu Tyr Thr Arg Phe Lys His Asp Glu Ile Tyr
                85                  90                  95

Thr Phe Thr Gly Asn Ile Leu Ile Ala Val Asn Pro Phe Thr Arg Leu
                100                 105                 110

Pro His Leu Phe Asn Thr Tyr Met Met Lys Gln Tyr Gln Asp Ala Gln
                115                 120                 125

Pro Gly Asp Leu Asn Pro His Val Tyr Ser Val Ala Asp Ala Ala Tyr
                130                 135                 140

Lys Ala Met Met Glu Glu Met Lys Ser Gln Ala Ile Leu Val Ser Gly
145                 150                 155                 160

Glu Ser Gly Ala Gly Lys Thr Glu Thr Thr Lys Gln Ile Met Gln Tyr
                165                 170                 175

Leu Ala Phe Val Gly Gly Arg Thr Val Gly Asp Glu Arg Ser Val Glu
                180                 185                 190

Gln Gln Val Leu Gln Ser Asn Pro Leu Leu Glu Ala Phe Gly Asn Ala
                195                 200                 205

Lys Thr Val Arg Asn Asn Asn Ser Ser Arg Phe Gly Lys Phe Val Glu
                210                 215                 220

Ile Gln Phe Asn Asn Gly Lys Ile Ser Gly Ala Ala Val Arg Thr Tyr
225                 230                 235                 240

Leu Leu Glu Arg Ser Arg Val Thr Gln Ile Ser Ser Pro Glu Arg Asn
```

```
                    245                 250                 255
Tyr His Cys Phe Tyr Gln Leu Val Ala Gly Ala Ser Pro Glu Asp Ala
                260                 265                 270
Glu Arg Leu Lys Leu Gly Pro Pro Asp Ser Phe His Tyr Leu Asn Gln
                275                 280                 285
Ser Lys Cys Val Glu Val Gly Ala Ile Asp Asp Cys Lys Glu Tyr Gln
                290                 295                 300
Leu Thr Arg Glu Ala Met Asp Ile Val Gly Ile Thr Thr Glu Glu Gln
305                 310                 315                 320
Glu Ala Ile Phe Arg Thr Ile Ala Ala Val Leu His Leu Gly Asn Ile
                325                 330                 335
Glu Phe Asp Ser Gly Glu Ser Asp Ala Ser Glu Val Ser Thr Glu Lys
                340                 345                 350
Ser Lys Phe His Leu Lys Ala Ala Ala Glu Met Leu Met Cys Asp Glu
                355                 360                 365
Gln Met Leu Glu Lys Ser Leu Thr Thr Arg Ile Met Lys Ala Thr Arg
                370                 375                 380
Thr Glu Ser Ile Thr Lys Ile Leu Asn Lys Ser Gln Ala Thr Asp Asn
385                 390                 395                 400
Arg Asp Ser Ile Ala Lys Thr Ile Tyr Ala Lys Leu Phe Asp Trp Leu
                405                 410                 415
Val Asn Lys Val Asn Lys Ser Ile Gly Gln Asp Pro His Ser Thr Val
                420                 425                 430
Leu Ile Gly Val Leu Asp Ile Tyr Gly Phe Glu Ser Phe Glu Ile Asn
                435                 440                 445
Ser Phe Glu Gln Phe Cys Ile Asn Leu Thr Asn Glu Lys Leu Gln Gln
                450                 455                 460
His Phe Asn Thr His Val Phe Lys Met Glu Gln Ala Glu Tyr Arg Lys
465                 470                 475                 480
Glu Glu Ile Asn Trp Asp Asn Ile Asp Phe Val Asp Asn Ile Asp Val
                485                 490                 495
Leu Asp Leu Ile Glu Lys Lys Pro Leu Gly Ile Ile Ala Leu Leu Asp
                500                 505                 510
Glu Ala Cys Met Leu Pro Arg Ser Thr Ala Glu Ser Phe Ala Arg Lys
                515                 520                 525
Leu Gly Asp Thr Phe Asn Asn His Arg Arg Phe Ser Lys His Lys Phe
                530                 535                 540
Lys Arg Thr Ala Phe Thr Ile Asp His Tyr Ala Gly Gln Val Glu Tyr
545                 550                 555                 560
Arg Ala Asp Leu Phe Leu Glu Lys Asn Lys Asp Phe Val Val Pro Glu
                565                 570                 575
His Gln Gln Leu Leu His Ala Ser Arg Cys Ala Phe Val Ser Gly Leu
                580                 585                 590
Phe Pro Ala Asp Glu Gly Thr Lys Ala Pro Ser Lys Phe Met Ser Ile
                595                 600                 605
Gly Ser Gln Phe Lys Leu Gln Leu Ala Ala Leu Met Glu Thr Leu Lys
                610                 615                 620
Leu Thr Ala Pro His Tyr Ile Arg Cys Val Lys Pro Asn Met Gln Leu
625                 630                 635                 640
Lys Pro Gln Ile Phe Glu Asn Lys Asn Val Leu Gln Gln Leu Arg Cys
                645                 650                 655
Ser Gly Val Leu Glu Ala Val Arg Ile Ser Cys Ala Gly Phe Pro Thr
                660                 665                 670
```

```
Arg Arg Thr Phe Glu Glu Phe Leu Asp Arg Phe Gly Leu Leu His Pro
        675                 680                 685

Glu Val Leu Ile Glu Ser Ala Glu Ser Ala Asp Glu Lys Val Ala
690             695                 700

Cys Gln Asn Leu Leu Glu Lys Cys Asn Leu Lys Gly Tyr Gln Ile Gly
705                 710                 715                 720

Lys Thr Lys Val Phe Leu Arg Ala Gly Gln Met Ala Ile Leu Asp Thr
                725                 730                 735

Leu Arg Ser Asn Val Leu Asn Glu Ala Ala Val Lys Ile Gln His Met
            740                 745                 750

Val Gln Ser Phe Leu Met Arg Arg Asp Tyr Glu Arg Met Lys Arg Ala
        755                 760                 765

Ser Leu Leu Val Gln Ala Tyr Trp Arg Gly Thr Met Ala Arg Met Glu
770                 775                 780

Phe Arg Phe Leu Arg Glu Gln Val Ser Ala Val Cys Phe Gln Arg Tyr
785                 790                 795                 800

Ile Arg Gly Tyr Leu Ala Gln Lys Asn Tyr Phe Glu Met Arg Gln Ala
                805                 810                 815

Ala Ile Arg Ile Gln Ser Ala Ile Arg Ser Leu Ala Ala Arg Arg Val
            820                 825                 830

Leu Cys Val Leu Gln Asp Asn His Ala Ala Thr Gln Ile Gln Ser Lys
        835                 840                 845

Trp Arg Ser Tyr Val Ala Phe Arg Ser Tyr Asp Glu Leu Leu Arg Ser
850                 855                 860

Cys Lys Val Phe Gln Gly Ala Trp Arg Cys Lys Glu Ala Arg Ser Glu
865                 870                 875                 880

Ile Lys Lys Leu Arg Gln Ala Ala Arg Glu Thr Gly Ala Leu Arg Glu
                885                 890                 895

Ala Lys Thr Arg Leu Glu Lys Lys Cys Glu Glu Leu Thr Leu Arg Leu
            900                 905                 910

Gly Leu Ala Lys Val Ser Leu Ile Ala Arg Asn Ser Glu Leu Ala Lys
        915                 920                 925

Leu Lys Phe Ala Met Glu Gly Ala Gln Ala Gln Val Glu Gln Met Lys
930                 935                 940

Ile Leu Leu Ala Lys Glu Arg Glu Gly His Glu Ala Asp Leu Ala Gln
945                 950                 955                 960

Ala Lys Val Ala Ala Ala Gln Leu Leu Glu Ala Glu Met Ser Ala Gln
                965                 970                 975

Ala Ser Lys Glu Val Leu Asp Lys Val Glu Ala Leu Ser Glu Glu Asn
            980                 985                 990

Ser Lys Leu Lys Glu Leu Val Glu Asp Tyr Glu Lys Lys Lys Ala Leu
        995                 1000                1005

Glu Glu Ser Ser Ala Lys Arg Ile Glu Glu Ala Asp Leu Lys Arg
1010                1015                1020

Asp Ala Ile Gln Glu Leu Leu Asn Arg Ser Glu Glu Gln Val Gln
1025                1030                1035

Asp Leu Ile Ser Glu Asn Gln Ser Leu Gln Ser Glu Lys Leu Asn
1040                1045                1050

Leu Gln Leu Asp Asn Arg Ile Leu Arg Gln Gln Ala Leu Ser Met
    1055                1060                1065

Lys Asp Leu Glu Leu Glu Lys Gln Asp Leu Gln Arg Asn Leu Gln
1070                1075                1080
```

| | | | | | | | | | | | |
|---|---|---|---|---|---|---|---|---|---|---|---|
|His|Leu|Glu|Ala|Asn|Ser|Gln|Ala|Leu|Arg|Ala|Glu|Asn|Gln|Thr|
|1085| | | | |1090| | | | |1095| | | | |

His Leu Glu Ala Asn Ser Gln Ala Leu Arg Ala Glu Asn Gln Thr
    1085                1090                1095

Leu Lys Gln Gln Leu Glu Gln Leu Glu Ser Gln Asp Leu Gln Arg
    1100                1105                1110

Asn Leu Gln His Leu Glu Ala Asn Ser Gln Ala Leu Arg Ala Glu
    1115                1120                1125

Asn Gln Thr Leu Lys Tyr Gln Leu Glu Gln Leu Glu Ser Gln Asp
    1130                1135                1140

Leu Gln Arg Asp Leu Gln His Leu Glu Ala Asn Ser Gln Ala Leu
    1145                1150                1155

Arg Ala Glu Asn Gln Thr Leu Lys Gln Gln Leu Glu Gln Leu Glu
    1160                1165                1170

Ser Gln Asp Leu Gln Arg Asn Leu Gln His Leu Glu Ala Asn Ser
    1175                1180                1185

Gln Ala Leu Arg Ala Glu Asn Gln Thr Leu Lys Gln Gln Leu Glu
    1190                1195                1200

Gln Leu Thr Ser Lys Gly Gly Thr Val Leu Lys Ile Gly Gly Ala
    1205                1210                1215

Ser Ser Lys Phe Asp Ile Ser Glu Pro Glu Pro Ala Ile Gly Glu
    1220                1225                1230

Thr Glu Phe Thr Glu Ala Asn Ser Gln Ala Leu Arg Ala Glu Asn
    1235                1240                1245

Gln Thr Leu Lys Tyr Gln Leu Glu Gln Leu Glu Ser Gln Asp Leu
    1250                1255                1260

Gln Arg Asn Leu Gln His Leu Glu Ala Asn Ser Gln Ala Leu Arg
    1265                1270                1275

Ala Glu Asn Gln Thr Leu Lys Gln Gln Leu Glu Gln Leu Glu Ser
    1280                1285                1290

Gln Asp Leu Gln Arg Thr Leu Gln His Leu Glu Ala Asn Ser Gln
    1295                1300                1305

Ala Leu Arg Ala Glu Asn Gln Thr Leu Lys Gln Gln Leu Glu Gln
    1310                1315                1320

Leu Thr Ser Lys Gly Gly Thr Val Leu Lys Ile Gly Gly Ala Ser
    1325                1330                1335

Ser Lys Phe Asp Ile Ser Glu Pro Glu Pro Ala Ile Gly Glu Thr
    1340                1345                1350

Glu Phe Thr Glu Ala Asn Ser Gln Ala Leu Arg Ala Glu Asn Gln
    1355                1360                1365

Thr Leu Lys Gln Gln Leu Glu Gln Leu Glu Ser Gln Asp Leu Gln
    1370                1375                1380

Arg Asn Leu Gln His Leu Glu Ala Asn Ser Gln Ala Leu Arg Ala
    1385                1390                1395

Glu Asn Gln Thr Leu Lys Gln Gln Leu Glu Gln Leu Glu Ser Gln
    1400                1405                1410

Asp Leu Gln Arg Asn Leu Gln His Leu Glu Ala Asn Ser His Ala
    1415                1420                1425

Leu Arg Ala Glu Asn Gln Thr Leu Lys Gln Gln Leu Glu Gln Leu
    1430                1435                1440

Thr Ser Lys Gly Gly Thr Val Leu Lys Ile Gly Gly Ala Ser Ser
    1445                1450                1455

Lys Phe Asp Ile Arg Glu Pro Glu Pro Ala Ile Gly Glu Thr Glu
    1460                1465                1470

Phe Thr Glu Ala Asn Ser Gln Ala Leu Arg Ala Glu Asn Gln Thr

-continued

```
            1475                1480                1485

Leu Lys Gln Gln Leu Glu Gln Leu Glu Ser Gln Asp Leu Gln Arg
            1490                1495                1500

Asn Leu Gln His Leu Glu Ala Asn Ser Gln Ala Leu Arg Ala Glu
            1505                1510                1515

Asn Gln Thr Leu Lys Gln Gln Leu Glu Gln Leu Glu Ser Gln Asp
            1520                1525                1530

Leu Gln Arg Asn Leu Gln His Leu Glu Ala Asn Ser Gln Ala Leu
            1535                1540                1545

Arg Ala Glu Asn Gln Thr Leu Lys Gln Gln Leu Glu Gln Leu Glu
            1550                1555                1560

Ser Gln Asp Leu Gln Arg Asn Leu Gln His Leu Glu Ala Lys Cys
            1565                1570                1575

Gln Ala Leu Arg Ala Glu Asn Glu Thr Leu Lys Gln Gln Leu Glu
            1580                1585                1590

Gln Leu Glu Ser Gln Asp Leu Gln Arg Asn Leu Gln His Leu Glu
            1595                1600                1605

Ala Asn Ser Gln Ala Leu Arg Ala Glu Asn Gln Thr Leu Lys Gln
            1610                1615                1620

Gln Leu Glu Gln Leu Thr Ser Lys Gly Gly Thr Val Val Lys Ile
            1625                1630                1635

Gly Arg Ala Ala Val Thr Arg Ile Lys Pro Thr Pro Glu Pro Val
            1640                1645                1650

Ile Thr Thr Ser Tyr Pro Asp Glu Gln Pro Ala Thr Pro Gly Val
            1655                1660                1665

Thr Gly Pro Gly Thr Pro Ser Arg Pro Leu Gly Arg Ser Gln His
            1670                1675                1680

Ile Arg Ser Glu Ser Ser Asp Phe Thr Ser Leu Tyr Phe Arg Glu
            1685                1690                1695

Asp Ser Pro Val Pro Glu Ala Lys Pro Val Asp His Glu Lys Ser
            1700                1705                1710

Lys Met Met Pro Asp Lys Leu Gln Tyr Leu Pro Glu Asp Ser Pro
            1715                1720                1725

Val Pro Glu Ala Lys Pro Val Asp Gln Lys Lys Ser Lys Met Met
            1730                1735                1740

Pro Asp Lys Leu Gln Tyr Leu Pro Glu Asp Ser Pro Val Pro Glu
            1745                1750                1755

Ala Lys Pro Val Asp Gln Lys Lys Ser Lys Met Met Pro Asp Lys
            1760                1765                1770

Leu Gln Ser Asp Gln Glu Ala Leu Leu Asp Cys Leu Met Gln Asp
            1775                1780                1785

Val Gly Phe Ser Lys Asp His Pro Val Ala Ala Val Ile Ile Phe
            1790                1795                1800

Lys Cys Leu Leu Gln Trp His Ser Phe Glu Ala Glu Arg Thr Asp
            1805                1810                1815

Val Phe Asp Arg Ile Ile Ser Ala Ile Gln Lys Ala Ile Glu Ser
            1820                1825                1830

His Ser Asp Asn Asn Asp Val Leu Ala Tyr Trp Leu Ser Asn Thr
            1835                1840                1845

Ser Thr Leu Leu His Leu Leu Gln Arg Thr Leu Lys Thr Gly Gly
            1850                1855                1860

Gly Gly Gly Thr Thr Pro Arg Arg Arg Arg Gln Ala Thr Leu Phe
            1865                1870                1875
```

```
Gly Arg Met Thr Gln Arg Phe Ser Ser Gln Gln Glu Asn Tyr Pro
    1880                1885                1890

Asn Gly Met Gly Pro Val Gly Leu Asp Asn Val Arg Gln Val Glu
    1895                1900                1905

Ala Lys Tyr Pro Ala Leu Leu Phe Lys Gln Gln Leu Ser Ala Tyr
    1910                1915                1920

Val Glu Lys Ile Tyr Gly Met Leu Arg Asp Arg Leu Lys Lys Glu
    1925                1930                1935

Ile Thr Pro Leu Leu Gly Ser Cys Ile Gln Ala Pro Arg Ala Pro
    1940                1945                1950

Arg His Gln Leu Val Arg Lys Leu Ser Leu Thr Pro Ala Gln Gln
    1955                1960                1965

Val Leu Ser Ser His Trp Gly Ser Ile Ile Asn Ser Leu Leu Thr
    1970                1975                1980

Leu Leu Asn Ala Leu Arg Gly Asn Lys Val Pro Pro Tyr Leu Val
    1985                1990                1995

Arg Asn Ile Phe Thr Gln Ile Phe Ser Phe Ile Asn Val Gln Leu
    2000                2005                2010

Val Asn Ser Leu Leu Leu Arg Arg Glu Cys Cys Ser Phe Ser Asn
    2015                2020                2025

Gly Glu Tyr Ile Lys Ala Gly Leu Ala Gln Leu Glu His Trp Ile
    2030                2035                2040

Tyr Glu Ala Gly Glu Glu Tyr Ala Gly Asp Ser Trp Glu Glu Leu
    2045                2050                2055

Arg Tyr Ile Arg Gln Ala Val Gly Phe Leu Val Ile His Gln Lys
    2060                2065                2070

Pro Lys Ile Ser Leu Asp Glu Ile Ile Asn Asp Leu Cys Pro Ala
    2075                2080                2085

Leu Ser Met Gln Gln Leu Tyr Arg Ile Ser Thr Met Tyr Trp Asp
    2090                2095                2100

Asp Lys Tyr Gly Thr His Thr Val Ala Pro Glu Val Ile Gln Asn
    2105                2110                2115

Met Arg Ile Leu Met Thr Glu Tyr Ser Tyr Asn Ala Gly Gly Asn
    2120                2125                2130

Ser Phe Leu Leu Asp Asp Asp Ser Gly Ile Pro Phe Ser Val Asp
    2135                2140                2145

Asp Ile Ser Lys Ser Met Pro Asp Val Asp Leu Ser Gln Val Asp
    2150                2155                2160

Pro Pro Pro Leu Leu Lys Asn Arg Pro Ser Phe Arg Phe Leu Gln
    2165                2170                2175

Pro Gly Lys Ala
    2180

<210> SEQ ID NO 3
<211> LENGTH: 1505
<212> TYPE: PRT
<213> ORGANISM: Arabidopsis thaliana
<220> FEATURE:
<223> OTHER INFORMATION: myosin XI-2 (MYA2) full length

<400> SEQUENCE: 3

Met Val Ala Asn Phe Asn Pro Ser Val Gly Ser Phe Val Trp Val Glu
1               5                   10                  15

Asp Pro Asp Glu Ala Trp Ile Asp Gly Glu Val Val Gln Val Asn Gly
            20                  25                  30
```

```
Asp Glu Ile Lys Val Leu Cys Thr Ser Gly Lys His Val Thr Lys
         35                  40                  45

Ile Ser Asn Ala Tyr Pro Lys Asp Val Glu Ala Pro Ala Ser Gly Val
 50                  55                  60

Asp Asp Met Thr Arg Leu Ala Tyr Leu His Glu Pro Gly Val Leu Gln
 65                  70                  75                  80

Asn Leu His Ser Arg Tyr Asp Ile Asn Glu Ile Tyr Thr Tyr Thr Gly
                 85                  90                  95

Ser Ile Leu Ile Ala Val Asn Pro Phe Arg Arg Leu Pro His Leu Tyr
                100                 105                 110

Ser Ser His Met Met Ala Gln Tyr Lys Gly Ala Ser Leu Gly Glu Leu
                115                 120                 125

Ser Pro His Pro Phe Ala Val Ala Asp Ala Ala Tyr Arg Gln Met Ile
                130                 135                 140

Asn Asp Gly Val Ser Gln Ser Ile Leu Val Ser Gly Glu Ser Gly Ala
145                 150                 155                 160

Gly Lys Thr Glu Ser Thr Lys Leu Leu Met Arg Tyr Leu Ala Tyr Met
                165                 170                 175

Gly Gly Arg Ala Ala Glu Gly Arg Ser Val Glu Lys Val Leu
                180                 185                 190

Glu Ser Asn Pro Val Leu Glu Ala Phe Gly Asn Ala Lys Thr Val Arg
                195                 200                 205

Asn Asn Asn Ser Ser Arg Phe Gly Lys Phe Val Glu Ile Gln Phe Asp
210                 215                 220

Glu Lys Gly Arg Ile Ser Gly Ala Ala Ile Arg Thr Tyr Leu Leu Glu
225                 230                 235                 240

Arg Ser Arg Val Cys Gln Val Ser Asp Pro Glu Arg Asn Tyr His Cys
                245                 250                 255

Phe Tyr Met Leu Cys Ala Ala Pro Gln Glu Asp Val Lys Lys Phe Lys
                260                 265                 270

Leu Glu Glu Pro Lys Lys Tyr His Tyr Leu Asn Gln Ser Lys Cys Leu
                275                 280                 285

Glu Leu Asp Ser Ile Asn Asp Ala Glu Glu Tyr His Ala Thr Arg Arg
290                 295                 300

Ala Met Asp Val Val Gly Ile Ser Thr Glu Glu Gln Asp Ala Ile Phe
305                 310                 315                 320

Ser Val Val Ala Ala Ile Leu His Ile Gly Asn Ile Glu Phe Ala Lys
                325                 330                 335

Gly Glu Glu Ile Asp Ser Ser Ile Pro Lys Asp Lys Ser Leu Phe
                340                 345                 350

His Leu Lys Thr Ala Ala Glu Leu Leu Ser Cys Asp Glu Lys Ala Leu
                355                 360                 365

Glu Asp Ser Leu Cys Lys Arg Ile Met Val Thr Arg Asp Glu Thr Ile
370                 375                 380

Thr Lys Thr Leu Asp Pro Glu Ala Ala Thr Leu Ser Arg Asp Ala Leu
385                 390                 395                 400

Ala Lys Val Met Tyr Ser Arg Leu Phe Asp Trp Leu Val Asp Lys Ile
                405                 410                 415

Asn Ser Ser Ile Gly Gln Asp His Asp Ser Lys Tyr Leu Ile Gly Val
                420                 425                 430

Leu Asp Ile Tyr Gly Phe Glu Ser Phe Lys Thr Asn Ser Phe Glu Gln
                435                 440                 445
```

-continued

```
Phe Cys Ile Asn Leu Thr Asn Glu Lys Leu Gln Gln His Phe Asn Gln
    450                 455                 460
His Val Phe Lys Met Glu Gln Glu Glu Tyr Lys Lys Glu Glu Ile Asn
465                 470                 475                 480
Trp Ser Tyr Ile Glu Phe Val Asp Asn Gln Asp Ile Leu Asp Leu Ile
                485                 490                 495
Glu Lys Lys Pro Gly Gly Ile Ile Ala Leu Leu Asp Glu Ala Cys Met
                500                 505                 510
Phe Pro Arg Ser Thr His Glu Thr Phe Ala Gln Lys Leu Tyr Gln Thr
            515                 520                 525
Phe Lys Thr His Lys Arg Phe Thr Lys Pro Lys Leu Ala Arg Ser Asp
        530                 535                 540
Phe Thr Ile Cys His Tyr Ala Gly Asp Val Thr Tyr Gln Thr Glu Leu
545                 550                 555                 560
Phe Leu Asp Lys Asn Lys Asp Tyr Val Ile Ala Glu His Gln Ala Leu
                565                 570                 575
Leu Asn Ser Ser Ser Cys Ser Phe Val Ala Ser Leu Phe Pro Pro Met
                580                 585                 590
Ser Asp Asp Ser Lys Gln Ser Lys Phe Ser Ser Ile Gly Thr Arg Phe
            595                 600                 605
Lys Gln Gln Leu Val Ser Leu Leu Glu Ile Leu Asn Thr Thr Glu Pro
        610                 615                 620
His Tyr Ile Arg Cys Ile Lys Pro Asn Asn Leu Leu Lys Pro Gly Ile
625                 630                 635                 640
Phe Glu Asn Glu Asn Ile Leu Gln Gln Leu Arg Cys Gly Gly Val Met
                645                 650                 655
Glu Ala Ile Arg Ile Ser Cys Ala Gly Tyr Pro Thr Arg Lys His Phe
                660                 665                 670
Asp Glu Phe Leu Ala Arg Phe Gly Ile Leu Ala Pro Glu Val Leu Val
            675                 680                 685
Lys Asn Ser Asp Asp Pro Ala Ala Cys Lys Lys Leu Leu Asp Lys Val
        690                 695                 700
Gly Leu Glu Gly Tyr Gln Ile Gly Lys Thr Lys Val Phe Leu Arg Ala
705                 710                 715                 720
Gly Gln Met Ala Asp Leu Asp Thr Arg Arg Thr Glu Val Leu Gly Arg
                725                 730                 735
Ser Ala Ser Ile Ile Gln Arg Lys Val Arg Ser Tyr Leu Ala Lys Lys
                740                 745                 750
Ser Phe Ile Val Leu Arg Asn Ser Ala Lys Gln Ile Gln Ser Val Cys
            755                 760                 765
Arg Gly Tyr Leu Ala Arg Ser Val Tyr Glu Gly Met Arg Arg Glu Ala
        770                 775                 780
Ala Ala Leu Lys Ile Gln Arg Asp Leu Arg Arg Phe Leu Ala Arg Lys
785                 790                 795                 800
Ala Tyr Thr Glu Leu Tyr Ser Ala Val Ser Val Gln Ala Gly Met
                805                 810                 815
Arg Gly Met Val Ala Arg Lys Glu Leu Cys Phe Arg Arg Gln Thr Lys
                820                 825                 830
Ala Ala Ile Ile Ile Gln Thr Trp Cys Arg Gly Tyr Leu Ala Arg Leu
            835                 840                 845
His Tyr Arg Lys Leu Lys Lys Ala Ala Ile Thr Thr Gln Cys Ala Trp
850                 855                 860
Arg Ser Lys Val Ala Arg Gly Glu Leu Arg Lys Leu Lys Met Ala Ala
```

-continued

```
              865                 870                 875                 880
Arg Glu Thr Gly Ala Leu Gln Ala Ala Lys Asn Lys Leu Glu Lys Gln
                    885                 890                 895

Val Glu Glu Leu Thr Trp Arg Leu Gln Leu Glu Lys Arg Ile Arg Thr
                    900                 905                 910

Asp Leu Glu Glu Ala Lys Lys Gln Glu Ser Ala Lys Ala Gln Ser Ser
                    915                 920                 925

Leu Glu Glu Leu Gln Leu Lys Cys Lys Glu Thr Glu Ala Leu Leu Ile
                    930                 935                 940

Lys Glu Arg Glu Ala Ala Lys Lys Ile Ala Glu Thr Ala Pro Ile Ile
945                 950                 955                 960

Lys Glu Ile Pro Val Val Asp Gln Glu Leu Met Asp Lys Ile Thr Asn
                    965                 970                 975

Glu Asn Glu Lys Leu Lys Ser Met Val Ser Ser Leu Glu Met Lys Ile
                    980                 985                 990

Gly Glu Thr Glu Lys Lys Leu Gln Glu Thr Thr Lys Ile Ser Gln Asp
                    995                 1000                1005

Arg Leu Asn Gln Ala Leu Glu Ala Glu Ser Lys Leu Val Lys Leu
    1010                1015                1020

Lys Thr Ala Met Gln Arg Leu Glu Glu Lys Ile Leu Asp Met Glu
    1025                1030                1035

Ala Glu Lys Lys Ile Met His Gln Gln Thr Ile Ser Thr Pro Val
    1040                1045                1050

Arg Thr Asn Leu Gly His Pro Thr Ala Pro Val Lys Asn Leu
    1055                1060                1065

Glu Asn Gly His Gln Thr Asn Leu Glu Lys Glu Phe Asn Glu Ala
    1070                1075                1080

Glu Phe Thr Thr Pro Val Asp Gly Lys Ala Gly Lys Ser Ala Ala
    1085                1090                1095

Glu Arg Gln Ile Met Asn Val Asp Ala Leu Ile Asp Cys Val Lys
    1100                1105                1110

Asp Asn Ile Gly Phe Ser Asn Gly Lys Pro Val Ala Ala Phe Thr
    1115                1120                1125

Ile Tyr Lys Cys Leu Leu His Trp Lys Cys Phe Glu Ser Glu Lys
    1130                1135                1140

Thr Asn Val Phe Asp Arg Leu Ile Gln Met Ile Gly Ser Ala Ile
    1145                1150                1155

Glu Asn Glu Asp Asp Asn Ser His Leu Ala Tyr Trp Leu Thr Ser
    1160                1165                1170

Thr Ser Ala Leu Leu Phe Leu Leu Gln Lys Ser Leu Lys Thr Asn
    1175                1180                1185

Gly Ser Gly Ala Thr Gln Ser Lys Lys Pro Pro Ala Ser Thr Ser
    1190                1195                1200

Leu Phe Gly Arg Met Ala Met Ser Phe Arg Ser Ser Pro Ala Ser
    1205                1210                1215

Gly Asn Leu Ala Ala Ala Ala Glu Ala Ala Ala Leu Ala Val Val
    1220                1225                1230

Arg Pro Val Glu Ala Lys Tyr Pro Ala Leu Leu Phe Lys Gln Gln
    1235                1240                1245

Leu Ala Ala Tyr Val Glu Lys Met Phe Gly Met Val Arg Asp Asn
    1250                1255                1260

Leu Lys Arg Glu Leu Ser Thr Leu Leu Ser Leu Cys Ile Gln Ala
    1265                1270                1275
```

```
Pro Arg Ser Ser Lys Gly Gly Met Leu Arg Ser Gly Arg Ser Phe
    1280                1285                1290

Gly Lys Asp Ser Pro Ala Val His Trp Gln Ser Ile Ile Asp Gly
    1295                1300                1305

Leu Asn Ser Leu Leu Val Thr Leu Lys Glu Asn His Val Pro Leu
    1310                1315                1320

Val Leu Ile Gln Lys Ile Tyr Ser Gln Thr Phe Ser Tyr Ile Asn
    1325                1330                1335

Val Gln Leu Phe Asn Ser Leu Leu Arg Lys Glu Cys Cys Thr
    1340                1345                1350

Phe Ser Asn Gly Glu Phe Val Lys Ser Gly Leu Ala Glu Leu Glu
    1355                1360                1365

Leu Trp Cys Cys Gln Ala Lys Glu Tyr Ser Gly Pro Ser Trp Glu
    1370                1375                1380

Glu Leu Lys His Ile Arg Gln Ala Val Gly Phe Leu Val Ile His
    1385                1390                1395

Gln Lys Tyr Arg Ile Ser Tyr Asp Glu Ile Ala Asn Asp Leu Cys
    1400                1405                1410

Pro Val Leu Ser Val Gln Gln Leu Tyr Arg Ile Cys Thr Leu Tyr
    1415                1420                1425

Trp Asp Asp Ser Tyr Asn Thr Arg Ser Val Ser Gln Glu Val Ile
    1430                1435                1440

Ser Ser Met Arg Thr Leu Met Thr Glu Glu Ser Asn Asp Ala Asp
    1445                1450                1455

Ser Asp Ser Phe Leu Leu Asp Asp Asp Ser Ser Ile Pro Phe Ser
    1460                1465                1470

Ile Asp Asp Ile Ser Ser Ser Met Glu Glu Lys Asp Phe Val Gly
    1475                1480                1485

Ile Lys Pro Ala Glu Glu Leu Leu Glu Asn Pro Ala Phe Val Phe
    1490                1495                1500

Leu His
    1505

<210> SEQ ID NO 4
<211> LENGTH: 1520
<212> TYPE: PRT
<213> ORGANISM: Arabidopsis thaliana
<220> FEATURE:
<223> OTHER INFORMATION: myosin XI-1 full length

<400> SEQUENCE: 4

Met Ala Ala Pro Val Ile Ile Val Gly Ser His Val Trp Val Glu Asp
1               5                   10                  15

Pro His Leu Ala Trp Ile Asp Gly Glu Val Thr Arg Ile Asp Gly Ile
                20                  25                  30

Asn Val His Val Lys Thr Lys Lys Gly Lys Thr Val Val Thr Asn Val
            35                  40                  45

Tyr Phe Pro Lys Asp Thr Glu Ala Pro Ser Gly Gly Val Asp Asp Met
    50                  55                  60

Thr Lys Leu Ser Tyr Leu His Glu Pro Gly Val Leu Arg Asn Leu Glu
65                  70                  75                  80

Thr Arg Tyr Glu Leu Asn Glu Ile Tyr Thr Tyr Thr Gly Asn Ile Leu
                85                  90                  95

Ile Ala Val Asn Pro Phe Gln Arg Leu Pro His Ile Tyr Glu Thr Asp
            100                 105                 110
```

-continued

```
Met Met Glu Gln Tyr Lys Gly Ile Ala Leu Gly Glu Leu Ser Pro His
        115                 120                 125
Val Phe Ala Ile Gly Asp Ala Ala Tyr Arg Ala Met Ile Asn Glu Gly
        130                 135                 140
Lys Asn Asn Ser Ile Leu Val Ser Gly Glu Ser Gly Ala Gly Lys Thr
145                 150                 155                 160
Glu Thr Thr Lys Met Leu Met Arg Tyr Leu Ala Phe Leu Gly Gly Arg
                165                 170                 175
Ser Gly Val Glu Gly Arg Thr Val Glu Gln Gln Val Leu Glu Ser Asn
            180                 185                 190
Pro Val Leu Glu Ala Phe Gly Asn Ala Lys Thr Leu Arg Asn Asn Asn
        195                 200                 205
Ser Ser Arg Phe Gly Lys Phe Val Glu Ile Gln Phe Asp Lys Asn Gly
    210                 215                 220
Arg Ile Ser Gly Ala Ala Ile Arg Thr Tyr Leu Leu Glu Arg Ser Arg
225                 230                 235                 240
Val Cys Gln Ile Ser Asp Pro Glu Arg Asn Tyr His Cys Phe Tyr Leu
                245                 250                 255
Leu Cys Ala Ala Pro Pro Glu Asp Ile Lys Lys Tyr Lys Leu Glu Asn
            260                 265                 270
Pro His Lys Phe His Tyr Leu Asn Gln Ser Ser Cys Tyr Lys Leu Asp
        275                 280                 285
Gly Val Asp Asp Ala Ser Glu Tyr Leu Glu Thr Arg Arg Ala Met Asp
    290                 295                 300
Val Val Gly Ile Ser Asn Glu Glu Gln Glu Ala Ile Phe Arg Val Val
305                 310                 315                 320
Ala Ala Ile Leu His Leu Gly Asn Ile Asp Phe Gly Lys Gly Glu Glu
                325                 330                 335
Ile Asp Ser Ser Val Ile Lys Asp Lys Asp Ser Arg Ser His Leu Asn
            340                 345                 350
Met Ala Ala Glu Leu Leu Met Cys Asn Ala Gln Ser Leu Glu Asp Ala
        355                 360                 365
Leu Ile Arg Arg Val Met Val Thr Pro Glu Glu Ile Ile Thr Arg Thr
    370                 375                 380
Leu Asp Pro Asp Asn Ala Ile Ala Ser Arg Asp Thr Leu Ala Lys Thr
385                 390                 395                 400
Ile Tyr Ser His Leu Phe Asp Trp Ile Val Asn Lys Ile Asn Thr Ser
                405                 410                 415
Ile Gly Gln Asp Pro Arg Ser Lys Ser Ile Ile Gly Val Leu Asp Ile
            420                 425                 430
Tyr Gly Phe Glu Ser Phe Lys Cys Asn Ser Phe Glu Gln Phe Cys Ile
        435                 440                 445
Asn Phe Thr Asn Glu Lys Leu Gln Gln His Phe Asn Gln His Val Phe
    450                 455                 460
Lys Met Glu Gln Glu Glu Tyr Thr Lys Glu Glu Ile Ala Trp Ser Tyr
465                 470                 475                 480
Ile Glu Phe Ile Asp Asn Gln Asp Val Leu Glu Leu Ile Glu Lys Lys
                485                 490                 495
Pro Gly Gly Ile Ile Ser Leu Leu Asp Glu Ala Cys Met Phe Pro Lys
            500                 505                 510
Ser Thr His Glu Thr Phe Ser Gln Lys Leu Phe Gln Thr Phe Lys Glu
        515                 520                 525
```

-continued

```
His Glu Arg Phe Ala Lys Pro Lys Leu Ser Arg Thr Asp Phe Thr Ile
    530                 535                 540

Ser His Tyr Ala Gly Glu Val Thr Tyr Gln Ser Asn His Phe Ile Asp
545                 550                 555                 560

Lys Asn Lys Asp Tyr Ile Val Ala Glu His Gln Ala Leu Phe Thr Ala
                565                 570                 575

Ser Asn Cys Lys Phe Val Ala Gly Leu Phe His Ala Leu His Glu Asp
            580                 585                 590

Ser Ser Arg Ser Ser Lys Phe Ser Ser Ile Gly Ser Arg Phe Lys Gln
        595                 600                 605

Gln Leu His Ser Leu Met Glu Ser Leu Asn Gly Thr Glu Pro His Tyr
    610                 615                 620

Ile Arg Cys Ile Lys Pro Asn Asn Val Leu Lys Pro Gly Ile Phe Glu
625                 630                 635                 640

Asn Phe Asn Val Ile His Gln Leu Arg Cys Gly Gly Val Leu Glu Ala
                645                 650                 655

Ile Arg Ile Ser Cys Ala Gly Tyr Pro Thr Arg Leu Ala Phe Tyr Asp
            660                 665                 670

Phe Leu Asp Arg Phe Gly Leu Leu Ala Pro Glu Val Leu Glu Gly Asn
        675                 680                 685

Tyr Asp Asp Lys Val Ala Cys Gln Met Ile Leu Asp Lys Lys Ser Leu
    690                 695                 700

Thr Asp Tyr Gln Ile Gly Lys Thr Lys Ile Phe Leu Arg Ala Gly Gln
705                 710                 715                 720

Met Ala Glu Leu Asp Ala Arg Arg Ala Glu Val Leu Gly Asn Ala Ala
                725                 730                 735

Arg Val Ile Gln Arg Gln Phe Arg Thr Cys Met Ala Arg Lys Asn Tyr
            740                 745                 750

Arg Ser Ile Arg Asn Ala Ala Ile Val Leu Gln Ser Phe Leu Arg Gly
        755                 760                 765

Glu Ile Ala Arg Ala Val His Lys Lys Leu Arg Ile Glu Ala Ala Ala
    770                 775                 780

Leu Arg Val Gln Lys Asn Phe Arg Arg Tyr Val Asp Arg Lys Ser Phe
785                 790                 795                 800

Val Thr Thr Arg Ser Ser Thr Ile Val Leu Gln Thr Gly Leu Arg Ala
                805                 810                 815

Met Ile Ala Arg Ser Glu Phe Arg Leu Arg Arg Gln Arg Lys Ala Ala
            820                 825                 830

Ile Val Leu Gln Ala His Trp Arg Gly Arg Gln Ala Phe Ser Tyr Tyr
        835                 840                 845

Thr Arg Leu Gln Lys Ala Ala Ile Val Thr Gln Cys Ala Trp Arg Cys
    850                 855                 860

Arg Leu Ala Arg Arg Glu Leu Arg Met Leu Lys Met Ala Ala Arg Asp
865                 870                 875                 880

Thr Gly Ala Leu Lys Asp Ala Lys Asn Lys Leu Glu Gln Arg Val Glu
                885                 890                 895

Glu Leu Ser Leu Arg Leu His Leu Glu Lys Arg Leu Arg Thr Asp Leu
            900                 905                 910

Glu Glu Ala Lys Val Gln Glu Val Ala Lys Leu Gln Glu Ala Leu His
        915                 920                 925

Thr Met Arg Leu Gln Leu Lys Glu Thr Thr Ala Met Val Val Lys Glu
    930                 935                 940

Gln Glu Ala Ala Arg Val Ala Ile Glu Glu Ala Ser Ser Val Asn Lys
```

```
            945                 950                 955                 960
       Glu Pro Val Val Glu Asp Thr Glu Lys Ile Asp Ser Leu Ser Asn
                       965                 970                 975
       Glu Ile Asp Arg Leu Lys Gly Leu Leu Ser Ser Glu Thr His Lys Ala
                       980                 985                 990
       Asp Glu Ala Gln His Ala Tyr Gln Ser Ala Leu Val Gln Asn Glu Glu
                       995                 1000                1005
       Leu Cys Lys Lys Leu Glu Glu Ala Gly Arg Lys Ile Asp Gln Leu
           1010                1015                1020
       Gln Asp Ser Val Gln Arg Phe Gln Glu Lys Val Phe Ser Leu Glu
           1025                1030                1035
       Ser Glu Asn Lys Val Leu Arg Gln Gln Thr Leu Thr Ile Ser Pro
           1040                1045                1050
       Thr Thr Arg Ala Leu Ala Leu Arg Pro Lys Thr Thr Ile Ile Gln
           1055                1060                1065
       Arg Thr Pro Glu Lys Asp Thr Phe Ser Asn Gly Glu Thr Thr Gln
           1070                1075                1080
       Leu Gln Glu Pro Glu Thr Glu Asp Arg Pro Gln Lys Ser Leu Asn
           1085                1090                1095
       Gln Lys Gln Gln Glu Asn Gln Glu Leu Leu Leu Lys Ser Ile Ser
           1100                1105                1110
       Glu Asp Ile Gly Phe Ser Glu Gly Lys Pro Val Ala Ala Cys Leu
           1115                1120                1125
       Ile Tyr Lys Cys Leu Ile His Trp Arg Ser Phe Glu Val Glu Arg
           1130                1135                1140
       Thr Ser Ile Phe Asn Arg Ile Ile Glu Thr Ile Ala Ser Ala Ile
           1145                1150                1155
       Glu Met Gln Glu Asn Ser Asp Val Leu Cys Tyr Trp Leu Ser Asn
           1160                1165                1170
       Ser Ala Thr Leu Leu Met Phe Leu Gln Arg Thr Leu Lys Ala Gly
           1175                1180                1185
       Ala Thr Gly Ser Ile Thr Thr Pro Arg Arg Gly Met Pro Ser
           1190                1195                1200
       Ser Leu Phe Gly Arg Val Ser Gln Ser Phe Arg Gly Ser Pro Gln
           1205                1210                1215
       Ser Ala Gly Phe Pro Phe Met Thr Gly Arg Ala Ile Gly Gly Gly
           1220                1225                1230
       Leu Asp Glu Leu Arg Gln Val Glu Ala Lys Tyr Pro Ala Leu Leu
           1235                1240                1245
       Phe Lys Gln Gln Leu Thr Ala Phe Leu Glu Lys Ile Tyr Gly Met
           1250                1255                1260
       Ile Arg Asp Lys Met Lys Lys Glu Ile Ser Pro Leu Leu Ala Ser
           1265                1270                1275
       Cys Ile Gln Val Pro Arg Thr Pro Arg Ser Gly Leu Val Lys Gly
           1280                1285                1290
       Arg Ser Gln Asn Thr Gln Asn Asn Val Val Ala Pro Lys Pro Met
           1295                1300                1305
       Ile Ala His Trp Gln Asn Ile Val Thr Cys Leu Asn Gly His Leu
           1310                1315                1320
       Arg Thr Met Arg Ala Asn Tyr Val Pro Ser Leu Leu Ile Ser Lys
           1325                1330                1335
       Val Phe Gly Gln Ile Phe Ser Phe Ile Asn Val Gln Leu Phe Asn
           1340                1345                1350
```

```
Ser Leu Leu Leu Arg Arg Glu Cys Cys Ser Phe Ser Asn Gly Glu
    1355                1360                1365

Tyr Val Lys Thr Gly Leu Ala Glu Leu Glu Lys Trp Cys His Asp
    1370                1375                1380

Ala Thr Glu Glu Phe Val Gly Ser Ala Trp Asp Glu Leu Lys His
    1385                1390                1395

Ile Arg Gln Ala Val Gly Phe Leu Val Ile His Gln Lys Pro Lys
    1400                1405                1410

Lys Ser Leu Lys Glu Ile Thr Thr Glu Leu Cys Pro Val Leu Ser
    1415                1420                1425

Ile Gln Gln Leu Tyr Arg Ile Ser Thr Met Tyr Trp Asp Asp Lys
    1430                1435                1440

Tyr Gly Thr His Ser Val Ser Thr Glu Val Ile Ala Thr Met Arg
    1445                1450                1455

Ala Glu Val Ser Asp Val Ser Lys Ser Ala Ile Ser Asn Ser Phe
    1460                1465                1470

Leu Leu Asp Asp Asp Ser Ser Ile Pro Phe Ser Leu Asp Asp Ile
    1475                1480                1485

Ser Lys Ser Met Gln Asn Val Glu Val Ala Glu Val Asp Pro Pro
    1490                1495                1500

Pro Leu Ile Arg Gln Asn Ser Asn Phe Met Phe Leu Leu Glu Arg
    1505                1510                1515

Ser Asp
    1520

<210> SEQ ID NO 5
<211> LENGTH: 1500
<212> TYPE: PRT
<213> ORGANISM: Arabidopsis thaliana
<220> FEATURE:
<223> OTHER INFORMATION: myosin XI-B full length

<400> SEQUENCE: 5

Met Val Ala Thr Phe Asn Pro Ala Val Gly Ser His Val Trp Val Glu
1               5                   10                  15

Asp Pro Asp Glu Ala Trp Leu Asp Gly Glu Val Val Glu Ile Asn Gly
                20                  25                  30

Asp Gln Ile Lys Val Leu Cys Ala Ser Gly Lys Gln Val Val Val Lys
            35                  40                  45

Asp Ser Asn Ile Tyr Pro Lys Asp Val Glu Ala Pro Ala Ser Gly Val
        50                  55                  60

Glu Asp Met Thr Arg Leu Ala Tyr Leu His Glu Pro Gly Val Leu Gln
65                  70                  75                  80

Asn Leu Gln Ser Arg Tyr Asp Ile Asn Glu Ile Tyr Thr Tyr Thr Gly
                85                  90                  95

Ser Ile Leu Ile Ala Val Asn Pro Phe Arg Arg Leu Pro His Leu Tyr
            100                 105                 110

Ser Ser His Met Met Thr Gln Tyr Lys Gly Ala Ser Leu Gly Glu Leu
        115                 120                 125

Ser Pro His Pro Phe Ala Val Ala Asp Ala Ala Tyr Arg Gln Met Val
    130                 135                 140

Asn Glu Gly Val Ser Gln Ser Ile Leu Val Ser Gly Glu Ser Gly Ala
145                 150                 155                 160

Gly Lys Thr Glu Ser Thr Lys Leu Leu Met Arg Tyr Leu Ala Phe Met
                165                 170                 175
```

```
Gly Gly Arg Gly Ala Ala Thr Glu Gly Arg Thr Val Glu Gln Lys Val
            180                 185                 190

Leu Glu Ser Asn Pro Val Leu Glu Ala Phe Gly Asn Ala Lys Thr Val
            195                 200                 205

Lys Asn Asn Asn Ser Ser Arg Phe Gly Lys Phe Val Glu Ile Gln Phe
210                 215                 220

Asp Gln Ser Gly Arg Ile Ser Gly Ala Ala Ile Arg Thr Tyr Leu Leu
225                 230                 235                 240

Glu Arg Ser Arg Val Cys Gln Val Ser Asp Pro Glu Arg Asn Tyr His
                245                 250                 255

Cys Phe Tyr Met Leu Cys Ala Ala Pro Glu Gly Asp Ala Lys Lys Phe
            260                 265                 270

Lys Leu Gly Asp Pro Lys Ile Tyr His Tyr Leu Asn Gln Ser Lys Cys
            275                 280                 285

Ile Gln Leu Asp Ala Met Asn Asp Ala Glu Glu Tyr His Ala Thr Lys
            290                 295                 300

Lys Ala Met Asp Val Val Gly Ile Ser Ser Glu Glu Gln Asp Ala Ile
305                 310                 315                 320

Phe Arg Val Val Ala Ser Ile Leu His Leu Gly Asn Ile Glu Phe Ala
                325                 330                 335

Lys Gly Thr Glu Ile Asp Ser Ser Ile Pro Arg Asp Glu Lys Ser Trp
            340                 345                 350

Phe His Leu Lys Thr Ala Ala Glu Leu Leu Met Cys Asn Glu Lys Ser
            355                 360                 365

Leu Glu Asp Ser Leu Cys Lys Arg Ile Met Ala Thr Arg Asp Glu Thr
            370                 375                 380

Ile Thr Lys Thr Leu Asp Pro Glu Ala Ala Leu Leu Ser Arg Asp Ala
385                 390                 395                 400

Leu Ala Lys Val Met Tyr Ser Arg Leu Phe Asp Trp Leu Val Glu Lys
                405                 410                 415

Ile Asn Thr Ser Ile Gly Gln Asp Pro Asp Ser Lys Tyr Leu Ile Gly
            420                 425                 430

Val Leu Asp Ile Tyr Gly Phe Glu Ser Phe Lys Thr Asn Ser Phe Glu
            435                 440                 445

Gln Phe Cys Ile Asn Leu Thr Asn Glu Lys Leu Gln Gln His Phe Asn
450                 455                 460

Gln His Val Phe Lys Met Glu Gln Glu Glu Tyr Lys Lys Glu Glu Ile
465                 470                 475                 480

Asn Trp Ser Tyr Ile Glu Phe Val Asp Asn Gln Asp Ile Leu Asp Leu
                485                 490                 495

Ile Glu Lys Lys Pro Gly Gly Ile Ile Ala Leu Leu Asp Glu Ala Cys
            500                 505                 510

Met Phe Pro Arg Ser Thr His Glu Thr Phe Ala Gln Lys Leu Tyr Gln
            515                 520                 525

Thr Tyr Lys Asn His Lys Arg Phe Thr Lys Pro Lys Leu Ala Arg Ser
            530                 535                 540

Asp Phe Thr Ile Cys His Tyr Ala Gly Asp Val Thr Tyr Gln Thr Glu
545                 550                 555                 560

Leu Phe Leu Asp Lys Asn Lys Asp Tyr Val Ile Ala Glu His Gln Ala
                565                 570                 575

Leu Leu Asn Ala Ser Thr Cys Ser Phe Val Ala Asn Leu Phe Pro Pro
            580                 585                 590
```

```
Val Ser Asp Asp Ser Lys Gln Ser Lys Phe Ser Ser Ile Gly Thr Arg
        595                 600                 605

Phe Lys Gln Gln Leu Val Ser Leu Leu Glu Ile Leu Asn Thr Thr Glu
    610                 615                 620

Pro His Tyr Ile Arg Cys Ile Lys Pro Asn Asn Leu Leu Lys Pro Gly
625                 630                 635                 640

Ile Phe Glu Asn Gln Asn Val Leu Gln Gln Leu Arg Cys Gly Gly Val
                645                 650                 655

Met Glu Ala Ile Arg Ile Ser Cys Ala Gly Tyr Pro Thr Arg Lys His
            660                 665                 670

Phe Asp Glu Phe Leu Asn Arg Phe Gly Ile Ile Ala Pro Gln Val Leu
        675                 680                 685

Asp Lys Asn Ser Asn Glu Pro Ala Ala Cys Lys Lys Leu Leu Asp Lys
    690                 695                 700

Ala Gly Leu Glu Gly Tyr Gln Ile Gly Lys Ser Lys Val Phe Leu Arg
705                 710                 715                 720

Ala Gly Gln Met Ala Asp Leu Asp Thr Arg Arg Thr Glu Ile Leu Gly
                725                 730                 735

Arg Ser Ala Ser Ile Ile Gln Arg Lys Val Arg Ser Tyr Leu Ala Gln
            740                 745                 750

Lys Thr Phe Ile Gln Leu Arg Ile Ser Ala Thr Gln Ile Gln Ala Val
        755                 760                 765

Cys Arg Gly Tyr Leu Ala Arg Ser Ile Tyr Glu Gly Met Arg Arg Glu
    770                 775                 780

Ala Ala Ala Leu Lys Ile Gln Arg Asp Leu Arg Lys Phe Leu Ala Arg
785                 790                 795                 800

Lys Ala Tyr Thr Glu Leu Phe Ser Ala Thr Ile Leu Ile Gln Ala Gly
                805                 810                 815

Met Arg Gly Met Val Ser Arg Lys Glu Leu Cys Leu Arg Arg Gln Thr
            820                 825                 830

Lys Ala Ala Thr Ile Ile Gln Thr Arg Cys Arg Val Tyr Leu Ala Arg
        835                 840                 845

Leu His Tyr Arg Lys Leu Lys Lys Ala Ala Ile Thr Thr Gln Cys Ala
    850                 855                 860

Trp Arg Gly Lys Val Ala Arg Lys Glu Leu Lys Asn Leu Lys Met Ala
865                 870                 875                 880

Ala Arg Glu Thr Gly Ala Leu Gln Glu Ala Lys Asn Lys Leu Glu Lys
                885                 890                 895

Gln Val Glu Glu Leu Thr Trp Arg Leu Gln Leu Glu Lys Arg Met Arg
            900                 905                 910

Thr Asp Leu Glu Glu Ala Lys Lys Gln Glu Asn Ala Lys Tyr Glu Ser
        915                 920                 925

Ser Leu Glu Glu Ile Gln Asn Lys Phe Lys Glu Thr Glu Ala Leu Leu
    930                 935                 940

Ile Lys Glu Arg Glu Ala Ala Lys Thr Val Ser Glu Val Leu Pro Ile
945                 950                 955                 960

Ile Lys Glu Val Pro Val Val Asp Gln Glu Leu Met Glu Lys Leu Thr
                965                 970                 975

Asn Glu Asn Glu Lys Leu Lys Gly Met Val Ser Ser Leu Glu Ile Lys
            980                 985                 990

Ile Asp Glu Thr Ala Lys Glu Leu  His Glu Thr Ala Arg  Ile Ser Gln
        995                 1000                 1005

Asp Arg  Leu Lys Gln Ala Leu  Ala Ala Glu Ser Lys  Val Ala Lys
```

```
                  1010                1015                1020

Leu Lys Thr Ala Met Gln Arg Leu Glu Glu Lys Ile Ser Asp Met
    1025                1030                1035

Glu Thr Glu Lys Gln Ile Met Leu Gln Gln Thr Ile Leu Asn Thr
    1040                1045                1050

Pro Val Lys Ser Val Ala Gly His Pro Pro Thr Ala Thr Ile Lys
    1055                1060                1065

Asn Leu Glu Asn Gly His Arg Thr Asn Leu Glu Asn Gln Phe Asn
    1070                1075                1080

Glu Val Glu Val Asn Gly Asn Ala Gly Lys Ser Ala Ala Glu Arg
    1085                1090                1095

Gln Leu Glu Asn Val Asp Thr Leu Ile Asp Cys Val Lys Glu Asn
    1100                1105                1110

Ile Gly Phe Ser Asn Gly Lys Pro Ile Ala Ala Phe Thr Ile Tyr
    1115                1120                1125

Lys Cys Leu Leu His Trp Lys Cys Phe Glu Ser Glu Lys Thr Ser
    1130                1135                1140

Ala Phe Asp Arg Leu Ile Glu Met Ile Gly Ser Ala Ile Glu Asn
    1145                1150                1155

Glu Asp Asp Asn Gly His Leu Ala Tyr Trp Leu Thr Asn Thr Ser
    1160                1165                1170

Ala Leu Leu Phe Leu Leu Gln Lys Ser Leu Lys Pro Ala Gly Ala
    1175                1180                1185

Gly Ala Thr Ala Ser Lys Lys Pro Pro Ile Thr Thr Ser Leu Phe
    1190                1195                1200

Gly Arg Met Ala Leu Ser Phe Arg Ser Ser Pro Asn Leu Ala Ala
    1205                1210                1215

Ala Ala Glu Ala Ala Ala Leu Ala Val Ile Arg Pro Val Glu Ala
    1220                1225                1230

Lys Tyr Pro Ala Leu Leu Phe Lys Gln Gln Leu Ala Ala Tyr Val
    1235                1240                1245

Glu Lys Ile Phe Gly Met Ile Arg Asp Asn Leu Lys Lys Glu Leu
    1250                1255                1260

Ser Ala Leu Ile Ser Met Cys Ile Gln Ala Pro Arg Ile Ser Lys
    1265                1270                1275

Gly Gly Ile Gln Arg Ser Ala Arg Ser Leu Gly Lys Asp Ser Pro
    1280                1285                1290

Ala Ile His Trp Gln Ser Ile Ile Asp Gly Leu Asn Ser Leu Leu
    1295                1300                1305

Ala Ile Leu Lys Asp Asn Tyr Val Pro Leu Val Leu Ile Gln Lys
    1310                1315                1320

Ile His Thr Gln Thr Phe Ser Phe Val Asn Val Gln Leu Phe Asn
    1325                1330                1335

Ser Leu Leu Leu Arg Lys Glu Cys Cys Thr Phe Ser Asn Gly Glu
    1340                1345                1350

Phe Val Lys Ser Gly Leu Ala Glu Leu Glu Leu Trp Cys Gly Gln
    1355                1360                1365

Val Asn Glu Tyr Ala Gly Pro Ser Trp Asp Glu Leu Lys His Ile
    1370                1375                1380

Arg Gln Ala Val Gly Phe Leu Val Ile His Gln Lys Tyr Arg Val
    1385                1390                1395

Ser Tyr Asp Asp Ile Val His Asp Leu Cys Pro Ile Leu Ser Val
    1400                1405                1410
```

Gln Gln Leu Tyr Arg Ile Cys Thr Leu Tyr Trp Asp Asp Cys Tyr
    1415                1420                1425

Asn Thr Arg Ser Val Ser Gln Glu Val Ile Ser Ser Met Arg Ala
    1430                1435                1440

Leu Met Thr Glu Glu Ser Asn Asp Ala Asp Ser Asn Ser Phe Leu
    1445                1450                1455

Leu Asp Asp Asn Ser Ser Ile Pro Phe Ser Ile Asp Glu Ile Ser
    1460                1465                1470

Asn Ser Met His Glu Lys Asp Phe Ala Ser Val Lys Pro Ala Lys
    1475                1480                1485

Glu Leu Leu Glu Asn Pro Glu Phe Val Phe Leu His
    1490                1495                1500

<210> SEQ ID NO 6
<211> LENGTH: 1531
<212> TYPE: PRT
<213> ORGANISM: Arabidopsis thaliana
<220> FEATURE:
<223> OTHER INFORMATION: myosin XI-K (Dolja) full length

<400> SEQUENCE: 6

Met Val Gly Pro Val Asn Ile Ile Val Gly Ser His Val Trp Ile Glu
1               5                   10                  15

Asp Pro Gly Ala Ala Trp Ile Asp Gly Glu Val Val Lys Ile Asn Gly
            20                  25                  30

Glu Glu Val His Ala His Thr Thr Asn Gly Lys Thr Val Val Ala Asn
        35                  40                  45

Ile Ala Asn Val Phe Pro Lys Asp Thr Glu Ala Pro Pro Gly Gly Val
50                  55                  60

Asp Asp Met Thr Lys Leu Ser Tyr Leu His Glu Pro Gly Val Leu Asn
65                  70                  75                  80

Asn Leu Ala Met Arg Tyr Glu Leu Asn Glu Ile Tyr Thr Tyr Thr Gly
            85                  90                  95

Asn Ile Leu Ile Ala Val Asn Pro Phe Gln Arg Leu Pro His Leu Tyr
        100                 105                 110

Asp Thr His Met Met Glu Gln Tyr Lys Gly Ala Gly Phe Gly Glu Leu
    115                 120                 125

Ser Pro His Val Phe Ala Ile Ala Glu Val Ala Tyr Arg Ala Met Ile
130                 135                 140

Asn Glu Gly Lys Ser Asn Ser Ile Leu Val Ser Gly Glu Ser Gly Ala
145                 150                 155                 160

Gly Lys Thr Glu Thr Thr Lys Met Leu Met Arg Tyr Leu Ala Tyr Leu
            165                 170                 175

Gly Gly Arg Ser Gly Val Glu Gly Arg Thr Val Glu Gln Gln Val Leu
        180                 185                 190

Glu Ser Asn Pro Val Leu Glu Ala Phe Gly Asn Ala Lys Thr Leu Arg
    195                 200                 205

Asn Asn Asn Ser Ser Arg Phe Gly Lys Phe Val Glu Leu Gln Phe Asp
210                 215                 220

Asn Cys Gly Arg Ile Ser Gly Ala Ala Val Arg Thr Tyr Leu Leu Glu
225                 230                 235                 240

Arg Ser Arg Val Cys Gln Ile Ser Asp Pro Glu Arg Asn Tyr His Cys
            245                 250                 255

Phe Tyr Leu Leu Cys Ala Ala Pro Pro Glu Glu Arg Glu Lys Phe Lys
        260                 265                 270

```
Leu Gly Asp Pro Lys Leu Phe His Tyr Leu Asn Gln Ser Lys Cys Tyr
        275                 280                 285
Lys Leu Asp Gly Val Asp Asp Thr Glu Glu Tyr Leu Ala Thr Arg Arg
290                 295                 300
Ala Met Asp Ile Val Gly Ile Ser Glu Glu Gln Asp Ala Ile Phe
305                 310                 315                 320
Arg Val Val Ala Ala Ile Leu His Leu Gly Asn Val Asn Phe Ala Lys
                        325                 330                 335
Gly Lys Glu Ile Asp Ser Ser Val Leu Lys Asp Glu Lys Ser Arg Tyr
                340                 345                 350
His Leu Asp Val Cys Ala Glu Leu Leu Arg Cys Asp Ala Lys Lys Met
                    355                 360                 365
Glu Asp Ala Leu Ile Lys Arg Val Met Val Thr Pro Glu Glu Val Ile
370                 375                 380
Thr Arg Thr Leu Asp Pro Asp Ser Ala Thr Gly Ser Arg Asp Ala Leu
385                 390                 395                 400
Ala Lys Thr Ile Tyr Ser Arg Leu Phe Asp Trp Leu Val Asp Lys Ile
                    405                 410                 415
Asn Asn Ser Ile Gly Gln Asp Pro Asn Ser Lys Thr Ile Ile Gly Val
                420                 425                 430
Leu Asp Ile Tyr Gly Phe Glu Ser Phe Lys Ile Asn Ser Phe Glu Gln
        435                 440                 445
Phe Cys Ile Asn Phe Thr Asn Glu Lys Leu Gln Gln His Phe Asn Gln
    450                 455                 460
His Val Phe Lys Met Glu Gln Glu Asp Tyr Thr Lys Glu Glu Ile Asn
465                 470                 475                 480
Trp Ser Tyr Ile Glu Phe Val Asp Asn Lys Asp Val Leu Glu Leu Ile
                485                 490                 495
Glu Lys Lys Pro Gly Gly Val Ile Ala Leu Leu Asp Glu Ala Cys Met
                500                 505                 510
Phe Pro Lys Ser Thr His Glu Thr Phe Ala Gln Lys Leu Tyr Gln Thr
            515                 520                 525
Phe Lys Asn Tyr Lys Arg Phe Thr Lys Pro Lys Leu Ser Arg Thr Ser
        530                 535                 540
Phe Ala Ile Ser His Tyr Ala Gly Glu Val Thr Tyr Gln Ala Asp Leu
545                 550                 555                 560
Phe Leu Asp Lys Asn Lys Asp Tyr Val Val Ala Glu His Gln Asp Leu
                565                 570                 575
Leu Ile Ala Ser Ser Asp Thr Phe Val Ala Gly Leu Phe Pro Arg Leu
                580                 585                 590
Pro Glu Glu Thr Ser Ser Lys Thr Lys Phe Ser Ser Ile Gly Ser Arg
            595                 600                 605
Phe Lys Leu Gln Leu Gln Ser Leu Met Glu Thr Leu Ser Ser Thr Glu
        610                 615                 620
Pro His Tyr Ile Arg Cys Val Lys Pro Asn Asn Val Leu Lys Pro Ala
625                 630                 635                 640
Ile Phe Glu Asn Val Asn Val Ile Gln Gln Leu Arg Cys Gly Gly Val
                645                 650                 655
Leu Glu Ala Ile Arg Ile Ser Cys Ala Gly Tyr Pro Thr Lys Arg Thr
                660                 665                 670
Phe Tyr Glu Phe Leu Asn Arg Phe Gly Val Leu Ala Pro Glu Val Leu
        675                 680                 685
```

-continued

```
Glu Gly Asn Tyr Asp Asp Lys Val Ala Cys Lys Met Leu Leu Asp Lys
690             695                 700
Ile Gly Leu Lys Gly Tyr Glu Leu Gly Lys Thr Lys Val Phe Leu Arg
705                 710                 715                 720
Ala Gly Gln Met Ala Glu Leu Asp Ala Arg Arg Ala Glu Val Leu Gly
            725                 730                 735
Asn Ala Ala Arg Arg Ile Gln Arg Gln Ser Arg Thr Phe Ile Ala Cys
            740                 745                 750
Lys Glu Phe Arg Ala Leu Arg Gly Ala Ala Ile Val Leu Gln Ser Asn
            755                 760                 765
Cys Arg Gly Lys Leu Ala Cys Asn Leu Tyr Glu Glu Met Arg Arg Gln
770                 775                 780
Ala Ala Ala Val Lys Ile Gln Lys Ile Phe Arg Arg His Ile Ala Arg
785                 790                 795                 800
Glu Ser Tyr Leu Arg Ile Arg His Ser Thr Ile Thr Val Gln Thr Ala
                805                 810                 815
Leu Arg Gly Met Val Ala Arg Asn Glu Phe Arg Phe Arg Lys Gln Met
            820                 825                 830
Lys Ala Ala Thr Ile Ile Gln Ala Arg Leu Arg Ser His Leu Thr His
            835                 840                 845
Ser Tyr Tyr Lys Gln Leu Gln Lys Ala Ala Leu Ser Thr Gln Cys Gly
850                 855                 860
Trp Arg Ser Arg Val Ala Arg Lys Glu Leu Arg Thr Leu Lys Met Ala
865                 870                 875                 880
Ala Arg Asp Thr Gly Ala Leu Arg Glu Ala Lys Asp Lys Leu Glu Lys
            885                 890                 895
Arg Val Glu Glu Leu Thr Trp Arg Leu Gln Leu Glu Lys Arg Gln Arg
            900                 905                 910
Thr Glu Leu Glu Glu Ala Lys Thr Gln Glu Tyr Ala Lys Gln Gln Glu
            915                 920                 925
Ala Leu Glu Thr Met Arg Leu Gln Val Glu Glu Ala Asn Ala Ala Val
            930                 935                 940
Ile Arg Glu Arg Glu Ala Ala Arg Lys Ala Ile Glu Glu Ala Pro Pro
945                 950                 955                 960
Val Ile Lys Glu Thr Pro Val Leu Val Glu Asp Thr Glu Lys Ile Asn
                965                 970                 975
Ser Leu Thr Ser Glu Val Glu Ala Leu Lys Ala Ser Leu Gln Ala Glu
            980                 985                 990
Arg Gln Ala Ala Glu Asn Leu Arg Lys Ala Phe Ser Glu Ala Glu Ala
            995                 1000                1005
Arg Asn Ser Glu Leu Ala Thr Glu Leu Glu Asn Ala Thr Arg Lys
        1010                1015                1020
Ala Asp Gln Leu His Glu Ser Val Gln Arg Leu Glu Glu Lys Leu
        1025                1030                1035
Ser Asn Ser Glu Ser Glu Ile Gln Val Leu Arg Gln Gln Ala Leu
        1040                1045                1050
Ala Ile Ser Pro Thr Ser Arg Thr Met Ala Thr Arg Ser Lys Thr
        1055                1060                1065
Met Leu Leu Pro Arg Thr Pro Glu Asn Gly Asn Tyr Leu Asn Gly
        1070                1075                1080
Gly Thr Lys Thr Thr Pro Asp Met Thr Leu Ala Val Arg Glu Pro
        1085                1090                1095
Glu Ser Glu Glu Lys Pro Gln Lys His Leu Asn Glu Lys Gln Gln
```

-continued

```
            1100                1105                1110

Glu  Asn  Gln  Asp  Leu  Leu  Val  Lys  Cys  Ile  Ser  Gln  Asn  Leu  Gly
    1115                1120                1125

Tyr  Asn  Gly  Asp  Lys  Pro  Val  Ala  Ala  Cys  Val  Ile  Tyr  Lys  Cys
    1130                1135                1140

Leu  Leu  His  Trp  Arg  Ser  Phe  Glu  Val  Glu  Arg  Thr  Ser  Val  Phe
    1145                1150                1155

Asp  Arg  Ile  Ile  Gln  Thr  Ile  Ala  Thr  Ala  Ile  Glu  Val  Pro  Asp
    1160                1165                1170

Asn  Asn  Glu  Val  Leu  Ala  Tyr  Trp  Leu  Ser  Asn  Ser  Ala  Thr  Leu
    1175                1180                1185

Leu  Leu  Leu  Leu  Gln  Arg  Thr  Leu  Lys  Ala  Thr  Gly  Ala  Ala  Ser
    1190                1195                1200

Leu  Thr  Pro  Gln  Arg  Arg  Thr  Thr  Ser  Ala  Ser  Leu  Phe  Gly
    1205                1210                1215

Arg  Met  Ser  Gln  Gly  Leu  Arg  Gly  Ser  Pro  Gln  Ser  Ala  Gly  Leu
    1220                1225                1230

Ser  Phe  Leu  Asn  Arg  Gln  Gly  Leu  Thr  Lys  Leu  Asp  Asp  Leu  Arg
    1235                1240                1245

Gln  Val  Glu  Ala  Lys  Tyr  Pro  Ala  Leu  Leu  Phe  Lys  Gln  Gln  Leu
    1250                1255                1260

Thr  Ala  Phe  Leu  Glu  Lys  Ile  Tyr  Gly  Met  Ile  Arg  Asp  Asn  Leu
    1265                1270                1275

Lys  Lys  Glu  Ile  Ser  Pro  Leu  Leu  Gly  Leu  Cys  Ile  Gln  Ala  Pro
    1280                1285                1290

Arg  Thr  Ser  Arg  Ala  Ser  Leu  Val  Lys  Gly  Arg  Ala  Gln  Ala  Asn
    1295                1300                1305

Ala  Val  Ala  Gln  Gln  Ala  Leu  Ile  Ala  His  Trp  Gln  Ser  Ile  Arg
    1310                1315                1320

Lys  Ser  Leu  Asn  Ser  Tyr  Leu  Asn  Leu  Met  Lys  Ala  Asn  Asn  Ala
    1325                1330                1335

Pro  Pro  Phe  Leu  Val  Arg  Lys  Val  Phe  Thr  Gln  Ile  Phe  Ser  Phe
    1340                1345                1350

Ile  Asn  Val  Gln  Leu  Phe  Asn  Ser  Leu  Leu  Leu  Arg  Arg  Glu  Cys
    1355                1360                1365

Cys  Ser  Phe  Ser  Asn  Gly  Glu  Tyr  Val  Lys  Ala  Gly  Leu  Ala  Glu
    1370                1375                1380

Leu  Glu  Gln  Trp  Cys  Ile  Glu  Ala  Thr  Asp  Glu  Tyr  Ala  Gly  Ser
    1385                1390                1395

Ala  Trp  Asp  Glu  Leu  Arg  His  Ile  Arg  Gln  Ala  Val  Gly  Phe  Leu
    1400                1405                1410

Val  Ile  His  Gln  Lys  Pro  Lys  Lys  Thr  Leu  Asp  Glu  Ile  Thr  Arg
    1415                1420                1425

Glu  Leu  Cys  Pro  Val  Leu  Ser  Ile  Gln  Gln  Leu  Tyr  Arg  Ile  Ser
    1430                1435                1440

Thr  Met  Tyr  Trp  Asp  Asp  Lys  Tyr  Gly  Thr  His  Ser  Val  Ser  Ser
    1445                1450                1455

Asp  Val  Ile  Ala  Asn  Met  Arg  Val  Met  Met  Thr  Glu  Asp  Ser  Asn
    1460                1465                1470

Asn  Ala  Val  Ser  Ser  Ser  Phe  Leu  Leu  Asp  Asp  Asp  Ser  Ser  Ile
    1475                1480                1485

Pro  Phe  Thr  Val  Glu  Asp  Ile  Ser  Lys  Ser  Met  Gln  Gln  Val  Asp
    1490                1495                1500
```

```
Val Asn Asp Ile Glu Pro Pro Gln Leu Ile Arg Glu Asn Ser Gly
    1505                1510                1515

Phe Gly Phe Leu Leu Thr Arg Lys Glu Gly Ser Thr Ser
    1520                1525                1530
```

<210> SEQ ID NO 7
<211> LENGTH: 1465
<212> TYPE: PRT
<213> ORGANISM: Arabidopsis thaliana
<220> FEATURE:
<223> OTHER INFORMATION: myosin XI-K (Ojangu) full length

<400> SEQUENCE: 7

```
Met Thr Lys Leu Ser Tyr Leu His Glu Pro Gly Val Leu Asn Asn Leu
1               5                   10                  15

Ala Met Arg Tyr Glu Leu Asn Glu Ile Tyr Thr Tyr Thr Gly Asn Ile
            20                  25                  30

Leu Ile Ala Val Asn Pro Phe Gln Arg Leu Pro His Leu Tyr Asp Thr
        35                  40                  45

His Met Met Glu Gln Tyr Lys Gly Ala Gly Phe Gly Glu Leu Ser Pro
    50                  55                  60

His Val Phe Ala Ile Ala Glu Val Ala Tyr Arg Ala Met Ile Asn Glu
65                  70                  75                  80

Gly Lys Ser Asn Ser Ile Leu Val Ser Gly Glu Ser Gly Ala Gly Lys
                85                  90                  95

Thr Glu Thr Thr Lys Met Leu Met Arg Tyr Leu Ala Tyr Leu Gly Gly
            100                 105                 110

Arg Ser Gly Val Glu Gly Arg Thr Val Glu Gln Gln Val Leu Glu Ser
        115                 120                 125

Asn Pro Val Leu Glu Ala Phe Gly Asn Ala Lys Thr Leu Arg Asn Asn
    130                 135                 140

Asn Ser Ser Arg Phe Gly Lys Phe Val Glu Leu Gln Phe Asp Asn Cys
145                 150                 155                 160

Gly Arg Ile Ser Gly Ala Ala Val Arg Thr Tyr Leu Leu Glu Arg Ser
                165                 170                 175

Arg Val Cys Gln Ile Ser Asp Pro Glu Arg Asn Tyr His Cys Phe Tyr
            180                 185                 190

Leu Leu Cys Ala Ala Pro Pro Glu Glu Arg Glu Lys Phe Lys Leu Gly
        195                 200                 205

Asp Pro Lys Leu Phe His Tyr Leu Asn Gln Ser Lys Cys Tyr Lys Leu
    210                 215                 220

Asp Gly Val Asp Asp Thr Glu Glu Tyr Leu Ala Thr Arg Arg Ala Met
225                 230                 235                 240

Asp Ile Val Gly Ile Ser Glu Glu Glu Gln Asp Ala Ile Phe Arg Val
                245                 250                 255

Val Ala Ala Ile Leu His Leu Gly Asn Val Asn Phe Ala Lys Gly Lys
            260                 265                 270

Glu Ile Asp Ser Ser Val Leu Lys Asp Glu Lys Ser Arg Tyr His Leu
        275                 280                 285

Asp Val Cys Ala Glu Leu Leu Arg Cys Asp Ala Lys Lys Met Glu Asp
    290                 295                 300

Ala Leu Ile Lys Arg Val Met Val Thr Pro Glu Glu Val Ile Thr Arg
305                 310                 315                 320

Thr Leu Asp Pro Asp Ser Ala Thr Gly Ser Arg Asp Ala Leu Ala Lys
                325                 330                 335
```

```
Thr Ile Tyr Ser Arg Leu Phe Asp Trp Leu Asp Lys Ile Asn Asn
            340                 345                 350

Ser Ile Gly Gln Asp Pro Asn Ser Lys Thr Ile Ile Gly Val Leu Asp
            355                 360                 365

Ile Tyr Gly Phe Glu Ser Phe Lys Ile Asn Ser Phe Glu Gln Phe Cys
    370                 375                 380

Ile Asn Phe Thr Asn Glu Lys Leu Gln Gln His Phe Asn Gln His Val
385                 390                 395                 400

Phe Lys Met Glu Gln Glu Asp Tyr Thr Lys Glu Ile Asn Trp Ser
            405                 410                 415

Tyr Ile Glu Phe Val Asp Asn Lys Asp Val Leu Glu Leu Ile Glu Lys
            420                 425                 430

Lys Pro Gly Gly Val Ile Ala Leu Leu Asp Glu Ala Cys Met Phe Pro
            435                 440                 445

Lys Ser Thr His Glu Thr Phe Ala Gln Lys Leu Tyr Gln Thr Phe Lys
            450                 455                 460

Asn Tyr Lys Arg Phe Thr Lys Pro Lys Leu Ser Arg Thr Ser Phe Ala
465                 470                 475                 480

Ile Ser His Tyr Ala Gly Glu Val Thr Tyr Gln Ala Asp Leu Phe Leu
                485                 490                 495

Asp Lys Asn Lys Asp Tyr Val Val Ala Glu His Gln Asp Leu Leu Ile
            500                 505                 510

Ala Ser Ser Asp Thr Phe Val Ala Gly Leu Phe Pro Arg Leu Pro Glu
            515                 520                 525

Glu Thr Ser Ser Lys Thr Lys Phe Ser Ser Ile Gly Ser Arg Phe Lys
            530                 535                 540

Leu Gln Leu Gln Ser Leu Met Glu Thr Leu Ser Ser Thr Glu Pro His
545                 550                 555                 560

Tyr Ile Arg Cys Val Lys Pro Asn Asn Val Leu Lys Pro Ala Ile Phe
                565                 570                 575

Glu Asn Val Asn Val Ile Gln Gln Leu Arg Cys Gly Gly Val Leu Glu
            580                 585                 590

Ala Ile Arg Ile Ser Cys Ala Gly Tyr Pro Thr Lys Arg Thr Phe Tyr
            595                 600                 605

Glu Phe Leu Asn Arg Phe Gly Val Leu Ala Pro Glu Val Leu Glu Gly
            610                 615                 620

Asn Tyr Asp Asp Lys Val Ala Cys Lys Met Leu Leu Asp Lys Ile Gly
625                 630                 635                 640

Leu Lys Gly Tyr Glu Leu Gly Lys Thr Lys Val Phe Leu Arg Ala Gly
                645                 650                 655

Gln Met Ala Glu Leu Asp Ala Arg Arg Ala Glu Val Leu Gly Asn Ala
            660                 665                 670

Ala Arg Arg Ile Gln Arg Gln Ser Arg Thr Phe Ile Ala Cys Lys Glu
            675                 680                 685

Phe Arg Ala Leu Arg Gly Ala Ala Ile Val Leu Gln Ser Asn Cys Arg
            690                 695                 700

Gly Lys Leu Ala Cys Asn Leu Tyr Glu Glu Met Arg Arg Gln Ala Ala
705                 710                 715                 720

Ala Val Lys Ile Gln Lys Ile Phe Arg Arg His Ile Ala Arg Glu Ser
            725                 730                 735

Tyr Leu Arg Ile Arg His Ser Thr Ile Thr Val Gln Thr Ala Leu Arg
            740                 745                 750
```

```
Gly Met Val Ala Arg Asn Glu Phe Arg Phe Arg Lys Gln Met Lys Ala
            755                 760                 765
Ala Thr Ile Ile Gln Ala Arg Leu Arg Ser His Leu Thr His Ser Tyr
    770                 775                 780
Tyr Lys Gln Leu Gln Lys Ala Ala Leu Ser Thr Gln Cys Gly Trp Arg
785                 790                 795                 800
Ser Arg Val Ala Arg Lys Glu Leu Arg Thr Leu Lys Met Ala Ala Arg
                805                 810                 815
Asp Thr Gly Ala Leu Arg Glu Ala Asp Lys Leu Glu Lys Arg Val
            820                 825                 830
Glu Glu Leu Thr Trp Arg Leu Gln Leu Glu Lys Arg Gln Arg Thr Glu
                835                 840                 845
Leu Glu Glu Ala Lys Thr Gln Glu Tyr Ala Lys Gln Gln Glu Ala Leu
    850                 855                 860
Glu Thr Met Arg Leu Gln Val Glu Glu Ala Asn Ala Ala Val Ile Arg
865                 870                 875                 880
Glu Arg Glu Ala Ala Arg Lys Ala Ile Glu Glu Ala Pro Pro Val Ile
                885                 890                 895
Lys Glu Thr Pro Val Leu Val Glu Asp Thr Glu Lys Ile Asn Ser Leu
            900                 905                 910
Thr Ser Glu Val Glu Ala Leu Lys Ala Ser Leu Gln Ala Glu Arg Gln
    915                 920                 925
Ala Ala Glu Asn Leu Arg Lys Ala Phe Ser Glu Ala Glu Arg Asn
930                 935                 940
Ser Glu Leu Ala Thr Glu Leu Glu Asn Ala Thr Arg Lys Ala Asp Gln
945                 950                 955                 960
Leu His Glu Ser Val Gln Arg Leu Glu Glu Lys Leu Ser Asn Ser Glu
                965                 970                 975
Ser Glu Ile Gln Val Leu Arg Gln Gln Ala Leu Ala Ile Ser Pro Thr
            980                 985                 990
Ser Arg Thr Met Ala Thr Arg Ser Lys Thr Met Leu Leu Pro Arg Thr
    995                 1000                1005
Pro Glu Asn Gly Asn Tyr Leu Asn Gly Gly Thr Lys Thr Thr Pro
    1010                1015                1020
Asp Met Thr Leu Ala Val Arg Glu Pro Glu Ser Glu Glu Lys Pro
    1025                1030                1035
Gln Lys His Leu Asn Glu Lys Gln Gln Glu Asn Gln Asp Leu Leu
    1040                1045                1050
Val Lys Cys Ile Ser Gln Asn Leu Gly Tyr Asn Gly Asp Lys Pro
    1055                1060                1065
Val Ala Ala Cys Val Ile Tyr Lys Cys Leu Leu His Trp Arg Ser
    1070                1075                1080
Phe Glu Val Glu Arg Thr Ser Val Phe Asp Arg Ile Ile Gln Thr
    1085                1090                1095
Ile Ala Thr Ala Ile Glu Val Pro Asp Asn Asn Glu Val Leu Ala
    1100                1105                1110
Tyr Trp Leu Ser Asn Ser Ala Thr Leu Leu Leu Leu Gln Arg
    1115                1120                1125
Thr Leu Lys Ala Thr Gly Ala Ala Ser Leu Thr Pro Gln Arg Arg
    1130                1135                1140
Arg Thr Thr Ser Ala Ser Leu Phe Gly Arg Met Ser Gln Gly Leu
    1145                1150                1155
Arg Gly Ser Pro Gln Ser Ala Gly Leu Ser Phe Leu Asn Arg Gln
```

```
               1160                1165                1170
Gly Leu Thr Lys Leu Asp Asp Leu Arg Gln Val Glu Ala Lys Tyr
    1175                1180                1185

Pro Ala Leu Leu Phe Lys Gln Gln Leu Thr Ala Phe Leu Glu Lys
    1190                1195                1200

Ile Tyr Gly Met Ile Arg Asp Asn Leu Lys Lys Glu Ile Ser Pro
    1205                1210                1215

Leu Leu Gly Leu Cys Ile Gln Ala Pro Arg Thr Ser Arg Ala Ser
    1220                1225                1230

Leu Val Lys Gly Arg Ala Gln Ala Asn Ala Val Ala Gln Gln Ala
    1235                1240                1245

Leu Ile Ala His Trp Gln Ser Ile Arg Lys Ser Leu Asn Ser Tyr
    1250                1255                1260

Leu Asn Leu Met Lys Ala Asn Asn Ala Pro Pro Phe Leu Val Arg
    1265                1270                1275

Lys Val Phe Thr Gln Ile Phe Ser Phe Ile Asn Val Gln Leu Phe
    1280                1285                1290

Asn Ser Leu Leu Leu Arg Arg Glu Cys Cys Ser Phe Ser Asn Gly
    1295                1300                1305

Glu Tyr Val Lys Ala Gly Leu Ala Glu Leu Glu Gln Trp Cys Ile
    1310                1315                1320

Glu Ala Thr Asp Glu Tyr Ala Gly Ser Ala Trp Asp Glu Leu Arg
    1325                1330                1335

His Ile Arg Gln Ala Val Gly Phe Leu Val Ile His Gln Lys Pro
    1340                1345                1350

Lys Lys Thr Leu Asp Glu Ile Thr Arg Glu Leu Cys Pro Val Leu
    1355                1360                1365

Ser Ile Gln Gln Leu Tyr Arg Ile Ser Thr Met Tyr Trp Asp Asp
    1370                1375                1380

Lys Tyr Gly Thr His Ser Val Ser Ser Asp Val Ile Ala Asn Met
    1385                1390                1395

Arg Val Met Met Thr Glu Asp Ser Asn Asn Ala Val Ser Ser Ser
    1400                1405                1410

Phe Leu Leu Asp Asp Asp Ser Ile Pro Phe Thr Val Glu Asp
    1415                1420                1425

Ile Ser Lys Ser Met Gln Gln Val Asp Val Asn Asp Ile Glu Pro
    1430                1435                1440

Pro Gln Leu Ile Arg Glu Asn Ser Gly Phe Gly Phe Leu Leu Thr
    1445                1450                1455

Arg Lys Glu Gly Ser Thr Ser
    1460                1465

<210> SEQ ID NO 8
<211> LENGTH: 1506
<212> TYPE: PRT
<213> ORGANISM: O. sativa
<220> FEATURE:
<223> OTHER INFORMATION: myosin XI-I full length

<400> SEQUENCE: 8

Met Leu Phe Arg Pro Gly Thr Ala Val Trp Val Glu His Pro Asp His
1               5                   10                  15

Ala Trp Ala Glu Ala Val Val Thr Ser Pro Ala Ser Ser Pro Ser
                20                  25                  30

Ser Val Thr Val Thr Leu Ala Gly Gly Ala Lys Ala Val Val Asp Gly
```

-continued

```
                35                  40                  45
Lys Lys Val Leu Pro Arg Asp Thr Glu Ala Asp Leu Gly Gly Val Asp
 50                  55                  60

Asp Met Thr Lys Leu Val Tyr Leu His Glu Pro Gly Val Leu Cys Asn
 65                  70                  75                  80

Leu Ala Arg Arg Tyr Gly Phe Asn Glu Ile Tyr Thr Tyr Thr Gly Arg
                 85                  90                  95

Ile Leu Ile Ala Val Asn Pro Phe Ala Lys Leu Pro His Leu Tyr Asp
                100                 105                 110

Met His Met Met Glu Gln Tyr Arg Gly Val Gln Phe Gly Glu Leu Ser
                115                 120                 125

Pro His Val Phe Ala Val Thr Asp Ala Ser Tyr Arg Ala Met Val Ser
                130                 135                 140

Glu Asp Arg Ser Gln Ser Ile Leu Val Ser Gly Glu Ser Gly Ala Gly
145                 150                 155                 160

Lys Thr Glu Thr Thr Lys Leu Ile Met Arg Tyr Leu Thr Phe Val Gly
                165                 170                 175

Gly Arg Ser Thr Gly Asp Ile Arg Ser Val Glu Gln Gln Val Leu Glu
                180                 185                 190

Ser Asn Pro Leu Leu Glu Ala Phe Gly Asn Ala Arg Thr Val Arg Asn
                195                 200                 205

Asp Asn Ser Ser Arg Phe Gly Lys Phe Val Glu Ile Gln Phe Asp Lys
210                 215                 220

Ser Gly Arg Ile Ser Gly Ala Ala Val Arg Thr Tyr Leu Leu Glu Arg
225                 230                 235                 240

Ser Arg Val Val Gln Ile Ser Glu Ser Glu Arg Asn Tyr His Cys Phe
                245                 250                 255

Tyr Gln Leu Cys Ala Ser Gly Gln Asp Ala Asp Lys Tyr Lys Leu Ala
                260                 265                 270

His Pro Arg Asn Phe Asn Tyr Leu Asn Gln Ser His Thr Tyr Glu Leu
                275                 280                 285

Glu Gly Val Asn Glu Ala Glu Glu Tyr Leu Lys Thr Arg Arg Ala Met
                290                 295                 300

Asp Ile Val Gly Ile Ser Phe Ser His Gln Glu Ala Ile Phe Arg Thr
305                 310                 315                 320

Val Ala Ala Ile Leu His Leu Gly Asn Ile Glu Phe Ser Pro Gly Lys
                325                 330                 335

Glu Phe Asp Ser Ser Ala Ile Lys Asp Glu Lys Ser Lys Phe His Leu
                340                 345                 350

Gln Met Ala Ala Asp Leu Leu Met Val Asp Gly Ser Leu Leu Leu Ser
                355                 360                 365

Thr Leu Cys Tyr Arg Thr Ile Lys Thr Pro Glu Gly Asn Ile Val Lys
                370                 375                 380

Ala Val Asp Ser Ser Ala Ala Ile Ser Arg Asp Ala Leu Ala Lys
385                 390                 395                 400

Thr Val Tyr Ala Gln Leu Phe Asp Trp Leu Val Asp Asn Ile Asn Met
                405                 410                 415

Ser Ile Gly Gln Asp Met Glu Ser Arg Ala Leu Ile Gly Val Leu Asp
                420                 425                 430

Ile Tyr Gly Phe Glu Cys Phe Lys Tyr Asn Ser Phe Glu Gln Leu Cys
                435                 440                 445

Ile Asn Phe Ala Asn Glu Lys Leu Gln Gln His Phe Asn Lys His Val
                450                 455                 460
```

```
Phe Lys Met Glu Gln Glu Tyr Lys Thr Glu Ile Asn Trp Ser
465                 470                 475                 480

Tyr Ile Glu Phe Val Asp Asn Gln Asp Ile Leu Asp Leu Ile Glu Lys
            485                 490                 495

Lys Pro Ile Gly Ile Val Ser Leu Leu Asp Glu Ala Cys Met Leu Gly
            500                 505                 510

Lys Ser Thr His Glu Thr Phe Ala Met Lys Leu Phe Gln Asn Phe Lys
            515                 520                 525

Ala His Pro Arg Leu Glu Lys Pro Lys Leu Ser Lys Thr Asp Phe Ala
            530                 535                 540

Leu Ser His Phe Ala Gly Lys Val Ile Tyr Gln Thr Glu Leu Phe Leu
545                 550                 555                 560

Glu Lys Asn Arg Asp Tyr Val Asn Leu Glu His Gln Asn Leu Leu Cys
            565                 570                 575

Ser Ser Lys Cys Ser Phe Leu Ser Arg Leu Phe Ala Leu Gln Gln Asp
            580                 585                 590

Asp Pro Ser Lys Ser Ser Tyr Lys Phe Ser Ser Ile Ala Ser Arg Phe
            595                 600                 605

Lys Gln Gln Leu Gln Ala Leu Met Glu Thr Leu Ser Ser Thr Glu Pro
            610                 615                 620

His Tyr Ile Arg Cys Val Lys Pro Asn Ser Leu Asn Tyr Pro Gln Lys
625                 630                 635                 640

Phe Glu Asn Gly Ser Val Leu Gln Gln Leu Arg Ser Gly Gly Val Leu
            645                 650                 655

Glu Ala Ile Arg Ile Ser Leu Ala Gly Tyr Pro Thr Arg Thr Thr Tyr
            660                 665                 670

Thr Glu Phe Ile Asp Arg Phe Gly Leu Leu Val Pro Glu His Met Asp
            675                 680                 685

Glu Arg Phe Asp Glu Lys Ser Leu Thr Glu Lys Ile Leu Arg Gln Leu
            690                 695                 700

His Leu Glu Asn Phe Gln Leu Gly Arg Thr Lys Val Phe Leu Arg Ala
705                 710                 715                 720

Gly Gln Ile Ala Val Leu Asp Ser Lys Arg Thr Glu Ile Leu Glu Lys
            725                 730                 735

Ala Ala Arg Ile Val Gln Gly Arg Phe Arg Thr Phe Val Ala Cys Lys
            740                 745                 750

Glu Phe His Ser Thr Lys Lys Ala Ser Val Ser Leu Gln Ala Tyr Cys
            755                 760                 765

Arg Gly Cys Leu Ala Arg Asn Leu Leu Asp Ala Lys Arg Gln Ile Ala
            770                 775                 780

Ala Ala Val Ser Val Glu Lys Tyr Ala Arg Arg Trp Phe Cys Arg Cys
785                 790                 795                 800

Glu Tyr Leu His Leu Arg Ser Ser Ala Leu Val Ile Gln Ser Gly Val
            805                 810                 815

Arg Tyr Met Leu Ala Ile Gln Lys Leu Gln Leu Lys Asn Asn Lys
            820                 825                 830

Ala Ala Thr Ile Ile Gln Ala Leu Trp Arg Met Lys Lys Leu Tyr Asp
            835                 840                 845

Phe His Arg Gln Tyr Arg His Ala Thr Ile Leu Ile Gln Cys Cys Trp
            850                 855                 860

Arg Gln Lys Leu Ala Lys Arg Ala Phe Arg Asn Leu Lys Gln Ala Ala
865                 870                 875                 880
```

```
Tyr Glu Thr Gly Ala Leu Arg Glu Ala Lys Gly Lys Leu Glu Arg Ser
            885                 890                 895

Leu Glu Asp Leu Thr Leu Arg Phe Thr Leu Glu Arg Arg Gln Arg Val
        900                 905                 910

Ala Ala Glu Glu Ser Lys Ala Leu Glu Val Ser Lys Leu Leu Lys Ile
        915                 920                 925

Val Glu Ser Leu Lys Cys Glu Leu Glu Ala Ala Asn Glu Glu Lys Ile
    930                 935                 940

Asn Gly Cys Lys Glu Val Ala Ser Met Gln Gln Leu Gly Leu Ser
945                 950                 955                 960

Ile Lys Asp Gln Glu Leu Leu His Ser Asn Leu Ala Gln Ile Glu Glu
                965                 970                 975

Leu Lys Arg Glu Asn Thr Leu Leu Lys Gly Lys Asn Ala Glu Met Glu
        980                 985                 990

Gln Glu Leu Leu Lys Ala Gln Lys Cys Ser His Asp Asn Met Asp Lys
            995                1000                1005

Leu His Gly Val Glu Arg Asn Tyr Leu His Leu Arg Asp Asn Leu
    1010                1015                1020

Lys Asn Leu Glu Asp Lys Ile Ser Asn Leu Glu Asp Glu Asn His
    1025                1030                1035

Leu Leu Arg Gln Lys Ala Leu Ser Leu Ser Pro Arg His Ser Arg
    1040                1045                1050

Thr Met Ser His Pro Ile Gly Ser Ser Pro Cys Ser Pro Lys Ser
    1055                1060                1065

Leu Ile Glu Ser Ser Pro Val Lys Ile Val Pro Leu Pro His Asn
    1070                1075                1080

Pro Thr Glu Leu Arg Arg Ser Arg Met Asn Ser Glu Arg His Glu
    1085                1090                1095

Glu Tyr His Glu Leu Leu Gln Arg Cys Ile Lys Asp Asp Met Gly
    1100                1105                1110

Phe Lys Lys Gly Lys Pro Val Ala Ala Cys Val Ile Tyr Lys Cys
    1115                1120                1125

Leu Leu His Trp Gly Val Phe Glu Ala Glu Arg Thr Thr Ile Phe
    1130                1135                1140

Asp Phe Ile Ile Gln Asn Ile Asn Thr Val Leu Lys Thr Glu Asn
    1145                1150                1155

Glu Asn Asp Ile Leu Pro Tyr Trp Leu Ala Asn Ala Ser Ala Leu
    1160                1165                1170

Leu Cys Leu Leu Gln Arg Asn Leu Arg Ser Lys Gly Phe Ile Ala
    1175                1180                1185

Ala Pro Ser Arg Ser Ser Ser Asp Pro His Leu Cys Glu Lys Ala
    1190                1195                1200

Asn Asp Ala Leu Arg Pro Pro Leu Lys Ala Phe Gly Gln Arg Asn
    1205                1210                1215

Ser Met Ser His Ile Asp Ala Lys Tyr Pro Ala Met Leu Phe Lys
    1220                1225                1230

Gln Gln Leu Thr Ala Ser Leu Glu Lys Ile Phe Gly Leu Ile Arg
    1235                1240                1245

Asp Asn Leu Lys Lys Glu Ile Ser Pro Leu Leu Ser Leu Cys Ile
    1250                1255                1260

Gln Ala Pro Lys Leu Ala Arg Gly Gly Ser Gly Arg Arg Ser Arg
    1265                1270                1275

Ser Pro Asp Val Thr Leu Gln Gln Pro Ile Ser Ala His Trp Asp
```

```
                    1280                1285                1290

Arg Ile  Ile Lys Phe Leu Asp  Ser Leu Met Asp Arg  Leu His Lys
    1295                1300                1305

Asn Phe  Val Pro Ser Phe Phe  Ile Arg Lys Leu Val  Thr Gln Val
    1310                1315                1320

Phe Ser  Phe Ile Asn Val Gln  Leu Phe Asn Ser Leu  Leu Leu Arg
    1325                1330                1335

Arg Glu  Cys Cys Thr Phe Ser  Asn Gly Glu Tyr Val  Lys Thr Gly
    1340                1345                1350

Leu Cys  Val Leu Glu Lys Trp  Ile Leu Asp Ala Thr  Glu Glu His
    1355                1360                1365

Ala Gly  Ala Ala Trp Asp Glu  Leu Lys Tyr Ile Arg  Glu Ala Val
    1370                1375                1380

Glu Phe  Leu Ile Ile Ala Gln  Lys Ser Lys Arg Thr  Leu Glu Gln
    1385                1390                1395

Ile Lys  Lys Asn Ile Cys Pro  Ala Leu Ser Val Arg  Gln Ile Tyr
    1400                1405                1410

Arg Leu  Cys Thr Met Tyr Trp  Asp Asp Lys Tyr Gly  Thr His Ser
    1415                1420                1425

Val Ser  Ala Glu Val Val Ala  Lys Met Arg Asp Met  Val Ser Ser
    1430                1435                1440

Asp Ala  Gln Asn Pro Val Ser  Asn Ser Phe Leu Leu  Asp Asp Asp
    1445                1450                1455

Leu Ser  Ile Pro Phe Thr Thr  Glu Glu Ile Ala Glu  Glu Val Pro
    1460                1465                1470

Asp Ile  Asp Met Ser Asn Ile  Glu Met Pro Ser Ser  Leu Arg His
    1475                1480                1485

Val His  Ser Ala Gln Phe Leu  Met Gln His Leu Gln  Thr Thr Tyr
    1490                1495                1500

Pro Leu  Arg
    1505

<210> SEQ ID NO 9
<211> LENGTH: 1533
<212> TYPE: PRT
<213> ORGANISM: O. sativa
<220> FEATURE:
<223> OTHER INFORMATION: myosin XI-K full length

<400> SEQUENCE: 9

Met Gln Ala Ser Met Leu Asn Ile Val Ile Gly Ser His Val Trp Val
1               5                   10                  15

Glu Asp Lys Asp Ser Ala Trp Val Asp Gly Glu Val Phe Arg Ile Asp
                20                  25                  30

Gly Lys Asn Ala His Val Arg Thr Thr Lys Gly Lys Thr Val Ile Ala
            35                  40                  45

Asn Val Ser Asp Ile His Pro Lys Asp Thr Glu Ala Pro Pro Asp Gly
        50                  55                  60

Val Asp Asp Met Thr Arg Leu Ser Tyr Leu His Glu Pro Gly Val Leu
65                  70                  75                  80

Asp Asn Leu Ala Val Arg Tyr Ala Arg Asn Leu Ile Tyr Thr Tyr Thr
                85                  90                  95

Gly Asn Ile Leu Ile Ala Ile Asn Pro Phe Gln Arg Leu Pro Asn Leu
            100                 105                 110

Val Asp Val Arg Thr Met Glu Lys Tyr Lys Gly Ala Asn Leu Gly Asp
```

-continued

```
            115                 120                 125
Leu Asp Pro His Val Phe Ala Ile Ala Asp Val Ser Tyr Arg Gln Met
            130                 135                 140
Met Asn Glu Gly Arg Asn Asn Ser Ile Leu Val Ser Gly Glu Ser Gly
145                 150                 155                 160
Ala Gly Lys Thr Glu Thr Thr Lys Leu Leu Met Arg Tyr Leu Ala Tyr
                    165                 170                 175
Leu Gly Gly Arg Ser Gly Thr Gly Gly Arg Thr Val Glu Gln Gln Val
                    180                 185                 190
Leu Glu Ser Asn Pro Val Leu Glu Ala Phe Gly Asn Ala Lys Thr Val
                    195                 200                 205
Arg Asn Asn Asn Ser Ser Arg Phe Gly Lys Phe Val Glu Ile Gln Phe
210                 215                 220
Asp Lys Ser Gly Lys Ile Ser Gly Ala Ala Ile Arg Thr Tyr Leu Leu
225                 230                 235                 240
Glu Arg Ser Arg Val Cys Gln Ile Asn Ser Pro Glu Arg Asn Tyr His
                    245                 250                 255
Cys Phe Tyr Phe Leu Cys Ala Ala Pro Pro Glu Asp Ile Lys Arg Tyr
                    260                 265                 270
Lys Leu Gly Asp Pro Ser Ser Phe His Tyr Leu Asn Gln Ser Ser Cys
                    275                 280                 285
Ile Arg Val Asp Gly Ile Asn Asp Ala Glu Glu Tyr Leu Val Thr Arg
                    290                 295                 300
Asn Ala Met Asp Thr Val Gly Ile Ile Glu Gln Glu Gln Ala Ile
305                 310                 315                 320
Phe Arg Val Val Ala Ala Val Leu His Leu Gly Asn Ile Asn Phe Ala
                    325                 330                 335
Lys Gly Ser Glu Val Asp Ser Ser Val Ile Lys Asp Asp Lys Ser Arg
                    340                 345                 350
Phe His Leu Asn Thr Ala Ala Glu Leu Leu Met Cys Asp Cys Lys Lys
                    355                 360                 365
Leu Glu Asn Ala Leu Ile Lys Arg Glu Ile Asn Thr Pro Glu Gly Val
                    370                 375                 380
Ile Thr Thr Thr Val Gly Pro Ser Ser Ala Thr Val Ser Arg Asp Gly
385                 390                 395                 400
Leu Ala Lys Gln Ile Tyr Ser Arg Leu Phe Asp Trp Leu Val Asn Arg
                    405                 410                 415
Ile Asn Ala Ser Ile Gly Gln Asp Pro Asn Ser Asp Lys Leu Ile Gly
                    420                 425                 430
Val Leu Asp Ile Tyr Gly Phe Glu Ser Phe Lys Thr Asn Ser Phe Glu
                    435                 440                 445
Gln Leu Cys Ile Asn Phe Thr Asn Glu Lys Leu Gln Gln His Phe Asn
                    450                 455                 460
Gln Asn Val Phe Lys Met Glu Gln Glu Glu Tyr Thr Arg Glu Gln Ile
465                 470                 475                 480
Asn Trp Ser Tyr Ile Glu Phe Val Asp Asn Gln Asp Val Leu Asp Leu
                    485                 490                 495
Ile Glu Lys Lys Pro Gly Gly Ile Ile Ala Leu Leu Asp Glu Ala Cys
                    500                 505                 510
Met Phe Pro Lys Ser Thr His Glu Thr Phe Ser Gln Lys Leu Tyr Glu
                    515                 520                 525
Lys Phe Lys Asn His Lys Arg Phe Thr Lys Pro Lys Leu Ser Arg Thr
                    530                 535                 540
```

```
Ala Phe Thr Ile Gln His Tyr Ala Gly Asp Val Ile Tyr Gln Ser Asp
545                 550                 555                 560

His Phe Leu Asp Lys Asn Lys Asp Tyr Val Val Ala Glu His Gln Glu
            565                 570                 575

Leu Leu Asn Ala Ser Arg Cys Ser Phe Val Ser Ala Leu Phe Pro Pro
                580                 585                 590

Ala Ser Glu Glu Asn Thr Lys Ser Ser Lys Ser Ser Ile Ala Thr Arg
            595                 600                 605

Phe Lys Val Gln Leu His Glu Leu Met Glu Thr Leu Ser Ser Thr Glu
        610                 615                 620

Pro His Tyr Ile Arg Cys Val Lys Pro Asn Ser Val Leu Lys Pro Ala
625                 630                 635                 640

Ile Phe Glu Asn Thr Asn Val Leu Gln Gln Leu Arg Cys Ser Gly Val
                645                 650                 655

Leu Glu Ala Ile Arg Ile Ser Cys Ala Gly Tyr Pro Thr Arg Lys Leu
            660                 665                 670

Phe His Asp Phe Leu His Arg Phe Arg Ile Leu Ala Ser Glu Ile Val
        675                 680                 685

Lys Glu Lys Asn Asp Glu Lys Val Thr Cys Gln Lys Val Leu Asp Lys
    690                 695                 700

Met Gly Leu Gln Gly Tyr Gln Ile Gly Arg Thr Lys Val Phe Leu Arg
705                 710                 715                 720

Ala Gly Gln Met Ala Glu Leu Asp Ala Arg Arg Thr Glu Val Arg Asn
                725                 730                 735

Asn Ala Ala Arg Gly Val Gln Gly Gln Phe Arg Thr His Val Ala Arg
            740                 745                 750

Glu Gln Phe Leu Ile Leu Arg Asn Ala Ser Val Cys Leu Gln Ser Phe
        755                 760                 765

Val Arg Ala Arg Leu Ala Cys Lys Leu His Glu Cys Leu Arg Arg Glu
    770                 775                 780

Ala Ala Ala Ile Lys Ile Gln Lys Asn Ile Arg Cys Tyr Phe Ala Trp
785                 790                 795                 800

Arg Thr Tyr Ser Gln Leu Arg Leu Ser Ala Ile Thr Leu Gln Thr Gly
                805                 810                 815

Leu Arg Thr Met Ala Ala Leu Lys Glu Phe Met Phe Arg Lys Gln Asn
            820                 825                 830

Lys Ala Thr Thr His Ile Gln Thr Gln Trp Arg Cys His Arg Asp Asn
        835                 840                 845

Ser Asn Tyr Leu Lys Leu Lys Arg Ala Ala Leu Thr Tyr Gln Cys Ala
    850                 855                 860

Trp Arg Arg Arg Val Ala Arg Arg Glu Leu Arg Gln Leu Arg Met Ala
865                 870                 875                 880

Ala Arg Asp Thr Gln Ala Leu Lys Val Ala Lys Glu Lys Leu Glu Glu
                885                 890                 895

Arg Val Glu Glu Leu Thr Asn Arg Leu Gly Leu Glu Lys Lys Leu Arg
            900                 905                 910

Thr Asp Leu Glu Lys Ser Lys Val Ala Glu Val Ser Lys Leu Gln Ala
        915                 920                 925

Ala Leu Asn Glu Met Glu Gln Arg Met Gln Asp Val Thr Ala Met Gln
    930                 935                 940

Glu Arg Glu Ser Ala Lys Lys Ala Val Glu Glu Ala Leu Glu Gln Glu
945                 950                 955                 960
```

```
Arg Glu Lys Ile Ser Ser Leu Thr Ser Glu Ile Glu Gly Leu Lys Lys
                965                 970                 975

Asp Ala Leu Leu Thr Thr Glu Arg Gln Glu Thr Glu Ala Thr Lys Lys
        980                 985                 990

Leu Leu Ser Glu Ala Gln Tyr Lys Asn Glu Glu Leu Leu Lys Lys Ile
            995                1000                1005

Glu Asp Ala Asp Lys Ser Ile Ala His Tyr His Asp Thr Thr Gln
    1010                1015                1020

Arg Leu Glu Gly Lys Ser Thr Asn Leu Glu Ala Glu Asn Gln Val
    1025                1030                1035

Leu Arg Gln Gln Ala Thr Ala Thr Pro Pro Ser Thr Ala Lys Ser
    1040                1045                1050

Ser Ala Ser Arg Ser Lys Ile Thr Arg Ile His Arg Ser Pro Glu
    1055                1060                1065

Asn Gly His Ile Leu Asn Gly Asp Thr Arg Gln Ala Glu Ile Lys
    1070                1075                1080

Pro Ser Thr Gly Thr Ser Glu Thr Ile Pro Ser Ile Gly Asn Pro
    1085                1090                1095

Pro Asp Leu Asn Asn Glu Lys His Val Glu Gln Gly Glu Lys Leu
    1100                1105                1110

Gln Lys Val Leu Asn Gln Lys Tyr Gln Asp Asp Gln Gln Trp Leu
    1115                1120                1125

Leu Thr Cys Ile Ser Gln Tyr Leu Gly Phe Phe Gly Ser Lys Pro
    1130                1135                1140

Val Ala Ala Leu Leu Ile Tyr Gln Cys Leu Ser His Trp Arg Ser
    1145                1150                1155

Phe Glu Ala Met Lys Thr Gly Val Phe Asp Ser Ile Leu Gln Ala
    1160                1165                1170

Ile Asn Ser Ala Thr Glu Ala Gln Asn Asp Thr Arg Ala Leu Ala
    1175                1180                1185

Tyr Trp Leu Ser Asn Leu Ser Thr Leu Thr Val Leu Leu Gln Arg
    1190                1195                1200

Ser Phe Lys Thr Thr Arg Thr Ala Ile Ser Thr Pro Gln Arg Arg
    1205                1210                1215

Arg Phe Ser Ser Glu Arg Ile Phe His Ala Ser Gln Thr Ser Asn
    1220                1225                1230

Ala Gly Leu Ala Tyr Leu Ser Gly Gln Pro Val Gly Ala Ala
    1235                1240                1245

Gly Leu Pro Gln Val Glu Ala Lys Tyr Pro Ala Leu Leu Phe Lys
    1250                1255                1260

Gln Gln Leu Val Asp Leu Ile Glu Lys Val Tyr Gly Met Ile Ser
    1265                1270                1275

Asp Ser Val Lys Lys Glu Leu Asn Pro Leu Leu Glu Leu Cys Ile
    1280                1285                1290

Gln Asp Pro Arg Thr Ser His Ser Pro Ala Lys Gly His Ala Asn
    1295                1300                1305

Gly Leu Gly Gln Lys Asn Gln Leu Gly His Trp Leu Ala Ile Val
    1310                1315                1320

Lys Val Leu Thr Asn Tyr Leu Asp Val Leu Arg Ala Asn His Val
    1325                1330                1335

Pro Ser Ile Leu Val His Lys Leu Phe Thr Gln Ile Phe Ser Leu
    1340                1345                1350

Ile Asp Val Gln Leu Phe Asn Arg Glu Cys Cys Ser Phe Ser Asn
```

-continued

```
                   1355                1360                1365

Gly Glu Tyr Val Lys Val Gly Leu Ala Glu Leu Lys His Trp Ser
               1370                1375                1380

Asp Asn Ala Thr Arg Glu Tyr Arg Leu Met Arg Phe Cys Leu Ile
           1385                1390                1395

Gln Phe Ala Gly Ser Ala Trp Asp Ala Leu Lys His Ile Arg Gln
       1400                1405                1410

Ala Val Asp Phe Leu Val Ile Ser Leu Lys Pro Met Arg Thr Leu
   1415                1420                1425

Lys Glu Ile Arg Thr Asp Val Cys Pro Ala Leu Ser Ile Gln Gln
1430                1435                1440

Leu Glu Arg Ile Val Ser Met Tyr Trp Asp Asp Ile Asn Gly Ser
   1445                1450                1455

Asn Ala Ile Ser Ala Glu Phe Thr Ser Ser Leu Lys Ser Ala Val
   1460                1465                1470

Arg Glu Glu Ser Asn Thr Val Thr Thr Phe Ser Ile Leu Leu Asp
   1475                1480                1485

Asp Asp Ser Cys Ile Pro Phe Ser Leu Asp Asp Ile Ala Lys Thr
   1490                1495                1500

Met Pro Ile Ile Glu Val Ala Glu Asp Asp Leu Leu Pro Phe Val
   1505                1510                1515

Arg Glu Asn Pro Ser Phe Ala Phe Leu Leu Gln Arg Gly Asn Ser
   1520                1525                1530

<210> SEQ ID NO 10
<211> LENGTH: 1478
<212> TYPE: PRT
<213> ORGANISM: O. sativa
<220> FEATURE:
<223> OTHER INFORMATION: myosin XI-G full length

<400> SEQUENCE: 10

Met Asp Gly Leu Val Glu Glu Ile Asn Glu Asn Asp Leu Val Val Asn
1               5                  10                  15

Cys Thr Ser Gly Lys Lys Val Thr Ile Asn Val Gly Ser Ala Tyr Pro
           20                  25                  30

Lys Asp Thr Glu Ser Pro Arg Gly Gly Val Glu Asp Met Thr Arg Leu
       35                  40                  45

Ala Tyr Leu His Glu Pro Gly Val Leu Gln Asn Leu Lys Ser Arg Tyr
   50                  55                  60

Ala Leu Asn Glu Ile Tyr Thr Tyr Thr Gly Asn Ile Leu Ile Ala Val
65                  70                  75                  80

Asn Pro Phe Gln Arg Leu Pro His Leu Tyr Asn Asn His Met Met Gly
               85                  90                  95

Ile Tyr Lys Gly Ala Glu Phe Gly Glu Leu Gly Pro His Pro Phe Ala
           100                 105                 110

Ile Ala Asp Arg Ser Tyr Arg Leu Met Ile Asn Asn Arg Ile Ser Gln
       115                 120                 125

Ala Ile Leu Val Ser Gly Glu Ser Gly Ala Gly Lys Thr Glu Ser Thr
   130                 135                 140

Lys Met Leu Met Gln Tyr Leu Ala Phe Met Gly Gly Lys Ala Gln Ala
145                 150                 155                 160

Glu Gly Arg Ser Val Gln Gln Gln Ile Leu Glu Ser Asn Pro Val Leu
               165                 170                 175

Glu Ala Phe Gly Asn Ala Lys Thr Val Arg Asn Asn Asn Ser Ser Arg
```

```
            180              185              190
Phe Gly Lys Phe Val Glu Ile Gln Phe Asp Asp Asn Gly Lys Ile Ser
        195              200              205
Gly Ala Ala Ile Arg Thr Tyr Leu Leu Glu Arg Ser Arg Val Cys Gln
        210              215              220
Ile Ser Asp Pro Glu Arg Asn Tyr His Cys Phe Tyr Met Leu Cys Ala
225              230              235              240
Ala Pro Ser Glu Asp Cys Lys Lys Tyr Lys Leu Gly Glu Ala Lys Thr
        245              250              255
Phe His Tyr Leu Asn Gln Ser Asn Cys Ile Glu Leu Asp Gly Leu Asp
        260              265              270
Asp Ser Lys Glu Tyr Thr Asp Thr Arg Arg Ala Met Ser Ile Val Gly
        275              280              285
Ile Ser Ser Asp Glu Gln Asp Ala Ile Phe Arg Val Val Ala Ala Ile
        290              295              300
Leu His Leu Gly Asn Val Glu Phe Ala Glu Gly Ser Glu Ala Asp Ser
305              310              315              320
Ser Met Pro Lys Asp Glu Lys Ser Gln Phe His Leu Arg Thr Ala Ala
        325              330              335
Glu Leu Phe Met Cys Asp Glu Lys Gly Leu Glu Ser Leu Cys Lys
        340              345              350
Arg Val Met Ala Thr Arg Gly Glu Ser Ile Thr Lys Asn Leu Asp Pro
        355              360              365
Arg Ala Ala Leu Ser Arg Asp Ala Leu Ser Arg Ile Val Tyr Ser
        370              375              380
Arg Leu Phe Asp Trp Leu Val Asn Lys Ile Asn Ser Ser Ile Gly Gln
385              390              395              400
Asp Pro Asp Ser Lys Ile Leu Ile Gly Val Leu Asp Ile Tyr Gly Phe
        405              410              415
Glu Ser Phe Lys Thr Asn Ser Phe Glu Gln Phe Cys Ile Asn Leu Thr
        420              425              430
Asn Glu Lys Leu Gln Gln His Phe Asn Gln His Val Phe Lys Met Glu
        435              440              445
Gln Glu Glu Tyr Thr Lys Glu Glu Ile Asp Trp Ser Tyr Ile Gln Phe
        450              455              460
Val Asp Asn Gln Glu Ile Leu Asp Leu Ile Glu Lys Lys Pro Gly Gly
465              470              475              480
Ile Ile Ala Leu Leu Asp Glu Thr Cys Met Leu Arg Asn Ser Thr His
        485              490              495
Glu Thr Phe Ala Glu Lys Leu Tyr Gln Lys Phe Lys Asp Asn Pro His
        500              505              510
Phe Ser Lys Pro Lys Phe Ser Arg Ser Asp Phe Thr Ile His His Tyr
        515              520              525
Ala Gly Asn Val Thr Tyr Gln Thr Asp Leu Phe Leu Asp Lys Asn Ile
        530              535              540
Asp Tyr Ala Val Asn Glu His Gln Ile Leu Leu Asn Ala Ser Lys Cys
545              550              555              560
Ser Phe Val Ser Ser Leu Phe Pro Pro Cys Glu Glu Thr Lys Ser
        565              570              575
Thr Lys Phe Ser Ser Ile Gly Ser Ser Phe Lys Gln Gln Leu Gln Ser
        580              585              590
Leu Leu Glu Thr Leu Ser Ala Ile Glu Pro His Tyr Ile Arg Cys Ile
        595              600              605
```

-continued

Lys Pro Asn Asn Val Leu Lys Pro Ala Ile Phe Glu Asn Ser Asn Val
610                     615                     620

Leu Gln Gln Leu Arg Cys Gly Gly Val Leu Glu Ala Ile Arg Ile Ser
625                     630                     635                     640

Cys Leu Gly Tyr Pro Thr Arg Arg Thr Phe Phe Glu Phe Ile Asn Arg
                645                     650                     655

Phe Gly Ile Leu Gln Pro Lys Val Leu Gly Arg Ser His Asp Glu Val
                660                     665                     670

Ala Ala Thr Lys Met Leu Leu Gly Lys Ala Asn Leu Thr Gly Tyr Gln
                675                     680                     685

Ile Gly Lys Thr Lys Val Phe Leu Arg Ala Gly Gln Met Ala Glu Leu
                690                     695                     700

Asp Ala Leu Arg Thr Glu Ile Leu Gly Leu Ser Ala Lys Lys Ile Gln
705                     710                     715                     720

Thr Lys Val Arg Ser His Val Ala Arg Lys Lys Tyr Val Met Leu Gln
                        725                     730                     735

His Phe Ala Thr Gln Leu Gln Ala Val Cys Arg Gly Thr Ile Ala Arg
                740                     745                     750

Trp Arg Tyr Glu Thr Met Arg Arg Glu Ala Ala Ser Leu Lys Ile Gln
                755                     760                     765

Thr Cys Tyr Arg Lys His Cys Ala Arg Lys Thr Tyr Lys Glu Ile Cys
770                     775                     780

Ser Ala Ser Thr Thr Ile Gln Ser Gly Leu Arg Gly Met Ala Ala Arg
785                     790                     795                     800

His Lys Leu His Phe Tyr Arg Gln Thr Lys Ala Ala Val Ile Ile Gln
                805                     810                     815

Ser His Cys Arg Cys Tyr Leu Val Leu Ser Asn Tyr Lys Arg Met Met
                820                     825                     830

Lys Ala Ile Ile Thr Thr Gln Cys Ala Trp Arg Gly Arg Val Ala Arg
                835                     840                     845

Arg Glu Leu Arg Glu Leu Lys Val Ala Ala Lys Glu Thr Gly Ala Leu
850                     855                     860

Gln Ala Ala Lys Ser Lys Leu Glu Lys Glu Val Glu Glu Leu Thr Trp
865                     870                     875                     880

Arg Leu Gln Leu Glu Lys Arg Ile Arg Tyr Ala Ser Ile Ile Ile Cys
                885                     890                     895

Ala Thr Tyr Asn Ile Asp Tyr Thr Cys Pro Phe Ile Ala Asp Val Glu
                900                     905                     910

Glu Ala Lys Ala Gln Glu Asn Lys Leu Gln Leu Gln Leu Gln Asp
                915                     920                     925

Leu Gln Met Gln Leu Asn Asp Thr Lys Glu Leu Leu Lys Arg Glu Lys
                930                     935                     940

Glu Ser Thr Lys Ala Glu Met Glu Lys Thr Leu Val Pro Glu Ile Cys
945                     950                     955                     960

Val Asp Thr Thr Gln Val Asn Glu Leu Thr Ala Glu Asn Asn Arg Leu
                965                     970                     975

Lys Ala Leu Val Val Ser Leu Glu Thr Asn Ile Glu Glu Met Lys Gln
                980                     985                     990

Lys Phe Gly Glu Thr Asp Asn Val Arg Asp Glu Trp Cys Lys Lys Ala
                995                     1000                    1005

Thr Asp Ala Glu Ser Gln Ile Asn Glu Leu Lys Ser Met Met Gln
    1010                    1015                    1020

```
Ser Leu Gln Glu Lys Leu Asn Ser Thr Glu Ala Glu Asn His Val
    1025                1030                1035

Leu Arg Gln Gln Ala Met Arg Thr Arg Pro Asp Asn Met Pro Leu
    1040                1045                1050

Leu Asn Met His Arg Lys Ser Thr Pro His Gly Thr Ser Met Glu
    1055                1060                1065

Tyr Gly Arg Thr Ser Tyr Ile Glu Arg Gln Gln Glu Ser Val Glu
    1070                1075                1080

Ala Leu Ile Asn Cys Val Val Glu Asn Val Gly Phe Ser Glu Gly
    1085                1090                1095

Lys Pro Val Ala Ala Val Thr Ile Tyr Lys Cys Leu Leu His Trp
    1100                1105                1110

Arg Thr Phe Glu Ala Glu Lys Thr Asn Val Phe Asp Arg Leu Ile
    1115                1120                1125

Gln Ile Phe Gly Ser Ala Met Gln Lys Gln Glu Ser Asn Ala Asp
    1130                1135                1140

Leu Ala Tyr Trp Leu Ser Asn Ser Ser Ser Leu Leu Ile Ile Leu
    1145                1150                1155

Gln Lys Ser Leu Lys Pro Val Gly Ser Ser Val Thr Thr Pro Leu
    1160                1165                1170

Lys Arg Thr Gln Thr Gln Thr Ser Phe Leu Gly Arg Met Val Phe
    1175                1180                1185

Arg Ala Ser Asn Ile Thr Val Asp Met Asp Leu Val Arg Gln Val
    1190                1195                1200

Glu Ala Lys Tyr Pro Ala Phe Leu Phe Lys Gln Gln Leu Thr Ala
    1205                1210                1215

Phe Val Glu Gly Leu Tyr Gly Met Ile Arg Asp Asn Val Lys Arg
    1220                1225                1230

Asp Ile Ser Ser Val Leu Thr Leu Ile Ile Gln Thr Pro Arg Ser
    1235                1240                1245

Ala Lys Ala Gly Leu Leu Thr Asp Gln Gly Asn Asn Trp Gln Ala
    1250                1255                1260

Ile Val Asn His Leu Asn Asp Leu Leu Lys Thr Leu Gln Glu Asn
    1265                1270                1275

Cys Val Pro Ser Ile Phe Ala Arg Lys Ile Phe Thr Gln Ile Phe
    1280                1285                1290

Ser Phe Ile Asn Ala Gln Leu Phe Asn Ser Leu Leu Val Arg Arg
    1295                1300                1305

Glu Cys Cys Ser Phe Ser Asn Gly Glu Tyr Val Lys Gln Gly Leu
    1310                1315                1320

Gln Glu Leu Glu Ala Trp Cys Thr Gln Ala Lys Pro Glu Tyr Ala
    1325                1330                1335

Gly Ser Ala Trp Asp Glu Leu Lys His Ile Ser Gln Ala Val Gly
    1340                1345                1350

Phe Leu Val Ile Phe Lys Lys Phe Arg Ile Ser Tyr Asp Glu Ile
    1355                1360                1365

Ile Asn Asp Leu Cys Thr Ala Leu Ser Val Gln Gln Leu Tyr Lys
    1370                1375                1380

Ile Cys Thr Gln Tyr Trp Asp Asp Lys Tyr Asn Thr Glu Ser Val
    1385                1390                1395

Ser Glu Glu Val Leu Asn Glu Met Lys Thr Leu Met Asn Gly Lys
    1400                1405                1410

Asp Ala Ser Asp Gly Thr Leu Lys Ser Leu Met Asn Glu Lys Asp
```

-continued

```
              1415                1420                1425

Ala Ser Asp Gly Thr Phe Leu Leu Asn Glu Glu Ile Ser Met Pro
        1430                1435                1440

Leu Ser Leu Glu Glu Ile Gly Asp Ser Met Asp Ala Lys Glu Phe
        1445                1450                1455

Gln Asn Val Val Pro Pro Gln Gln Leu Leu Asp Asn Pro Ala Phe
        1460                1465                1470

Gln Phe Leu Lys Ser
        1475

<210> SEQ ID NO 11
<211> LENGTH: 1529
<212> TYPE: PRT
<213> ORGANISM: O. sativa
<220> FEATURE:
<223> OTHER INFORMATION: myosin XI-J full length

<400> SEQUENCE: 11

Met Gly Thr Lys Val Asn Ile Ile Val Gly Ser His Val Trp Ala Glu
1               5                   10                  15

Asp Pro Glu Ile Ala Trp Val Asp Gly Glu Val Val Lys Ile Lys Gly
            20                  25                  30

Glu Glu Ala Glu Ile Gln Ala Thr Asn Gly Lys Thr Ile Thr Ala Asn
        35                  40                  45

Leu Ser Lys Leu Tyr Pro Lys Asp Met Glu Ala Ala Gly Gly Val
    50                  55                  60

Asp Asp Met Thr Lys Leu Ser Tyr Leu His Glu Pro Gly Val Leu Gln
65                  70                  75                  80

Asn Leu Ala Thr Arg Tyr Glu Leu Asn Glu Ile Tyr Thr Tyr Thr Gly
                85                  90                  95

Asn Ile Leu Ile Ala Val Asn Pro Phe Gln Arg Leu Pro His Leu Tyr
            100                 105                 110

Asp Pro His Met Met Gln Gln Tyr Lys Gly Ala Pro Phe Gly Glu Leu
        115                 120                 125

Ser Pro His Val Phe Ala Val Ala Asp Val Ala Tyr Arg Ala Met Ile
    130                 135                 140

His Glu Gly Lys Ser Asn Ser Ile Leu Val Ser Gly Glu Ser Gly Ala
145                 150                 155                 160

Gly Lys Thr Glu Thr Thr Lys Met Leu Met Arg Tyr Leu Ala Tyr Leu
                165                 170                 175

Gly Gly Arg Ala Ala Thr Glu Gly Arg Thr Val Glu Gln Gln Val Leu
            180                 185                 190

Glu Ser Asn Pro Val Leu Glu Ala Phe Gly Asn Ala Lys Thr Val Arg
        195                 200                 205

Asn Asn Asn Ser Ser Arg Phe Gly Lys Phe Val Glu Ile Gln Phe Asp
    210                 215                 220

Lys Gln Gly Arg Ile Ser Gly Ala Ala Val Arg Thr Tyr Leu Leu Glu
225                 230                 235                 240

Arg Ser Arg Val Cys Gln Ile Ser Asp Pro Glu Arg Asn Tyr His Cys
                245                 250                 255

Phe Tyr Leu Leu Cys Ala Ala Pro Gln Glu Val Glu Lys Tyr Lys
            260                 265                 270

Leu Gly Asn Pro Lys Thr Phe His Tyr Leu Asn Gln Ser Asn Cys Tyr
        275                 280                 285

Glu Leu Val Gly Val Ser Asp Ala His Glu Tyr Leu Ala Thr Arg Arg
```

```
              290                 295                 300
Ala Met Asp Ile Val Gly Ile Ser Thr Gln Glu Gln Asp Ala Ile Phe
305                 310                 315                 320

Arg Val Val Ala Ala Ile Leu His Ile Gly Asn Ile Glu Phe Ala Lys
                    325                 330                 335

Gly Lys Glu Val Asp Ser Ser Val Leu Lys Asp Asp Lys Ser Lys Phe
                340                 345                 350

His Leu Asp Thr Thr Ala Glu Leu Leu Met Cys Asp Ser Gly Ala Leu
            355                 360                 365

Gly Asp Ala Leu Cys Lys Arg Val Met Val Thr Pro Glu Glu Val Ile
        370                 375                 380

Lys Arg Ser Leu Asp Pro Tyr Asn Ala Thr Val Ser Arg Asp Gly Leu
385                 390                 395                 400

Ala Lys Thr Ile Tyr Ser Arg Leu Phe Asp Trp Leu Val Asp Lys Ile
                405                 410                 415

Asn Ser Ser Ile Gly Gln Asp Pro Asn Ser Lys Ser Leu Ile Gly Val
                420                 425                 430

Leu Asp Ile Tyr Gly Phe Glu Ser Phe Lys Leu Asn Ser Phe Glu Gln
            435                 440                 445

Phe Cys Ile Asn Tyr Thr Asn Glu Lys Leu Gln Gln His Phe Asn Gln
        450                 455                 460

His Val Phe Lys Met Glu Gln Glu Glu Tyr Thr Lys Glu Gln Ile Asp
465                 470                 475                 480

Trp Ser Tyr Ile Glu Phe Val Asp Asn Gln Asp Val Leu Asp Leu Ile
                485                 490                 495

Glu Lys Lys Pro Gly Gly Val Ile Ala Leu Leu Asp Glu Ala Cys Met
                500                 505                 510

Phe Pro Lys Ser Thr His Glu Thr Phe Ser Gln Lys Leu Tyr Gln Thr
            515                 520                 525

Phe Gln Lys His Lys Arg Phe Val Lys Pro Lys Leu Ser Arg Thr Asp
        530                 535                 540

Phe Thr Ile Cys His Tyr Ala Gly Glu Val Leu Tyr Gln Ser Asp Gln
545                 550                 555                 560

Phe Leu Asp Lys Asn Lys Asp Tyr Val Val Ala Glu His Gln Glu Leu
                565                 570                 575

Leu Ser Ala Ser Lys Cys Ser Phe Ile Ser Gly Leu Phe Pro Pro Leu
                580                 585                 590

Pro Glu Glu Thr Ser Lys Ser Ser Lys Phe Ser Ser Ile Gly Ala Arg
            595                 600                 605

Phe Lys Gln Gln Leu Gln Ala Leu Met Glu Thr Leu Asn Ser Thr Glu
        610                 615                 620

Pro His Tyr Ile Arg Cys Val Lys Pro Asn Asn Val Leu Lys Pro Ala
625                 630                 635                 640

Ile Phe Glu Asn Val Asn Val Met Gln Gln Leu Arg Cys Gly Gly Val
                645                 650                 655

Leu Glu Ala Ile Arg Ile Ser Cys Ala Gly Tyr Pro Thr Arg Arg Thr
                660                 665                 670

Phe Tyr Glu Phe Leu His Arg Phe Gly Ile Leu Ala Gln Glu Ala Leu
            675                 680                 685

Glu Gly Asn Cys Asp Glu Lys Val Ala Cys Lys Arg Ile Leu Glu Lys
        690                 695                 700

Lys Gly Leu Val Gly Phe Gln Ile Gly Lys Thr Lys Val Phe Leu Arg
705                 710                 715                 720
```

```
Ala Gly Gln Met Ala Glu Leu Asp Ala Arg Arg Thr Glu Val Leu Gly
                725                 730                 735

Ala Ala Ala Lys Thr Ile Gln Gly Lys Ile Arg Thr His Ile Met Arg
                740                 745                 750

Lys Lys Phe Val Asn Trp Arg Lys Ala Ser Ile Ser Val Gln Ala Ile
                755                 760                 765

Trp Arg Gly Arg Leu Ala Cys Lys Leu Phe Asp Gln Met Arg Arg Val
770                 775                 780

Ala Ala Ala Ile Lys Val Gln Lys Asn Gln Arg Met His Gln Ala Arg
785                 790                 795                 800

Arg Ser Tyr Lys His Leu Asn Ala Ser Val Leu Val Gln Thr Ala
                805                 810                 815

Leu Arg Ala Met Ala Ala Arg Asn Thr Phe Arg Tyr Lys Lys Gln Ser
                820                 825                 830

Lys Ala Ala Val Lys Ile Gln Ala Arg Tyr Arg Cys His Thr Ala His
                835                 840                 845

Val Tyr His Lys Lys Leu Lys Arg Ala Ala Ile Val Ala Gln Cys Arg
                850                 855                 860

Trp Arg Gly Lys Ile Ala Arg Lys Glu Leu Arg Lys Leu Lys Met Glu
865                 870                 875                 880

Ala Arg Glu Thr Gly Ala Leu Lys Glu Ala Lys Asp Lys Leu Glu Lys
                885                 890                 895

Lys Val Glu Glu Leu Thr Trp Arg Val Gln Leu Glu Lys Arg Met Arg
                900                 905                 910

Thr Asp Leu Glu Glu Ala Lys Ala Gln Glu Leu Ser Lys Leu Gln Ser
                915                 920                 925

Ser Met Glu Ala Leu Gln Ala Lys Leu Asp Glu Thr Ser Ala Lys Leu
                930                 935                 940

Val Lys Glu Arg Glu Val Ala Arg Ala Ile Glu Glu Ala Pro Pro Val
945                 950                 955                 960

Val Gln Gln Thr Glu Val Leu Val Gln Asp Thr Glu Lys Val Asp Ser
                965                 970                 975

Leu Thr Ala Glu Val Glu Glu Leu Lys Thr Ser Leu Gln Ser Glu Lys
                980                 985                 990

Gln Arg Ala Asp Asp Leu Glu Lys Lys Arg Ser Glu Glu Gln Gln Ala
                995                 1000                1005

Asn Glu Glu Lys Gln Lys Lys Met Glu Glu Thr Asp Val Lys Met
                1010                1015                1020

Arg Gln Phe Gln Glu Tyr Leu Arg Arg Leu Glu Glu Lys Leu Ala
                1025                1030                1035

Asn Val Glu Ser Glu Asn Lys Val Leu Arg Gln Gln Ala Val Ser
                1040                1045                1050

Met Ala Pro Ser Lys Ile Leu Ser Gly Arg Ser Lys Ser Ile Leu
                1055                1060                1065

Gln Arg Asn Ala Glu Ser Val His Val Ser Ser Gly Asp Ser Lys
                1070                1075                1080

Ala Ala Pro Glu Ser Asn Asn Ile Ser Ser Pro Lys Lys Glu Phe
                1085                1090                1095

Asp Phe Asp Asp Lys Pro Gln Lys Ser Leu Asn Glu Lys Gln Gln
                1100                1105                1110

Glu Asn Gln Asp Leu Leu Ile Arg Cys Ile Ala Gln His Leu Gly
                1115                1120                1125
```

-continued

```
Phe Ala Gly Asn Arg Pro Val Ala Ala Cys Ile Ile Tyr Lys Cys
1130                1135                1140

Leu Leu His Trp Arg Ser Phe Glu Val Glu Arg Thr Ser Val Phe
1145                1150                1155

Asp Arg Ile Ile Gln Thr Ile Gly His Ala Ile Glu Thr Gln Asp
1160                1165                1170

Asn Asn Glu Val Leu Ala Tyr Trp Leu Ser Asn Ala Ser Thr Leu
1175                1180                1185

Leu Leu Leu Leu Gln Arg Thr Leu Lys Ala Ser Gly Ser Thr Gly
1190                1195                1200

Met Ala Pro Gln Arg Arg Ser Ser Ser Ala Thr Leu Phe Gly
1205                1210                1215

Arg Met Thr Gln Ser Phe Arg Gly Thr Pro Gln Gly Val Asn Leu
1220                1225                1230

Ser Leu Ile Asn Gly Ser Met Val Ser Gly Val Glu Thr Leu Arg
1235                1240                1245

Gln Val Glu Ala Lys Tyr Pro Ala Leu Leu Phe Lys Gln Gln Leu
1250                1255                1260

Thr Ala Tyr Val Glu Lys Ile Tyr Gly Met Ile Arg Asp Asn Leu
1265                1270                1275

Lys Lys Glu Ile Ser Pro Leu Leu Gly Leu Cys Ile Gln Ala Pro
1280                1285                1290

Arg Thr Ser Arg Ala Ser Leu Met Lys Gly Ser Ser Arg Ser Asn
1295                1300                1305

Thr Asn Thr Ala Ala Gln Gln Ala Leu Ile Ala His Trp Gln Gly
1310                1315                1320

Ile Val Lys Ser Leu Gly Asn Phe Leu Asn Met Leu Lys Leu Asn
1325                1330                1335

Asn Val Pro Pro Phe Leu Val Arg Lys Val Phe Thr Gln Ile Phe
1340                1345                1350

Ser Phe Ile Asn Val Gln Leu Phe Asn Ser Leu Leu Leu Arg Arg
1355                1360                1365

Glu Cys Cys Ser Phe Ser Asn Gly Glu Tyr Val Lys Ala Gly Leu
1370                1375                1380

Ala Glu Leu Glu His Trp Cys Tyr Arg Ala Thr Asp Glu Tyr Ala
1385                1390                1395

Gly Ser Ala Trp Asp Glu Leu Lys His Ile Arg Gln Ala Ile Gly
1400                1405                1410

Phe Leu Val Ile His Gln Lys Pro Lys Lys Thr Leu Asp Glu Ile
1415                1420                1425

Ser His Asp Leu Cys Pro Val Leu Ser Ile Gln Gln Leu Tyr Arg
1430                1435                1440

Ile Ser Thr Met Tyr Trp Asp Asp Lys Tyr Gly Thr His Ser Val
1445                1450                1455

Ser Pro Glu Val Ile Ser Asn Met Arg Val Leu Met Thr Glu Asp
1460                1465                1470

Ser Asn Asn Pro Val Ser Ser Phe Leu Leu Asp Asp Asp Ser
1475                1480                1485

Ser Ile Pro Phe Ser Val Asp Asp Ile Ser Lys Ser Met Glu Gln
1490                1495                1500

Ile Asp Ile Ser Asp Ile Glu Pro Pro Pro Leu Ile Arg Glu Asn
1505                1510                1515

Ser Gly Phe Val Phe Leu Leu Pro Pro Pro Glu
```

-continued

```
                1520                1525
```

```
<210> SEQ ID NO 12
<211> LENGTH: 1501
<212> TYPE: PRT
<213> ORGANISM: Brachypodium distachyon
<220> FEATURE:
<223> OTHER INFORMATION: XI-I full length

<400> SEQUENCE: 12

Met Ser Tyr Arg Arg Gly Ser Lys Val Trp Val Glu Glu Lys Gly Glu
1               5                   10                  15

Gly Trp Val Glu Ala Glu Val Val Glu Val Lys Asp Arg Ala Val Leu
            20                  25                  30

Val Leu Thr Ser Gln Arg Lys Lys Ile Thr Val Leu Pro Glu Lys Leu
        35                  40                  45

Leu Pro Arg Asn Thr Asp Glu Asp Leu Gly Gly His Val Asp Asp
    50                  55                  60

Met Thr Lys Leu Thr Tyr Leu Asn Glu Pro Gly Val Leu Tyr Asn Leu
65                  70                  75                  80

Lys Arg Arg Tyr Ala Leu Asn Glu Ile Tyr Thr Tyr Thr Gly Ser Ile
                85                  90                  95

Leu Ile Ala Val Asn Pro Phe Thr Arg Leu Pro His Leu Tyr Asn Glu
            100                 105                 110

Tyr Met Met Glu Gln Tyr Lys Gly Val Arg Leu Gly Glu Leu Ser Pro
        115                 120                 125

His Val Phe Ala Val Ala Asp Ala Ser Tyr Arg Ala Met Val Asn Asp
    130                 135                 140

Ser Arg Ser Gln Ser Ile Leu Val Ser Gly Glu Ser Gly Ala Gly Lys
145                 150                 155                 160

Thr Glu Thr Thr Lys Leu Ile Met Gln Tyr Leu Thr Tyr Val Gly Gly
                165                 170                 175

Arg Ala Val Leu Asp Asp Arg Ser Val Glu Gln Gln Val Leu Glu Ser
            180                 185                 190

Asn Pro Leu Leu Glu Ala Phe Gly Asn Ala Lys Thr Val Arg Asn Asp
        195                 200                 205

Asn Ser Ser Arg Phe Gly Lys Phe Val Glu Ile Gln Phe Asp Arg Asn
    210                 215                 220

Gly Arg Ile Ser Gly Ala Ala Ile Arg Thr Tyr Leu Leu Glu Arg Ser
225                 230                 235                 240

Arg Val Val Gln Ile Thr Asp Pro Glu Arg Asn Phe His Cys Phe Tyr
                245                 250                 255

Gln Leu Cys Ala Ser Gly Lys Asp Ala Glu Leu Tyr Lys Leu Gly His
            260                 265                 270

Ala Ser Thr Phe His Tyr Leu Asn Gln Ser Lys Thr Tyr Glu Leu Glu
        275                 280                 285

Gly Ile Asn Asn Glu Asp Glu Tyr Trp Lys Thr Lys Arg Ala Met Asp
    290                 295                 300

Ile Val Gly Ile Ser Thr Lys Asp Gln Asp Ala Ile Phe Arg Thr Leu
305                 310                 315                 320

Ala Ala Ile Leu His Leu Gly Asn Ile Glu Phe Ser Pro Gly Lys Glu
                325                 330                 335

Pro Asp Ser Ser Ile Ile Lys Asp Ser Thr Ser Asn Phe His Leu Gln
            340                 345                 350

Met Thr Ala Lys Leu Leu Met Cys Asp Pro Asp Val Leu Val Ala Ser
```

```
                355                 360                 365
Leu Cys Ser Arg Ser Ile His Thr Asn Glu Gly Ile Ile Lys Ala
    370                 375                 380
Leu Asp Cys Ala Ala Ala Ala Asn Arg Asp Thr Leu Ala Lys Thr
385                 390                 395                 400
Val Tyr Ala Lys Leu Phe Asp Trp Leu Val Glu Asn Ile Asn Lys Ser
                405                 410                 415
Ile Gly Gln Asp Val Asp Ser Lys Ala Gln Ile Gly Val Leu Asp Ile
                420                 425                 430
Tyr Gly Phe Glu Ser Phe Lys Asn Asn Ser Phe Glu Gln Phe Cys Ile
                435                 440                 445
Asn Phe Ala Asn Glu Lys Leu Gln Gln His Phe Asn Glu His Val Phe
                450                 455                 460
Lys Met Glu Gln Glu Glu Tyr Lys Ser Glu Lys Ile Asn Trp Ser Tyr
465                 470                 475                 480
Ile Glu Phe Ile Asp Asn Gln Asp Met Leu Asp Leu Ile Glu Lys Lys
                485                 490                 495
Pro Ile Gly Ile Ile Ala Leu Leu Asp Glu Ala Cys Met Phe Pro Lys
                500                 505                 510
Ser Thr His Val Thr Phe Ala Thr Lys Met Phe Arg Asn Phe Ser Ser
                515                 520                 525
His Pro Arg Leu Glu Lys Thr Lys Phe Ser Glu Thr Asp Phe Thr Ile
                530                 535                 540
Ser His Tyr Ala Gly Lys Val Thr Tyr Gln Thr Asp Ser Phe Leu Glu
545                 550                 555                 560
Lys Asn Arg Asp Tyr Ile Val Ala Glu His Cys Asn Leu Leu Ser Ser
                565                 570                 575
Ser Arg Cys Pro Phe Val Ser Gly Leu Phe Thr Ser Leu Pro Glu Glu
                580                 585                 590
Ser Leu Arg Ser Ser Tyr Lys Phe Ser Ser Val Ala Ser Arg Phe Lys
                595                 600                 605
Gln Gln Leu Gln Ala Leu Met Glu Thr Leu Ser Ser Thr Glu Pro His
                610                 615                 620
Tyr Val Arg Cys Val Lys Pro Asn Ser Val Asn Arg Pro Gln Leu Phe
625                 630                 635                 640
Glu Asn Gln Ser Val Leu His Gln Leu Arg Cys Gly Gly Val Leu Glu
                645                 650                 655
Ala Val Arg Ile Ser Leu Ala Gly Tyr Pro Thr Arg Arg Ser Tyr Ala
                660                 665                 670
Glu Phe Val Asp Arg Phe Gly Val Leu Val Pro Glu Leu Ile Leu Gly
                675                 680                 685
Ser Tyr Asp Glu Arg Ala Leu Thr Glu Ala Ile Leu Glu Lys Met Lys
                690                 695                 700
Leu Asp Asn Phe Gln Leu Gly Arg Ala Lys Val Phe Leu Arg Ala Gly
705                 710                 715                 720
Gln Ile Ala Ile Leu Asp Val Arg Arg Ala Glu Val Leu Asp Asn Ala
                725                 730                 735
Ala Arg His Ile Gln Gly Arg Phe Arg Thr Phe Val Ala Arg Lys Glu
                740                 745                 750
Phe Val Lys Thr Lys Lys Ala Ser Ile Ser Ile Gln Ala Phe Cys Arg
                755                 760                 765
Gly Cys Leu Ala Arg Lys Met Tyr Met Ile Arg Arg Glu Thr Ala Ala
                770                 775                 780
```

```
Ala Ile Thr Ile Gln Lys Tyr Val Arg Arg Leu Leu Arg Arg Asn
785                 790                 795                 800

Tyr Gln Gln Ala Cys Ser Ala Ser Leu Leu Ile Gln Ser Cys Ile Arg
            805                 810                 815

Gly Phe Ile Ala Arg Leu Tyr Phe Ser Ala Met Arg Glu Gln Lys Ala
            820                 825                 830

Ala Leu Val Ile Gln Ser Leu Trp Arg Lys Arg Lys Ala Val Met Leu
            835                 840                 845

Phe Gln His Tyr Arg Gln Ala Ser Ile Ala Ile Gln Cys Ala Trp Arg
850                 855                 860

Gln Lys Leu Ala Arg Arg Glu Leu Arg Lys Leu Arg Met Ala Ala Asn
865                 870                 875                 880

Glu Ala Gly Ala Leu Arg Asp Ala Lys Asn Lys Leu Glu Lys Gln Leu
            885                 890                 895

Asp Asp Leu Thr Leu Arg Leu Thr Leu Glu Arg Arg Met Arg Ala Thr
            900                 905                 910

Gly Glu Glu Thr Lys Leu Val Glu Ile Ser Lys Arg Glu Lys Ile Ile
            915                 920                 925

Glu Thr Leu Ser Ala Glu Cys Ala Glu Ala Lys Ser Ser Ala Arg Ser
930                 935                 940

Glu His Asp Lys Asn Leu Leu Leu Gln Arg Gln Leu Asp Asp Ser Leu
945                 950                 955                 960

Arg Glu Ile Ala Met Leu Arg Ser Asn Lys Ile Leu Lys Ala Glu Thr
            965                 970                 975

Glu Lys Glu Asn Ser Asn Leu Lys Asn Ile Val Glu Ser Leu Ser Lys
            980                 985                 990

Lys Asn Thr Leu Leu Glu Asn Glu  Leu Ser Thr Ala Arg  Arg Ser Ser
            995                 1000                1005

Asp Asp  Thr Met Glu Lys Leu  Lys Asp Val Glu Gly  Lys Cys Thr
    1010                1015                1020

His Leu  Gln Gln Asn Leu Asp  Lys Leu Gln Glu Lys  Leu Thr Asn
    1025                1030                1035

Leu Glu  Asn Glu Asn His Val  Leu Arg Gln Lys Ala  Phe Asn Ile
    1040                1045                1050

Ser Pro  Lys Thr Leu Ser Glu  Lys Phe Ser Ala Ser  Ile Gly Leu
    1055                1060                1065

Gly Asn  Ser Glu Gln Lys Arg  Ile Phe Glu Ser Pro  Thr Pro Ala
    1070                1075                1080

Lys Tyr  Leu Ser Pro Ile Pro  Gln Ser Thr Gly Ser  Arg Arg Thr
    1085                1090                1095

Arg Leu  Pro Val Glu Arg His  Glu Gly Asn His Glu  Ile Leu Leu
    1100                1105                1110

Arg Cys  Ile Lys Glu Asn Leu  Gly Phe Lys Asp Gly  Lys Pro Val
    1115                1120                1125

Ala Ala  Cys Ile Ile Tyr Lys  Cys Leu Leu His Trp  Arg Ala Phe
    1130                1135                1140

Glu Ser  Glu Arg Thr Ala Val  Phe Asp His Val Ile  Glu Ala Ile
    1145                1150                1155

Asn Asp  Val Leu Lys Ala Lys  Glu Ser Asp Gly Arg  Leu Pro Tyr
    1160                1165                1170

Trp Leu  Ser Asn Thr Ser Ala  Leu Leu Cys Leu Leu  Gln Lys Asn
    1175                1180                1185
```

Leu Arg Ser Asn Gly Phe Phe Gly Thr Pro Ser Arg Arg Ser Ala
    1190            1195                1200

Gly Pro Leu Gly Leu Gly Lys Met Ala Gln Leu Val Gly Arg
    1205            1210                1215

Gly Asp Thr Leu Ala Gln Val Asp Ala Arg Tyr Pro Ala Ile Leu
    1220            1225                1230

Phe Lys Gln Gln Leu Thr Ala Cys Val Glu Lys Ile Phe Gly Gln
    1235            1240                1245

Leu Arg Asp Asn Leu Lys Lys Glu Ile Ser Pro Leu Leu Ser Val
    1250            1255                1260

Cys Ile Gln Ala Pro Lys Ala Thr Arg Ala Gln Thr Gly Lys Ala
    1265            1270                1275

Ser Lys Ser Pro Gly Val Gly Ala Gln Pro Pro Asn Ser His
    1280            1285                1290

Trp Asp Asn Ile Val Lys Phe Leu Asn Leu Leu Met Asp Thr Leu
    1295            1300                1305

Arg Glu Asn Tyr Val Pro Ser Phe Phe Ile Arg Lys Leu Ile Thr
    1310            1315                1320

Gln Leu Phe Ser Phe Ile Asn Ile Gln Leu Phe Asn Ser Leu Leu
    1325            1330                1335

Leu Arg Arg Glu Cys Cys Thr Phe Thr Asn Gly Glu Tyr Val Lys
    1340            1345                1350

Ala Gly Leu Ser Leu Leu Glu Lys Trp Ile Thr Asp Val Thr Glu
    1355            1360                1365

Glu Phe Ala Gly Thr Ser Trp His Glu Leu Asn Tyr Ile Arg Gln
    1370            1375                1380

Ala Val Gly Phe Leu Val Ile His Gln Lys Arg Lys Lys Thr Leu
    1385            1390                1395

Glu Glu Ile Ser Gln Asp Leu Cys Pro Ser Leu Ser Val Arg Gln
    1400            1405                1410

Ile Tyr Arg Ile Cys Ser Met Tyr Trp Asp Asp Lys Tyr Asn Thr
    1415            1420                1425

Gln Gly Ile Ser Asn Glu Val Val Gly Ala Met Arg Glu Met Val
    1430            1435                1440

Asn Lys Asp Ser Gln Asn Leu Val Ser Asn Ser Phe Leu Leu Asp
    1445            1450                1455

Asp Asp Leu Ser Ile Pro Phe Ser Thr Glu Asp Leu Ser Met Ala
    1460            1465                1470

Ile Pro Ala Ile Glu Tyr Ala Gly Val Glu Leu Pro Glu Ser Leu
    1475            1480                1485

His Gln Tyr Pro Ser Ala Gln Phe Leu Leu Glu Ala Ser
    1490            1495                1500

<210> SEQ ID NO 13
<211> LENGTH: 1556
<212> TYPE: PRT
<213> ORGANISM: Brachypodium distachyon
<220> FEATURE:
<223> OTHER INFORMATION: XI-F full length

<400> SEQUENCE: 13

Met Gly Thr Pro Val Asn Ile Ile Val Gly Ser Gln Val Trp Leu Glu
1               5                   10                  15

Asp Pro Asp Asp Ala Trp Val Asp Gly Glu Val Thr Gly Ile Lys Gly
                20                  25                  30

```
Gly Asp Val Thr Val Ala Thr Thr Asn Gly Lys Thr Val Val Ala Ser
         35                  40                  45

Leu Ala Ser Ile His Pro Lys Asp Thr Glu Ala Pro Pro Ala Gly Val
 50                  55                  60

Asp Asp Met Thr Lys Leu Ala Tyr Leu His Glu Pro Gly Val Leu His
 65                  70                  75                  80

Asn Leu Ala Cys Arg Tyr Gly Leu Asn Glu Ile Tyr Thr Tyr Thr Gly
                 85                  90                  95

Asn Ile Leu Ile Ala Val Asn Pro Phe Gln Arg Leu Pro His Leu Tyr
            100                 105                 110

Asp Val His Met Met Glu Gln Tyr Lys Gly Ala Thr Phe Gly Glu Leu
            115                 120                 125

Ser Pro His Leu Phe Ala Ile Ala Asp Ser Cys Tyr Arg Ala Met Ile
    130                 135                 140

Asn Glu His Gly Ser Gln Ser Ile Leu Val Ser Gly Glu Ser Gly Ala
145                 150                 155                 160

Gly Lys Thr Glu Thr Thr Lys Met Leu Met Arg Tyr Leu Ala Phe Met
                165                 170                 175

Gly Gly Arg Ser Gly Thr Glu Gly Arg Thr Val Glu Gln Gln Val Leu
            180                 185                 190

Glu Ser Asn Pro Val Leu Glu Ala Phe Gly Asn Ala Lys Thr Val Lys
        195                 200                 205

Asn Asn Asn Ser Ser Arg Phe Gly Lys Phe Val Glu Ile Gln Phe Asp
210                 215                 220

Lys Tyr Gly Lys Ile Ser Gly Ala Ala Val Arg Thr Tyr Leu Leu Glu
225                 230                 235                 240

Arg Ser Arg Val Cys Gln Val Ser Asp Pro Glu Arg Asn Tyr His Cys
                245                 250                 255

Phe Tyr Met Leu Cys Ser Ala Pro Pro Glu Asp Val Lys Arg Phe Lys
            260                 265                 270

Val Gly Asp Pro Arg Ser Phe His Tyr Leu Asn Gln Thr Asn Cys Tyr
        275                 280                 285

Glu Val Ala Asn Val Asp Asp Ala Arg Glu Tyr Leu Glu Thr Arg Asn
290                 295                 300

Ala Met Asp Ile Val Gly Ile Cys Glu Glu Glu Gln Asp Ala Ile Phe
305                 310                 315                 320

Arg Val Val Ala Ala Ile Leu His Leu Gly Asn Ile Asn Phe Ser Lys
                325                 330                 335

Gly Glu Glu Ile Asp Ser Ser Arg Leu Arg Asp Glu Lys Ser Val Tyr
            340                 345                 350

His Leu Lys Thr Val Ala Glu Leu Leu Met Cys Asp Glu Lys Tyr Leu
        355                 360                 365

Glu Asp Ser Leu Cys Lys Arg Val Ile Val Thr Pro Asp Gly Asn Ile
370                 375                 380

Thr Lys Pro Leu Asp Pro Asp Ser Ala Leu Gln Ser Arg Asp Ala Leu
385                 390                 395                 400

Ala Lys Thr Val Tyr Ser Arg Leu Phe Asp Trp Ile Val Asp Lys Ile
                405                 410                 415

Asn Asn Ser Ile Gly Gln Asp Pro Asp Ala Ile Ser Ile Gly Val
            420                 425                 430

Leu Asp Ile Tyr Gly Phe Glu Ser Phe Lys Ile Asn Ser Phe Glu Gln
        435                 440                 445

Leu Cys Ile Asn Met Thr Asn Glu Lys Leu Gln Gln His Phe Asn Gln
```

-continued

```
            450                 455                 460
His Val Phe Lys Met Glu Gln Glu Tyr Thr Arg Asp Glu Ile Asp
465                 470                 475                 480

Trp Ser Tyr Val Glu Phe Val Asp Asn Gln Asp Val Leu Asp Leu Ile
                    485                 490                 495

Glu Lys Lys Pro Gly Gly Ile Ile Ala Leu Leu Asp Glu Ala Cys Met
                500                 505                 510

Phe Pro Lys Ser Thr His Glu Thr Phe Ala Gln Lys Met Tyr Gln Thr
            515                 520                 525

Tyr Lys Ala His Lys Arg Phe Ser Lys Pro Lys Leu Ala Arg Thr Ala
            530                 535                 540

Phe Thr Ile Asn His Tyr Ala Gly Asp Val Thr Tyr Gln Ala Asp Gln
545                 550                 555                 560

Phe Leu Asp Lys Asn Lys Asp Tyr Val Val Ala Glu His Gln Ala Leu
                565                 570                 575

Leu Asn Tyr Ser Arg Cys Pro Phe Val Ala Asn Leu Phe Pro Pro Leu
                580                 585                 590

Pro Glu Glu Ser Ser Lys Gln Ser Lys Phe Ser Ser Ile Gly Thr Arg
            595                 600                 605

Phe Lys Gln Gln Leu Gln Ala Leu Met Glu Thr Leu Ser Thr Thr Glu
            610                 615                 620

Pro His Tyr Ile Arg Cys Val Lys Pro Asn Thr Val Leu Lys Pro Gly
625                 630                 635                 640

Ile Phe Glu Asn Tyr Asn Val Leu Asn Gln Leu Arg Cys Gly Gly Val
                645                 650                 655

Leu Glu Ala Ile Arg Ile Ser Cys Ala Gly Tyr Pro Thr Lys Arg Thr
                660                 665                 670

Phe Asp Glu Phe Ile Asp Arg Phe Gly Val Leu Ala Pro Glu Leu Val
            675                 680                 685

Asp Ser Ser Asp Glu Lys Ala Ala Cys Ala Ala Ile Cys Asp Arg Met
            690                 695                 700

Gly Leu Lys Gly Tyr Gln Ile Gly Lys Thr Lys Val Phe Leu Arg Ala
705                 710                 715                 720

Gly Gln Met Ala Glu Leu Asp Ala Arg Arg Ala Glu Val Leu Ala Asn
                725                 730                 735

Ala Val Arg Leu Ile Gln Arg Ile Arg Thr His Leu Met Arg Lys
                740                 745                 750

Glu Phe Thr Asn Leu Arg Lys Ala Ser Ile Gln Thr Gln Lys Phe Trp
            755                 760                 765

Arg Ala Arg Leu Ala Arg Lys Leu Phe Glu His Met Arg Arg Val Ala
770                 775                 780

Ala Ala Ile Thr Ile Gln Lys His Thr Arg Thr Arg Ser Ala Trp Lys
785                 790                 795                 800

Ala Tyr Leu Gln Ile Tyr Arg Ser Ser Ile Thr Ile Gln Thr Gly Leu
                805                 810                 815

Arg Ala Met Ala Ala Arg Asn Glu His Arg Phe Arg Arg Gln Thr Lys
                820                 825                 830

Ala Ala Ile Ile Ile Gln Thr Arg Trp Arg Gln His Lys Ala Tyr Val
                835                 840                 845

Ala Tyr Lys Gln Gln Lys Lys Ala Ser Leu Ile Leu Gln Cys Ser Trp
            850                 855                 860

Arg Ala Arg Val Ala Arg Lys Glu Leu Arg Lys Leu Lys Met Glu Ala
865                 870                 875                 880
```

```
Arg Asp Asn Gly Ala Leu Lys Glu Ala Lys Asp Lys Leu Glu Lys Arg
            885                 890                 895

Val Glu Glu Leu Thr Trp Arg Leu Asp Val Glu Lys His Leu Arg Ile
            900                 905                 910

Asp Leu Glu Ile Ser Lys Gly Gln Glu Ile Ala Lys Leu Gln Ser Ala
            915                 920                 925

Leu Gln Glu Met Arg Glu Lys Leu Glu Ala His Thr Ala Ile Ile
        930                 935                 940

Lys Glu Lys Glu Asp Ala Lys Leu Ala Ile Glu Gln Ala Pro Pro Lys
945                 950                 955                 960

Ile Val Glu Val Pro Val Asp Asn Glu Lys Val Glu Leu Leu Thr
            965                 970                 975

Ser Gln Asn Glu Glu Leu Glu Gly Lys Phe Gly Met Phe Lys Lys Lys
            980                 985                 990

Ala Asp Asp Leu Glu Asn Lys Val Ile Glu Ile Gln Lys Gln Phe Asp
            995                 1000                1005

Lys Leu Ser Arg Glu Thr Gln Glu Arg Asp Ser Lys Ile Asn Gln
        1010                1015                1020

Leu Glu Glu Met Ile Ser Arg Leu Glu Thr Asn Leu Ser Ser Met
        1025                1030                1035

Glu Ser Glu Asn His Val Leu Arg Gln Gln Ser Leu Leu Ala Ser
        1040                1045                1050

Ala Asp Asp Lys Ser Arg Gln Ile Glu Ser Leu Glu Ser Lys
        1055                1060                1065

Ile Ala Asn Leu Glu Ser Glu Asn Gln Leu Leu Arg Asn Asn Ser
        1070                1075                1080

Ala Leu Ala Val Gln Ala Ala Val Thr Pro Glu Val Ile Gln Pro
        1085                1090                1095

Ser Val Ile Glu Val Leu Glu Asn Gly Gln Gln Leu Gly Glu Leu
        1100                1105                1110

Lys Ile Phe Asn Glu Gln Val Val Pro Pro Val Lys Asn Leu
        1115                1120                1125

Ser Lys Gln Lys Ser Leu Thr Asp Arg Gln Gln Glu Asn His Asp
        1130                1135                1140

Val Leu Ile Lys Ser Leu Ala Glu Asp Arg Arg Tyr Asp Asn Arg
        1145                1150                1155

Arg Pro Ala Ala Ala Cys Ile Val Tyr Lys Ser Leu Leu His Trp
        1160                1165                1170

His Ser Phe Glu Ala Glu Lys Thr Asn Ile Phe Asp Arg Ile Ile
        1175                1180                1185

His Thr Ile Arg Ser Ser Ile Glu Ser Ala Glu Gly Ser Gly Glu
        1190                1195                1200

Leu Ala Tyr Trp Leu Ser Thr Thr Ser Thr Leu Leu Tyr Leu Leu
        1205                1210                1215

Gln Asn Thr Leu Lys Thr Ser Ser Ser Ser Thr Lys Gly Ser Asn
        1220                1225                1230

Arg Ser Arg Thr Ser Thr Gly Asn Leu Phe Asn Arg Met Met Gln
        1235                1240                1245

Asn Ala Arg Ser Ser Ser Ser Gly Leu Gly Ile Ser Ser Gly Tyr
        1250                1255                1260

Ser Gly Met Ile Gly Arg Thr Asp Ile Ala Ser Met Val Glu Ala
        1265                1270                1275
```

```
Lys Tyr Pro Ala Val Arg Phe Lys Gln Gln Leu Thr Ala Tyr Val
    1280                1285                1290

Glu Lys Ile Tyr Gly Met Met Arg Asp Ser Leu Lys Lys Glu Ile
    1295                1300                1305

Ser Thr Ile Leu Ile Met Cys Ile Gln Ala Pro Arg Ala Val Arg
    1310                1315                1320

Val Arg Ser Ser Arg Gly Ser Leu Lys Ser Ile His Ser Ser Ala
    1325                1330                1335

Leu Ser Arg Gln Val Ser Asn Val His Trp Gln Asn Ile Val Met
    1340                1345                1350

Cys Leu Asn Asn Thr Leu Glu Thr Met Asn Ser Asn Tyr Val Pro
    1355                1360                1365

Pro Met Ile Ile Arg Lys Thr Phe Ser Gln Val Phe Ala Phe Met
    1370                1375                1380

Asn Val Gln Leu Phe Asn Ser Leu Leu Leu Arg Arg Glu Cys Cys
    1385                1390                1395

Ser Phe Ser Asn Gly Glu Phe Leu Lys Ala Gly Leu Gln Glu Leu
    1400                1405                1410

Glu Gln Trp Cys Ser Arg Thr Thr Glu Glu Phe Ala Gly Thr Ser
    1415                1420                1425

Trp Asp Glu Met Lys His Ile Arg Gln Ala Val Gly Phe Leu Val
    1430                1435                1440

Leu His Gln Lys Ser His Lys Thr Leu Asp Glu Ile Thr Asp Glu
    1445                1450                1455

Leu Cys Pro Val Leu Ser Ile Thr Gln Ile Cys Arg Ile Gly Thr
    1460                1465                1470

Met Phe Trp Asp Asp Lys Tyr Gly Ala Gln Gly Leu Ser Gln Glu
    1475                1480                1485

Val Ile Gly Asn Met Arg Thr Leu Thr Thr Asp Asp Ser Val Ala
    1490                1495                1500

Thr Pro Asn Ser Ser Phe Leu Leu Asp Asp Ser Ser Ile Pro
    1505                1510                1515

Ile Ser Leu Asp Asp Ile Ser Arg Leu Met Leu Asp Ile Asn Pro
    1520                1525                1530

Ser Asp Val Glu Pro Pro Leu Leu Arg Gln Asn Ser Gln Phe
    1535                1540                1545

His Phe Leu Leu Gln Gln Cys Thr
    1550                1555

<210> SEQ ID NO 14
<211> LENGTH: 1514
<212> TYPE: PRT
<213> ORGANISM: Brachypodium distachyon
<220> FEATURE:
<223> OTHER INFORMATION: XI-G full length

<400> SEQUENCE: 14

Met Glu Ile Leu Leu Gln Gly Ser Ile Ala Arg Phe Thr Val Gly Ser
1               5                   10                  15

His Val Trp Val Glu Asp Ala Asp Val Ala Trp Ile Asp Gly Leu Val
            20                  25                  30

Glu Glu Val Asn Gly Asp Asn Leu Thr Val Asn Cys Thr Ser Gly Lys
        35                  40                  45

Lys Val Thr Ala Asn Val Ser Ser Val Tyr Pro Lys Asp Val Glu Val
    50                  55                  60
```

-continued

```
Lys Arg Cys Gly Val Glu Asp Met Thr Arg Leu Ala Tyr Leu His Glu
 65                  70                  75                  80

Pro Gly Val Leu Arg Asn Leu Lys Ser Arg Tyr Gly Met Asn Glu Ile
                 85                  90                  95

Tyr Thr Tyr Thr Gly Asn Ile Leu Ile Ala Val Asn Pro Phe Gln Arg
            100                 105                 110

Leu Pro His Leu Tyr Asn Asp His Met Met Gly Met Tyr Lys Gly Ala
        115                 120                 125

Glu Phe Gly Glu Leu Ser Pro His Pro Phe Ala Ile Ala Asp Arg Ala
130                 135                 140

Tyr Arg Leu Met Met Asn Tyr Gly Ile Ser Gln Ala Ile Leu Val Ser
145                 150                 155                 160

Gly Glu Ser Gly Ala Gly Lys Thr Glu Ser Thr Lys Met Leu Met Gln
                165                 170                 175

Tyr Leu Ala Phe Met Gly Gly Lys Val Glu Ser Gly Gly Arg Ser Val
            180                 185                 190

Gln Gln Gln Val Leu Glu Ser Asn Pro Val Leu Glu Ala Phe Gly Asn
        195                 200                 205

Ala Lys Thr Val Arg Asn Asn Asn Ser Ser Arg Phe Gly Lys Phe Val
210                 215                 220

Glu Leu Gln Phe Asp Gln Asn Gly Lys Ile Ser Gly Ala Ala Ile Arg
225                 230                 235                 240

Thr Tyr Leu Leu Glu Arg Ser Arg Val Cys Gln Ile Ser Asp Pro Glu
                245                 250                 255

Arg Asn Tyr His Cys Phe Tyr Met Leu Cys Ala Ala Pro Pro Glu Asp
            260                 265                 270

Arg Glu Arg Tyr Lys Leu Gly Asp Ala Ala Ser Phe His Tyr Leu Asn
        275                 280                 285

Gln Ser Asn Cys Ile Lys Leu Asp Gly Met Asp Asp Ser Ser Glu Tyr
290                 295                 300

Ile Ala Thr Arg Arg Ala Met Glu Ile Val Gly Ile Ser Ser Asp Glu
305                 310                 315                 320

Gln Asp Ala Ile Phe Arg Val Val Ala Ala Ile Leu His Leu Gly Asn
                325                 330                 335

Val Asp Phe Ser Glu Gly Ser Glu Ala Asp Ser Ser Val Pro Lys Asp
            340                 345                 350

Glu Lys Ser Gln Phe His Leu Arg Thr Ala Ala Glu Leu Phe Met Cys
        355                 360                 365

Asp Glu Lys Ser Leu Glu Glu Ser Leu Cys Lys Arg Val Met Val Thr
370                 375                 380

Arg Gly Glu Ser Ile Val Arg Asn Leu Asp Ser Arg Gly Ala Ala Leu
385                 390                 395                 400

Ser Arg Asp Ala Leu Ala Arg Ile Val Tyr Ser Arg Leu Phe Asp Trp
                405                 410                 415

Leu Val Asn Lys Ile Asn Thr Ser Ile Gly Gln Asp Pro Thr Ser Lys
            420                 425                 430

Leu Leu Ile Gly Val Leu Asp Ile Tyr Gly Phe Glu Ser Phe Lys Thr
        435                 440                 445

Asn Ser Phe Glu Gln Phe Cys Ile Asn Leu Thr Asn Glu Lys Leu Gln
450                 455                 460

Gln His Phe Asn Gln His Val Phe Lys Met Glu Gln Glu Glu Tyr Thr
465                 470                 475                 480

Lys Glu Glu Ile Asp Trp Ser Tyr Ile Gln Phe Val Asp Asn Gln Glu
```

```
            485            490            495
Ile Leu Asp Leu Ile Glu Lys Lys Pro Gly Ile Ile Ser Leu Leu
            500            505            510

Asp Glu Thr Cys Met Leu Arg Asn Ser Asn His Glu Ile Phe Ala Glu
            515            520            525

Lys Leu Tyr Gln Lys Phe Lys Asp Asn Pro His Phe Ser Arg Pro Lys
            530            535            540

Phe Ser Arg Ser Asp Phe Thr Ile His His Tyr Ala Gly Asn Val Thr
545            550            555            560

Tyr Gln Thr Asp Leu Phe Leu Asp Lys Asn Ile Asp Tyr Ala Val Asn
            565            570            575

Glu His Gln Asp Leu Leu His Ala Ser Arg Cys Pro Phe Val Ser Ser
            580            585            590

Leu Phe Pro Pro Ser Glu Glu Ser Thr Lys Ser Thr Lys Phe Thr Ser
            595            600            605

Ile Gly Ser Ser Phe Lys Gln Gln Leu Gln Ala Leu Leu Glu Thr Leu
            610            615            620

Ser Thr Thr Glu Pro His Tyr Met Arg Cys Ile Lys Pro Asn Asn Val
625            630            635            640

Leu Lys Pro Ala Ile Phe Glu Asn Ser Asn Val Leu Gln Gln Leu Arg
            645            650            655

Cys Gly Gly Val Leu Glu Ala Ile Arg Ile Ser Cys Leu Gly Tyr Pro
            660            665            670

Thr Arg Arg Thr Phe Asp Glu Phe Val Asp Arg Phe Gly Ile Leu Leu
            675            680            685

Pro Glu Val Leu Gly Glu Ser Tyr Asp Glu Val Thr Ala Thr Asn Met
            690            695            700

Leu Leu Glu Lys Val Asn Leu Thr Gly Tyr Gln Ile Gly Lys Thr Lys
705            710            715            720

Val Phe Leu Arg Ala Gly Gln Met Ala Glu Leu Asp Ala Arg Arg Thr
            725            730            735

Glu Val Leu Asn Cys Ser Ala Ser Lys Ile Gln Arg Lys Val Arg Ser
            740            745            750

Tyr Leu Ala Arg Arg Asn Phe Ile Glu Leu Arg Met Ser Ser Thr Gln
            755            760            765

Leu Gln Ala Ile Cys Arg Gly Gln Ile Ala Arg Phe His Tyr Glu Asp
            770            775            780

Leu Arg Arg Lys Ala Ala Ser Leu Lys Ile Gln Thr Tyr Tyr Arg Met
785            790            795            800

His Phe Ala Arg Lys Asn Tyr Arg Asp Ile Cys Ser Ala Ser Thr Thr
            805            810            815

Ile Gln Ser Gly Leu Arg Gly Met Ala Ala Arg Glu Leu His Phe
            820            825            830

Arg Gln Gln Thr Lys Ala Ala Val Ile Ile Gln Ser Cys Cys Arg Ser
            835            840            845

Asp Leu Ala Ser Ser Arg Tyr Met Gly Leu Lys Lys Ala Ala Ile Thr
            850            855            860

Thr Gln Cys Ala Trp Arg Gly Arg Val Ala Arg Arg Glu Leu Arg Lys
865            870            875            880

Leu Lys Met Ala Ala Lys Glu Ser Gly Ala Leu Gln Ala Ala Lys Asn
            885            890            895

Lys Leu Glu Lys Gln Val Glu Glu Leu Thr Trp Arg Leu Gln Leu Glu
            900            905            910
```

```
Lys Arg Met Arg Thr Asp Met Glu Glu Ala Lys Thr Gln Glu Asn Arg
        915                 920                 925

Lys Leu Gln Gln Lys Val Gln Glu Leu Gln Leu Gln Ser Lys Glu Thr
        930                 935                 940

Lys Asp Leu Leu Lys Arg Glu Gln Glu Asn Ala Lys Thr Ala Trp Glu
945                 950                 955                 960

Lys Ala Ala Leu Val Pro Glu Ile His Ala Asp Thr Thr Leu Val Asp
                965                 970                 975

Glu Leu Thr Ala Glu Asn Glu Lys Leu Lys Thr Leu Val Val Ser Leu
                980                 985                 990

Glu Thr Lys Ile Asp Glu Thr Glu Gln Lys Phe Glu Glu Met Lys Asn
                995                 1000                1005

Ala Arg Glu Glu Leu Leu Lys Lys Ala Ile Asp Ala Glu Ser Lys
    1010                1015                1020

Ile Asn Gly Leu Thr Asn Thr Met Leu Ser Phe Gln Glu Lys Met
    1025                1030                1035

Thr Asn Met Glu Ala Glu Asn Gln Leu Leu Arg Gln Gln Ala Leu
    1040                1045                1050

Leu Arg Thr Pro Val Arg Thr Ile Pro Glu Asn Thr Ser Pro Lys
    1055                1060                1065

Ser Asn Leu Thr Asn Gly Ser Pro His Ser Glu Gln Met Thr
    1070                1075                1080

Pro His Gly Thr Pro Arg Ala Pro Lys Asp Tyr Gly Asn Leu Ala
    1085                1090                1095

Gln Pro Arg Ala Ser Phe Phe Glu Arg Gln His Glu Ser Val Asp
    1100                1105                1110

Ala Leu Ile Asp Cys Val Ala Glu Asn Val Gly Phe Ser Glu Gly
    1115                1120                1125

Lys Pro Val Ala Ala Ile Thr Ile Tyr Lys Cys Leu Val His Trp
    1130                1135                1140

Lys Ile Phe Glu Thr Glu Lys Thr Ser Val Phe Asp Arg Leu Ile
    1145                1150                1155

Gln Ile Phe Gly Ser Ala Met Gln Asn His Asp Ser Asn Glu Asp
    1160                1165                1170

Leu Ala Tyr Trp Leu Ser Asn Ser Ser Thr Leu Leu Ile Ile Leu
    1175                1180                1185

Gln Lys Ser Leu Lys Ala Val Gly Ser Ser Gly Thr Thr Pro Arg
    1190                1195                1200

Lys Arg Pro Gln Pro Gln Ser Ser Phe Leu Gly Arg Met Val Phe
    1205                1210                1215

Arg Ser Ser Thr Ile Thr Val Asp Met Asp Leu Val Arg Gln Ile
    1220                1225                1230

Glu Ala Lys Tyr Pro Ala Phe Leu Phe Lys Gln Gln Leu Ala Ala
    1235                1240                1245

Phe Val Glu Gly Leu Tyr Gly Met Ile Arg Asp Asn Val Lys Lys
    1250                1255                1260

Glu Leu Ser Ser Leu Leu Leu His Ala Ile Gln Val Pro Arg Ile
    1265                1270                1275

Met Lys Ala Ser Met Val Arg Gly His Ser Phe Gly Ser Ser Thr
    1280                1285                1290

Leu Pro Arg Gly Arg Ser Phe Ser Asn Gln Gly Ser Tyr Trp Gln
    1295                1300                1305
```

```
Ala Ile Val Asp Asn Leu Asn Glu Leu Leu Asn Ile Leu Arg Glu
    1310                1315                1320

Asn Cys Val Pro Ala Ile Phe Ile Arg Lys Ile Phe Thr Gln Leu
    1325                1330                1335

Phe Ser Phe Ile Asn Ala Gln Leu Phe Asn Ser Leu Leu Val Arg
    1340                1345                1350

His Glu Cys Cys Ser Phe Ser Asn Gly Glu Tyr Val Lys Gln Gly
    1355                1360                1365

Leu Ala Gln Leu Glu Val Trp Cys Gly Glu Val Lys Pro Glu Tyr
    1370                1375                1380

Ala Gly Ser Ala Leu Asp Glu Leu Arg His Ile Arg Gln Ala Val
    1385                1390                1395

Gly Phe Leu Val Ile Phe Lys Lys Phe Arg Ile Ser Tyr Asp Glu
    1400                1405                1410

Ile Val His Asp Leu Cys Pro Val Leu Ser Val Gln Gln Leu Tyr
    1415                1420                1425

Lys Ile Cys Thr Gln Tyr Trp Asp Asp Lys Tyr Asn Thr Glu Ser
    1430                1435                1440

Val Ser Glu Glu Val Leu Asp Glu Met Arg Thr Leu Met Thr Glu
    1445                1450                1455

Glu Ser Ser His Ser Thr Ser Asp Ser Thr Phe Leu Leu Asp Asp
    1460                1465                1470

Glu Ile Ser Met Pro Ile Ser Leu Glu Glu Ile Ala Asp Ser Met
    1475                1480                1485

Asp Val Lys Glu Phe Gln Asn Val Ala Pro Pro Ser Glu Leu Val
    1490                1495                1500

Ala Val Pro Ala Phe Gln Phe Leu Arg Ser Arg
    1505                1510

<210> SEQ ID NO 15
<211> LENGTH: 1852
<212> TYPE: PRT
<213> ORGANISM: Brachypodium distachyon
<220> FEATURE:
<223> OTHER INFORMATION: XI-J full length

<400> SEQUENCE: 15

Met Thr Gly Arg Leu His Val Gly Gly Pro Thr Tyr Ser Thr Lys
1               5                   10                  15

Cys Pro Thr Glu Gln Arg Lys Leu Trp Phe Val Ala Ser Ser Leu Ala
                20                  25                  30

Ala Gly Ser Thr Thr Gly Leu Leu Asp Gly Glu Asn Ala Gly Pro Thr
        35                  40                  45

Cys His Gly Gly Lys Leu Lys Cys Pro Ala Phe Met Tyr Gln Arg Leu
50                  55                  60

Phe Ser Phe Leu Val Ala Gly Lys Pro Arg Leu Thr Arg Thr Lys
65                  70                  75                  80

Ser Ser Leu Lys Ser Lys Gly Gly Ala Arg Pro Pro Gly Thr Thr
                85                  90                  95

Thr Gln Arg Arg Lys Ser Arg Lys Arg Met Ala Gly Glu Gly Ala Ala
                100                 105                 110

Ala Ser Ala Ala Ala Ala Glu Val Ala Ala Asp Trp Arg Asp Gly Trp
            115                 120                 125

Arg Gly Gly Glu Leu Leu Gly Ala Trp Glu Ala Asp Leu Val Glu Leu
    130                 135                 140
```

```
Glu Cys Lys Phe Trp Ala Asn Glu Gly Lys Asn Val Lys Tyr Glu Ala
145                 150                 155                 160

Tyr Arg Arg Gln Gln His Arg Trp Thr Cys Gly Ala Ala Asn Leu Phe
                165                 170                 175

Arg Lys Met Gly Ala Glu Ile Leu Leu Thr Lys Glu Val Ser Phe Trp
            180                 185                 190

Arg Lys Leu Tyr Leu Leu Tyr Ser Phe Phe Val Arg Lys Val Val
        195                 200                 205

Ala His Val Val Pro Phe Met Leu Tyr Cys Val Val Ile Pro Leu Ser
    210                 215                 220

Val Leu Val Pro Glu Val Thr Ile Pro Val Trp Gly Met Val Tyr Ile
225                 230                 235                 240

Pro Thr Ala Ile Thr Leu Leu Tyr Ala Ile Arg Asn Pro Arg Ala Ser
                245                 250                 255

Leu Gln Phe Tyr Pro Leu His Thr Ile Leu Asp Pro Leu Arg Glu Cys
            260                 265                 270

Tyr Val Val Ser Pro Tyr Lys Gly Asp Val His Arg Phe Ala Arg Ala
        275                 280                 285

Arg Glu Arg Glu Arg Val Gly Gly His Arg Glu Thr Trp Gln Phe Asn
290                 295                 300

Gln His Lys Ala His Ile Ser Asp Thr Arg Lys Ala Ser Leu Gln Val
305                 310                 315                 320

Leu Gly Gln Gly Thr Lys Val Asn Ile Ile Val Gly Ser His Val Trp
                325                 330                 335

Ala Glu Asp Ser Glu Ile Ala Trp Ile Asp Gly Glu Val Val Lys Ile
            340                 345                 350

Asn Gly Glu Glu Ala Glu Ile Gln Ala Thr Asn Gly Lys Lys Ile Val
        355                 360                 365

Gln Asn Leu Ser Lys Leu Tyr Pro Lys Asp Met Glu Ala Ala Ala Gly
370                 375                 380

Gly Val Asp Asp Met Thr Lys Leu Ser Tyr Leu His Glu Pro Gly Val
385                 390                 395                 400

Leu Gln Asn Leu Ala Ile Arg Tyr Glu Leu Asn Glu Ile Tyr Thr Tyr
                405                 410                 415

Thr Gly Asn Ile Leu Ile Ala Val Asn Pro Phe Gln Arg Leu Pro His
            420                 425                 430

Leu Tyr Asp Pro His Met Met Gln Gln Tyr Lys Gly Ala Pro Phe Gly
        435                 440                 445

Glu Leu Ser Pro His Val Phe Ala Val Ala Asp Val Ala Tyr Arg Ala
450                 455                 460

Met Ile Asn Glu Lys Lys Ser Asn Ser Ile Leu Val Ser Gly Glu Ser
465                 470                 475                 480

Gly Ala Gly Lys Thr Glu Thr Thr Lys Met Leu Met Arg Tyr Leu Ala
                485                 490                 495

Tyr Leu Gly Gly Arg Ala Ala Thr Glu Gly Arg Thr Val Glu Gln Gln
            500                 505                 510

Val Leu Glu Ser Asn Pro Val Leu Glu Ala Phe Gly Asn Ala Lys Thr
        515                 520                 525

Val Arg Asn Asn Asn Ser Ser Arg Phe Gly Lys Phe Val Glu Ile Gln
530                 535                 540

Phe Asp Lys Gln Gly Arg Ile Ser Gly Ala Ala Val Arg Thr Tyr Leu
545                 550                 555                 560

Leu Glu Arg Ser Arg Val Cys Gln Ile Ser Asp Pro Glu Arg Asn Tyr
```

```
                  565                 570                 575
His Cys Phe Tyr Leu Leu Cys Ala Ala Pro Gln Glu Glu Val Glu Lys
                580                 585                 590

Tyr Lys Leu Gly Asn Pro Lys Thr Phe His Tyr Leu Asn Lys Ser Asn
                595                 600                 605

Cys Tyr Glu Leu Val Gly Val Ser Asp Ala His Glu Tyr Leu Ala Thr
            610                 615                 620

Arg Arg Ala Met Asp Ile Val Gly Ile Ser Thr Gln Glu Gln Asp Ala
625                 630                 635                 640

Ile Phe Arg Val Val Ala Ala Ile Leu His Ile Gly Asn Ile Glu Phe
                645                 650                 655

Ala Lys Gly Lys Glu Ala Asp Ser Ser Val Leu Lys Asp Asp Lys Ser
                660                 665                 670

Lys Phe His Leu Asp Thr Ala Ala Glu Leu Leu Met Cys Asp Pro Gly
                675                 680                 685

Ala Leu Thr Asp Ala Leu Cys Lys Arg Val Met Val Thr Pro Glu Glu
            690                 695                 700

Val Ile Lys Arg Ser Leu Asp Pro Tyr Asn Ala Thr Ile Ser Arg Asp
705                 710                 715                 720

Gly Leu Ala Lys Thr Ile Tyr Ser Arg Leu Phe Asp Trp Leu Val Asp
                725                 730                 735

Lys Ile Asn Ser Ser Ile Gly Gln Asp Ala Asn Ser Lys Cys Leu Ile
                740                 745                 750

Gly Val Leu Asp Ile Tyr Gly Phe Glu Ser Phe Lys Leu Asn Ser Phe
            755                 760                 765

Glu Gln Phe Cys Ile Asn Tyr Thr Asn Glu Lys Leu Gln Gln His Phe
770                 775                 780

Asn Gln His Val Phe Lys Met Glu Gln Glu Glu Tyr Thr Lys Glu Gln
785                 790                 795                 800

Ile Asp Trp Ser Tyr Ile Glu Phe Val Asp Asn Gln Asp Val Leu Asp
                805                 810                 815

Leu Ile Glu Lys Lys Pro Gly Gly Val Ile Ala Leu Leu Asp Glu Ala
                820                 825                 830

Cys Met Phe Pro Lys Ser Thr His Glu Thr Phe Ala Gln Lys Leu Tyr
            835                 840                 845

Gln Thr Phe Gln Lys His Lys Arg Phe Val Lys Pro Lys Leu Ser Arg
            850                 855                 860

Thr Asp Phe Ala Ile Ala His Tyr Ala Gly Glu Val Met Tyr Gln Ser
865                 870                 875                 880

Asp Gln Phe Leu Asp Lys Asn Lys Asp Tyr Val Val Ala Glu His Gln
                885                 890                 895

Glu Leu Leu Ser Ala Ser Arg Cys Ser Phe Ile Ala Gly Leu Phe Pro
                900                 905                 910

Thr Leu Pro Asp Glu Thr Ser Lys Ser Ser Lys Phe Ser Ser Ile Gly
            915                 920                 925

Ala Arg Phe Lys Gln Gln Leu Gln Ala Leu Met Glu Thr Leu Asn Ser
            930                 935                 940

Thr Glu Pro His Tyr Ile Arg Cys Val Lys Pro Asn Asn Val Leu Lys
945                 950                 955                 960

Pro Ala Ile Phe Glu Asn Val Asn Val Met Gln Gln Leu Arg Cys Gly
                965                 970                 975

Gly Val Leu Glu Ala Ile Arg Ile Ser Cys Ala Gly Tyr Pro Thr Arg
            980                 985                 990
```

```
Arg Thr Phe Tyr Glu Phe Leu His Arg Phe Gly Ile Leu Ala Pro Asp
    995                 1000                1005

Ala Val Glu Val Asn Cys Asp Glu Lys Val Ala Cys Lys Arg Ile
    1010                1015                1020

Leu Glu Lys Lys Gly Leu Leu Gly Phe Gln Ile Gly Lys Thr Lys
    1025                1030                1035

Val Phe Leu Arg Ala Gly Gln Met Ala Glu Leu Asp Ala Arg Arg
    1040                1045                1050

Thr Glu Val Leu Ser Ala Ala Lys Thr Ile Gln Gly Lys Met
    1055                1060                1065

Arg Thr His Ile Met Arg Lys Lys Phe Val Ser Leu Arg Lys Ala
    1070                1075                1080

Ser Val Cys Phe Gln Ala Val Trp Arg Gly Thr Leu Ala Cys Lys
    1085                1090                1095

Leu Tyr Asp Arg Met Arg Arg Glu Ala Ala Ser Val Lys Ile Gln
    1100                1105                1110

Lys Asn Gln Arg Arg His His Ala Arg Arg Ser Tyr Lys Leu Leu
    1115                1120                1125

Asn Ala Ser Val Leu Val Val Gln Thr Ala Leu Arg Ala Met Ala
    1130                1135                1140

Ala Arg Asn Asp Phe Arg Asn Lys Lys Arg Ser Gln Ala Ala Ile
    1145                1150                1155

Thr Ile Gln Ala Arg Tyr Arg Cys His Arg Ala His Leu Tyr His
    1160                1165                1170

Asn Lys Leu Lys Ser Ala Ala Ile Val Ala Gln Cys Arg Trp Arg
    1175                1180                1185

Gly Arg Ile Ala Arg Lys Glu Leu Arg Lys Leu Lys Met Glu Ala
    1190                1195                1200

Arg Glu Thr Gly Ala Leu Lys Glu Ala Lys Asp Lys Leu Glu Lys
    1205                1210                1215

Thr Val Glu Glu Leu Thr Trp Arg Val Gln Leu Glu Lys Arg Met
    1220                1225                1230

Arg Thr Asp Ser Glu Glu Gly Lys Ala Gln Glu Leu Ser Lys Leu
    1235                1240                1245

Gln Ser Ser Met Asp Ala Leu Gln Ala Lys Leu Asp Glu Thr Asn
    1250                1255                1260

Ala Met Leu Val Lys Glu Arg Glu Ala Ala Lys Lys Ala Ile Ala
    1265                1270                1275

Glu Ala Pro Ser Leu Val Lys Glu Thr Glu Val Val Gln Asp
    1280                1285                1290

Thr Glu Lys Val Asn Ser Leu Glu Ala Glu Val Asp Gly Leu Lys
    1295                1300                1305

Thr Ser Leu Gln Ser Glu Lys Gln Arg Ala Asp Glu Leu Glu Lys
    1310                1315                1320

Lys Cys Ser Glu Glu Ala Gln Ala Asn Glu Glu Lys Gln Lys Lys
    1325                1330                1335

Leu Glu Glu Thr Glu Ile Lys Ile Arg Gln Phe Gln Asp Tyr Leu
    1340                1345                1350

Arg Arg Leu Glu Glu Lys Leu Ser Asn Val Glu Ser Glu Asn Lys
    1355                1360                1365

Val Leu Arg Gln Gln Ala Val Ser Met Ala Pro Ser Lys Ile Leu
    1370                1375                1380
```

```
Ser Gly Arg Ser Lys Ser Asn Leu Gln Arg Asn Ala Glu Ser Gly
    1385                1390                1395

His Val Ser Val Ala Asp Ser Lys Ile Thr Pro Glu Ser Thr Asn
    1400                1405                1410

Val Ser Ser Pro Lys Arg Glu Tyr Asp Ile Asp Lys Pro Gln
    1415                1420                1425

Lys Ser Leu Asn Glu Lys Gln Gln Glu Asn Gln Asp Leu Leu Ile
    1430                1435                1440

Arg Cys Ile Ala Gln His Leu Gly Phe Gly Gly Asn Arg Pro Val
    1445                1450                1455

Ala Ala Cys Ile Ile Tyr Lys Cys Leu Leu His Trp Arg Ser Phe
    1460                1465                1470

Glu Val Glu Arg Thr Ser Val Phe Asp Arg Ile Ile Gln Thr Ile
    1475                1480                1485

Gly His Ala Ile Glu Thr Gln Asp Asn Asn Glu Val Leu Ala Tyr
    1490                1495                1500

Trp Leu Ser Asn Ala Ser Thr Leu Leu Leu Leu Leu Gln Arg Thr
    1505                1510                1515

Leu Lys Ala Ser Gly Ser Thr Gly Met Ala Pro Gln Arg Arg Arg
    1520                1525                1530

Ser Ser Ser Ala Thr Leu Phe Gly Arg Met Thr Gln Ser Phe Arg
    1535                1540                1545

Gly Thr Pro Gln Gly Val Asn Leu Ala Leu Ile Asn Gly Ser Met
    1550                1555                1560

Val Ser Gly Val Glu Thr Leu Arg Gln Val Glu Ala Lys Tyr Pro
    1565                1570                1575

Ala Leu Leu Phe Lys Gln Gln Leu Thr Ala Tyr Val Glu Lys Ile
    1580                1585                1590

Tyr Gly Met Ile Arg Asp Asn Leu Lys Lys Glu Ile Ser Pro Leu
    1595                1600                1605

Leu Gly Leu Cys Ile Gln Ala Pro Arg Thr Ser Arg Ala Ser Leu
    1610                1615                1620

Met Lys Gly Ser Ser Arg Ser Asn Thr Asn Thr Ala Ala Gln Gln
    1625                1630                1635

Ala Leu Ile Ala His Trp Gln Gly Ile Val Lys Ser Leu Gly Asn
    1640                1645                1650

Phe Leu Asn Ile Leu Lys Val Asn Asn Val Pro Pro Phe Leu Val
    1655                1660                1665

Arg Lys Val Phe Thr Gln Ile Phe Ser Phe Ile Asn Val Gln Leu
    1670                1675                1680

Phe Asn Ser Leu Leu Leu Arg Arg Glu Cys Cys Ser Phe Ser Asn
    1685                1690                1695

Gly Glu Tyr Val Lys Ala Gly Leu Ala Glu Leu Glu His Trp Cys
    1700                1705                1710

Tyr Arg Ala Thr Asp Glu Tyr Ala Gly Ser Ala Trp Asp Glu Leu
    1715                1720                1725

Lys His Ile Arg Gln Ala Ile Gly Phe Leu Val Ile His Gln Lys
    1730                1735                1740

Pro Lys Lys Thr Leu Asp Glu Ile Ser His Asp Leu Cys Pro Val
    1745                1750                1755

Leu Ser Ile Gln Gln Leu Tyr Arg Ile Ser Thr Met Tyr Trp Asp
    1760                1765                1770

Asp Lys Tyr Gly Thr His Ser Val Ser Pro Glu Val Ile Ser Asn
```

```
                    1775                1780                1785

Met Arg Val Leu Met Thr Glu  Asp Ser Asn Asn Pro  Val Ser Asn
            1790                1795                1800

Ser Phe Leu Leu Asp Asp Asp  Ser Ser Ile Pro Phe  Ser Val Asp
            1805                1810                1815

Asp Ile Ser Lys Ser Met Gln  Gln Ile Asp Ile Ser  Asp Ile Glu
            1820                1825                1830

Pro Pro Pro Leu Ile Arg Glu  Asn Ser Gly Phe Val  Phe Leu Leu
            1835                1840                1845

Pro Pro Pro Glu
            1850

<210> SEQ ID NO 16
<211> LENGTH: 1520
<212> TYPE: PRT
<213> ORGANISM: Sorghum bicoler
<220> FEATURE:
<223> OTHER INFORMATION: XI-I full length

<400> SEQUENCE: 16

Met Ser Phe Arg Lys Gly Leu Lys Val Trp Val Glu Glu Lys Gly Glu
1               5                   10                  15

Gly Trp Val Glu Ala Glu Val Ala Glu Ala Lys Glu Arg Ala Val Val
                20                  25                  30

Val Leu Thr Ser Gln Arg Lys Lys Ile Thr Val Ser Pro Glu Lys Leu
            35                  40                  45

Leu Pro Arg Asp Thr Asp Glu Asp Leu Gly Gly Gly His Val Asp Asp
        50                  55                  60

Met Thr Lys Leu Thr Tyr Leu Asn Glu Pro Gly Val Leu Tyr Asn Leu
65                  70                  75                  80

Lys Lys Arg Tyr Ala Leu Asn Glu Ile Tyr Thr Tyr Thr Gly Ser Ile
                85                  90                  95

Leu Ile Ala Val Asn Pro Phe Thr Arg Leu Pro His Leu Tyr Asn Glu
            100                 105                 110

Tyr Met Met Glu Gln Tyr Lys Gly Ile Arg Leu Gly Glu Leu Ser Pro
        115                 120                 125

His Val Phe Ala Val Ala Asp Ala Ser Tyr Arg Ala Met Val Asn Asp
        130                 135                 140

Ser Arg Ser Gln Ser Ile Leu Val Ser Gly Glu Ser Gly Ala Gly Lys
145                 150                 155                 160

Thr Glu Thr Thr Lys Leu Ile Met Gln Tyr Leu Thr Phe Val Gly Gly
                165                 170                 175

Arg Ala Ala Leu Asp Asp Arg Thr Val Glu Gln Gln Val Leu Glu Ser
            180                 185                 190

Asn Pro Leu Leu Glu Ala Phe Gly Asn Ala Lys Thr Val Arg Asn Asp
        195                 200                 205

Asn Ser Ser Arg Phe Gly Lys Phe Val Glu Ile Gln Phe Asp Gly Ser
    210                 215                 220

Gly Arg Ile Ser Gly Ala Ala Ile Arg Thr Tyr Leu Leu Glu Arg Ser
225                 230                 235                 240

Arg Val Val Gln Ile Thr Asp Pro Glu Arg Asn Phe His Cys Phe Tyr
                245                 250                 255

Gln Leu Cys Ala Ser Gly Lys Asp Ala Glu Leu Tyr Lys Leu Gly His
            260                 265                 270

Ala Ser Ser Phe His Tyr Leu Asn Gln Ser Asn Thr Tyr Asp Leu Glu
```

```
            275                 280                 285
Gly Thr Asn Asn Glu Asp Glu Tyr Trp Lys Thr Lys Arg Ala Met Asp
            290                 295                 300
Ile Val Gly Ile Ser Arg Glu Asp Gln Asp Ala Ile Phe Arg Thr Leu
305                 310                 315                 320
Ala Ala Ile Leu His Leu Gly Asn Ile Glu Phe Ala Pro Gly Lys Asp
                    325                 330                 335
Thr Asp Ser Ser Lys Ile Lys Asp Ser Thr Ser Asn Phe His Leu Gln
                340                 345                 350
Thr Ala Ala Lys Leu Phe Met Cys Asp Ser Asp Leu Leu Val Ser Thr
                355                 360                 365
Leu Cys Ser Arg Ser Ile His Thr Arg Glu Gly Ile Ile Val Lys Ala
            370                 375                 380
Leu Asp Cys Ala Ala Ala Ala Asn Arg Asp Ala Leu Ala Lys Thr
385                 390                 395                 400
Val Tyr Ala Arg Leu Phe Asp Trp Leu Val Glu Asn Ile Asn Lys Ser
                    405                 410                 415
Ile Gly Gln Asp Val Asp Ser Lys Val Gln Ile Gly Val Leu Asp Ile
                420                 425                 430
Tyr Gly Phe Glu Ser Phe Lys Asn Asn Ser Phe Glu Gln Phe Cys Ile
            435                 440                 445
Asn Phe Ala Asn Glu Lys Leu Gln Gln His Phe Asn Glu His Val Phe
450                 455                 460
Lys Met Glu Gln Glu Glu Tyr Lys Ser Glu Glu Ile Asn Trp Ser Tyr
465                 470                 475                 480
Ile Glu Phe Ile Asp Asn Gln Asp Val Leu Asp Leu Ile Glu Lys Lys
                    485                 490                 495
Pro Ile Gly Ile Ile Ala Leu Leu Asp Glu Ala Cys Met Phe Pro Lys
                500                 505                 510
Ser Thr His Glu Thr Phe Ala Thr Lys Met Phe Arg Asn Phe Ser Ser
            515                 520                 525
His Pro Arg Leu Glu Lys Thr Lys Phe Ser Glu Thr Asp Phe Thr Ile
            530                 535                 540
Ser His Tyr Ala Gly Lys Val Thr Tyr Gln Thr Asp Ser Phe Leu Glu
545                 550                 555                 560
Lys Asn Arg Asp Tyr Ile Val Ala Glu His Cys Asn Leu Leu Ser Ser
                    565                 570                 575
Ser Arg Cys Pro Phe Val Ser Gly Leu Phe Thr Ser Leu Pro Glu Glu
                580                 585                 590
Ser Ile Arg Ser Ser Tyr Lys Phe Ser Ser Val Ala Ser Arg Phe Lys
            595                 600                 605
Leu Gln Leu Gln Ala Leu Met Glu Thr Leu Asn Ser Thr Glu Pro His
            610                 615                 620
Tyr Val Arg Cys Val Lys Pro Asn Ser Ala Asn Arg Pro Gln Leu Phe
625                 630                 635                 640
Glu Asn Gln Ser Val Leu His Gln Leu Arg Cys Gly Gly Val Leu Glu
                    645                 650                 655
Ala Val Arg Ile Ser Leu Ala Gly Tyr Pro Thr Arg Arg Thr Tyr Ala
                660                 665                 670
Glu Phe Val Asp Arg Phe Ala Val Leu Val Pro Glu Leu Met Ile Gly
            675                 680                 685
Ser Tyr Asp Glu Arg Met Leu Thr Lys Gly Ile Leu Glu Lys Met Glu
            690                 695                 700
```

```
Leu Glu Asn Phe Gln Leu Gly Arg Thr Lys Val Phe Leu Arg Ala Gly
705                 710                 715                 720

Gln Ile Ala Ile Leu Asp Met Arg Arg Ala Glu Val Leu Asp Asn Ala
            725                 730                 735

Ala Arg His Ile Gln Gly Arg Phe Arg Thr Phe Ile Thr Arg Lys Glu
            740                 745                 750

Phe Val Lys Thr Arg Glu Ala Ser Val Ser Val Gln Ala Tyr Cys Arg
            755                 760                 765

Gly Cys Leu Ala Arg Lys Met Tyr Ala Ile Arg Arg Glu Thr Ala Ala
            770                 775                 780

Ala Val Ile Val Gln Lys Tyr Val Arg Arg Trp Ile Leu Arg Arg Ala
785                 790                 795                 800

His Leu Gln Ala Cys Leu Ala Ala Leu Leu Ile Gln Ser Tyr Ile Arg
            805                 810                 815

Gly Phe Ile Ala Arg Arg Tyr Phe Ser Ala Ile Arg Glu His Lys Ala
            820                 825                 830

Ala Thr Val Ile Gln Ser Ile Trp Arg Arg Lys Val Val Met Leu
            835                 840                 845

Phe Gln Asn Cys Arg Gln Ala Ala Val Thr Ile Gln Cys Ser Trp Arg
            850                 855                 860

Gln Lys Leu Ala Arg Lys Glu Leu Arg Arg Leu Lys Met Ala Ala Asn
865                 870                 875                 880

Glu Ala Gly Ala Leu Arg Glu Ala Lys Asn Lys Leu Glu Lys Lys Met
            885                 890                 895

Asp Asp Leu Ala Leu Arg Leu Thr Leu Glu Arg Arg Leu Arg Ala Ala
            900                 905                 910

Ser Glu Asp Ser Lys Ser Ala Glu Ile Leu Arg Arg Asp Lys Ile Ile
            915                 920                 925

Glu Ser Leu Ser Ala Glu Cys Ala Ala Lys Ser Ala Ala Gln Asn
            930                 935                 940

Glu His Asp Lys Asn Leu Leu Gln Lys Gln Leu Asp Asp Ser Leu
945                 950                 955                 960

Arg Glu Ile Ala Met Leu Gln Ser Lys Lys Ile Met Ser Ala Glu Ala
            965                 970                 975

Glu Lys Glu Asn Ser Asn Leu Lys Asn Leu Val Glu Ser Leu Ser Met
            980                 985                 990

Lys Asn Ser Ile Leu Glu Asn Glu Leu Thr Val Thr Arg Lys Ser Ser
            995                 1000                1005

Asp Asp Thr Met Glu Lys Leu Lys Asp Val Glu Gly Lys Cys Asn
    1010                1015                1020

His Leu Gln Gln Asn Leu Asp Lys Leu Gln Glu Lys Leu Thr Asn
    1025                1030                1035

Leu Glu Asn Glu Asn His Val Leu Arg Gln Lys Ala Phe Asn Met
    1040                1045                1050

Pro Thr Met Asn Asn Leu Pro Val Ala Pro Lys Thr Leu Ser Glu
    1055                1060                1065

Lys Phe Ser Ala Ser Ile Gly Leu Pro Ile Ser Glu Pro Lys His
    1070                1075                1080

Ile Tyr Glu Ser Pro Thr Pro Thr Lys Tyr Leu Ala Ser Leu Pro
    1085                1090                1095

Gln Ser Leu Ser Ala Ser Arg Arg Ser Arg Leu Pro Val Glu Arg
    1100                1105                1110
```

```
His Glu Gln Asn His Glu Ile Leu Leu Lys Cys Ile Lys Glu Asn
1115                1120                1125

Leu Gly Tyr Lys Asp Gly Lys Pro Val Ala Ala Cys Ile Ile Tyr
    1130                1135                1140

Lys Cys Leu Leu His Trp Arg Ala Phe Glu Ser Glu Arg Thr Ala
1145                1150                1155

Ile Phe Asp His Val Ile Glu Ala Ile Asn Asp Val Leu Lys Gly
    1160                1165                1170

Thr Glu Ala Asp Gly Arg Leu Pro Tyr Trp Leu Ser Asn Thr Ser
1175                1180                1185

Ala Leu Leu Cys Leu Leu Gln Arg Asn Leu Arg Ser Asn Gly Leu
    1190                1195                1200

Phe Ala Thr Pro Ser Arg Arg Ser Gly Gly Ala Ile Gly Lys Ile
1205                1210                1215

Ala Gln Thr Leu Arg Ser Pro Ser Lys Phe Val Gly Arg Ser Asp
    1220                1225                1230

Thr Leu Pro Gln Val Asp Ala Arg Tyr Pro Ala Ile Leu Phe Lys
1235                1240                1245

Gln Gln Leu Thr Ala Cys Val Glu Lys Ile Phe Gly Gln Leu Arg
    1250                1255                1260

Asp Asn Leu Lys Lys Glu Ile Ser Pro Leu Leu Asn Leu Cys Ile
1265                1270                1275

Gln Ala Pro Lys Ser Thr Arg Gly Gln Pro Gly Lys Thr Ser Lys
    1280                1285                1290

Ser Pro Gly Val Gly Ala His Leu Ala Ser Asn Ser Asn Trp Asp
1295                1300                1305

Asn Ile Val Asn Phe Leu Asp Leu Leu Met Asp Thr Leu Arg Glu
    1310                1315                1320

Asn Tyr Val Pro Ser Phe Phe Ile Arg Lys Leu Ile Thr Gln Leu
1325                1330                1335

Phe Ser Phe Ile Asn Ile Gln Leu Phe Asn Ser Leu Leu Leu Arg
    1340                1345                1350

Arg Glu Cys Cys Thr Phe Ser Asn Gly Glu Tyr Val Lys Ala Gly
1355                1360                1365

Leu Ser Leu Leu Glu Lys Trp Ile Thr Asp Val Thr Glu Glu Phe
    1370                1375                1380

Ala Gly Thr Ser Trp His Glu Leu Asn Tyr Ile Arg Glu Ala Val
1385                1390                1395

Gly Phe Leu Val Ile His Gln Lys Arg Lys Lys Thr Leu Gln Glu
    1400                1405                1410

Ile Arg Gln Asp Leu Cys Pro Ser Leu Ser Val Arg Gln Ile Tyr
1415                1420                1425

Arg Ile Cys Ser Met Tyr Trp Asp Asp Lys Tyr Asn Thr Gln Gly
    1430                1435                1440

Ile Ser Thr Glu Val Val Ala Ala Met Arg Glu Val Val Asn Lys
1445                1450                1455

Asp Thr Gln Asn Leu Leu Ser Asn Ser Phe Leu Leu Asp Asp Asp
    1460                1465                1470

Leu Ser Ile Pro Phe Ser Thr Glu Asp Leu Ser Met Ala Ile Pro
1475                1480                1485

Ala Ile Asp Tyr Ala Asp Val Asp Leu Pro Glu Cys Leu Gln His
    1490                1495                1500

Tyr Thr Ser Val Gln Phe Leu Ile Arg Gln Gln Asp Leu Gln Pro
```

-continued

```
             1505                1510                1515

Ala Gln
    1520

<210> SEQ ID NO 17
<211> LENGTH: 1529
<212> TYPE: PRT
<213> ORGANISM: Sorghum bicoler
<220> FEATURE:
<223> OTHER INFORMATION: XI-K full length

<400> SEQUENCE: 17

Met Pro Lys Gly Leu Cys Cys Leu Pro Cys Cys Asn Phe Ile Pro Leu
1               5                  10                  15

Glu Val Gly Phe Ser Ile Phe Phe Pro Ser Phe Pro Leu Asn Asp Val
            20                  25                  30

Leu Lys Gln Ile Gly Phe Thr Phe Cys Pro Lys Ser His Pro Met Tyr
        35                  40                  45

Leu Gly Gly Leu Gly Thr Pro Val Asn Ile Ile Val Gly Ser His Val
    50                  55                  60

Trp Val Glu Asp Pro Asn Leu Ala Trp Ile Asp Gly Glu Val Val Ser
65                  70                  75                  80

Ile Lys Asn Asn Glu Val His Val Gln Thr Ser Ser Gly Lys Lys Val
                85                  90                  95

Thr Thr Asp Arg Ser Lys Val Phe Pro Lys Asp Met Glu Ala Pro Pro
            100                 105                 110

Gly Gly Val Asp Asp Met Thr Arg Leu Ser Tyr Leu His Glu Pro Gly
        115                 120                 125

Val Leu Gln Asn Leu Ala Thr Arg Tyr Glu Leu Asn Glu Ile Tyr Thr
    130                 135                 140

Tyr Thr Gly Ser Ile Leu Ile Ala Val Asn Pro Phe Gln Arg Leu Pro
145                 150                 155                 160

His Leu Tyr Asp Thr His Met Met Glu Gln Tyr Lys Gly Ala Asp Phe
                165                 170                 175

Gly Glu Leu Ser Pro His Val Phe Ala Ile Ala Asp Thr Ala Tyr Arg
            180                 185                 190

Ala Met Ile Asn Glu Gly Lys Ser Asn Ser Ile Leu Val Ser Gly Glu
        195                 200                 205

Ser Gly Ala Gly Lys Thr Glu Thr Thr Lys Met Leu Met Arg Tyr Leu
    210                 215                 220

Ala His Leu Gly Gly Arg Ser Gly Val Glu Gly Arg Thr Val Glu Gln
225                 230                 235                 240

Gln Val Leu Glu Ser Asn Pro Val Leu Glu Ala Phe Gly Asn Ala Lys
                245                 250                 255

Thr Val Arg Asn Asn Asn Ser Ser Arg Phe Gly Lys Phe Val Glu Ile
            260                 265                 270

Gln Phe Asp Lys Thr Gly Arg Ile Ser Gly Ala Ala Ile Arg Thr Tyr
        275                 280                 285

Leu Leu Glu Arg Ser Arg Val Cys Gln Ile Asn Ser Pro Glu Arg Asn
    290                 295                 300

Tyr His Cys Phe Tyr Phe Leu Cys Ala Ala Pro Pro Glu Glu Thr Gln
305                 310                 315                 320

Arg Tyr Lys Leu Ser Asp Pro Arg Ser Phe His Tyr Leu Asn Gln Ser
                325                 330                 335

Ser Cys Ile Glu Val Asp Gly Ile Asn Asp Ala Glu Glu Tyr Leu Ala
```

```
                340                 345                 350
Thr Arg Arg Ala Met Asp Ile Val Gly Ile Asn Glu Glu Gln Glu
            355                 360                 365
Ala Ile Phe Arg Val Val Ala Val Leu His Leu Gly Asn Ile Asn
            370                 375                 380
Phe Ala Lys Gly Thr Glu Ile Asp Ser Ser Val Ile Lys Asp Asp Lys
385                 390                 395                 400
Ser Arg Phe His Leu Asn Thr Ala Ala Glu Leu Leu Lys Cys Asp Cys
            405                 410                 415
Gln Asn Leu Glu Lys Ala Leu Ile Thr Arg Val Ile Val Thr Pro Glu
            420                 425                 430
Glu Val Ile Thr Arg Thr Leu Asp Pro Ala Ser Ala Leu Ala Ser Arg
            435                 440                 445
Asp Ala Leu Ala Lys Ile Ile Tyr Cys Arg Leu Phe Asp Trp Ile Val
            450                 455                 460
Glu Lys Ile Asn Val Ser Ile Gly Gln Asp Pro Asn Ser Lys Gln Leu
465                 470                 475                 480
Ile Gly Val Leu Asp Ile Tyr Gly Phe Glu Ser Phe Lys Val Asn Ser
            485                 490                 495
Phe Glu Gln Leu Cys Ile Asn Tyr Thr Asn Glu Lys Leu Gln Gln His
            500                 505                 510
Phe Asn Gln His Val Phe Lys Met Glu Gln Glu Glu Tyr Thr Arg Glu
            515                 520                 525
Glu Ile Asn Trp Ser Tyr Ile Glu Phe Val Asp Asn Gln Asp Val Leu
            530                 535                 540
Asp Leu Ile Glu Lys Lys Gly Gly Leu Ile Ala Leu Leu Asp Glu Ala
545                 550                 555                 560
Cys Met Phe Pro Arg Ser Thr His Glu Thr Phe Ala Gln Lys Leu Tyr
            565                 570                 575
Thr Thr Phe Lys Asn Asn Lys Arg Phe Ala Lys Pro Lys Leu Ser Arg
            580                 585                 590
Thr Asp Phe Thr Val Val His Tyr Ala Gly Asp Val Thr Tyr Gln Ala
            595                 600                 605
Asp Tyr Phe Leu Asp Lys Asn Lys Asp Tyr Val Val Ala Glu His Gln
            610                 615                 620
Asp Leu Leu Asn Ala Ser Ser Cys Pro Phe Val Ala Gly Leu Phe Pro
625                 630                 635                 640
Pro Leu Pro Gln Glu Thr Ala Lys Ser Ser Lys Phe Ser Ser Ile Gly
            645                 650                 655
Ser Arg Phe Lys Leu Gln Leu Gln Ser Leu Met Glu Thr Leu Ser Ser
            660                 665                 670
Thr Glu Pro His Tyr Ile Arg Cys Val Lys Pro Asn Asn Leu Leu Lys
            675                 680                 685
Pro Ala Ile Phe Glu Asn Thr Asn Val Ile Gln Gln Leu Arg Cys Gly
            690                 695                 700
Gly Val Leu Glu Ala Ile Arg Ile Ser Cys Ala Gly Tyr Pro Thr Arg
705                 710                 715                 720
Lys Thr Phe Tyr Glu Phe Val Asn Arg Phe Gly Val Leu Ala Pro Glu
            725                 730                 735
Val Leu Glu Gly Ser Asn Asp Asp Lys Ile Ala Cys Gln Lys Ile Leu
            740                 745                 750
Glu Lys Val Gly Leu Glu Asn Tyr Gln Ile Gly Lys Thr Lys Val Phe
            755                 760                 765
```

```
Leu Arg Ala Gly Gln Met Ala Asp Leu Asp Ala Arg Arg Ala Glu Val
    770                 775                 780

Leu Gly Arg Ala Ala Arg Ile Ile Gln Arg Gln Ile Cys Thr Tyr Ile
785                 790                 795                 800

Ala Arg Lys Gln Phe Ala Glu Leu Lys Arg Ser Ala Met Gln Leu Gln
                805                 810                 815

Ser Phe Val Arg Gly Thr Leu Ala Arg Lys Leu Tyr Glu Cys Met Arg
                820                 825                 830

Lys Glu Ala Ala Ala Val Lys Ile Gln Lys Asn Met Arg Arg His Lys
            835                 840                 845

Ala Arg Glu Ser Tyr Leu Gln Leu Gln Ala Ala Ile Thr Leu Gln
    850                 855                 860

Thr Gly Leu Arg Ala Met Ser Ala Arg Lys Glu Phe Arg Phe Arg Lys
865                 870                 875                 880

Glu Thr Lys Ala Ala Val His Ile Gln Ala Gln Trp Arg Arg His Arg
                885                 890                 895

Asp Tyr Ser Tyr Tyr Lys Asn Leu Gln Gly Ala Ala Leu Thr Tyr Gln
                900                 905                 910

Cys Ala Trp Arg Gln Arg Leu Ala Arg Arg Glu Leu Arg Lys Leu Lys
            915                 920                 925

Met Ala Ala Arg Glu Thr Gly Ala Leu Lys Glu Ala Lys Asp Lys Leu
930                 935                 940

Glu Lys Arg Val Glu Glu Leu Thr Trp Arg Leu Gly Leu Glu Lys Arg
945                 950                 955                 960

Leu Arg Thr Asp Leu Glu Ala Lys Ala Gln Glu Ile Ala Lys Leu
                965                 970                 975

Gln Glu Thr Leu His Asp Met Gln Leu Gln Val Glu Glu Ser Lys Ala
                980                 985                 990

Met Val Val Lys Glu Arg Glu Ala  Ala Arg Lys Ala Ile  Glu Glu Ala
                995                 1000                 1005

Pro Pro  Val Ile Lys Glu Thr  Pro Val Leu Val Glu  Asp Thr Glu
        1010                 1015                 1020

Lys Ile  Asn Ser Leu Thr Ala  Glu Val Glu Gln Leu  Arg Ala Leu
        1025                 1030                 1035

Leu Leu  Thr Glu Arg Gln Ala  Thr Glu Ala Ala Lys  Arg Glu His
        1040                 1045                 1050

Ala Glu  Ser Glu Arg Arg Asn  Glu Glu Leu Ile Lys  Lys Phe Glu
        1055                 1060                 1065

Ser Ala  Glu Lys Lys Ile Glu  Gln Leu Gln Asp Thr  Val Gln Arg
        1070                 1075                 1080

Leu Glu  Glu Lys Ala Thr Asn  Met Glu Ser Glu Asn  Lys Val Leu
        1085                 1090                 1095

Arg Gln  Gln Ala Val Ala Ile  Ser Pro Thr Ala Lys  Ser Leu Ala
        1100                 1105                 1110

Ala Tyr  Pro Lys Ser Pro Phe  Gln Leu Lys Thr Pro  Glu Asn Gly
        1115                 1120                 1125

Asn Ala  Leu Asn Gly Glu Val  Lys Ser Ser Pro Asp  Val Thr Pro
        1130                 1135                 1140

Ile Ser  Pro Ile Pro Lys Glu  Leu Glu Ala Glu Glu  Lys Pro Gln
        1145                 1150                 1155

Lys Ser  Leu Asn Glu Lys Gln  Gln Glu Asn Gln Asp  Leu Leu Ile
        1160                 1165                 1170
```

| | | | | | | | | | | | |
|---|---|---|---|---|---|---|---|---|---|---|---|
| Lys | Cys | Val | Ser | Gln | Asp | Leu | Gly | Phe | Ser | Ser | Gly | Lys | Pro | Ile |
| 1175 | | | | 1180 | | | | | 1185 | | |

Lys Cys Val Ser Gln Asp Leu Gly Phe Ser Ser Gly Lys Pro Ile
1175                1180                1185

Ala Ala Cys Leu Ile Tyr Arg Cys Leu Leu His Trp Arg Ser Phe
1190                1195                1200

Glu Val Glu Arg Thr Gly Val Phe Asp Arg Ile Ile Gln Thr Ile
1205                1210                1215

Gly Ser Ala Ile Glu Gly Met Arg Ala Ser Pro Gln Ser Ala Gly
1220                1225                1230

Arg Ala Phe Leu Gly Ser Arg Leu Ile Gly Gly Leu Gly Asp Leu
1235                1240                1245

Arg Gln Val Glu Ala Lys Tyr Pro Ala Leu Leu Phe Lys Gln Gln
1250                1255                1260

Leu Thr Ala Phe Leu Glu Lys Ile Tyr Gly Met Ile Arg Asp Asn
1265                1270                1275

Leu Lys Lys Glu Ile Phe Pro Leu Leu Gly Leu Cys Ile Gln Ala
1280                1285                1290

Pro Arg Thr Ser Arg Ala Ser Leu Ile Lys Gly Ser Arg Ser Gln
1295                1300                1305

Ala Asn Ala Leu Ala Gln Gln Thr Leu Ile Ala His Trp Gln Ser
1310                1315                1320

Ile Val Lys Ile Leu Thr Asn Tyr Leu Asn Val Leu Lys Ala Asn
1325                1330                1335

Tyr Val Pro Ser Phe Leu Ile Cys Lys Val Phe Thr Gln Ile Phe
1340                1345                1350

Ser Phe Ile Asn Val Gln Leu Phe Asn Ser Leu Leu Leu Arg Arg
1355                1360                1365

Glu Cys Cys Ser Phe Ser Asn Gly Glu Tyr Val Lys Ala Gly Leu
1370                1375                1380

Ala Glu Leu Glu Gln Trp Cys Ile Tyr Ala Thr Glu Glu Tyr Ala
1385                1390                1395

Gly Ser Ser Trp Glu Glu Leu Lys His Ile Arg Gln Ala Val Gly
1400                1405                1410

Phe Leu Val Ile His Gln Lys Pro Lys Lys Thr Leu Lys Glu Ile
1415                1420                1425

Thr Asn Asp Leu Cys Pro Val Leu Ser Ile Gln Gln Leu Tyr Arg
1430                1435                1440

Ile Ser Thr Met Tyr Trp Asp Asp Lys Tyr Gly Thr His Thr Val
1445                1450                1455

Ser Ser Asp Val Ile Ser Ser Met Arg Val Met Met Thr Glu Asp
1460                1465                1470

Ser Asn Asn Ala Val Ser Ser Ser Phe Leu Leu Asp Asp Asp Ser
1475                1480                1485

Ser Ile Pro Phe Ser Val Asp Asp Ile Ser Lys Ser Met Thr Glu
1490                1495                1500

Ile Glu Val Thr Asp Val Asp Met Pro Pro Leu Ile Arg Glu Asn
1505                1510                1515

Ser Gly Phe Thr Phe Leu His Gln Arg Lys Asp
1520                1525

<210> SEQ ID NO 18
<211> LENGTH: 1464
<212> TYPE: PRT
<213> ORGANISM: Sorghum bicoler
<220> FEATURE:
<223> OTHER INFORMATION: XI-F full length

<400> SEQUENCE: 18

```
Met Gln Gly Thr Pro Val Asn Ile Ile Val Gly Ser His Val Trp Leu
1               5                   10                  15

Glu Asp Pro Gly Glu Ala Trp Val Asp Gly Val Val Thr Asp Ile Lys
            20                  25                  30

Gly Gly Asn Ala Thr Ile Ala Thr Thr Asn Gly Lys Thr Val Val Ala
        35                  40                  45

Ser Leu Gly Ser Ile Tyr Pro Lys Asp Thr Glu Ala Pro Pro Ser Gly
    50                  55                  60

Val Asp Asp Met Thr Lys Leu Ala Tyr Leu His Glu Pro Gly Val Leu
65                  70                  75                  80

His Asn Leu Ser Cys Arg Tyr Gly Leu Asn Glu Ile Tyr Thr Tyr Thr
                85                  90                  95

Gly Asn Ile Leu Ile Ala Val Asn Pro Phe Gln Arg Leu Pro His Leu
            100                 105                 110

Tyr Asp Val His Met Met Glu Gln Tyr Lys Gly Ala Ser Phe Gly Glu
        115                 120                 125

Leu Ser Pro His Leu Phe Ala Ile Ala Asp Ala Cys Tyr Arg Ala Leu
    130                 135                 140

Ile Asn Asp Gln Gly Ser Gln Ala Ile Leu Val Ser Gly Glu Ser Gly
145                 150                 155                 160

Ala Gly Lys Thr Glu Thr Thr Lys Met Leu Met Arg Tyr Leu Ala Phe
                165                 170                 175

Met Gly Gly Arg Ser Gly Thr Glu Gly Arg Thr Val Glu Gln Gln Val
            180                 185                 190

Leu Glu Ser Asn Pro Val Leu Glu Ala Phe Gly Asn Ala Lys Thr Val
    195                 200                 205

Lys Asn Asn Asn Ser Ser Arg Phe Gly Lys Phe Val Glu Ile Gln Phe
210                 215                 220

Asp Lys Tyr Gly Lys Ile Ser Gly Ala Ala Val Arg Thr Tyr Leu Leu
225                 230                 235                 240

Glu Arg Ser Arg Val Cys Gln Val Ser Asp Pro Glu Arg Asn Tyr His
                245                 250                 255

Cys Phe Tyr Met Leu Cys Ser Ala Pro Pro Glu Asp Val Lys Arg Phe
            260                 265                 270

Lys Val Gly Asp Pro Arg Gln Phe His Tyr Leu Asn Gln Thr Asn Cys
        275                 280                 285

Tyr Glu Val Ala Asn Val Asp Asp Ala Arg Glu Tyr Leu Glu Thr Arg
    290                 295                 300

Asn Ala Met Asp Ile Val Gly Ile Asp Gln Glu Glu Gln Asp Ala Ile
305                 310                 315                 320

Phe Arg Val Val Ala Ala Ile Leu His Leu Gly Asn Ile Asn Phe Ser
                325                 330                 335

Lys Gly Gln Glu Ile Asp Ser Ser Lys Leu Arg Asp Asp Lys Ser Val
            340                 345                 350

Tyr His Leu Lys Thr Val Ala Glu Leu Leu Met Cys Asp Glu Lys Ala
        355                 360                 365

Leu Glu Asp Ser Leu Cys Gln Arg Val Ile Val Thr Pro Asp Gly Asn
    370                 375                 380

Ile Thr Lys Pro Leu Asp Pro Asp Ser Ala Ala Leu Ser Arg Asp Ala
385                 390                 395                 400

Leu Ala Lys Thr Val Tyr Ser Arg Leu Phe Asp Trp Ile Val Asp Lys
```

```
            405                 410                 415
Ile Asn Asn Ser Ile Gly Gln Asp Pro Asp Ala Thr Asn Ile Ile Gly
            420                 425                 430

Val Leu Asp Ile Tyr Gly Phe Glu Ser Phe Lys Ile Asn Ser Phe Glu
            435                 440                 445

Gln Leu Cys Ile Asn Leu Thr Asn Glu Lys Leu Gln Gln His Phe Asn
            450                 455                 460

Gln His Val Phe Lys Met Glu Gln Glu Glu Tyr Thr Arg Glu Glu Ile
465                 470                 475                 480

Asp Trp Ser Tyr Val Glu Phe Val Asp Asn Gln Asp Val Leu Asp Leu
                485                 490                 495

Ile Glu Lys Lys Pro Gly Gly Ile Ile Ala Leu Leu Asp Glu Ala Cys
                500                 505                 510

Met Phe Pro Lys Ser Thr His Glu Thr Phe Ala Gln Lys Met Tyr Gln
                515                 520                 525

Thr Tyr Lys Ala His Lys Arg Phe Ser Lys Pro Lys Leu Ala Arg Thr
            530                 535                 540

Ala Phe Thr Ile Asn His Tyr Ala Gly Asp Val Thr Tyr Gln Ala Asp
545                 550                 555                 560

His Phe Leu Asp Lys Asn Lys Asp Tyr Val Val Ala Glu His Gln Ala
                565                 570                 575

Leu Leu Asn Ser Ser Arg Cys Pro Phe Val Ala Asn Leu Phe Pro Pro
                580                 585                 590

Leu Pro Glu Glu Thr Ser Lys Gln Ser Lys Phe Ser Ser Ile Gly Thr
                595                 600                 605

Arg Phe Lys Gln Gln Leu Gln Ser Leu Met Glu Thr Leu Asn Thr Thr
            610                 615                 620

Glu Pro His Tyr Ile Arg Cys Val Lys Pro Asn Ala Val Leu Lys Pro
625                 630                 635                 640

Gly Ile Phe Glu Asn His Asn Val Leu Asn Gln Leu Arg Cys Gly Gly
                645                 650                 655

Val Leu Glu Ala Ile Arg Ile Ser Cys Ala Gly Tyr Pro Thr Lys Arg
                660                 665                 670

Thr Phe Asp Glu Phe Ile Asp Arg Phe Gly Met Leu Ala Pro Glu Leu
            675                 680                 685

Val Asp Ser Ser Asp Glu Lys Ala Ala Cys Ala Ala Ile Cys Asp Arg
            690                 695                 700

Met Gly Leu Lys Gly Tyr Gln Ile Gly Lys Thr Lys Val Phe Leu Arg
705                 710                 715                 720

Ala Gly Gln Met Ala Glu Leu Asp Ala Arg Arg Ala Glu Ile Leu Ala
                725                 730                 735

Asn Ala Ala Arg Leu Ile Gln Arg His Ile Lys Ala His Leu Met Arg
            740                 745                 750

Lys Glu Phe Ile Asn Leu Arg Lys Ala Ser Val Gln Ser Gln Lys Phe
            755                 760                 765

Trp Arg Ala Arg Leu Ala Arg Lys Leu Phe Glu Tyr Met Arg Arg Asp
            770                 775                 780

Ala Ala Ser Ile Arg Ile Gln Lys His Val Arg Thr His Ser Ala Arg
785                 790                 795                 800

Lys Ala Tyr Leu Gln Val Tyr Glu Ser Ala Ile Val Ile Gln Thr Gly
                805                 810                 815

Leu Arg Ala Met Ala Ala Arg Asn Glu His Arg Phe Arg Arg Glu Thr
                820                 825                 830
```

-continued

```
Lys Ala Ser Ile Ile Ile Gln Thr Arg Trp Arg Gln His Arg Ala Tyr
        835                 840                 845
Val Ala Tyr Lys Gln Gln Lys Arg Ala Ala Leu Ile Leu Gln Cys Leu
    850                 855                 860
Trp Arg Ala Arg Ile Ala Arg Lys Glu Leu Arg Lys Leu Lys Met Glu
865                 870                 875                 880
Ala Arg Glu Thr Gly Ala Leu Lys Glu Ala Lys Asp Lys Leu Glu Lys
                885                 890                 895
Arg Val Glu Glu Leu Thr Trp Arg Leu Asp Val Glu Lys Arg Leu Arg
                900                 905                 910
Thr Asp Leu Glu Glu Ala Lys Gly His Glu Ile Glu Lys Leu Gln Ser
        915                 920                 925
Ala Leu Gln Lys Leu Gln Glu Asn Leu Glu Glu Ala His Ala Ala Ile
        930                 935                 940
Val Lys Glu Lys Glu Ala Ala Lys Leu Ala Ile Glu Gln Ala Pro Pro
945                 950                 955                 960
Lys Ile Val Glu Val Pro Val Val Asp Asn Ala Lys Leu Glu Glu Leu
                965                 970                 975
Thr Thr Gln Asn Lys Glu Leu Glu Asp Glu Leu Thr Thr Phe Lys Gln
        980                 985                 990
Lys Ala Glu Asp Leu Glu Asn Lys Leu Leu Glu Leu Gln Lys Gln Ser
        995                 1000                1005
Asp Glu Leu Ser Gln Glu Thr Gln Glu Gln Ala Ser Lys Val Thr
    1010                1015                1020
Gln Leu Gln Glu Leu Ile Glu Arg Leu Glu Ala Ser Leu Ser Asn
    1025                1030                1035
Met Glu Ser Glu Asn Gln Val Leu Arg Gln Gln Ser Leu Val Val
    1040                1045                1050
Thr Ser Ala Asp Glu Asp Lys Ser Lys Gln Ile Glu Arg Phe Glu
    1055                1060                1065
Ser Lys Ile Ser Thr Leu Glu Ser Glu Ile Glu Leu Leu Arg Cys
    1070                1075                1080
Asn Ser Ala Leu Ala Val Gln Ala Val Val Thr Pro Glu Met Asn
    1085                1090                1095
Gln Thr Thr Val Ile Glu Leu Asp Lys Gly His Gln Leu Glu
    1100                1105                1110
Glu Val Lys Thr Val Asn Glu Gln Val Val Ile Pro Pro Val Lys
    1115                1120                1125
Asn Leu Ser Lys Gln Lys Ser Leu Thr Asp Arg Gln Gln Glu Asn
    1130                1135                1140
His Asp Ala Leu Ile Lys Ser Leu Val Glu Asp Arg Arg Phe Asp
    1145                1150                1155
Asp Lys Lys Ser Ala Ala Ala Cys Ile Ala Tyr Lys Ser Leu Leu
    1160                1165                1170
His Trp His Ser Phe Glu Ala Glu Lys Thr Asn Ile Phe Asp Arg
    1175                1180                1185
Ile Ile Gln Thr Ile Arg Ser Ser Val Glu Gly Ala Glu Ser Ser
    1190                1195                1200
Gly Glu Leu Ala Tyr Trp Leu Ser Thr Ser Thr Leu Leu Tyr
    1205                1210                1215
Leu Leu Gln Asn Thr Leu Lys Ala Ser Ser Ser Leu Ser Lys Gly
    1220                1225                1230
```

-continued

Thr Asn Arg Ser Arg Thr Thr Thr Gly Ser Leu Phe Ser Arg Met
1235               1240                    1245

Val Gln Ser Ala Arg Ala Ser Ser Gly Leu Gly Ile Pro Ser Gly
1250                1255                    1260

Tyr Ser Gly Met Val Arg Arg Pro Asp Thr Ala Ser Met Val Glu
1265                1270                    1275

Ala Lys Tyr Pro Ala Leu Arg Phe Lys Gln Gln Leu Thr Ala Tyr
1280                1285                    1290

Val Glu Lys Ile Tyr Gly Ile Ile Arg Asp Asn Leu Lys Lys Glu
1295                1300                    1305

Ile Ser Pro Phe Leu Thr Met Cys Ile Gln Ala Pro Arg Ala Asn
1310                1315                    1320

Arg Val Arg Pro Ser Arg Gly Ser Leu Lys Ser Ile His Ser Asn
1325                1330                    1335

Gly Leu Ala Arg Gln Ala Ser Ser Leu His Trp Gln Asn Ile Val
1340                1345                    1350

Lys Cys Leu Asp His Thr Leu Glu Thr Met Lys Asn Asn Tyr Val
1355                1360                    1365

Pro Pro Val Ile Ile Arg Lys Thr Phe Ser Gln Val Phe Ala Tyr
1370                1375                    1380

Leu Asn Val Gln Leu Leu Asn Ser Leu Leu Arg Arg Glu Cys
1385                1390                    1395

Cys Ser Phe Ser Asn Gly Glu Phe Leu Lys Ala Gly Leu Gln Asp
1400                1405                    1410

Leu Glu Gln Trp Cys Ser Thr Ile Thr Glu Glu Tyr Val Gly Thr
1415                1420                    1425

Ser Trp Asp Glu Leu Gln His Ile Arg Gln Ala Val Gly Phe Leu
1430                1435                    1440

Val Cys Leu Lys Thr Cys Ser Tyr Phe Asn Gly Tyr Thr Ser Leu
1445                1450                    1455

Ile Cys Leu Leu Ile Lys
1460

<210> SEQ ID NO 19
<211> LENGTH: 1539
<212> TYPE: PRT
<213> ORGANISM: Sorghum bicoler
<220> FEATURE:
<223> OTHER INFORMATION: XI-J full length

<400> SEQUENCE: 19

Met Ile Pro Glu Thr Pro Lys Phe Pro Leu Gln Gly Thr Lys Val Asn
1               5                   10                  15

Ile Ile Val Gly Ser His Val Trp Ala Glu Asp Pro Asp Thr Cys Trp
                20                  25                  30

Val Asp Gly Glu Val Val Lys Ile Asn Gly Glu Glu Ala Glu Ile Gln
            35                  40                  45

Ala Thr Asn Gly Lys Lys Ile Val Ala Asn Leu Ser Lys Leu Tyr Pro
        50                  55                  60

Lys Asp Met Glu Ala Ala Ala Gly Gly Val Asp Asp Met Thr Lys Leu
65                  70                  75                  80

Ser Tyr Leu His Glu Pro Gly Val Leu Glu Asn Leu Ala Ile Arg Tyr
                85                  90                  95

Glu Leu Asn Glu Ile Tyr Thr Tyr Thr Gly Asn Ile Leu Ile Ala Val
            100                 105                 110

```
Asn Pro Phe Gln Arg Leu Pro His Leu Tyr Asp Pro His Met Met Gln
            115                 120                 125

Gln Tyr Lys Gly Ala Pro Phe Gly Glu Leu Ser Pro His Val Phe Ala
    130                 135                 140

Val Ala Asp Val Ala Tyr Arg Ala Met Ile Asn Glu Asn Lys Ser Asn
145                 150                 155                 160

Ala Ile Leu Val Ser Gly Glu Ser Gly Ala Gly Lys Thr Glu Thr Thr
                165                 170                 175

Lys Met Leu Met Arg Tyr Leu Ala Tyr Leu Gly Gly Arg Ala Ala Thr
            180                 185                 190

Glu Gly Arg Thr Val Glu Gln Gln Val Leu Glu Ser Asn Pro Val Leu
    195                 200                 205

Glu Ala Phe Gly Asn Ala Lys Thr Val Arg Asn Asn Asn Ser Ser Arg
210                 215                 220

Phe Gly Lys Phe Val Glu Ile Gln Phe Asp Lys His Gly Arg Ile Ser
225                 230                 235                 240

Gly Ala Ala Ile Arg Thr Tyr Leu Leu Glu Arg Ser Arg Val Cys Gln
                245                 250                 255

Ile Ser Asp Pro Glu Arg Asn Tyr His Cys Phe Tyr Leu Leu Cys Ala
            260                 265                 270

Ala Pro Gln Glu Asp Val Glu Lys Tyr Lys Leu Gly Asn Arg Lys Thr
    275                 280                 285

Phe His Tyr Leu Asn Gln Ser Asn Cys Tyr Glu Leu Val Gly Val Ser
290                 295                 300

Asp Ala His Glu Tyr Leu Ala Thr Arg Arg Ala Met Asp Ile Val Gly
305                 310                 315                 320

Ile Ser Thr Gln Glu Gln Asp Ala Ile Phe Arg Val Val Ala Ala Ile
                325                 330                 335

Leu His Val Gly Asn Ile Glu Phe Ser Lys Gly Lys Glu Val Asp Ser
            340                 345                 350

Ser Val Leu Lys Asp Glu Lys Ser Lys Phe His Leu Glu Thr Thr Ala
    355                 360                 365

Glu Leu Leu Met Cys Asn Pro Gly Ala Leu Glu Asp Ala Leu Cys Lys
370                 375                 380

Arg Val Met Val Thr Pro Glu Glu Val Ile Lys Arg Ser Leu Asp Pro
385                 390                 395                 400

Tyr Asn Ala Thr Ile Ser Arg Asp Gly Leu Ala Lys Thr Ile Tyr Ser
                405                 410                 415

Arg Leu Phe Asp Trp Leu Val Lys Ile Asn Ser Ser Ile Gly Gln
            420                 425                 430

Asp Ala Ser Ser Lys Cys Leu Ile Gly Val Leu Asp Ile Tyr Gly Phe
    435                 440                 445

Glu Ser Phe Lys Ala Asn Ser Phe Glu Gln Phe Cys Ile Asn Tyr Thr
450                 455                 460

Asn Glu Lys Leu Gln Gln His Phe Asn Gln His Val Phe Lys Met Glu
465                 470                 475                 480

Gln Glu Glu Tyr Thr Lys Glu Gln Ile Asp Trp Ser Tyr Ile Glu Phe
                485                 490                 495

Val Asp Asn Gln Asp Val Leu Asp Leu Ile Glu Lys Lys Pro Gly Gly
            500                 505                 510

Val Ile Ala Leu Leu Asp Glu Ala Cys Met Phe Pro Lys Ser Thr His
    515                 520                 525

Glu Thr Phe Ala Gln Lys Leu Tyr Gln Thr Phe Gln Lys His Lys Arg
```

```
            530                 535                 540
Phe Val Lys Pro Lys Leu Ser Arg Thr Asp Phe Thr Ile Cys His Tyr
545                 550                 555                 560

Ala Gly Glu Val Leu Tyr Gln Ser Asp Gln Phe Leu Asp Lys Asn Lys
                565                 570                 575

Asp Tyr Val Val Ala Glu His Gln Glu Leu Leu Ser Ala Ser Lys Cys
                580                 585                 590

Ser Phe Ile Ser Gly Leu Phe Pro Pro Pro Glu Glu Thr Ser Lys
            595                 600                 605

Ser Ser Lys Phe Ser Ser Ile Gly Ala Arg Phe Lys Gln Gln Leu Gln
            610                 615                 620

Ala Leu Met Asp Thr Leu Asn Ser Thr Glu Pro His Tyr Ile Arg Cys
625                 630                 635                 640

Val Lys Pro Asn Asn Val Leu Lys Pro Ala Ile Phe Glu Asn Val Asn
                645                 650                 655

Val Met Gln Gln Leu Arg Cys Gly Gly Val Leu Glu Ala Ile Arg Ile
                660                 665                 670

Ser Cys Ala Gly Tyr Pro Thr Arg Arg Thr Phe Tyr Glu Phe Leu His
            675                 680                 685

Arg Phe Gly Ile Leu Ala Pro Glu Ala Leu Glu Gly Asn Ser Asp Glu
            690                 695                 700

Lys Val Ala Cys Lys Arg Ile Leu Glu Lys Lys Gly Leu Leu Gly Phe
705                 710                 715                 720

Gln Ile Gly Lys Thr Lys Val Phe Leu Arg Ala Gly Gln Met Ala Glu
                725                 730                 735

Leu Asp Ala Arg Arg Thr Glu Val Leu Ser Ala Ala Ala Lys Thr Ile
                740                 745                 750

Gln Gly Lys Met Arg Thr His Ile Met Arg Lys Lys Phe Leu Ser Leu
            755                 760                 765

Arg Lys Ala Ser Val Cys Val Gln Ala Ile Trp Arg Gly Arg Leu Ala
770                 775                 780

Cys Lys Leu Tyr Asp Asn Met Arg Arg Glu Ala Ala Ala Ile Lys Val
785                 790                 795                 800

Gln Lys Asn Gln Arg Arg His Gln Ala Arg Arg Ser Tyr Lys Leu His
            805                 810                 815

Tyr Ala Ser Val Leu Val Gln Thr Ala Leu Arg Ala Met Ala Ala
            820                 825                 830

Arg Lys Glu Phe Arg Phe Lys Lys Gln Ser Thr Gly Ala Val Thr Ile
            835                 840                 845

Gln Ala Arg Tyr Arg Cys His Arg Ala His Lys Tyr His Lys Lys Leu
850                 855                 860

Lys Trp Ala Ala Ile Val Ala Gln Cys Arg Trp Arg Gly Arg Ile Ala
865                 870                 875                 880

Arg Lys Glu Leu Lys Lys Leu Lys Met Glu Ala Arg Glu Thr Gly Ala
                885                 890                 895

Leu Lys Glu Ala Lys Asp Lys Leu Glu Lys Val Glu Glu Leu Thr
            900                 905                 910

Trp Arg Val Gln Leu Glu Lys Arg Leu Arg Thr Asp Leu Glu Glu Ala
            915                 920                 925

Lys Ala Gln Glu Leu Ser Lys Met Gln Ile Ser Met Glu Ala Leu Gln
            930                 935                 940

Ala Lys Leu Asp Glu Ala Asn Thr Lys Leu Ala Lys Glu Arg Glu Ala
945                 950                 955                 960
```

-continued

```
Ala Lys Thr Ile Glu Glu Ala Pro Pro Val Val Lys Glu Thr Gln Val
                965                 970                 975
Ile Val Gln Asp Thr Glu Lys Ile Asp Ser Leu Thr Thr Glu Val Gln
                980                 985                 990
Glu Leu Lys Thr Ser Leu Gln Leu Glu Lys Gln Arg Ala Asp Asp Leu
                995                1000                1005
Glu Lys Lys Arg Ser Glu Glu Gln Ala Asn Glu Glu Lys Gln
           1010                1015                1020
Lys Lys Leu Asp Glu Thr Glu Asn Lys Met Arg Gln Phe Gln Asp
           1025                1030                1035
Tyr Leu Arg Arg Leu Glu Glu Lys Leu Ala Asn Val Glu Ser Glu
           1040                1045                1050
Asn Lys Val Leu Arg Gln Gln Ala Val Ser Met Ala Pro Ser Lys
           1055                1060                1065
Ile Leu Ser Gly Arg Ser Lys Ser Asn Leu Gln Arg Asn Ser Glu
           1070                1075                1080
Asn Val Gln Val Ser Ser Asn Asp Pro Lys Ile Thr Pro Glu Ser
           1085                1090                1095
Asn Asn Thr Ser Ser Pro Lys Lys Glu Tyr Asp Ile Asp Asp Lys
           1100                1105                1110
Pro Gln Lys Ser Leu Asn Glu Lys Gln Gln Glu Asn Gln Asp Leu
           1115                1120                1125
Leu Ile Arg Cys Ile Ala Gln His Leu Gly Tyr Ala Gly Asn Arg
           1130                1135                1140
Pro Val Ala Ala Cys Ile Ile Tyr Lys Cys Leu Leu His Trp Arg
           1145                1150                1155
Ser Phe Glu Val Glu Arg Thr Ser Val Phe Asp Arg Ile Ile Gln
           1160                1165                1170
Thr Val Gly His Ala Ile Glu Thr Gln Asp Asn Asn Glu Val Leu
           1175                1180                1185
Ala Tyr Trp Leu Ser Asn Ala Ser Thr Leu Leu Leu Leu Leu Gln
           1190                1195                1200
Arg Thr Leu Lys Ala Ser Gly Ser Thr Gly Met Ala Pro Gln Arg
           1205                1210                1215
Arg Arg Ser Ser Ser Ala Thr Leu Phe Gly Arg Met Thr Gln Ser
           1220                1225                1230
Phe Arg Gly Ala Pro Gln Gly Val Asn Leu Ser Leu Ile Asn Gly
           1235                1240                1245
Ser Met Val Thr Gly Val Glu Thr Leu Arg Gln Val Glu Ala Lys
           1250                1255                1260
Tyr Pro Ala Leu Leu Phe Lys Gln Gln Leu Thr Ala Tyr Val Glu
           1265                1270                1275
Lys Ile Tyr Gly Met Ile Arg Asp Asn Leu Lys Lys Glu Ile Ser
           1280                1285                1290
Pro Leu Leu Gly Leu Cys Ile Gln Ala Pro Arg Thr Ser Arg Ala
           1295                1300                1305
Ser Leu Met Lys Gly Ser Ser Arg Ser Asn Thr Asn Thr Ala Ala
           1310                1315                1320
Gln Gln Ala Leu Ile Ala His Trp Gln Gly Ile Val Lys Ser Leu
           1325                1330                1335
Gly Asn Phe Val Asn Ile Leu Lys Ala Asn Asn Val Pro Pro Phe
           1340                1345                1350
```

```
Leu Val Arg Lys Val Phe Thr Gln Ile Phe Ser Phe Ile Asn Val
    1355                1360                1365

Gln Leu Phe Asn Ser Leu Leu Arg Arg Glu Cys Cys Ser Phe
1370                1375                1380

Ser Asn Gly Glu Tyr Val Lys Ala Gly Leu Ala Glu Leu Glu His
1385                1390                1395

Trp Cys Tyr Arg Ala Thr Asp Glu Tyr Ala Gly Ser Ala Trp Asp
1400                1405                1410

Glu Leu Lys His Ile Lys Gln Ala Ile Gly Phe Leu Val Ile His
    1415                1420                1425

Gln Lys Pro Lys Lys Thr Phe Asp Glu Ile Ser His Asp Leu Cys
    1430                1435                1440

Pro Val Leu Ser Ile Gln Gln Leu Tyr Arg Ile Ser Thr Met Tyr
    1445                1450                1455

Trp Asp Asp Lys Tyr Gly Thr His Ser Val Ser Pro Glu Val Ile
    1460                1465                1470

Ser Asn Met Arg Val Leu Met Thr Glu Asp Ser Asn Asn Pro Val
    1475                1480                1485

Ser Asn Ser Phe Leu Leu Asp Asp Asp Ser Ser Ile Pro Phe Ser
    1490                1495                1500

Val Asp Asp Ile Ser Lys Ser Met Gln Gln Ile Asp Ile Ser Asp
    1505                1510                1515

Ile Glu Pro Pro Pro Leu Ile Arg Glu Asn Ser Gly Phe Val Phe
    1520                1525                1530

Leu Leu Pro Pro Pro Glu
    1535

<210> SEQ ID NO 20
<211> LENGTH: 1539
<212> TYPE: PRT
<213> ORGANISM: Populus trichocarpa
<220> FEATURE:
<223> OTHER INFORMATION: XI-M full length

<400> SEQUENCE: 20

Met Trp Glu Val Phe Leu Leu Gly Glu Arg Ala Thr Thr Asp Asn Ile
1               5                   10                  15

Ile Val Gly Ser His Val Trp Val Glu Asp Pro Val Leu Ala Trp Ile
                20                  25                  30

Asp Gly Glu Val Leu Arg Ile Asn Gly Glu Gln Val His Val Gln Ala
            35                  40                  45

Thr Asn Gly Lys Thr Val Val Ala Asn Ile Ser Lys Val Phe Pro Lys
    50                  55                  60

Asp Thr Glu Ala Pro Pro Gly Gly Val Asp Asp Met Thr Lys Leu Ser
65                  70                  75                  80

Tyr Leu His Glu Pro Gly Val Leu His Asn Leu Ala Ala Arg Tyr Glu
                85                  90                  95

Leu Asn Glu Ile Tyr Thr Tyr Thr Gly Asn Ile Leu Ile Ala Ile Asn
            100                 105                 110

Pro Phe Gln Arg Leu Pro His Leu Tyr Asp Thr His Met Met Glu Gln
        115                 120                 125

Tyr Lys Gly Ala Ala Phe Gly Glu Leu Ser Pro His Val Phe Ala Val
    130                 135                 140

Ala Asp Val Ala Tyr Arg Gln Met Ile Asn Glu Gly Lys Ser Asn Ser
145                 150                 155                 160
```

-continued

Ile Leu Val Ser Gly Glu Ser Gly Ala Gly Lys Thr Glu Thr Thr Lys
                165                 170                 175
Met Leu Met Arg Tyr Leu Ala Tyr Met Gly Gly Arg Ser Gly Val Glu
            180                 185                 190
Gly Arg Thr Val Glu Gln Gln Val Leu Glu Ser Asn Pro Val Leu Glu
        195                 200                 205
Ala Phe Gly Asn Ala Lys Thr Val Arg Asn Asn Ser Ser Arg Phe
    210                 215                 220
Gly Lys Phe Val Glu Ile Gln Phe Asp Lys Asn Gly Arg Ile Ser Gly
225                 230                 235                 240
Ala Ala Ile Arg Thr Tyr Leu Leu Glu Arg Ser Arg Val Cys Gln Val
                245                 250                 255
Ser Asp Pro Glu Arg Asn Tyr His Cys Phe Tyr Leu Leu Cys Ala Ala
            260                 265                 270
Pro Leu Glu Glu Arg Glu Arg Tyr Lys Leu Glu Asn Pro Lys Ser Phe
        275                 280                 285
His Tyr Leu Asn Gln Thr Asn Cys Tyr Lys Leu Asp Gly Val Asn Asp
    290                 295                 300
Ala Glu Glu Tyr Leu Ala Thr Arg Arg Ala Met Asp Ile Val Gly Ile
305                 310                 315                 320
Ser Glu Glu Glu Gln Glu Ala Ile Phe Arg Val Val Ala Ala Ile Leu
                325                 330                 335
His Leu Gly Asn Ile Glu Phe Ala Lys Gly Glu Glu Ile Asp Ser Ser
            340                 345                 350
Val Ile Lys Asp Gln Lys Ser Arg Phe His Leu Asn Met Thr Ala Glu
        355                 360                 365
Leu Leu Lys Cys Asp Ala Lys Ser Leu Glu Asp Ala Leu Ile Gln Arg
    370                 375                 380
Val Met Val Thr Pro Glu Glu Val Ile Thr Arg Thr Leu Asp Pro Leu
385                 390                 395                 400
Ala Ala Val Leu Ser Arg Asp Ala Leu Ala Lys Thr Ile Tyr Ser Arg
                405                 410                 415
Leu Phe Asp Trp Leu Val Asp Lys Ile Asn Asn Ser Ile Gly Gln Asp
            420                 425                 430
Pro Asn Ser Lys Ser Leu Ile Gly Val Leu Asp Ile Tyr Gly Phe Glu
        435                 440                 445
Ser Phe Lys Phe Asn Ser Phe Glu Gln Phe Cys Ile Asn Phe Thr Asn
    450                 455                 460
Glu Lys Leu Gln Gln His Phe Asn Gln His Val Phe Lys Met Glu Gln
465                 470                 475                 480
Glu Glu Tyr Thr Lys Glu Glu Ile Asn Trp Ser Tyr Ile Glu Phe Val
                485                 490                 495
Asp Asn Gln Asp Val Leu Asp Leu Ile Glu Lys Pro Gly Gly Ile
            500                 505                 510
Ile Ala Leu Leu Asp Glu Ala Cys Met Phe Pro Lys Ser Thr His Glu
        515                 520                 525
Thr Phe Ala Gln Lys Leu Tyr Gln Thr Phe Lys Asn Asn Lys Arg Phe
    530                 535                 540
Ile Lys Pro Lys Leu Ser Arg Thr Ser Phe Thr Ile Ser His Tyr Ala
545                 550                 555                 560
Gly Glu Val Met Tyr Leu Ala Asp Gln Phe Leu Asp Lys Asn Lys Asp
                565                 570                 575
Tyr Val Val Ala Glu His Gln Asp Leu Leu Thr Ala Ser Lys Cys Pro

```
                    580               585               590
      Phe Ala Ala Ser Leu Phe Pro Pro Leu Pro Glu Glu Ser Ser Lys Ser
                          595               600               605

Ser Lys Phe Ser Ser Ile Gly Ser Arg Phe Lys Leu Gln Leu Gln Ser
              610               615               620

Leu Met Glu Thr Leu Asn Ser Thr Glu Pro His Tyr Ile Arg Cys Val
      625               630               635               640

Lys Pro Asn Asn Leu Leu Lys Pro Ala Ile Phe Glu Asn Ala Asn Ile
                      645               650               655

Ile Gln Gln Leu Arg Cys Gly Val Leu Glu Ala Ile Arg Ile Ser
                  660               665               670

Cys Ala Gly Tyr Pro Thr Arg Thr Phe Tyr Glu Phe Leu Leu Arg
              675               680               685

Phe Gly Val Leu Ala Pro Glu Val Leu Glu Gly Asn His Asp Asp Lys
          690               695               700

Val Ala Cys Gln Met Ile Leu Asp Lys Met Gly Leu Lys Gly Tyr Gln
      705               710               715               720

Leu Gly Lys Thr Lys Val Phe Leu Arg Ala Gly Gln Met Ala Glu Leu
                      725               730               735

Asp Ala Arg Arg Thr Glu Val Leu Gly Asn Ala Ala Arg Thr Ile Gln
                      740               745               750

Arg Gln Ile Arg Thr Tyr Ile Ala Arg Lys Glu Phe Ile Ser Leu Arg
                  755               760               765

Arg Ala Ala Phe His Leu Gln Ser His Cys Arg Gly Val Ser Ala Arg
              770               775               780

Met Leu Tyr Glu Gly Leu Arg Gln Glu Ala Ala Ala Leu Lys Ile Gln
      785               790               795               800

Lys Asn Phe Arg Arg His Thr Ala Arg Lys Ala Tyr Leu Thr Leu Cys
                      805               810               815

Leu Ser Ala Ile Ser Leu Gln Thr Gly Leu Arg Ala Met Thr Ala Arg
                  820               825               830

Asn Glu Phe Arg Phe Arg Lys Gln Thr Lys Ala Ala Ile Ile Ile Gln
              835               840               845

Ala Lys Leu Arg His His Ile Ala Tyr Ser Tyr Tyr Lys Arg Leu Gln
      850               855               860

Lys Ala Ala Leu Val Ser Gln Cys Gly Trp Arg Gln Arg Val Ala Arg
      865               870               875               880

Arg Glu Leu Arg Lys Leu Lys Met Ala Ala Lys Glu Thr Gly Ala Leu
                      885               890               895

Lys Glu Ala Lys Asp Lys Leu Glu Lys Arg Val Glu Glu Leu Thr Trp
                      900               905               910

Arg Leu Gln Leu Glu Lys Arg Leu Arg Ala Asp Leu Glu Glu Lys
                  915               920               925

Ala Gln Glu Ile Ala Lys Leu Gln Asp Ala Leu Arg Glu Met Gln Ile
      930               935               940

Gln Val Glu Asp Ala Asn Ala Arg Val Ile Lys Glu Arg Glu Glu Ala
      945               950               955               960

Gln Lys Ala Ile Glu Glu Ala Pro Pro Ile Ile Lys Glu Thr Pro Val
                      965               970               975

Ile Val Gln Asp Thr Glu Lys Val Glu Ser Leu Thr Ala Glu Val Glu
                  980               985               990

Ser Leu Lys Ala Leu Leu Leu Ser  Glu Arg Gln Ala Ala  Glu Glu Ala
                  995              1000              1005
```

-continued

```
Arg Lys Ala His Ala Asp Gly Glu Ala Arg Asn Ser Glu Leu Ala
    1010            1015                1020

Lys Lys Leu Glu Asp Ala Ala Lys Lys Met Asp Gln Leu Gln Glu
    1025            1030                1035

Ser Val Gln Arg Leu Glu Lys Leu Ser Asn Ser Glu Ser Glu
    1040            1045                1050

Asn Gln Val Leu Arg Gln Gln Ala Leu Thr Met Ser Pro Thr Gly
    1055            1060                1065

Lys Ser Leu Ser Ala Arg Pro Lys Ser Met Ile Ile Gln Arg Thr
    1070            1075                1080

Pro Val Asn Gly Asn Val Ala Asn Gly Glu Val Lys Val Ala Ser
    1085            1090                1095

Asp Ile Ile Leu Ala Ala Ser Asn Ala Arg Glu Pro Glu Ser Glu
    1100            1105                1110

Glu Lys Pro Gln Lys Ser Leu Asn Glu Lys Gln Gln Glu Asn Gln
    1115            1120                1125

Asp Leu Leu Ile Lys Cys Val Ser Gln Asn Leu Gly Phe Ser Gly
    1130            1135                1140

Gly Lys Pro Val Ala Ala Cys Val Ile Tyr Lys Cys Leu Leu His
    1145            1150                1155

Trp Arg Ser Phe Glu Val Glu Arg Thr Thr Val Phe Asp Arg Ile
    1160            1165                1170

Ile Gln Thr Ile Ala Ser Ser Ile Glu Val Pro Asp Asn Asn Asp
    1175            1180                1185

Val Leu Ala Tyr Trp Leu Ser Asn Ser Ser Thr Leu Leu Leu Leu
    1190            1195                1200

Leu Gln His Thr Leu Lys Ala Ser Gly Ala Ala Ser Leu Thr Pro
    1205            1210                1215

Gln Arg Arg Arg Thr Ser Ser Ala Ser Leu Phe Gly Arg Met Ser
    1220            1225                1230

Gln Gly Leu Arg Ala Ser Pro Gln Ser Ser Gly Leu Ser Phe Leu
    1235            1240                1245

Asn Ser Arg Gly Leu Ser Arg Leu Asp Asp Leu Arg Gln Val Glu
    1250            1255                1260

Ala Lys Tyr Pro Ala Leu Leu Phe Lys Gln Gln Leu Thr Ala Phe
    1265            1270                1275

Leu Glu Lys Ile Tyr Gly Met Ile Arg Asp Asn Leu Lys Lys Glu
    1280            1285                1290

Ile Ser Pro Leu Leu Gly Leu Cys Ile Gln Ala Pro Arg Thr Ser
    1295            1300                1305

Arg Ala Ser Leu Val Lys Gly Arg Ser Gln Ala Asn Ala Val Ala
    1310            1315                1320

Gln Gln Ala Leu Ile Ala His Trp Gln Ser Ile Val Lys Ser Leu
    1325            1330                1335

Asn Ser Tyr Leu Lys Thr Met Lys Ala Asn Asn Val Pro Pro Phe
    1340            1345                1350

Leu Val Arg Lys Val Phe Thr Gln Ile Phe Ser Phe Ile Asn Val
    1355            1360                1365

Gln Leu Phe Asn Ser Leu Leu Leu Arg Arg Glu Cys Cys Ser Phe
    1370            1375                1380

Ser Asn Gly Glu Tyr Val Lys Ala Gly Leu Ala Glu Leu Glu Gln
    1385            1390                1395
```

```
Trp Cys Tyr Glu Ala Thr Glu Glu Phe Ala Gly Ser Ala Trp Asp
    1400                1405                1410

Glu Leu Lys His Ile Arg Gln Ala Val Gly Phe Leu Val Ile His
    1415                1420                1425

Gln Lys Pro Lys Lys Thr Leu Asn Glu Ile Thr Lys Glu Leu Cys
    1430                1435                1440

Pro Val Leu Ser Ile Gln Gln Leu Tyr Arg Ile Ser Thr Met Tyr
    1445                1450                1455

Trp Asp Asp Lys Tyr Gly Thr His Ser Val Ser Ser Asp Val Ile
    1460                1465                1470

Ser Ser Met Arg Val Met Met Thr Glu Asp Ser Asn Asn Ala Val
    1475                1480                1485

Ser Asn Ser Phe Leu Leu Asp Asp Ser Ser Ile Pro Phe Ser
    1490                1495                1500

Val Asp Asp Ile Ser Lys Ser Met Gln Gln Val Asp Ile Ala Asp
    1505                1510                1515

Ile Asp Pro Pro Ser Ile Ile Arg Glu Asn Ser Gly Phe Gly Phe
    1520                1525                1530

Leu Leu Pro Arg Ser Glu
    1535

<210> SEQ ID NO 21
<211> LENGTH: 1509
<212> TYPE: PRT
<213> ORGANISM: Populus trichocarpa
<220> FEATURE:
<223> OTHER INFORMATION: XI-M full length

<400> SEQUENCE: 21

Met Val Gly Ser Phe Val Trp Val Glu Asp Pro Glu Glu Ala Trp Met
1               5                   10                  15

Asp Gly Glu Val Leu Glu Val Asn Gly Glu Glu Ile Thr Val Asn Cys
                20                  25                  30

Ala Ser Arg Lys Ala Val Val Ala Lys Ala Ser Asn Val Phe Pro Lys
            35                  40                  45

Asp Pro Glu Phe Pro Pro Cys Gly Val Asp Asp Met Thr Lys Leu Ala
        50                  55                  60

Tyr Leu His Glu Pro Gly Val Leu Gln Asn Leu Arg Cys Arg Tyr Asp
65                  70                  75                  80

Ile Asn Glu Ile Tyr Thr Tyr Thr Gly Asn Ile Leu Ile Ala Val Asn
                85                  90                  95

Pro Phe Arg Arg Leu Pro His Leu Tyr Asp Asn His Met Met Glu Gln
                100                 105                 110

Tyr Lys Gly Ala Thr Ile Gly Glu Leu Ser Pro His Pro Phe Ala Val
            115                 120                 125

Ala Asp Ser Ala Tyr Arg Trp Phe Met Ile Asn Glu Gly Ile Ser Gln
        130                 135                 140

Ser Ile Leu Val Ser Gly Glu Ser Gly Ala Gly Lys Thr Glu Ser Thr
145                 150                 155                 160

Lys Met Leu Met Arg Tyr Leu Ala Tyr Met Gly Gly Arg Ala Ala Ala
                165                 170                 175

Glu Gly Arg Ser Val Glu Gln Gln Val Leu Glu Ser Asn Pro Val Leu
                180                 185                 190

Glu Ala Phe Gly Asn Ala Lys Thr Leu Arg Asn Asn Asn Ser Ser Arg
            195                 200                 205
```

-continued

```
Phe Gly Lys Phe Val Glu Ile Gln Phe Asp Gln Ser Gly Arg Ile Ser
    210                 215                 220
Gly Ala Ala Ile Arg Thr Tyr Leu Leu Glu Arg Ser Arg Val Cys Gln
225                 230                 235                 240
Val Ser Asp Ala Glu Arg Asn Tyr His Cys Phe Tyr Met Leu Cys Ala
                245                 250                 255
Ala Pro Glu Glu Val Ile Glu Lys Tyr Lys Leu Gly Asn Pro Arg Thr
            260                 265                 270
Phe His Tyr Leu Asn Gln Ser Asn Phe Tyr Asp Leu Asp Gly Val Asn
        275                 280                 285
Glu Ser Glu Glu Tyr Leu Ala Thr Arg Arg Ala Met Asp Ile Val Gly
    290                 295                 300
Ile Asn Ala Asn Glu Gln Asp Ala Ile Phe Arg Val Val Ala Ala Ile
305                 310                 315                 320
Leu His Leu Gly Asn Val Glu Phe Ala Lys Gly Asn Glu Ile Asp Ser
                325                 330                 335
Ser Glu Pro Lys Asp Asp Lys Ser Gln Phe His Leu Lys Thr Ala Ala
            340                 345                 350
Glu Leu Leu Met Cys Asn Glu Lys Ser Leu Glu Asn Ser Leu Cys Lys
        355                 360                 365
Arg Val Ile Val Thr Arg Asp Glu Ser Ile Thr Lys Trp Leu Asp Pro
    370                 375                 380
Asp Ala Ala Thr Val Asn Arg Asp Thr Leu Ala Lys Ile Val Tyr Ser
385                 390                 395                 400
Arg Leu Phe Asp Trp Ile Val Ser Thr Ile Asn Asn Ser Ile Gly Gln
                405                 410                 415
Asp Pro Asn Ser Lys Ser Leu Ile Gly Val Leu Asp Ile Tyr Gly Phe
            420                 425                 430
Glu Ser Phe Lys Thr Asn Ser Phe Glu Gln Phe Cys Ile Asn Leu Thr
        435                 440                 445
Asn Glu Lys Leu Gln Gln His Phe Asn Gln His Val Phe Lys Ala Glu
    450                 455                 460
Gln Glu Glu Tyr Thr Lys Glu Glu Ile Asp Trp Ser Tyr Ile Glu Phe
465                 470                 475                 480
Ile Asp Asn Gln Asp Ile Leu Asp Leu Ile Glu Lys Lys Pro Gly Gly
                485                 490                 495
Ile Ile Ala Leu Leu Asp Glu Ala Cys Met Phe Pro Arg Ser Thr His
            500                 505                 510
Glu Thr Phe Ala Glu Lys Leu Tyr Gln Thr Phe Lys Asp His Lys Arg
        515                 520                 525
Phe Asn Lys Pro Lys Leu Ala Arg Ser Asp Phe Thr Ile Cys His Tyr
    530                 535                 540
Ala Gly Asp Val Thr Tyr Gln Thr Glu His Phe Leu Asp Lys Asn Lys
545                 550                 555                 560
Asp Tyr Val Val Ala Glu His Gln Ser Leu Leu Ser Glu Ser Met Cys
                565                 570                 575
Ser Phe Val Ser Gly Leu Phe Pro Pro Leu Pro Glu Glu Ser Ala Lys
            580                 585                 590
Ser Ser Lys Phe Ser Ser Ile Gly Ser Arg Cys Lys Gln Gln Leu Gln
        595                 600                 605
Ala Leu Leu Glu Thr Leu Ser Ala Thr Glu Pro His Tyr Ile Arg Cys
    610                 615                 620
Val Lys Pro Asn Asn Ala Leu Lys Pro Ser Ile Phe Glu Asn Asn Asn
```

-continued

```
                625                 630                 635                 640
Val Leu Gln Gln Leu Cys Cys Gly Gly Val Met Glu Ala Ile Arg Ile
                    645                 650                 655

Ser Cys Ala Gly Tyr Pro Thr Arg Lys Thr Phe Asp Glu Phe Val Arg
                    660                 665                 670

Arg Phe Ala Ile Leu Ala Pro Asp Val Leu His Gly Cys Asp Glu
                675                 680                 685

Val Ser Ala Cys Lys Met Leu Leu Glu Lys Val Asn Leu Lys Gly Tyr
690                 695                 700

Gln Ile Gly Lys Thr Lys Val Phe Leu Arg Ala Gly Gln Met Ala Glu
705                 710                 715                 720

Leu Asp Ala His Arg Ser Glu Leu Leu Gly Arg Ser Ala Ser Ile Ile
                    725                 730                 735

Gln Arg Lys Val Arg Ser Tyr Phe Cys Arg Lys Ser Phe Ile Leu Leu
                    740                 745                 750

Arg Gln Ser Ala Ile His Ile Gln Thr Leu Cys Arg Ala Glu Val Ala
                755                 760                 765

Arg Asn Arg Phe Glu Cys Leu Arg Arg Glu Ala Ala Cys Leu Lys Ile
                770                 775                 780

Gln Lys Tyr Ser Arg Arg Tyr Leu Ala Ser Lys Ala Tyr Asn Asn Leu
785                 790                 795                 800

Cys Phe Ser Ala Val Ser Ile Gln Ser Cys Met Arg Gly Met Ala Ala
                    805                 810                 815

Arg Asn Glu Leu Cys Phe Arg Lys Gln Met Arg Ala Val Ile Val Ile
                820                 825                 830

Gln Ser Gln Cys Arg Lys His Ser Ala Gln Leu His Tyr Leu Arg Leu
                835                 840                 845

Lys Arg Ala Ala Ile Ala Thr Gln Cys Ala Trp Arg Gly Arg Val Ala
                850                 855                 860

Arg Lys Glu Leu Arg Lys Leu Lys Met Ala Ala Lys Glu Thr Gly Ala
865                 870                 875                 880

Leu Gln Ala Ala Lys Ser Lys Leu Glu Lys Glu Val Glu Glu Leu Thr
                    885                 890                 895

Trp Arg Leu Gln Leu Glu Lys Arg Met Arg Ala Asp Leu Glu Glu Ser
                    900                 905                 910

Lys Thr Gln Glu Asn Ala Lys Leu Arg Thr Thr Leu Gln Glu Met Gln
                915                 920                 925

Leu Glu Phe Gln Glu Ser Lys Ala Leu Leu Ile Lys Glu Arg Glu Ser
                930                 935                 940

Ile Lys Lys Glu Ala Glu Lys Val Pro Thr Ile Gln Glu Val Pro Val
945                 950                 955                 960

Ile Asp Asn Glu Leu Val Asn Lys Leu Thr Ala Glu Asn Glu Met Leu
                    965                 970                 975

Lys Ala Met Val Ser Ser Leu Glu Lys Arg Ile Asp Glu Thr Glu Lys
                980                 985                 990

Lys Tyr Glu Glu Thr Ser Lys Leu Ser Glu Glu His Leu Lys Gln Ala
                995                 1000                1005

Leu Asp Ala Glu Ser Lys Ile Ile Glu Leu Lys Thr Ala Met Gln
                1010                1015                1020

Arg Leu Glu Glu Lys Leu Ser Asp Met Glu Ala Glu Asp Gln Val
                1025                1030                1035

Leu Gln His Gln Ala Leu Phe Ser Ser Ser Ser Arg Lys Met Ser
                1040                1045                1050
```

-continued

```
Glu His Leu Glu Ile Thr Ser Gln Val Lys Cys Met Asn Ile Phe
    1055                1060                1065

Phe Val Lys His Leu Tyr Phe Ser Ser Arg Lys Trp Ser Ser
    1070                1075                1080

Leu Ile Met Leu Leu Gln Glu Pro Pro Thr Pro Ser Lys Arg Leu
    1085                1090                1095

Gly Thr Asp Ala Asp Lys Lys Met Arg Lys Ser Gln Ile Glu Arg
    1100                1105                1110

Leu His Glu Ser Val Asp Ala Leu Ile Lys Cys Val Glu Gln Asn
    1115                1120                1125

Pro Gly Phe Ser Gln Gly Lys Pro Val Gly Ala Phe Thr Ile Tyr
    1130                1135                1140

Arg Cys Leu Val Gln Trp Arg Ser Phe Glu Ala Glu Lys Thr Ser
    1145                1150                1155

Val Phe Asp Arg Leu Ile Gln Met Ile Gly Ser Ala Ile Glu Asn
    1160                1165                1170

Gln Asp Asp Asn Asn His Met Ala Tyr Trp Leu Ser Asn Thr Ser
    1175                1180                1185

Met Leu Leu Phe Leu Leu Gln Arg Thr Leu Lys Asp Ser Gly Ala
    1190                1195                1200

Asn Ser Asn Pro Pro Pro Pro Thr Ser Phe Phe Gly Arg Met Ala
    1205                1210                1215

Gln Gly Phe Arg Ser Ser Pro Ser Ser Ala Asn Leu Arg Val Gly
    1220                1225                1230

Arg Asp Ile Gln Met Val Glu Ala Lys Tyr Pro Ala Leu Leu Phe
    1235                1240                1245

Lys Gln Gln Leu Thr Ala Tyr Val Glu Thr Ile Tyr Gly Ile Val
    1250                1255                1260

Arg Asp Asn Phe Lys Lys Asp Leu Ser Pro Leu Leu Ser Ser Cys
    1265                1270                1275

Ile Gln Ala Pro Arg Ala Ser Arg Gly Thr Ala Leu Lys Ser Ser
    1280                1285                1290

Leu Ser Phe Gly His Asn Thr Pro Ala Asp Ser Trp Arg Ser Ile
    1295                1300                1305

Val Asn Ser Leu Asp Gly Leu Leu Cys Thr Leu Lys Glu Asn Phe
    1310                1315                1320

Val Pro Pro Ile Phe Val Gln Lys Ile Phe Thr Gln Ile Phe Ser
    1325                1330                1335

Tyr Ile Asn Val Gln Leu Phe Asn Ser Leu Leu Leu Arg Arg Glu
    1340                1345                1350

Cys Cys Thr Phe Ser Asn Gly Glu Tyr Val Lys Ala Gly Leu Ala
    1355                1360                1365

Glu Leu Glu Leu Trp Cys Gly Gln Ala Lys Glu Glu Tyr Val Gly
    1370                1375                1380

Ala Ser Trp Asp Glu Leu Lys Asn Thr Arg Gln Ala Val Gly Phe
    1385                1390                1395

Leu Val Ile His Gln Lys Ser Arg Ile Ser Tyr Asp Glu Ile Thr
    1400                1405                1410

Asn Asp Leu Cys Pro Val Leu Ser Val Gln Gln Leu Tyr Arg Val
    1415                1420                1425

Cys Thr Leu Tyr Trp Asp Asp Tyr Asn Thr Arg Ser Val Ser
    1430                1435                1440
```

```
Pro Asp Val Ile Ser Ser Met Lys Thr Leu Ala Asn Asp Ser Asn
    1445                1450                1455

Asp Asp Asp Ser Asn Ser Phe Leu Ile Asp Asp Asn Ser Ser Ile
    1460                1465                1470

Pro Phe Ser Val Asp Asp Leu Ser Gly Ser Phe His Glu Lys Asp
    1475                1480                1485

Phe Ser Asp Val Lys Pro Ala Ala Asp Leu Leu Glu Asn Pro Ala
    1490                1495                1500

Phe Gln Phe Leu Gln Asp
    1505

<210> SEQ ID NO 22
<211> LENGTH: 1513
<212> TYPE: PRT
<213> ORGANISM: Populus trichocarpa
<220> FEATURE:
<223> OTHER INFORMATION: XI-M full length

<400> SEQUENCE: 22

Met Ala Ser Ala Ala Ser Leu Val Val Gly Ser Leu Val Trp Leu Glu
1               5                   10                  15

Asp Pro Asp Glu Ala Trp Ile Asp Gly Glu Val Val Glu Ile Asn Lys
            20                  25                  30

Glu Asp Ile Lys Val Leu Cys Thr Ser Gly Lys Thr Val Thr Val Lys
        35                  40                  45

Ala Ser Lys Thr Tyr Pro Lys Asp Ala Glu Ala Pro Pro Cys Gly Val
    50                  55                  60

Asp Asp Met Thr Lys Leu Ala Tyr Leu His Glu Pro Gly Val Leu Gln
65                  70                  75                  80

Asn Leu Arg Ser Arg Tyr Asp Met Asn Glu Ile Tyr Thr Tyr Val Gly
                85                  90                  95

Asn Ile Leu Ile Ala Val Asn Pro Phe Thr Arg Leu Pro His Leu Tyr
            100                 105                 110

Asn Ser His Met Met Ala Gln Tyr Lys Gly Ala Ser Phe Gly Glu Leu
        115                 120                 125

Ser Pro His Pro Phe Ala Val Ala Asp Ala Ser Tyr Arg Leu Met Met
    130                 135                 140

Asn Glu Gly Ile Ser Gln Ser Ile Leu Val Ser Gly Glu Ser Gly Ala
145                 150                 155                 160

Gly Lys Thr Glu Ser Thr Lys Leu Leu Met Arg Tyr Leu Ala Tyr Met
                165                 170                 175

Gly Gly Arg Ala Ala Thr Glu Gly Arg Thr Val Glu Gln Gln Val Leu
            180                 185                 190

Glu Ser Asn Pro Val Leu Glu Ala Phe Gly Asn Ala Lys Thr Val Arg
        195                 200                 205

Asn Asn Asn Ser Ser Arg Phe Gly Lys Phe Val Glu Ile Gln Phe Asp
    210                 215                 220

Gln Gly Gly Arg Ile Ser Gly Ala Ala Ile Arg Thr Tyr Leu Leu Glu
225                 230                 235                 240

Arg Ser Arg Val Cys Gln Leu Ser Asp Pro Glu Arg Asn Tyr His Cys
                245                 250                 255

Phe Tyr Met Leu Cys Ala Ala Pro Pro Glu Asp Val Gln Lys Tyr Lys
            260                 265                 270

Leu Gly Asn Pro Arg Thr Phe His Tyr Leu Asn Gln Ser Asn Cys Tyr
        275                 280                 285
```

```
Glu Leu Asp Val Val Asp Asp Ser Lys Glu Tyr Ile Ala Thr Arg Arg
    290                 295                 300

Ala Met Glu Ile Val Gly Ile Ser Ala Glu Glu Gln Asp Ala Ile Phe
305                 310                 315                 320

Arg Val Val Ala Ala Val Leu His Leu Gly Asn Ile Glu Phe Ala Lys
                325                 330                 335

Gly Lys Glu Met Asp Ser Ser Val Pro Lys Asp Glu Lys Ser Trp Phe
                340                 345                 350

His Leu Arg Thr Val Ala Glu Leu Leu Met Cys Asp Ser Lys Ala Leu
            355                 360                 365

Glu Asp Ser Leu Cys Lys Arg Val Ile Val Thr Arg Asp Glu Thr Ile
370                 375                 380

Thr Lys Trp Leu Asp Pro Glu Ser Ala Ala Val Ser Arg Asp Ala Leu
385                 390                 395                 400

Ala Lys Val Val Tyr Ser Arg Leu Phe Asp Trp Leu Val Asp Lys Ile
                405                 410                 415

Asn Ser Ser Ile Gly Gln Asp Pro His Ser Lys Tyr Leu Ile Gly Val
                420                 425                 430

Leu Asp Ile Tyr Gly Phe Glu Ser Phe Lys Thr Asn Ser Phe Glu Gln
            435                 440                 445

Phe Cys Ile Asn Leu Thr Asn Glu Lys Leu Gln Gln His Phe Asn Gln
450                 455                 460

His Val Phe Lys Met Glu Gln Glu Glu Tyr Thr Lys Glu Glu Ile Asp
465                 470                 475                 480

Trp Ser Tyr Ile Glu Phe Val Asp Asn Gln Asp Ile Leu Asp Leu Ile
                485                 490                 495

Glu Lys Lys Pro Gly Gly Ile Ile Ala Leu Leu Asp Glu Ala Cys Met
                500                 505                 510

Phe Pro Arg Ser Thr His Glu Thr Phe Ala Gln Lys Leu Tyr Gln Thr
            515                 520                 525

Phe Lys Asn His Lys Arg Phe Ala Lys Pro Lys Leu Ala Arg Ser Asp
530                 535                 540

Phe Thr Ile Cys His Tyr Ala Gly Asp Val Thr Tyr Gln Thr Glu Leu
545                 550                 555                 560

Phe Leu Asp Lys Asn Lys Asp Tyr Val Val Ala Glu His Gln Ala Leu
                565                 570                 575

Met Gly Ala Ser Lys Cys Ser Phe Val Ser Gly Leu Phe Pro Pro Leu
                580                 585                 590

Ala Glu Glu Ser Ser Lys Gln Ser Lys Phe Ser Ser Ile Gly Ser Arg
            595                 600                 605

Phe Lys Gln Gln Leu Gln Ala Leu Leu Glu Thr Leu Ser Ala Thr Glu
610                 615                 620

Pro His Tyr Ile Arg Cys Val Lys Pro Asn Asn Leu Leu Lys Pro Ala
625                 630                 635                 640

Ile Phe Glu Asn Lys Asn Ala Leu Gln Gln Leu Arg Cys Gly Gly Val
                645                 650                 655

Met Glu Ala Ile Arg Ile Ser Cys Ala Gly Phe Pro Thr Arg Lys Thr
            660                 665                 670

Phe Asp Glu Phe Val Asp Arg Phe Gly Leu Leu Ala Pro Glu Val Leu
            675                 680                 685

Asp Gly Ser Ser Asp Glu Val Thr Ala Cys Lys Arg Leu Leu Glu Lys
690                 695                 700

Val Gly Leu Thr Gly Tyr Gln Ile Gly Lys Thr Lys Val Phe Leu Arg
```

```
            705                 710                 715                 720
        Ala Gly Gln Met Ala Glu Leu Asp Ala Arg Arg Ser Glu Val Leu Gly
                        725                 730                 735

Arg Ser Ala Ser Ile Ile Gln Arg Lys Val Arg Ser Tyr Leu Ser Arg
                        740                 745                 750

Arg Ser Phe Ile Thr Leu Arg Arg Ser Ala Ile Gln Ile Gln Ser Ala
                        755                 760                 765

Cys Arg Gly Gln Ile Ala Arg His Val Tyr Glu Asn Met Arg Arg Glu
                        770                 775                 780

Ala Ala Ser Leu Arg Ile Gln Arg Asp Leu Arg Met Tyr Ile Ala Arg
        785                 790                 795                 800

Lys Ala Tyr Lys Asp Leu Cys Tyr Ser Ala Ile Ser Ile Gln Thr Gly
                        805                 810                 815

Met Arg Gly Met Ala Ala Arg Asp Asp Leu Arg Phe Arg Arg Gln Thr
                        820                 825                 830

Arg Ala Ala Ile Met Ile Gln Ser Gln Cys Arg Lys Tyr Leu Ala Arg
                        835                 840                 845

Leu His Tyr Lys Lys Leu Lys Lys Ala Ala Ile Thr Thr Gln Cys Ala
                        850                 855                 860

Trp Arg Gly Arg Val Ala Arg Lys Glu Leu Arg Asn Leu Lys Met Ala
        865                 870                 875                 880

Ala Arg Glu Thr Gly Ala Leu Gln Ala Ala Lys Asn Lys Leu Glu Lys
                        885                 890                 895

Gln Val Glu Glu Leu Thr Trp Arg Leu Gln Leu Glu Lys Arg Met Arg
                        900                 905                 910

Ala Asp Val Glu Glu Ala Lys Thr Gln Glu Asn Ala Lys Leu Gln Ser
                        915                 920                 925

Ala Leu Gln Glu Met Gln Leu Gln Phe Lys Glu Thr Lys Glu Met Leu
                        930                 935                 940

Val Lys Glu Arg Glu Ala Ala Ile Lys Val Thr Glu Lys Val Pro Val
        945                 950                 955                 960

Ile Gln Glu Val Pro Val Val Asp His Val Ala Leu Glu Lys Leu Thr
                        965                 970                 975

Ile Glu Asn Glu Lys Leu Lys Ala Leu Val Thr Ser Leu Glu Lys Lys
                        980                 985                 990

Ile Asp Glu Thr Glu Lys Lys Phe Glu Glu Thr Ser Arg Ile Ser Glu
                        995                 1000                1005

Glu Arg Leu Lys Gln Ala Leu Glu Ala Glu Ser Lys Ile Val Glu
                        1010                1015                1020

Leu Lys Thr Ala Met His Arg Leu Glu Glu Lys Phe Ser Asp Ile
                        1025                1030                1035

Glu Thr Glu Asn Gln Val Leu Arg Gln Gln Gly Leu Leu Gln Thr
                        1040                1045                1050

Pro Ala Lys Lys Leu Ser Glu Arg Pro Ile Pro Pro Thr Gln
                        1055                1060                1065

Ser Leu Glu Asn Gly His His Leu Asn Asp Glu Asn Lys Ala Asn
                        1070                1075                1080

Glu Pro Gln Ser Ala Thr Pro Val Lys Thr Tyr Gly Thr Glu Ser
                        1085                1090                1095

Asp Ser Lys Phe Arg Arg Ser His Ile Glu Arg Gln His Glu Asn
                        1100                1105                1110

Ile Asp Ala Leu Ile Ser Cys Val Thr Asn Asn Ile Gly Phe Ser
                        1115                1120                1125
```

```
His Gly Lys Pro Val Ala Ala Leu Thr Ile Tyr Arg Cys Leu Leu
    1130            1135                1140

His Trp Lys Ser Phe Glu Ala Glu Arg Thr Ser Val Phe Asp Arg
    1145            1150                1155

Leu Ile Gln Met Ile Gly Ser Ala Ile Glu Asn Glu Glu Asn Asn
    1160            1165                1170

Glu His Met Ala Tyr Trp Leu Ser Asn Thr Ser Thr Leu Leu Phe
    1175            1180                1185

Leu Leu Gln Arg Ser Ile Lys Ala Ala Gly Ala Ser Ala Thr Pro
    1190            1195                1200

Gln Arg Lys Pro Pro Ser Ala Thr Ser Leu Phe Gly Arg Met Thr
    1205            1210                1215

Met Gly Phe Arg Ser Ser Pro Ser Ser Ser Asn Leu Ala Ala Ala
    1220            1225                1230

Ala Ala Leu Ala Val Val Arg Gln Val Glu Ala Lys Tyr Pro Ala
    1235            1240                1245

Leu Leu Phe Lys Gln Gln Leu Ala Ala Tyr Val Glu Lys Ile Tyr
    1250            1255                1260

Gly Ile Ile Arg Asp Asn Leu Lys Lys Glu Leu Ala Ser Leu Leu
    1265            1270                1275

Ser Leu Cys Ile Gln Ala Pro Arg Thr Ser Lys Gly Ser Val Leu
    1280            1285                1290

Arg Ser Gly Arg Ser Phe Gly Lys Asp Ser Pro Leu Ser His Trp
    1295            1300                1305

Gln Ser Ile Val Asp Ser Leu Asn Thr Leu Leu Ser Thr Leu Lys
    1310            1315                1320

Gln Asn Phe Val Pro Pro Val Leu Ile Gln Lys Ile Tyr Thr Gln
    1325            1330                1335

Thr Phe Ser Tyr Ile Asn Val Gln Leu Phe Asn Ser Leu Leu Leu
    1340            1345                1350

Arg Arg Glu Cys Cys Thr Phe Ser Asn Gly Glu Tyr Val Lys Ser
    1355            1360                1365

Gly Leu Ala Glu Leu Glu Leu Trp Ser Ala Gln Ala Lys Glu Glu
    1370            1375                1380

Tyr Ala Gly Ser Ser Trp Asp Glu Leu Lys His Ile Arg Gln Ala
    1385            1390                1395

Val Gly Phe Leu Val Ile His Gln Lys Tyr Arg Ile Ser Tyr Asp
    1400            1405                1410

Glu Ile Thr Asn Asp Leu Cys Pro Ile Leu Ser Val Gln Gln Leu
    1415            1420                1425

Tyr Arg Ile Cys Thr Leu Tyr Trp Asp Asp Asn Tyr Asn Thr Arg
    1430            1435                1440

Ser Val Ser Pro Gly Val Ile Ser Ser Met Arg Val Leu Met Thr
    1445            1450                1455

Glu Asp Ser Asn Ser Ala Val Ser Asn Ser Phe Leu Leu Asp Asp
    1460            1465                1470

Asn Ser Gly Ile Pro Phe Ser Val Asp Asp Leu Ser Asn Ser Leu
    1475            1480                1485

Gln Glu Lys Asp Phe Met Asp Val Gln Pro Ala Glu Glu Leu Leu
    1490            1495                1500

Glu Asn Pro Ala Phe Gln Phe Leu His Glu
    1505            1510
```

<210> SEQ ID NO 23
<211> LENGTH: 25
<212> TYPE: DNA
<213> ORGANISM: Artificial
<220> FEATURE:
<223> OTHER INFORMATION: primer

<400> SEQUENCE: 23
caccatggtt gctaacttca atcca                                          25

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
ttagtgcaag aatacaaatg c                                              21

<210> SEQ ID NO 25
<211> LENGTH: 2226
<212> TYPE: DNA
<213> ORGANISM: Chara corallina
<220> FEATURE:
<223> OTHER INFORMATION: N-terminal region

<400> SEQUENCE: 25
atggatccag aaaaggcgag gtcttcggca ctggggattg gctcgccggc gtgggttgaa      60
gatgtggaga ccgtatggat agaagcgacc gtggtgaaac tcgatggcga tgccatcacg     120
gcacggacgg ttaacggcga tctggtggag acgacaatgg cgaatgctct tcccagggat     180
gaagatgtta cgatgcgggg ggttgatgac atgacgaagc tgtcgtattt gcacgagcct     240
ggcgttctgc acaatctcta caccagattc aagcacgatg agatctatac tttcacgggg     300
aatattttga ttgccgtcaa tccttttcaca aggcttccgc accttttcaa cacatacatg     360
atgaagcagt accaggatgc ccagccaggg gatctgaacc ctcatgttta ttctgtggct     420
gatgcggctt ataaagcaat gatggaagag atgaagagcc aggccatttt ggtgagtgga     480
gaaagtggcg ctggtaaaac agagacaaca aaacaaatca tgcagtacct ggctttcgtg     540
ggaggacgga cagtgggtga cgagagatca gttgagcagc aagtactcca gtcaaatcca     600
ttgctcgagg catttggaaa tgcgaagact gtgcggaata caactccag tcgctttggc     660 aagtttgtgg agatccagtt caacaatggg aaaatatctg cgcgggctgt gaggacgtat     720
ttattggaaa ggtcacgtgt cacgcagata tccagtccgg agcgaaacta tcattgcttc     780
tatcagcttg ttgctggtgc atcacctgag gatgcagaac ggttgaagct aggacctcct     840
gactcatttc attacttaaa tcagagcaag tgcgtggaag tcggagctat tgatgattgc     900
aaggagtacc aactcacgcg ggaggcgatg gatattgtgg gcatcactac agaagagcag     960
gaagcaattt ttcgaacaat tgctgctgtt cttcaccttg gcaacattga atttgattct    1020
ggagaatccg atgcatcaga ggtgtccact gagaagtcaa agtttcactt gaaagcggct    1080
gccgaaatgc tcatgtgcga tgagcaaatg ctggagaagt cgttgacaac acgaatcatg    1140
aaggcaacac gcactgagag catcacaaag atactgaaca gagccaggc cacagacaac    1200 agagactcca ttgcgaagac aatatatgcg aagctgtttg attggctggt caacaaggtc    1260
aacaagtcta ttggtcagga ccctcactcg actgttctta taggtgttct ggatatctat    1320
ggttttgaga gctttgagat caacagcttt gaacagttct gcatcaatct gacaaacgag    1380

```
aagctacagc agcatttcaa cacgcatgtg ttcaagatgg agcaagctga atatcggaag   1440
gaagagatca actgggacaa catagacttt gtggataaca ttgacgtgtt agaccttata   1500
gagaagaagc ctctcgggat cattgcactg ttggatgaag catgcatgtt accaagatca   1560
acagctgagt cgtttgcgag gaagctggga gacaccttca ataaccatag aaggttctcg   1620
aagcataagt tcaagagaac agcattcaca atcgatcatt atgcaggaca ggtggaatac   1680
agggcagatc ttttcttgga gaagaataaa gactttgtgg tacccgagca tcagcagctg   1740
cttcatgcat cgagatgtgc atttgtgtca ggactgtttc cagcagatga ggggacaaag   1800
gcaccatcga agtttatgtc cattggtagc caattcaagc tgcaactggc cgctcttatg   1860
gagacattga agctcacagc acctcactac atccgttgtg tgaagccaaa catgcaattg   1920
aagccacaga tcttcgagaa caagaacgtt cttcagcagc ttcgttgtag tggtgtattg   1980
gaggctgtcc gaatcagctg tgcagggttc cctacacgcc gcactttcga ggagttcctt   2040
gataggtttg gattgctgca tcctgaagta ctcatagaaa gtgctgaaga atctgctgat   2100
gagaaagtgg catgccaaaa tctcttggag aagtgcaacc tcaagggcta tcagattggc   2160
aagacaaagg tgttcctgcg cgccggtcaa atggctattt tagatacctt aagatctaat   2220
gttctc                                                              2226
```

<210> SEQ ID NO 26
<211> LENGTH: 2311
<212> TYPE: DNA
<213> ORGANISM: A. thaliana
<220> FEATURE:
<223> OTHER INFORMATION: Neck domain & Tail domain

<400> SEQUENCE: 26

```
atcagcaagc attattcaga gaaaagttcg gtcatatctc gctaaaaaga gtttcatcgt     60
tctgcgtaat tctgctaaac agattcagtc agtttgcaga ggttatctcg ctagaagtgt    120
atatgaaggc atgcgtaggg aagctgctgc tttaaaaatc cagagagact tgcgtaggtt    180
tctggctagg aaggcttaca cagagctata ttctgctgct gtttcggttc aagctggtat    240
gcgtggtatg gttgcccgga agaactatg ttttagaaga caaaccaaag ctgcaataat    300
aattcagact tggtgccgtg gataccggc tcgcctgcat tacagaaaac taagaaaagc    360
agctatcacg acccaatgtg catggagatc aaaagtggct cgtggagaac ttcgaaagct    420
taagatggct gctagagaaa ctggagcact ccaagcagcc aagaacaagc tagagaagca    480
agttgaagag ctgacctgga gattgcagtt agagaaacgg ataaggactg acctggaaga    540
ggccaaaaaa caagaaagtg caaaagcaca gtcttctttg gaggaattgc aactgaagtg    600
caaagaaacg gaggcattgc ttattaaaga acgtgaagct gccaagaaga ttgctgagac    660
tgccccgatt attaaggaga ttcctgtggt tgatcaggaa ttaatggata agatcacgaa    720
tgaaaatgaa aagctgaaga gtatggtgag ttcactggaa atgaaaatcg gtgagacaga    780
gaaaaaactt caagagacca ccaagattag ccaggataga ctaaatcaag cattggaggc    840
tgaatctaaa ctagtgaagt tgaagactgc aatgcagagg cttgaagaga aaatattaga    900
tatggaagct gagaagaaaa ttatgcatca gcaaacaata agcactcctg tgaggacaaa    960
tctaggacat cctccaactg cacctgttaa gaatttggaa aatggccacc aaacgaactt   1020
ggaaaaggag ttcaatgaag ccgagtttac aacaccagtt gatggcaagg ctgggaaatc   1080
tgctgcagaa cgtcaaatta tgaatgttga tgctctcatt gactgtgtaa aagacaacat   1140
```

```
cggtttcagt aatggaaaac ctgtggctgc atttacaatt tacaagtgtc tacttcactg    1200
gaagtgtttc gaatctgaga agactaatgt gtttgatcgt ctgattcaga tgattggttc    1260
cgcgattgag aatgaggatg acaatagtca cttggcgtat tggttgacaa gcacatcggc    1320
actactattt ttgcttcaaa aaagtcttaa aaccaatggc agcggagcaa cacaaagcaa    1380
gaagccacct gcttcaactt ctttatttgg aaggatggcc atgagcttcc gctcttcacc    1440
cgcttcaggc aaccttgctg ctgcagctga agctgctgct cttgcagtgg tccgcccagt    1500
ggaggcaaag tacccggctc tgcttttcaa gcaacagctt gcagcctatg ttgagaaaat    1560
gtttgggatg gttagggata acttgaagag agagttatca actttacttt ctctatgcat    1620
tcaggcaccc agatcttcta aaggagggat gctaagatct ggcaggtcct ttggaaaaga    1680
ttctcctgca gttcactggc aaagcattat cgacggtctt aattcgcttc ttgtcacact    1740
gaaagaaaat catgttcctt tagtactcat ccagaagata tactctcaaa cttttctcata   1800 cattaacgta caacttttca acagtctcct tctgcgtaaa gagtgctgta catttagcaa    1860
tggtgaattt gtaaaatccg ggcttgcgga gctagagcta tggtgttgtc aagccaaaga    1920
atattctggg ccgtcttggg aagaactgaa acatattaga caagccgttg ggttcttggt    1980
tatccaccag aaatacagaa tctcatacga tgaaatagca acgatctttt gcccggtcct    2040
cagtgtccag cagctttacc gtatttgcac cttatactgg gacgatagct ataacacccg    2100
aagcgtctca caagaagtga tatcgagtat gcggacactc atgacagagg aatccaatga    2160
tgcagacagt gattccttct tgttggatga tgattccagc attcctttct caatcgatga    2220
tatttcaagt tcgatggaag agaaggattt tgtaggaatc aaaccagcag aagaacttct    2280
tgaaaatcca gcatttgtat tcttgcacta a                                   2311
```

<210> SEQ ID NO 27
<211> LENGTH: 34
<212> TYPE: DNA
<213> ORGANISM: Artificial
<220> FEATURE:
<223> OTHER INFORMATION: primer

<400> SEQUENCE: 27

```
cacccgggta tgttcttaaa tttgaggcat agac                                  34
```

<210> SEQ ID NO 28
<211> LENGTH: 36
<212> TYPE: DNA
<213> ORGANISM: Artificial
<220> FEATURE:
<223> OTHER INFORMATION: primer

<400> SEQUENCE: 28

```
aggcctccat ggttcgtttc gtagatcaaa gacttc                                36
```

<210> SEQ ID NO 29
<211> LENGTH: 714
<212> TYPE: DNA
<213> ORGANISM: Aequorea victoria
<220> FEATURE:
<223> OTHER INFORMATION: sGFP gene

<400> SEQUENCE: 29

```
atggtgagca agggcgagga gctgttcacc ggggtggtgc ccatcctggt cgagctggac      60
ggcgacgtga acggccacaa gttcagcgtg tccggcgagg gcgagggcga tgccacctac     120
ggcaagctga ccctgaagtt catctgcacc accggcaagc tgcccgtgcc ctggcccacc     180
```

```
ctcgtgacca ccttcaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctgggggcac   420 aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actcacggca tggacgagct gtac          714
```

<210> SEQ ID NO 30
<211> LENGTH: 1540
<212> TYPE: PRT
<213> ORGANISM: Vitis vinifera

<400> SEQUENCE: 30

```
Met Leu Tyr Ala Val Lys Ala Arg Gln Ala Trp Asp Cys Ile Ala Arg
1               5                   10                  15

Arg Pro Gln Phe Leu Ile Arg Leu Ile Ala Glu Met Ala Ala Ser
                20                  25                  30

Val Ser Leu Gly Val Gly Ser Leu Val Trp Val Glu Asp Pro Glu Leu
        35                  40                  45

Ala Trp Leu Asp Gly Glu Val Glu Val Asn Gly Asp Thr Ile Lys
    50                  55                  60

Val Ala Cys Thr Ser Gly Lys Thr Val Val Lys Gly Ser Asn Val
65                  70                  75                  80

Tyr Pro Lys Asp Ala Glu Ala Pro Pro Cys Gly Val Asp Asp Met Thr
                85                  90                  95

Lys Leu Ala Tyr Leu His Glu Pro Gly Val Leu Gln Asn Leu Arg Ser
            100                 105                 110

Arg Tyr Asp Met Asn Glu Ile Tyr Thr Tyr Thr Gly Ser Ile Leu Ile
        115                 120                 125

Ala Val Asn Pro Phe Thr Arg Leu Pro His Leu Tyr Asp Asn His Met
    130                 135                 140

Met Ala Gln Tyr Lys Gly Ala Ala Phe Gly Glu Leu Ser Pro His Pro
145                 150                 155                 160

Phe Ala Val Ala Asp Ala Ala Tyr Arg Leu Met Met Asn Glu Lys Ile
                165                 170                 175

Ser Gln Ser Ile Leu Val Ser Gly Glu Ser Gly Ala Gly Lys Thr Glu
            180                 185                 190

Ser Thr Lys Leu Leu Met Arg Tyr Leu Ala Tyr Met Gly Gly Arg Ser
        195                 200                 205

Val Ala Glu Gly Arg Thr Val Glu Gln Gln Val Leu Glu Ser Asn Pro
    210                 215                 220

Val Leu Glu Ala Phe Gly Asn Ala Lys Thr Val Arg Asn Asn Asn Ser
225                 230                 235                 240

Ser Arg Phe Gly Lys Phe Val Glu Ile Gln Phe Asp Gln Arg Gly Arg
                245                 250                 255

Ile Ser Gly Ala Ala Ile Arg Thr Tyr Leu Leu Glu Arg Ser Arg Val
            260                 265                 270

Cys Gln Val Ser Asp Pro Glu Arg Asn Tyr His Cys Phe Tyr Met Leu
```

-continued

```
            275                 280                 285
Cys Ala Ala Pro Ala Glu Asp Val Gln Arg Phe Lys Leu Gly Asn Ala
290                 295                 300

Arg Thr Phe His Tyr Leu Asn Gln Ser Asn Cys Tyr Glu Leu Glu Gly
305                 310                 315                 320

Val Asp Asp Ser Lys Glu Tyr Ile Ala Thr Arg Lys Ala Met Asp Ile
                325                 330                 335

Val Gly Ile Ser Ser Asp Glu Gln Glu Gly Ile Phe Arg Val Val Ala
                340                 345                 350

Ala Ile Leu His Leu Gly Asn Ile Glu Phe Lys Lys Gly Lys Glu Thr
                355                 360                 365

Asp Ser Ser Glu Pro Lys Asp Glu Lys Ser Arg Phe His Leu Arg Thr
370                 375                 380

Ala Ala Glu Leu Phe Met Cys Asp Glu Lys Ala Leu Glu Asp Ser Leu
385                 390                 395                 400

Cys Lys Arg Ile Ile Val Thr Arg Asp Glu Thr Ile Thr Lys Cys Leu
                405                 410                 415

Asp Pro His Ser Ala Thr Leu Ser Arg Asp Ala Leu Ala Lys Ile Val
                420                 425                 430

Tyr Ser Arg Leu Phe Asp Trp Leu Val Asp Asn Ile Asn Cys Ser Ile
                435                 440                 445

Gly Gln Asp Pro Asp Ser Lys Cys Leu Ile Gly Val Leu Asp Ile Tyr
450                 455                 460

Gly Phe Glu Ser Phe Asn Thr Asn Ser Phe Glu Gln Phe Cys Ile Asn
465                 470                 475                 480

Leu Thr Asn Glu Lys Leu Gln Gln His Phe Asn Gln His Val Phe Lys
                485                 490                 495

Met Glu Gln Glu Glu Tyr Thr Lys Glu Glu Ile Asp Trp Ser Tyr Ile
                500                 505                 510

Asp Phe Val Asp Asn Lys Asp Val Leu Glu Leu Ile Glu Lys Lys Pro
                515                 520                 525

Gly Gly Ile Ile Ala Leu Leu Asp Glu Ala Cys Met Phe Pro Arg Ser
530                 535                 540

Thr His Glu Thr Phe Ser Gln Lys Leu Tyr Gln Thr Phe Lys Asn His
545                 550                 555                 560

Lys Arg Phe Ser Lys Pro Lys Leu Ser Arg Thr Asp Phe Thr Ile Cys
                565                 570                 575

His Tyr Ala Gly Asp Val Thr Tyr Gln Thr Asp Leu Phe Leu Asp Lys
                580                 585                 590

Asn Lys Asp Tyr Val Val Ala Glu His Gln Ala Leu Leu Ser Ala Ser
                595                 600                 605

Asn Cys Ser Phe Val Ala Gly Leu Phe Pro Pro Leu Ser Glu Glu Ser
                610                 615                 620

Ser Lys Ser Ser Lys Phe Ser Ser Ile Gly Ser Arg Phe Lys Gln Gln
625                 630                 635                 640

Leu Gln Ala Leu Leu Glu Thr Leu Ser Val Thr Glu Pro His Tyr Ile
                645                 650                 655

Arg Cys Val Lys Pro Asn Asn Leu Leu Lys Pro Ala Ile Phe Glu Asn
                660                 665                 670

Lys Asn Val Leu Gln Gln Leu Arg Cys Gly Gly Val Met Glu Ala Ile
                675                 680                 685

Arg Ile Ser Cys Ala Gly Tyr Pro Thr Lys Lys Pro Phe Asp Glu Phe
690                 695                 700
```

Ile Asp Arg Phe Gly Ile Leu Ala Pro Glu Val Leu Asp Gly Ser Ser
705                 710                 715                 720

Asp Glu Val Ala Ala Cys Lys Arg Leu Leu Glu Lys Val Gly Leu Lys
            725                 730                 735

Gly Tyr Gln Ile Gly Lys Thr Lys Val Phe Leu Arg Ala Gly Gln Met
        740                 745                 750

Ala Asp Leu Asp Ala Arg Arg Ser Glu Val Leu Gly Arg Ser Ala Ser
        755                 760                 765

Ile Ile Gln Arg Lys Val Arg Ser Tyr Leu Ser Arg Arg Ser Phe Ile
770                 775                 780

Ser Leu Arg His Ser Ala Ile Gln Leu Gln Ala Ala Cys Arg Gly Gln
785                 790                 795                 800

Leu Ala Arg Lys Val Tyr Glu Ser Met Arg Arg Glu Ala Ser Ala Leu
            805                 810                 815

Arg Ile Gln Lys Asp Leu Arg Met Phe Leu Ala Arg Lys Ala Tyr Lys
            820                 825                 830

Glu Leu Cys Ser Ser Ala Leu Cys Ile Gln Arg Gly Met Arg Gly Leu
            835                 840                 845

Ala Ala Arg Asn Glu Leu Arg Phe Arg Arg Gln Thr Arg Ala Ala Ile
850                 855                 860

Val Ile Gln Ser Gln Cys Arg Lys Tyr Leu Ala His Leu His Tyr Met
865                 870                 875                 880

Arg Leu Lys Lys Ala Ala Ile Thr Thr Gln Cys Ala Trp Arg Gly Arg
            885                 890                 895

Val Ala Arg Lys Glu Leu Arg Lys Leu Lys Met Ala Ala Lys Glu Thr
            900                 905                 910

Gly Ala Leu Gln Ala Ala Lys Asn Lys Leu Glu Lys Gln Val Glu Glu
            915                 920                 925

Leu Thr Trp Arg Leu Gln Leu Glu Lys Arg Met Arg Ala Asp Leu Glu
930                 935                 940

Glu Ala Lys Thr Gln Glu Asn Ala Lys Leu Gln Ser Ala Leu Gln Glu
945                 950                 955                 960

Val Gln Leu Glu Phe Lys Glu Thr Lys Glu Leu Leu Met Lys Glu Arg
            965                 970                 975

Glu Val Ala Lys Arg Ala Ala Glu Gln Ile Pro Val Ile Gln Glu Val
            980                 985                 990

Ser Val Ile Asp His Ala Met Leu Asp Lys Leu Thr Ala Glu Asn Glu
        995                 1000                1005

Lys Leu Lys Ser Leu Val Ser Ser Leu Glu Lys Arg Ile Asp Glu
    1010                1015                1020

Thr Gln Lys Lys Tyr Glu Glu Thr Asn Lys Leu Ser Glu Glu Arg
    1025                1030                1035

Leu Lys Gln Ala Leu Glu Ala Asp Gln Lys Ile Val Gln Leu Lys
    1040                1045                1050

Thr Ala Met Gln Arg Leu Glu Glu Lys Phe Ser Asp Val Glu Ser
    1055                1060                1065

Glu Asn Gln Ile Leu Arg Gln Gln Ala Leu Leu Lys Thr Pro Val
    1070                1075                1080

Lys Arg Ile Ala Asp Ile Leu Ser Thr Pro Glu Lys Ser Gln Gly
    1085                1090                1095

Leu Glu Asn Gly His His Leu Ser Glu Glu Asn Gly Ala Asn Glu
    1100                1105                1110

```
Pro Met Ser Ala Met Pro Ile Lys Glu Val Glu Thr Asp Ser Asp
    1115                1120                1125

Ser Lys Met Arg Lys Ser His Ile Glu Arg Gln Tyr Asp Asp Ile
    1130                1135                1140

Asp Ala Leu Ile Lys Cys Val Ser Lys Asp Ile Gly Phe Ser Gln
    1145                1150                1155

Gly Lys Pro Val Ala Ala Phe Thr Ile Tyr Lys Cys Leu Leu Gln
    1160                1165                1170

Trp Lys Ser Phe Glu Ala Glu Arg Thr Ser Val Phe Asp Arg Leu
    1175                1180                1185

Ile Gln Met Ile Gly Ser Ala Ile Glu Asn Gln Asp Asn Asn Asp
    1190                1195                1200

His Met Ala Tyr Trp Leu Ser Asn Thr Ser Thr Leu Leu Phe Leu
    1205                1210                1215

Leu Gln Lys Ser Leu Thr Ser Thr Gly Ala Ala Gly Ala Ala Pro
    1220                1225                1230

Arg Arg Lys Pro Pro Thr Ser Leu Phe Gly Arg Met Ala Met
    1235                1240                1245

Gly Phe Arg Ser Ser Pro Ser Ala Tyr Leu Ala Ala Pro Pro Phe
    1250                1255                1260

Glu Val Val Arg Gln Val Glu Ala Lys Tyr Pro Ala Leu Leu Phe
    1265                1270                1275

Lys Gln Gln Leu Thr Ala Tyr Val Glu Lys Ile Tyr Gly Ile Val
    1280                1285                1290

Arg Asp Asn Leu Lys Lys Glu Leu Thr Pro Leu Leu Ser Leu Cys
    1295                1300                1305

Ile Gln Ala Pro Arg Thr Ser Lys Gly Thr Ala Leu Arg Ser Gly
    1310                1315                1320

Arg Ser Phe Gly Lys Asp Ser Pro Ser His Trp Gln Ser Ile
    1325                1330                1335

Ile Glu Cys Leu Asn Thr Leu Leu Cys Thr Phe Lys Glu Asn Phe
    1340                1345                1350

Val Pro Pro Ile Leu Val Glu Lys Ile Phe Thr Gln Thr Phe Ser
    1355                1360                1365

Tyr Ile Asn Val Gln Leu Phe Asn Ser Leu Leu Leu Arg Arg Glu
    1370                1375                1380

Cys Cys Thr Phe Ser Asn Gly Glu Tyr Val Lys Ser Gly Leu Ala
    1385                1390                1395

Glu Leu Glu Leu Trp Cys Ala Gln Ala Lys Glu Glu Tyr Ala Gly
    1400                1405                1410

Ser Ser Trp Asp Glu Leu Lys His Ile Arg Gln Ala Val Gly Phe
    1415                1420                1425

Leu Val Ile His Gln Lys Tyr Arg Ile Ser Tyr Asp Glu Ile Thr
    1430                1435                1440

Asn Asp Leu Cys Pro Ile Leu Ser Val Gln Gln Leu Tyr Arg Ile
    1445                1450                1455

Cys Thr Leu Tyr Trp Asp Ser Asn Tyr Asn Thr Arg Ser Val Ser
    1460                1465                1470

Pro Asp Val Ile Ser Ser Met Arg Val Leu Met Thr Glu Asp Ser
    1475                1480                1485

Asn Asn Ala Val Ser Ser Ser Phe Leu Leu Asp Glu Asn Ser Ser
    1490                1495                1500

Ile Pro Phe Ser Val Asp Asp Leu Ser Asn Ser Leu Gln Glu Lys
```

Asp Phe Thr Asp Val Lys Pro Ala Glu Glu Leu Leu Asp Asn Ser
    1520                1525                1530

Ala Phe Gln Phe Leu Gln Glu
    1535                1540

<210> SEQ ID NO 31
<211> LENGTH: 1547
<212> TYPE: PRT
<213> ORGANISM: Vitis vinifera

<400> SEQUENCE: 31

Met Val Phe Ile Tyr Phe Phe Tyr Lys Glu Arg Asp Ser Ser Ala Gln
1               5                   10                  15

Ser Ala Met Ala Ala Pro Val Asn Ile Ile Val Gly Ser His Val Trp
            20                  25                  30

Val Glu Asp Pro Val Leu Ala Trp Ile Asp Gly Glu Val Phe Arg Ile
        35                  40                  45

Asn Ser Gln Glu Val His Val His Ile Thr Asn Gly Lys Thr Val Val
    50                  55                  60

Thr Asn Ile Ser Lys Val Phe Pro Lys Asp Thr Glu Ala Pro Pro Gly
65                  70                  75                  80

Gly Val Asp Asp Met Thr Lys Leu Ser Tyr Leu His Glu Pro Gly Val
                85                  90                  95

Leu Gln Asn Leu Ala Thr Arg Tyr Glu Leu Asn Glu Ile Tyr Thr Tyr
            100                 105                 110

Thr Gly Asn Ile Leu Ile Ala Val Asn Pro Phe Gln Arg Leu Pro His
        115                 120                 125

Leu Tyr Asp Thr His Met Met Glu Gln Tyr Lys Gly Ala Thr Phe Gly
    130                 135                 140

Glu Leu Ser Pro His Val Phe Ala Val Ala Asp Val Ala Phe Arg Ala
145                 150                 155                 160

Met Met Asn Glu Gly Lys Ser Asn Ser Ile Leu Val Ser Gly Glu Ser
                165                 170                 175

Gly Ala Gly Lys Thr Glu Thr Thr Lys Met Leu Met Arg Tyr Leu Ala
            180                 185                 190

Tyr Leu Gly Gly Arg Ser Gly Val Glu Gly Arg Thr Val Glu Gln Gln
        195                 200                 205

Val Leu Glu Ser Asn Pro Val Leu Glu Ala Phe Gly Asn Ala Lys Thr
    210                 215                 220

Val Arg Asn Asn Asn Ser Ser Arg Phe Gly Lys Phe Val Glu Ile Gln
225                 230                 235                 240

Phe Asp Lys Asn Gly Arg Ile Ser Gly Ala Ala Ile Arg Thr Tyr Leu
                245                 250                 255

Leu Glu Arg Ser Arg Val Cys Gln Ile Ser Asp Pro Glu Arg Asn Tyr
            260                 265                 270

His Cys Phe Tyr Leu Leu Cys Ala Ala Pro Pro Glu Glu Arg Glu Lys
        275                 280                 285

Tyr Lys Leu Gly Asn Pro Lys Ser Phe His Tyr Leu Asn Gln Ser Asn
    290                 295                 300

Cys Tyr Glu Leu Asp Gly Val Asn Asp Ala His Glu Tyr His Ala Thr
305                 310                 315                 320

Arg Arg Ala Met Asp Val Val Gly Ile Ser Glu Glu Glu Gln Glu Ala
                325                 330                 335

```
Ile Phe Arg Val Val Ala Ala Val Leu His Leu Gly Asn Ile Glu Phe
            340                 345                 350
Ala Lys Gly Lys Asp Ile Asp Ser Ser Ile Ile Lys Asp Glu Glu Ser
        355                 360                 365
Arg Phe His Leu Asn Met Thr Ala Glu Leu Leu Asn Cys Asp Ala Lys
    370                 375                 380
Gly Leu Glu Asp Ala Met Ile Lys Arg Val Met Val Thr Pro Glu Glu
385                 390                 395                 400
Val Ile Thr Arg Pro Leu Asp Pro Asp Ser Ala Leu Gly Ser Arg Asp
                405                 410                 415
Ala Leu Ala Lys Thr Ile Tyr Ser Arg Leu Phe Asp Trp Leu Val Asn
            420                 425                 430
Lys Ile Asn Asp Ser Ile Gly Gln Asp Pro Asn Ser Lys Ser Leu Ile
        435                 440                 445
Gly Val Leu Asp Ile Tyr Gly Phe Glu Ser Phe Lys Phe Asn Ser Phe
    450                 455                 460
Glu Gln Phe Cys Ile Asn Phe Thr Asn Glu Lys Leu Gln Gln His Phe
465                 470                 475                 480
Asn Gln His Val Phe Lys Met Glu Gln Glu Glu Tyr Thr Lys Glu Glu
                485                 490                 495
Ile Asn Trp Ser Tyr Ile Glu Phe Val Asp Asn Gln Asp Val Leu Asp
            500                 505                 510
Leu Ile Glu Lys Lys Pro Gly Gly Ile Ile Ala Leu Leu Asp Glu Ala
        515                 520                 525
Cys Met Phe Pro Lys Ser Thr His Glu Thr Phe Ala Gln Lys Leu Tyr
    530                 535                 540
Gln Thr Phe Lys Asn Asn Lys Arg Phe Ile Lys Pro Lys Leu Ser Arg
545                 550                 555                 560
Thr Ser Phe Ser Ile Ser His Tyr Ala Gly Glu Val Thr Tyr Leu Ala
                565                 570                 575
Asp Leu Phe Leu Asp Lys Asn Lys Asp Tyr Val Val Ala Glu His Gln
            580                 585                 590
Asp Leu Leu Ser Ala Ser Lys Cys Pro Phe Val Ala Ser Leu Phe Pro
        595                 600                 605
Leu Leu Pro Glu Glu Ser Ser Lys Ser Ser Lys Phe Ser Ser Ile Gly
    610                 615                 620
Ser Arg Phe Lys Leu Gln Leu Gln Ser Leu Met Glu Thr Leu Asn Ser
625                 630                 635                 640
Thr Glu Pro His Tyr Ile Arg Cys Val Lys Pro Asn Asn Val Leu Lys
                645                 650                 655
Pro Ala Ile Phe Glu Asn Leu Asn Ile Ile Gln Gln Leu Arg Cys Gly
            660                 665                 670
Gly Val Leu Glu Ala Ile Arg Ile Ser Cys Ala Gly Tyr Pro Thr Arg
        675                 680                 685
Arg Thr Phe Tyr Glu Phe Leu Arg Phe Gly Val Leu Ala Pro Glu
    690                 695                 700
Val Leu Glu Gly Asn Tyr Asp Asp Lys Val Ala Cys Gln Met Ile Leu
705                 710                 715                 720
Asp Lys Lys Gly Leu Lys Gly Tyr Gln Val Gly Lys Thr Lys Val Phe
                725                 730                 735
Leu Arg Ala Gly Gln Met Ala Glu Leu Asp Ala Arg Arg Ala Glu Val
            740                 745                 750
Leu Gly Asn Ala Ala Arg Ile Ile Gln Arg Gln Ile Arg Thr Tyr Ile
```

```
                 755                 760                 765
Ala Arg Lys Glu Phe Met Ala Leu Arg Lys Ala Ala Ile Gln Leu Gln
             770                 775                 780

Ser Gln Trp Arg Gly Lys Leu Ala Cys Lys Leu Tyr Glu Gln Met Arg
785                 790                 795                 800

Arg Glu Ala Ser Ala Val Arg Ile Gln Lys Asn Leu Arg Arg Tyr Thr
                 805                 810                 815

Ala Arg Lys Ser Tyr Leu Thr Val Trp Ser Thr Ala Ile Thr Leu Gln
             820                 825                 830

Thr Gly Leu Arg Ala Met Thr Ala Arg Asn Glu Phe Arg Phe Arg Lys
                 835                 840                 845

Gln Thr Lys Ala Ala Ile Leu Ile Gln Ala His Leu Arg Cys His Arg
850                 855                 860

Ala Tyr Ser Tyr Tyr Lys Ser Leu Gln Lys Ala Ala Ile Val Ser Gln
865                 870                 875                 880

Cys Gly Trp Arg Arg Val Ala Arg Arg Glu Leu Arg Lys Leu Lys
                 885                 890                 895

Met Ala Ala Arg Glu Thr Gly Ala Leu Lys Glu Ala Lys Asp Lys Leu
                 900                 905                 910

Glu Lys Arg Val Glu Glu Leu Thr Trp Arg Leu Gln Phe Glu Lys Arg
             915                 920                 925

Leu Arg Thr Asp Leu Glu Glu Ala Lys Ala Gln Glu Ile Ala Lys Phe
         930                 935                 940

Gln Asp Ala Leu His Glu Met Gln Leu Gln Val Glu Glu Ala Asn Ala
945                 950                 955                 960

Arg Val Ile Lys Glu Gln Glu Ala Ala Arg Lys Ala Ile Glu Glu Ala
                 965                 970                 975

Pro Pro Val Ile Lys Glu Thr Pro Val Ile Val Gln Asp Thr Glu Lys
                 980                 985                 990

Ile Asp Leu Leu Thr Ala Glu Val  Glu Ser Leu Lys Ala  Leu Leu Leu
                 995                 1000                1005

Ser Glu  Ser Lys Ala Ala Glu  Glu Ala Arg Lys Ala  Ser Thr Asp
     1010                1015                1020

Ala Glu  Ala Arg Asn Ala Glu  Leu Val Lys Lys Leu  Glu Asp Ala
     1025                1030                1035

Asp Arg  Lys Met Asp Gln Leu  Gln Asp Ser Met Gln  Arg Leu Glu
     1040                1045                1050

Glu Lys  Leu Ser Asn Ser Glu  Ser Glu Asn Gln Val  Leu Arg Gln
     1055                1060                1065

Gln Ala  Leu Ala Met Ser Pro  Thr Arg Lys Ala Val  Ser Ala Leu
     1070                1075                1080

Pro Lys  Pro Thr Ile Val Gln  Arg Thr Pro Glu Asn  Gly Asn Ile
     1085                1090                1095

Val Asn  Gly Glu Met Lys Val  Ala Ser Asp Leu Thr  Leu Ser Ile
     1100                1105                1110

Ser Asn  Pro Arg Glu Thr Glu  Ser Glu Glu Lys Pro  Gln Lys Ser
     1115                1120                1125

Leu Asn  Glu Lys His Gln Glu  Asn Gln Asp Leu Leu  Ile Arg Cys
     1130                1135                1140

Ile Thr  Gln Asn Leu Gly Phe  Ser Gly Ser Lys Pro  Val Ala Ala
     1145                1150                1155

Cys Val  Ile Tyr Lys Cys Leu  Leu His Trp Arg Ser  Phe Glu Val
     1160                1165                1170
```

Glu Arg Thr Ser Val Phe Asp Arg Ile Ile Gln Thr Ile Ala Ser
1175                1180                1185

Ala Ile Glu Val His Asp Asn Asn Asp Val Leu Ala Tyr Trp Leu
1190                1195                1200

Ser Asn Ser Ser Thr Leu Leu Leu Leu Gln His Thr Leu Lys
1205                1210                1215

Ala Ser Gly Ala Ala Ser Leu Thr Pro Gln Arg Arg Arg Ala Thr
1220                1225                1230

Ser Ala Ser Leu Phe Gly Arg Met Ser Gln Gly Leu Arg Thr Pro
1235                1240                1245

Pro Gln Ser Ala Gly Ile Ser Phe Leu Asn Gly Arg Met Leu Gly
1250                1255                1260

Arg Pro Asp Asp Leu Arg Gln Val Glu Ala Lys Tyr Pro Ala Leu
1265                1270                1275

Leu Phe Lys Gln Gln Leu Thr Ala Phe Leu Glu Lys Ile Tyr Gly
1280                1285                1290

Met Ile Arg Asp Ser Leu Lys Lys Glu Ile Ala Pro Leu Ile Gly
1295                1300                1305

Leu Cys Ile Gln Ala Pro Arg Thr Ser Arg Ala Ser Leu Val Lys
1310                1315                1320

Gly Arg Ser Gln Ala Asn Ala Val Ala Gln Gln Ala Leu Met Ala
1325                1330                1335

His Trp Gln Ser Ile Val Lys Ser Leu Asn Ser Tyr Leu Lys Thr
1340                1345                1350

Met Lys Ala Asn Tyr Val Pro Pro Phe Leu Val Arg Lys Val Phe
1355                1360                1365

Thr Gln Ile Phe Ser Phe Ile Asn Val Gln Leu Phe Asn Ser Leu
1370                1375                1380

Leu Leu Arg Arg Glu Cys Cys Ser Phe Ser Asn Gly Glu Tyr Val
1385                1390                1395

Lys Ser Gly Leu Ala Glu Leu Glu Gln Trp Cys Ser Tyr Ala Thr
1400                1405                1410

Glu Glu Tyr Ala Gly Ser Ala Trp Asp Glu Leu Lys His Ile Arg
1415                1420                1425

Gln Ala Val Glu Phe Leu Val Ile His Gln Lys Pro Lys Lys Thr
1430                1435                1440

Leu Asn Glu Ile Met Lys Glu Leu Cys Pro Val Leu Ser Ile Gln
1445                1450                1455

Gln Leu Tyr Arg Ile Ser Thr Met Tyr Trp Asp Asp Lys Tyr Gly
1460                1465                1470

Thr His Ser Val Ser Ser Glu Val Ile Ser Ser Met Arg Ile Met
1475                1480                1485

Met Thr Glu Ala Ser Asn Asn Ser Val Ser Ser Phe Leu Leu
1490                1495                1500

Asp Asp Asp Ser Ser Ile Pro Phe Thr Val Asp Asp Ile Ser Lys
1505                1510                1515

Ser Met Lys Gln Val Asp Thr Asp Val Asp Pro Pro Ser Leu Ile
1520                1525                1530

Arg Glu Asn Ser Gly Phe Val Phe Leu Leu Gln Arg Ser Glu
1535                1540                1545

<210> SEQ ID NO 32
<211> LENGTH: 1630

<212> TYPE: PRT
<213> ORGANISM: Vitis vinifera

<400> SEQUENCE: 32

Met Arg Val Ile His Lys Val Ala Thr Phe Leu Glu Lys Ile Leu His
1               5                   10                  15

Leu His Lys Ser Ile Val Val Ser Phe Tyr Met Leu Cys Gly Thr Ala
            20                  25                  30

Val Asn Ile Ile Val Gly Ser Gln Val Trp Val Glu Asp Pro Glu Ala
        35                  40                  45

Ala Trp Ile Asp Gly Leu Val Thr Lys Ile Asn Gly Ala Glu Ala Glu
    50                  55                  60

Ile Glu Leu Thr Lys Gly Lys Lys Val Val Asn Leu Leu Lys Ile
65                  70                  75                  80

Tyr Pro Lys Asp Thr Glu Ala Pro Ala Gly Gly Val Asp Asp Met Thr
                85                  90                  95

Lys Leu Ser Tyr Leu His Glu Pro Gly Val Leu Gln Asn Leu Lys Ser
            100                 105                 110

Arg Tyr Glu Leu Asn Glu Ile Tyr Thr Tyr Thr Gly Asn Ile Leu Ile
        115                 120                 125

Ala Ile Asn Pro Phe Gln Arg Leu Pro His Ile Tyr Asp Ala His Met
    130                 135                 140

Met Gln Gln Tyr Lys Gly Ala Pro Phe Gly Glu Leu Ser Pro His Val
145                 150                 155                 160

Phe Ala Val Ala Asp Val Ala Tyr Arg Ala Met Ile Asn Glu Gly Lys
                165                 170                 175

Ser Asn Ser Ile Leu Val Ser Gly Glu Ser Gly Ala Gly Lys Thr Glu
            180                 185                 190

Thr Thr Lys Met Leu Met Arg Tyr Leu Ala Phe Leu Gly Gly Arg Val
        195                 200                 205

Ala Thr Glu Gly Arg Thr Val Glu Gln Gln Val Leu Glu Ser Asn Pro
    210                 215                 220

Val Leu Glu Ala Phe Gly Asn Ala Lys Thr Val Arg Asn Asn Asn Ser
225                 230                 235                 240

Ser Arg Phe Gly Lys Phe Val Glu Ile Gln Phe Asp Lys Gln Gly Arg
                245                 250                 255

Ile Ser Gly Ala Ala Ile Arg Thr Tyr Leu Leu Glu Arg Ser Arg Val
            260                 265                 270

Cys Gln Ile Ser Asp Pro Glu Arg Asn Tyr His Cys Phe Tyr Leu Leu
        275                 280                 285

Cys Ala Ala Pro Gln Glu Glu Ile Glu Lys Tyr Lys Leu Gly Asn Pro
    290                 295                 300

Lys Ser Phe His Tyr Leu Asn Gln Ser Asn Cys Tyr Glu Leu Val Gly
305                 310                 315                 320

Val Ser Asp Ala His Asp Tyr Leu Ala Thr Arg Arg Ala Met Asp Ile
                325                 330                 335

Val Gly Ile Ser Glu Lys Glu Gln Glu Ala Ile Phe Arg Val Val Ala
            340                 345                 350

Ser Ile Leu His Ile Gly Asn Ile Glu Phe Thr Lys Gly Lys Glu Val
        355                 360                 365

Asp Ser Ser Val Pro Lys Asp Asp Lys Ala Lys Phe His Leu Lys Met
    370                 375                 380

Thr Ala Glu Leu Leu Met Cys Asp Pro Leu Ala Leu Glu Asp Ala Leu
385                 390                 395                 400

-continued

Cys Lys Arg Val Met Ile Thr Pro Glu Glu Val Ile Lys Arg Ser Leu
                405                 410                 415
Asp Pro Leu Ala Ala Thr Val Ser Arg Asp Gly Phe Ala Lys Thr Ile
            420                 425                 430
Tyr Ser Arg Leu Phe Asp Trp Leu Val Asp Lys Ile Asn Val Ser Ile
        435                 440                 445
Gly Gln Asp Pro Asn Ser Lys Ser Leu Ile Gly Val Leu Asp Ile Tyr
    450                 455                 460
Gly Phe Glu Ser Phe Lys Thr Asn Ser Phe Glu Gln Phe Cys Ile Asn
465                 470                 475                 480
Phe Thr Asn Glu Lys Leu Gln Gln His Phe Asn Gln His Val Phe Lys
                485                 490                 495
Met Glu Gln Glu Glu Tyr Thr Lys Glu Glu Ile Asp Trp Ser Tyr Ile
            500                 505                 510
Glu Phe Val Asp Asn Gln Asp Val Leu Asp Leu Ile Glu Lys Lys Pro
        515                 520                 525
Gly Gly Ile Val Ala Leu Leu Asp Glu Ala Cys Met Phe Pro Lys Ser
    530                 535                 540
Thr His Glu Thr Phe Ser Gln Lys Leu Tyr Gln Thr Phe Lys Val His
545                 550                 555                 560
Lys Arg Phe Ile Lys Pro Lys Leu Ser Arg Thr Asp Phe Thr Ile Ser
                565                 570                 575
His Tyr Ala Gly Glu Val Leu Tyr Gln Ser Asp Gln Phe Leu Asp Lys
            580                 585                 590
Asn Lys Asp Tyr Val Val Pro Glu His Gln Asp Leu Leu Gly Ala Ser
        595                 600                 605
Lys Cys Thr Phe Val Ala Gly Leu Phe Pro Pro Leu Pro Glu Glu Ser
    610                 615                 620
Ala Lys Ser Ser Lys Phe Ser Ser Ile Gly Ser Arg Phe Lys Leu Gln
625                 630                 635                 640
Leu Gln Gln Leu Met Asp Thr Leu Asn Ser Thr Glu Pro His Tyr Ile
                645                 650                 655
Arg Cys Val Lys Pro Asn Asn Leu Leu Lys Pro Ala Ile Phe Glu Asn
            660                 665                 670
Val Asn Ile Met Gln Gln Leu Arg Cys Gly Gly Val Leu Glu Ala Ile
        675                 680                 685
Arg Ile Ser Cys Ala Gly Tyr Pro Thr Arg Arg Pro Phe Phe Glu Phe
    690                 695                 700
Leu Asn Arg Phe Gly Ile Leu Ala Gln Glu Val Leu Glu Gly Asn Tyr
705                 710                 715                 720
Asp Glu Lys Val Ala Cys Arg Lys Ile Leu Glu Lys Lys Gly Leu Lys
                725                 730                 735
Gly Phe Gln Ile Gly Lys Thr Lys Val Phe Leu Arg Ala Gly Gln Met
            740                 745                 750
Ala Glu Leu Asp Ala Arg Arg Ala Glu Val Leu Ser Asn Ala Ala Lys
        755                 760                 765
Ala Ile Gln Arg Arg Ile Arg Thr Tyr His Ala Arg Lys Arg Phe Ile
    770                 775                 780
Ala Leu Arg Lys Ala Thr Ile His Val Gln Ser Leu Trp Arg Gly Met
785                 790                 795                 800
Leu Ala Cys Lys Leu Tyr Glu Ser Met Arg Arg Glu Ala Ala Ala Val
                805                 810                 815

Lys Ile Gln Lys Asn Ile Arg Arg His Glu Ala Arg Lys Thr Phe Asn
        820                 825                 830

Lys Leu Arg Val Ser Val Leu Val Leu Gln Thr Gly Leu Arg Ala Met
        835                 840                 845

Ala Ala His Arg Glu Phe Arg Phe Arg Lys Gln Thr Lys Ala Ala Ile
        850                 855                 860

Val Ile Gln Ala Arg Trp Arg Cys His Arg Ala Phe Ser Phe Tyr Lys
865                 870                 875                 880

Lys Leu Lys Arg Gly Ala Ile Val Ser Gln Cys Arg Trp Arg Gly Arg
                885                 890                 895

Val Ala Lys Lys Glu Leu Arg Lys Leu Lys Met Ala Ala Arg Glu Thr
        900                 905                 910

Gly Ala Leu Lys Glu Ala Lys Asp Lys Leu Glu Lys Thr Val Glu Asp
        915                 920                 925

Leu Thr Trp Arg Leu Gln Leu Glu Lys Arg Leu Arg Thr Asp Leu Glu
        930                 935                 940

Glu Ala Lys Ala Gln Glu Ile Ala Lys Leu Gln Asn Ser Leu Gln Ala
945                 950                 955                 960

Met Gln Thr Lys Val Asp Glu Thr Asn Ala Leu Leu Val Lys Glu Arg
                965                 970                 975

Glu Ala Ala Arg Lys Ala Ile Glu Glu Ala Pro Pro Val Ile Lys Glu
        980                 985                 990

Thr Pro Val Ile Val Glu Asp Thr Lys Lys Val Glu Ser Leu Thr Ala
        995                 1000                1005

Glu Val Glu Ser Phe Lys Ala Leu Leu Gln Ser Glu Lys Glu Arg
        1010                1015                1020

Ala Asp Asn Ser Glu Lys Lys Tyr Thr Glu Ala Gln Glu Ser Ser
        1025                1030                1035

Glu Glu Arg His Lys Lys Leu Glu Glu Thr Glu Lys Lys Val Gln
        1040                1045                1050

Gln Leu Gln Glu Ser Leu Ser Ser Val Lys Ser Asp Lys Val Ser
        1055                1060                1065

Asn Asp His Asp Ser Asn Gln Ile Ser Val Arg Lys Ile Val Lys
        1070                1075                1080

Pro Thr Thr Phe Ser Asn Val Trp Phe Ala Ile Pro Ile Glu Ser
        1085                1090                1095

Ser His Asn Gln Leu Leu Asp Arg Ser Ile Asp Gln Leu Leu Asp
        1100                1105                1110

Tyr Ser Tyr Lys Cys Lys Lys Cys Leu Lys Gln Ile Asn Leu
        1115                1120                1125

His Leu His Leu Met Leu Glu Glu Lys Leu Thr Asn Leu Glu Ser
        1130                1135                1140

Glu Asn Gln Val Leu Arg Gln Gln Ala Val Ser Met Ala Pro Asn
        1145                1150                1155

Lys Phe Leu Ser Gly Arg Ser Lys Ser Ile Val Gln Arg Ser Ser
        1160                1165                1170

Glu Gly Gly His Val Ala Gly Asp Ala Arg Thr Ser Leu Asp Leu
        1175                1180                1185

His Ser Pro Ser Leu Asn Gln Arg Glu Phe Ser Glu Val Glu Glu
        1190                1195                1200

Lys Pro Gln Lys Ser Leu Asn Glu Lys Gln Gln Glu Asn Gln Glu
        1205                1210                1215

Leu Leu Ile Arg Cys Ile Ala Gln His Leu Gly Phe Ala Gly Ser

```
              1220                1225                1230

Arg  Pro  Ile  Ala  Ala  Cys  Ile  Ile  Tyr  Lys  Cys  Leu  Leu  Gln  Trp
     1235                1240                1245

Arg  Ser  Phe  Glu  Val  Glu  Arg  Thr  Ser  Val  Phe  Asp  Arg  Ile  Ile
     1250                1255                1260

Gln  Thr  Ile  Gly  Gln  Ala  Ile  Glu  Thr  Gln  Asp  Asn  Asn  Asp  Ile
     1265                1270                1275

Leu  Ala  Tyr  Trp  Leu  Ser  Asn  Ala  Ser  Thr  Leu  Leu  Leu  Leu  Leu
     1280                1285                1290

Gln  Arg  Thr  Leu  Lys  Ala  Ser  Gly  Ala  Ala  Gly  Met  Ala  Pro  Gln
     1295                1300                1305

Arg  Arg  Arg  Ser  Ser  Ser  Ala  Thr  Leu  Phe  Gly  Arg  Met  Thr  Gln
     1310                1315                1320

Ser  Phe  Arg  Gly  Ala  Pro  Gln  Gly  Val  Asn  Leu  Ser  Phe  Thr  Asn
     1325                1330                1335

Gly  Gly  Leu  Thr  Gly  Gly  Val  Glu  Thr  Leu  Arg  Gln  Val  Glu  Ala
     1340                1345                1350

Lys  Tyr  Pro  Ala  Leu  Leu  Phe  Lys  Gln  Gln  Leu  Thr  Ala  Tyr  Val
     1355                1360                1365

Glu  Lys  Ile  Tyr  Gly  Met  Ile  Arg  Asp  Asn  Leu  Lys  Lys  Glu  Ile
     1370                1375                1380

Ser  Pro  Leu  Leu  Gly  Leu  Cys  Ile  Gln  Ala  Pro  Arg  Ile  Ser  Arg
     1385                1390                1395

Ala  Ser  Leu  Val  Lys  Gly  Pro  Ser  Arg  Ser  Val  Ala  Asn  Thr  Ala
     1400                1405                1410

Ala  Gln  Gln  Ala  Leu  Ile  Ala  His  Trp  Gln  Gly  Ile  Val  Lys  Ser
     1415                1420                1425

Leu  Gly  Asn  Phe  Leu  Asn  Thr  Leu  Lys  Ala  Asn  His  Val  Pro  Pro
     1430                1435                1440

Phe  Leu  Val  Arg  Lys  Val  Phe  Thr  Gln  Ile  Phe  Ser  Phe  Ile  Asn
     1445                1450                1455

Val  Gln  Leu  Phe  Asn  Ser  Leu  Leu  Leu  Arg  Arg  Glu  Cys  Cys  Ser
     1460                1465                1470

Phe  Ser  Asn  Gly  Glu  Tyr  Val  Lys  Ala  Gly  Leu  Ala  Glu  Leu  Glu
     1475                1480                1485

His  Trp  Cys  Tyr  Lys  Ala  Thr  Asp  Glu  Tyr  Ala  Gly  Ser  Ala  Trp
     1490                1495                1500

Asp  Glu  Leu  Lys  His  Ile  Arg  Gln  Ala  Ile  Gly  Phe  Leu  Val  Ile
     1505                1510                1515

His  Gln  Lys  Pro  Lys  Lys  Thr  Leu  Asp  Glu  Ile  Ser  His  Asp  Leu
     1520                1525                1530

Cys  Pro  Val  Leu  Ser  Ile  Gln  Gln  Leu  Tyr  Arg  Ile  Ser  Thr  Met
     1535                1540                1545

Tyr  Trp  Asp  Asp  Lys  Tyr  Gly  Thr  His  Ser  Val  Ser  Pro  Asp  Val
     1550                1555                1560

Ile  Ser  Asn  Met  Arg  Val  Leu  Met  Thr  Glu  Asp  Ser  Asn  Asn  Ala
     1565                1570                1575

Val  Ser  Asn  Ser  Phe  Leu  Leu  Asp  Asp  Asp  Ser  Ser  Ile  Pro  Phe
     1580                1585                1590

Ser  Val  Asp  Asp  Ile  Ser  Lys  Ser  Met  Glu  Gln  Ile  Asp  Ile  Ser
     1595                1600                1605

Asp  Ile  Glu  Pro  Pro  Pro  Leu  Ile  Arg  Glu  Asn  Ser  Gly  Phe  Ser
     1610                1615                1620
```

```
Phe Leu  Leu Pro Arg Ala Asp
    1625         1630

<210> SEQ ID NO 33
<211> LENGTH: 1587
<212> TYPE: PRT
<213> ORGANISM: Vitis vinifera

<400> SEQUENCE: 33

Met Asp Leu Arg Ser Phe Phe Ile Arg Phe Trp Ser Val Cys Lys Asn
1               5                   10                  15

Ile His Tyr Leu Tyr Ser Phe Phe Ile Leu Phe Leu Phe Phe Trp Met
            20                  25                  30

Ile Lys Gly Thr Pro Val Asn Ile Ile Val Gly Ser His Ala Trp Ala
        35                  40                  45

Glu Asp Pro Asp Ala Ala Trp Ile Asp Gly Glu Val Ile Gly Ile Glu
    50                  55                  60

Gly Arg Asn Ala Thr Ile Val Thr Thr Asp Gly Lys Thr Ile Val Ala
65                  70                  75                  80

Asp Ile Ser Asn Ile Tyr Pro Lys Asp Thr Glu Ala Pro Pro Ala Gly
                85                  90                  95

Val Asp Asp Met Thr Lys Leu Ala Tyr Leu His Glu Pro Gly Val Leu
            100                 105                 110

His Asn Leu Ala Ser Arg Phe Ala Leu Asn Glu Ile Tyr Thr Tyr Thr
        115                 120                 125

Gly Asn Ile Leu Ile Ala Val Asn Pro Phe Gln Arg Leu Pro His Leu
    130                 135                 140

Tyr Asp Ile His Met Met Gly Gln Tyr Lys Gly Ala Ala Phe Gly Glu
145                 150                 155                 160

Leu Ser Pro His Leu Phe Ala Val Ala Asp Thr Cys Tyr Arg Ala Met
                165                 170                 175

Ile Asn Glu Gln Lys Ser Gln Ser Ile Leu Val Ser Gly Glu Ser Gly
            180                 185                 190

Ala Gly Lys Thr Glu Thr Thr Lys Met Leu Met Arg Tyr Leu Ala Phe
        195                 200                 205

Met Gly Gly Arg Ser Gly Thr Glu Gly Arg Thr Val Glu Gln Gln Val
    210                 215                 220

Leu Glu Ser Asn Pro Val Leu Glu Ala Phe Gly Asn Ala Lys Thr Val
225                 230                 235                 240

Lys Asn Asn Asn Ser Ser Arg Phe Gly Lys Phe Val Glu Ile Gln Phe
                245                 250                 255

Asp Lys His Gly Lys Ile Ser Gly Ala Ala Val Arg Thr Tyr Leu Leu
            260                 265                 270

Glu Arg Ser Arg Val Cys Gln Val Ser Asp Pro Glu Arg Asn Tyr His
        275                 280                 285

Cys Phe Tyr Met Leu Cys Ala Ala Pro Pro Glu Asp Val Lys Lys Phe
    290                 295                 300

Lys Leu Gly Asp Pro Arg Ser Phe His Tyr Leu Asn Gln Thr Asn Cys
305                 310                 315                 320

Tyr Glu Val Ala Asn Val Asn Asp Ala Arg Glu Tyr Leu Glu Thr Arg
                325                 330                 335

Asn Ala Met Asp Val Val Gly Ile Ser Gln Asp Glu Gln Asp Ala Ile
            340                 345                 350

Phe Arg Val Val Ala Ala Ile Leu His Leu Gly Asn Ile Gly Phe Ile
```

-continued

```
                355                 360                 365
Lys Gly Lys Glu Ala Asp Ser Ser Lys Leu Lys Asp Glu Lys Ala Leu
            370                 375                 380
Tyr His Leu Arg Thr Ala Ala Glu Leu Leu Met Cys Asp Glu Lys Ala
385                 390                 395                 400
Leu Glu Asp Ser Leu Cys Gln Arg Val Ile Val Thr Pro Asp Gly Asn
                405                 410                 415
Ile Thr Lys Pro Leu Asp Pro Asp Leu Ala Val Phe Ser Arg Asp Ala
            420                 425                 430
Leu Ala Lys Thr Val Tyr Ser Arg Leu Phe Asp Trp Ile Val Asp Lys
            435                 440                 445
Ile Asn Ser Ser Ile Gly Gln Asp Pro Asn Ala Thr Ser Ile Ile Gly
            450                 455                 460
Val Leu Asp Ile Tyr Gly Phe Glu Ser Phe Lys Ile Asn Ser Phe Glu
465                 470                 475                 480
Gln Leu Cys Ile Asn Leu Thr Asn Glu Lys Leu Gln Gln His Phe Asn
                485                 490                 495
Gln His Val Phe Lys Met Glu Gln Glu Glu Tyr Lys Arg Glu Glu Ile
                500                 505                 510
Asn Trp Ser Tyr Val Glu Phe Ile Asp Asn Gln Asp Val Leu Asp Leu
            515                 520                 525
Ile Glu Lys Lys Pro Gly Gly Ile Ile Ala Leu Leu Asp Glu Ala Cys
            530                 535                 540
Met Phe Pro Lys Ser Thr His Glu Thr Phe Ala Gln Lys Met Tyr Gln
545                 550                 555                 560
Thr Tyr Lys Gly His Lys Arg Phe Ser Lys Pro Lys Leu Ala Arg Thr
                565                 570                 575
Asp Phe Thr Ile Asn His Tyr Ala Gly Asp Val Ile Tyr Gln Ala Asp
                580                 585                 590
Gln Phe Leu Asp Lys Asn Lys Asp Tyr Val Val Ala Glu His Gln Ala
            595                 600                 605
Leu Leu Asn Ala Ser Lys Cys Pro Phe Val Ala Asn Leu Phe Pro Leu
            610                 615                 620
Leu Ser Glu Glu Ala Ser Lys Gln Ser Lys Phe Ser Ser Ile Gly Thr
625                 630                 635                 640
Arg Phe Lys Gln Gln Leu Gln Ala Leu Met Glu Thr Leu Ser Thr Thr
                645                 650                 655
Glu Pro His Tyr Ile Arg Cys Val Lys Pro Asn Ala Val Leu Lys Pro
                660                 665                 670
Ala Ile Phe Glu Asn Phe Asn Val Leu Asn Gln Leu Arg Cys Gly Gly
            675                 680                 685
Val Leu Glu Ala Ile Arg Ile Ser Cys Ala Gly Tyr Pro Thr Lys Arg
            690                 695                 700
Thr Phe Asp Glu Phe Phe Asp Arg Phe Gly Met Leu Ala Pro Asp Val
705                 710                 715                 720
Leu Asp Gly Ala Asp Glu Lys Ser Ala Cys Ile Ala Ile Cys Asp Arg
            725                 730                 735
Met Gly Leu Lys Gly Tyr Gln Ile Gly Lys Thr Lys Val Phe Leu Arg
            740                 745                 750
Ala Gly Gln Met Ala Glu Leu Asp Ala Arg Arg Thr Glu Val Leu Ala
            755                 760                 765
Asn Ala Ala Arg Arg Ile Gln Arg Gln Ile Gln Thr His Leu Thr Arg
            770                 775                 780
```

```
Lys Glu Phe Ile Arg Gln Arg Arg Ala Thr Ile His Met Gln Lys Leu
785                 790                 795                 800

Trp Arg Ala Gln Leu Ala Arg Lys Leu Tyr Glu Ser Met Arg Arg Glu
            805                 810                 815

Ala Ala Ser Val Cys Val Gln Lys Asn Val Arg Ala His Thr Ala Arg
            820                 825                 830

Arg Asn Tyr Thr Asn Leu Gln Ala Ser Ala Met Ala Ile Gln Thr Gly
            835                 840                 845

Leu Arg Ala Met Ala Ala Arg Asn Glu Phe Arg Tyr Arg Arg Arg Thr
            850                 855                 860

Lys Ala Ala Thr Leu Ile Gln Thr Gln Trp Arg Gly Phe Gln Ala Phe
865                 870                 875                 880

Ser Ala Tyr Asn Gln Gln Lys Lys Ala Thr Leu Thr Leu Gln Cys Leu
            885                 890                 895

Trp Arg Gly Arg Ala Ala Arg Lys Glu Leu Arg Lys Leu Arg Met Ala
            900                 905                 910

Ala Arg Glu Thr Gly Ala Leu Lys Glu Ala Lys Asp Lys Leu Glu Lys
            915                 920                 925

Arg Val Glu Glu Leu Thr Trp Arg Leu Glu Phe Glu Lys His Leu Arg
930                 935                 940

Ile Asp Val Glu Glu Ala Lys Gly Gln Glu Ile Ser Lys Leu Gln Asn
945                 950                 955                 960

Ala Leu Leu Glu Met Gln Val Gln Leu Glu Glu Ala His Ala Ala Ile
            965                 970                 975

Ile Arg Glu Lys Glu Ala Ala Lys Ile Ala Ile Glu Gln Ala Pro Pro
            980                 985                 990

Val Leu Lys Glu Val Pro Val Val Asp Asn Thr Lys Met Asp Leu Leu
            995                 1000                1005

Lys Asn Gln Asn Glu Glu Leu Glu Gly Glu Val Ser Glu Leu Lys
1010                1015                1020

Lys Met Val Ala Glu Phe Glu Gln Lys Tyr Cys Glu Ala Gln Lys
1025                1030                1035

Glu Asn Thr Ala Arg Leu Lys Glu Ala Glu Glu Ser Phe Thr Arg
1040                1045                1050

Thr Ser Gln Leu Gln Glu Thr Ile Glu Arg Leu Glu Leu Asn Leu
1055                1060                1065

Ser Asn Leu Glu Ala Glu Asn Gln Val Leu Arg Gln Gln Ala Leu
1070                1075                1080

Val Ala Ser Thr Asn Glu Asp Leu Phe Glu Glu Met Lys Ile Leu
1085                1090                1095

Lys Asp Lys Ile Ala Asn Leu Glu Ser Glu Asn Glu Val Leu Arg
1100                1105                1110

Asn Gln Pro Thr Ser Ile Glu Gln Val Ala Ala Leu Glu Arg Val
1115                1120                1125

Pro Pro Gln Val Lys Ser Phe Asp Asn Gly His Lys Met Glu Glu
1130                1135                1140

Glu Leu Gln Thr Thr Lys Glu Leu Val Pro Phe Ala Pro Ile Leu
1145                1150                1155

Thr Lys Gln Arg Ser Leu Thr Asp Arg Gln Gln Glu Asn His Asp
1160                1165                1170

Val Leu Ile Lys Cys Leu Met Glu Asp Lys Arg Phe Asp Lys Asn
1175                1180                1185
```

Arg Pro Val Ala Ala Cys Ile Val Tyr Lys Ala Leu Leu Gln Trp
1190             1195                 1200

Arg Ser Phe Glu Ala Glu Lys Thr Asn Ile Phe Asp Arg Ile Ile
1205             1210                 1215

His Thr Ile Arg Ser Ser Ile Glu Ser Gln Glu Ser Ile Ser Asn
1220             1225                 1230

Leu Ala Tyr Trp Leu Ser Thr Thr Ser Thr Leu Leu Phe Leu Val
1235             1240                 1245

Gln Ser Thr Leu Lys Ala Ser Asn Thr Pro Asn Val Thr Ser Phe
1250             1255                 1260

Arg Ser Arg Asn Ser Pro Thr Thr Leu Phe Gly Arg Met Ala Gln
1265             1270                 1275

Gly Leu Arg Ser Ser Phe Pro Met Gly Val Ser Ser Gly Tyr
1280             1285                 1290

Ser Gly Met Val Gly Lys Pro Asn Thr His Ser Lys Val Glu Pro
1295             1300                 1305

Lys Tyr Pro Ala Leu Leu Phe Lys Gln His Leu Thr Ala Tyr Leu
1310             1315                 1320

Glu Lys Ile Tyr Gly Met Ile Arg Asp Ser Leu Lys Lys Glu Ile
1325             1330                 1335

Ser Pro Phe Leu Asn Leu Cys Ile Gln Ala Pro Arg Ser Thr Arg
1340             1345                 1350

Ala Arg Ser Ile Arg Gly Ser Ser Lys Asn Ile His Ser Asn Ile
1355             1360                 1365

Val Ala Lys Gln Gln Ala Ser Asn Ile His Trp Gln Asn Ile Val
1370             1375                 1380

Asn Ser Leu Asp His Thr Leu Gly Ile Met Ser Glu Asn His Val
1385             1390                 1395

Pro Ser Met Ile Thr Arg Lys Ile Phe Ser Gln Val Phe Ser Phe
1400             1405                 1410

Ile Asn Val Gln Leu Phe Asn Ser Leu Leu Leu Arg Arg Glu Cys
1415             1420                 1425

Cys Ser Phe Ser Asn Gly Glu Tyr Val Lys Ala Gly Leu Gln Glu
1430             1435                 1440

Leu Glu Gln Trp Cys Phe Lys Ala Lys Asp Glu Phe Ala Gly Ser
1445             1450                 1455

Ser Trp Asp Glu Leu Gln His Ile Arg Gln Ala Val Gly Phe Leu
1460             1465                 1470

Val Leu His Gln Lys Pro Gln Lys Phe Leu Asp Asp Ile Thr Asn
1475             1480                 1485

Glu Leu Cys Pro Met Leu Ser Ile Pro Gln Ile Tyr Arg Ile Gly
1490             1495                 1500

Thr Met Phe Trp Asp Asp Lys Tyr Gly Thr His Gly Leu Ser Pro
1505             1510                 1515

Asp Val Ile Gly Lys Met Arg Val Leu Met Thr Glu Asp Ser Ile
1520             1525                 1530

Asn Met Pro Asn Asn Ser Phe Leu Leu Asp Val Asp Ser Arg Ile
1535             1540                 1545

Pro Phe Ser Met Glu Glu Met Ser Arg Ser Leu Ile Asp Ile Asn
1550             1555                 1560

Leu Ser Tyr Val Asp Pro Pro Leu Leu Arg Gln Arg Ser Asp
1565             1570                 1575

Phe His Phe Leu Leu Gln Pro Thr Asp

<210> SEQ ID NO 34
<211> LENGTH: 1669
<212> TYPE: PRT
<213> ORGANISM: Vitis vinifera

<400> SEQUENCE: 34

Met Gln Ser Val Pro Val Lys Val Val Gly Ser His Val Trp Val
1               5                   10                  15

Glu Asp Pro Glu Ile Ala Trp Ile Asp Gly Glu Val Val Glu Val Asn
            20                  25                  30

Gly Glu Glu Ile Lys Ile Ile Cys Thr Ser Gly Lys Thr Ile Val Ala
        35                  40                  45

Asn Pro Ser Asp Val Tyr Pro Lys Asp Thr Glu Ala Pro Pro His Gly
50                  55                  60

Ile Asp Asp Met Thr Lys Leu Ala Tyr Leu His Glu Pro Gly Val Leu
65                  70                  75                  80

Gln Asn Leu Arg Cys Arg Tyr Asp Ile Asn Glu Ile Tyr Thr Tyr Thr
                85                  90                  95

Gly Ser Ile Leu Ile Ala Val Asn Pro Phe Gln Arg Leu Pro His Leu
            100                 105                 110

Tyr Asp Asn His Val Met Glu Gln Tyr Lys Gly Ala Val Phe Gly Glu
        115                 120                 125

Leu Ser Pro His Pro Phe Ala Val Ala Asp Ser Ala Tyr Arg Leu Met
    130                 135                 140

Ile Asn Asp Gly Val Ser Gln Ser Ile Leu Val Ser Gly Glu Ser Gly
145                 150                 155                 160

Ala Gly Lys Thr Glu Ser Thr Lys Met Leu Met Gln Tyr Leu Ala Tyr
                165                 170                 175

Met Gly Gly Arg Ala Ala Glu Gly Arg Thr Val Glu Gln Gln Val
            180                 185                 190

Leu Glu Ser Asn Pro Val Leu Glu Ala Phe Gly Asn Ala Lys Thr Val
        195                 200                 205

Arg Asn Asn Asn Ser Ser Arg Phe Gly Lys Phe Val Glu Ile Gln Phe
    210                 215                 220

Asp Gln Arg Gly Arg Ile Ser Gly Ala Ala Ile Arg Thr Tyr Leu Leu
225                 230                 235                 240

Glu Arg Ser Arg Val Cys Gln Val Ser Asp Pro Glu Arg Asn Tyr His
                245                 250                 255

Cys Phe Tyr Met Leu Cys Ala Ala Pro Pro Glu Asp Val Glu Lys Tyr
            260                 265                 270

Lys Leu Gly Asp Pro Arg Thr Phe His Tyr Leu Asn Gln Ser Asn Cys
        275                 280                 285

Tyr Glu Leu Asp Gly Val Asn Asp Ser Lys Glu Tyr Leu Ala Thr Arg
    290                 295                 300

Arg Ala Met Asn Val Val Gly Ile Ser Ser Val Glu Gln Asp Ala Ile
305                 310                 315                 320

Phe Arg Val Val Ala Ala Val Leu His Leu Gly Asn Ile Glu Phe Ala
                325                 330                 335

Lys Gly Gln Glu Ile Asp Ser Ser Glu Pro Lys Asp Asp Lys Ser Arg
            340                 345                 350

Phe His Leu Arg Met Ala Ala Glu Leu Phe Met Cys Asp Glu Lys Ser
        355                 360                 365

```
Leu Glu Asp Ser Leu Cys Lys Arg Val Ile Val Thr Arg Asp Glu Thr
370                 375                 380

Ile Thr Lys Trp Leu Asp Pro Asp Ser Ala Ala Val Ser Arg Asp Ala
385                 390                 395                 400

Leu Ala Lys Ile Val Tyr Ser Arg Leu Phe Asp Trp Ile Val Asp Lys
                405                 410                 415

Ile Asn Asn Ser Ile Gly Gln Asp Pro Asp Ser Lys Val Leu Ile Gly
            420                 425                 430

Val Leu Asp Ile Tyr Gly Phe Glu Ser Phe Lys Thr Asn Ser Phe Glu
        435                 440                 445

Gln Phe Cys Ile Asn Leu Thr Asn Glu Lys Leu Gln Gln His Phe Asn
450                 455                 460

Gln His Val Phe Lys Met Glu Gln Glu Glu Tyr Thr Lys Glu Glu Ile
465                 470                 475                 480

Asp Trp Ser Tyr Ile Asp Tyr Val Asp Asn Gln Asp Ile Leu Asp Leu
                485                 490                 495

Ile Glu Lys Lys Pro Gly Gly Ile Ile Ala Leu Leu Asp Glu Ala Cys
            500                 505                 510

Met Phe Pro Arg Ser Thr His Glu Thr Phe Ser Gln Lys Leu Tyr Gln
        515                 520                 525

Thr Phe Lys Ser His Lys Arg Phe Ser Lys Pro Lys Leu Ser Pro Thr
530                 535                 540

Asp Phe Thr Ile Tyr His Tyr Ala Gly Asp Val Thr Tyr Gln Thr Glu
545                 550                 555                 560

His Phe Leu Asp Lys Asn Lys Asp Tyr Val Val Ala Glu His Gln Ser
                565                 570                 575

Leu Leu Ser Ala Ser Arg Cys Ser Phe Val Ala Asp Leu Phe Pro Pro
            580                 585                 590

Leu Pro Glu Glu Ser Ser Lys Thr Ser Lys Phe Ser Ser Ile Gly Ser
        595                 600                 605

Arg Phe Lys Gln Gln Leu Gln Ser Leu Leu Glu Thr Leu Ser Ala Thr
610                 615                 620

Glu Pro His Tyr Val Arg Cys Val Lys Pro Asn Asn Leu Leu Lys Pro
625                 630                 635                 640

Ser Ile Phe Glu Asn Asn Asn Val Leu Gln Gln Leu Arg Cys Gly Gly
                645                 650                 655

Val Leu Glu Ala Ile Arg Ile Ser Cys Ala Gly Phe Pro Thr Arg Arg
            660                 665                 670

Thr Phe Val Glu Phe Ile Ala Arg Phe Gly Ile Leu Ala Pro Asp Val
        675                 680                 685

Leu Lys Gly Ser Cys Asp Glu Val Thr Thr Ser Lys Arg Ile Leu Glu
690                 695                 700

Lys Val Asp Leu Lys Gly Tyr Gln Ile Gly Lys Thr Lys Val Phe Leu
705                 710                 715                 720

Arg Ala Gly Gln Met Ala Glu Leu Asp Ala Arg Arg Asn Glu Val Leu
                725                 730                 735

Gly Arg Ser Ala Ser Ile Ile Gln Arg Lys Val Arg Ser Tyr Leu Ser
            740                 745                 750

Arg Lys Ser Phe Val Leu Leu Arg Gln Ser Ala Ile Gln Ile Gln Ala
        755                 760                 765

Ser Cys Arg Val Gln Val Ala Cys His Arg Tyr Glu Lys Met Arg Lys
770                 775                 780

Glu Ala Ala Cys Arg Thr Ile Gln Lys Asp Leu Arg Met Tyr Leu Ala
```

```
                785                 790                 795                 800
Arg Lys Ala Tyr Asn Arg Phe Cys Ser Ser Ala Leu Ser Ile Gln Thr
                    805                 810                 815
Gly Met Arg Ala Met Gly Ala Cys Asn Glu Leu Arg Phe Arg Lys Gln
                    820                 825                 830
Thr Lys Ala Ala Ile Ile Ile Lys Ser Arg Cys Arg Gly Tyr Leu Ala
                    835                 840                 845
His Leu His Tyr Leu Arg Ile Lys Lys Ala Ala Ile Ser Thr Gln Cys
            850                 855                 860
Ala Trp Arg Gly Lys Val Ala Arg Arg Glu Leu Arg Lys Leu Lys Ile
865                 870                 875                 880
Ala Ala Lys Glu Thr Gly Ala Leu Gln Ala Ala Lys Thr Met Leu Glu
                    885                 890                 895
Lys Gln Val Glu Glu Leu Thr Cys Gln Leu Gln Leu Glu Lys Arg Met
                900                 905                 910
Arg Asn Ile Cys Phe Cys Cys Leu Ser Tyr Phe Leu Pro Asp Pro Ser
            915                 920                 925
Ala Ile Leu Glu Val Gly Cys Val Asn Arg Phe Leu Ile Tyr Ser Leu
        930                 935                 940
Trp Val Leu Ile Pro Ile Ile Gln Glu Arg Trp Ile Asn Asn Leu
945                 950                 955                 960
Glu Arg Lys Gly Thr Thr Ile Lys Gln Glu Ile Arg Ser Ala Lys His
                965                 970                 975
Asp Glu Ile Lys Asp Thr Asn Tyr Ser Val Leu Gly Ser Leu Tyr His
            980                 985                 990
Lys Val Val Leu Lys Ser Ser Glu Leu Tyr Leu Ser Leu Pro Thr Lys
        995                 1000                1005
Asn Asn Leu Leu Met Thr Glu Arg Thr Leu Glu Ser Leu Ser Leu
        1010                1015                1020
Asp Phe Ser Cys Leu Ser Ala Leu Leu Leu Ser Val Arg Val Cys
        1025                1030                1035
Gln Ala Phe Gly His Met Leu Pro Glu Gln Cys Arg Lys Ser Ser
        1040                1045                1050
Ser Leu Phe Ser Arg Arg Asp Val Asp Phe Cys Leu Val Tyr His
        1055                1060                1065
Lys His Tyr Tyr Val Ile Tyr Ala Glu Lys Leu Val Lys Ala Ser
        1070                1075                1080
Leu Met Phe Trp Asp Val Ser Thr Leu Phe Gln Ala Asp Ile Glu
        1085                1090                1095
Glu Ala Lys Thr Gln Glu Asn Ala Lys Leu Gln Asn Ala Leu Gln
        1100                1105                1110
Glu Met Gln Val Gln Phe Gln Glu Thr Lys Glu Met Leu Ile Lys
        1115                1120                1125
Glu Arg Glu Asn Ala Lys Lys Ala Asp Glu Lys Val Pro Ile Ile
        1130                1135                1140
Gln Glu Val Pro Ala Ile Asp His Glu Met Met Asn Lys Leu Thr
        1145                1150                1155
Ala Glu Asn Glu Lys Leu Lys Asp Leu Val Ser Ser Leu Glu Lys
        1160                1165                1170
Lys Ile Asp Glu Thr Gln Arg Lys Tyr Glu Glu Thr Asn Lys Ile
        1175                1180                1185
Ser Glu Glu Arg Leu Lys Gln Ala Leu Asp Ala Glu Ser Lys Ile
        1190                1195                1200
```

Ile Gln Leu Lys Thr Asp Met Gln Arg Leu Glu Glu Lys Leu Ser
1205                1210                1215

Asp Met Glu Thr Glu Asp Gln Ile Leu Arg Gln Gln Val Ser Leu
1220                1225                1230

His Ser Pro Val Gly Lys Met Ser Glu His Leu Ala Ile Ala Ser
1235                1240                1245

Glu Pro His Leu Glu Asn Gly His His Gly Thr Glu Glu Lys Lys
1250                1255                1260

Thr Ser Glu Pro Glu Ser Ala Thr Pro Val Lys Lys Phe Gly Thr
1265                1270                1275

Glu Ser Asp Asn Lys Leu Arg Lys Ser Gln Ile Glu Arg Gln His
1280                1285                1290

Glu Ser Val Asp Ser Leu Ile Lys Cys Val Ser Gln Asp Leu Gly
1295                1300                1305

Phe Ser Asn Gly Lys Pro Val Ala Ala Val Thr Ile Tyr Lys Cys
1310                1315                1320

Leu Leu His Trp Lys Ser Phe Glu Ala Glu Lys Thr Ser Val Phe
1325                1330                1335

Asp Arg Leu Ile Gln Met Ile Gly Ser Ala Phe Glu Asn Gln Asp
1340                1345                1350

Asn Asn Glu His Met Ala Tyr Trp Leu Ser Asn Thr Ser Thr Leu
1355                1360                1365

Leu Leu Leu Leu Gln Arg Ser Leu Arg Thr Thr Gly Ala Ala Ser
1370                1375                1380

Leu Gln Gln Lys Pro Pro Ala Pro Ser Leu Phe Gly Arg Met
1385                1390                1395

Ala Gln Gly Phe Arg Ser Ser Phe Ser Ser Ala Asn Val Ser Val
1400                1405                1410

Asp Val Val Arg Gln Val Glu Ala Lys Tyr Pro Ala Leu Leu Phe
1415                1420                1425

Lys Gln Gln Leu Thr Ala Tyr Val Glu Thr Ile Tyr Gly Ile Ile
1430                1435                1440

Arg Asp Asn Leu Lys Lys Asp Leu Ser Ser Val Leu Ser Ser Cys
1445                1450                1455

Ile Gln Glu Pro Glu Thr Ser Arg Glu Ser Ser Gly Gln Ser Pro
1460                1465                1470

Gly Asn Ser Pro Leu Ala Ser Pro Trp Gln Ser Ile Ile Lys Ser
1475                1480                1485

Leu Asn Glu Leu Leu Ser Thr Leu Thr Glu Asn Phe Val Ser Pro
1490                1495                1500

Val Leu Val Gln Lys Ile Phe Ser Gln Ile Phe Ser Tyr Ile Asn
1505                1510                1515

Ser Gln Leu Phe Asn Ser Leu Leu Leu Arg Arg Glu Cys Cys Thr
1520                1525                1530

Phe Arg Asn Gly Glu Tyr Val Lys Ser Gly Leu Ala Glu Leu Glu
1535                1540                1545

Leu Trp Cys Gly Gln Thr Lys Glu Glu Tyr Val Gly Ser Ser Trp
1550                1555                1560

Asp Glu Leu Lys His Ile Arg Gln Ala Val Gly Phe Leu Val Ile
1565                1570                1575

His Gln Lys Ser Arg Ile Ser Tyr Asp Asp Leu Thr Asn Asp Leu
1580                1585                1590

```
Cys Pro Ser Leu Ser Val Gln Gln Leu Tyr Arg Ile Cys Thr Leu
    1595                1600                1605

Tyr Trp Asp Asp Asn Tyr Asn Thr Arg Ser Val Ser Pro Asp Val
    1610                1615                1620

Ile Ser Ser Met Arg Glu Gln Met Pro Glu Asp Ser Asn Asp Thr
    1625                1630                1635

Ala Thr Thr His Phe Cys Trp Val Thr Ile Pro Ala Phe Leu Ser
    1640                1645                1650

Gln Leu Met Thr Phe Leu Val Leu Phe Met Arg Arg Ile Ser Gln
    1655                1660                1665

Met

<210> SEQ ID NO 35
<211> LENGTH: 764
<212> TYPE: PRT
<213> ORGANISM: Homo sapiens
<220> FEATURE:
<223> OTHER INFORMATION: myosin Vb motor domain

<400> SEQUENCE: 35

Met Ser Val Gly Glu Leu Tyr Ser Gln Cys Thr Arg Val Trp Ile Pro
 1               5                  10                  15

Asp Pro Asp Glu Val Trp Arg Ser Ala Glu Leu Thr Lys Asp Tyr Lys
            20                  25                  30

Glu Gly Asp Lys Ser Leu Gln Leu Arg Leu Glu Asp Thr Ile Leu
        35                  40                  45

Glu Tyr Pro Ile Asp Val Gln Arg Asn Gln Leu Pro Phe Leu Arg Asn
    50                  55                  60

Pro Asp Ile Leu Val Gly Glu Asn Asp Leu Thr Ala Leu Ser Tyr Leu
65                  70                  75                  80

His Glu Pro Ala Val Leu His Asn Leu Lys Val Arg Phe Leu Glu Ser
                85                  90                  95

Asn His Ile Tyr Thr Tyr Cys Gly Ile Val Leu Val Ala Ile Asn Pro
            100                 105                 110

Tyr Glu Gln Leu Pro Ile Tyr Gly Gln Asp Val Ile Tyr Thr Tyr Ser
        115                 120                 125

Gly Gln Asn Met Gly Asp Met Asp Pro His Ile Phe Ala Val Ala Glu
    130                 135                 140

Glu Ala Tyr Lys Gln Met Ala Arg Asp Glu Lys Asn Gln Ser Ile Ile
145                 150                 155                 160

Val Ser Gly Glu Ser Gly Ala Gly Lys Thr Val Ser Ala Lys Tyr Ala
                165                 170                 175

Met Arg Tyr Phe Ala Thr Val Gly Gly Ser Ala Ser Glu Thr Asn Ile
            180                 185                 190

Glu Glu Lys Val Leu Ala Ser Ser Pro Ile Met Glu Ala Ile Gly Asn
        195                 200                 205

Ala Lys Thr Thr Arg Asn Asp Asn Ser Ser Arg Phe Gly Lys Tyr Ile
    210                 215                 220

Gln Ile Gly Phe Asp Lys Arg Tyr His Ile Ile Gly Ala Asn Met Arg
225                 230                 235                 240

Thr Tyr Leu Leu Glu Lys Ser Arg Val Val Phe Gln Ala Asp Asp Glu
                245                 250                 255

Arg Asn Tyr His Ile Phe Tyr Gln Leu Cys Ala Ala Ala Gly Leu Pro
            260                 265                 270

Glu Phe Lys Glu Leu Ala Leu Thr Ser Ala Glu Asp Phe Phe Tyr Thr
```

-continued

```
            275                 280                 285
Ser Gln Gly Gly Asp Thr Ser Ile Glu Gly Val Asp Asp Ala Glu Asp
            290                 295                 300
Phe Glu Lys Thr Arg Gln Ala Phe Thr Leu Leu Gly Val Lys Glu Ser
305                 310                 315                 320
His Gln Met Ser Ile Phe Lys Ile Ile Ala Ser Ile Leu His Leu Gly
                    325                 330                 335
Ser Val Ala Ile Gln Ala Glu Arg Asp Gly Asp Ser Cys Ser Ile Ser
                340                 345                 350
Pro Gln Asp Val Tyr Leu Ser Asn Phe Cys Arg Leu Leu Gly Val Glu
            355                 360                 365
His Ser Gln Met Glu His Trp Leu Cys His Arg Lys Leu Val Thr Thr
        370                 375                 380
Ser Glu Thr Tyr Val Lys Thr Met Ser Leu Gln Gln Val Ile Asn Ala
385                 390                 395                 400
Arg Asn Ala Leu Ala Lys His Ile Tyr Ala Gln Leu Phe Gly Trp Ile
                    405                 410                 415
Val Glu His Ile Asn Lys Ala Leu His Thr Ser Leu Lys Gln His Ser
                420                 425                 430
Phe Ile Gly Val Leu Asp Ile Tyr Gly Phe Glu Thr Phe Glu Val Asn
            435                 440                 445
Ser Phe Glu Gln Phe Cys Ile Asn Tyr Ala Asn Glu Lys Leu Gln Gln
        450                 455                 460
Gln Phe Asn Ser His Val Phe Lys Leu Glu Gln Glu Glu Tyr Met Lys
465                 470                 475                 480
Glu Gln Ile Pro Trp Thr Leu Ile Asp Phe Tyr Asp Asn Gln Pro Cys
                    485                 490                 495
Ile Asp Leu Ile Glu Ala Lys Leu Gly Ile Leu Asp Leu Leu Asp Glu
                500                 505                 510
Glu Cys Lys Val Pro Lys Gly Thr Asp Gln Asn Trp Ala Gln Lys Leu
            515                 520                 525
Tyr Asp Arg His Ser Ser Gln His Phe Gln Lys Pro Arg Met Ser
        530                 535                 540
Asn Thr Ala Phe Ile Ile Val His Phe Ala Asp Lys Val Glu Tyr Leu
545                 550                 555                 560
Ser Asp Gly Phe Leu Glu Lys Asn Arg Asp Thr Val Tyr Glu Glu Gln
                    565                 570                 575
Ile Asn Ile Leu Lys Ala Ser Lys Phe Pro Leu Val Ala Asp Leu Phe
                580                 585                 590
His Asp Asp Lys Asp Pro Val Pro Ala Thr Thr Pro Gly Lys Gly Ser
            595                 600                 605
Ser Ser Lys Ile Ser Val Arg Ser Ala Arg Pro Pro Met Lys Val Ser
        610                 615                 620
Asn Lys Glu His Lys Lys Thr Val Gly His Gln Phe Arg Thr Ser Leu
625                 630                 635                 640
His Leu Leu Met Glu Thr Leu Asn Ala Thr Thr Pro His Tyr Val Arg
                    645                 650                 655
Cys Ile Lys Pro Asn Asp Glu Lys Leu Pro Phe His Phe Asp Pro Lys
                660                 665                 670
Arg Ala Val Gln Gln Leu Arg Ala Cys Gly Val Leu Glu Thr Ile Arg
            675                 680                 685
Ile Ser Ala Ala Gly Tyr Pro Ser Arg Trp Ala Tyr His Asp Phe Phe
        690                 695                 700
```

```
Asn Arg Tyr Arg Val Leu Val Lys Lys Arg Glu Leu Ala Asn Thr Asp
705                 710                 715                 720

Lys Lys Ala Ile Cys Arg Ser Val Leu Glu Asn Leu Ile Lys Asp Pro
                725                 730                 735

Asp Lys Phe Gln Phe Gly Arg Thr Lys Ile Phe Phe Arg Ala Gly Gln
            740                 745                 750

Val Ala Tyr Leu Glu Lys Leu Arg Ala Asp Lys Phe
        755                 760
```

<210> SEQ ID NO 36
<211> LENGTH: 5547
<212> TYPE: DNA
<213> ORGANISM: Homo sapiens
<220> FEATURE:
<223> OTHER INFORMATION: myosin Vb

<400> SEQUENCE: 36

| | | | | | |
|---|---|---|---|---|---|
| atgtcggtgg | gcgagctcta | cagccagtgc | acaagggtct | ggatccctga | ccctgatgag | 60 |
| gtatggcgct | cagctgagtt | aaccaaggac | tacaaagaag | gagacaagag | cctacagctc | 120 |
| agactggagg | atgaaacgat | tctggaatac | ccaattgatg | tacaacgcaa | ccagctgccc | 180 |
| ttcttacgga | atccagatat | cttggtggga | gaaaatgacc | tgactgccct | tagctatctt | 240 |
| catgagcctg | cagttttgca | taatttgaag | gtccgtttcc | tggagtccaa | ccatatctac | 300 |
| acttactgtg | gtatcgtact | tgttgccatt | aatccttatg | aacagttgcc | aatctatgga | 360 |
| caagatgtca | tctataccta | cagtggccaa | acatgggag | acatggaccc | ccacatcttt | 420 |
| gctgtggcag | aagaagccta | caagcagatg | gccagagatg | agaagaatca | gtccatcata | 480 |
| gtcagtgggg | agtctggagc | cgggaagacg | gtatcagcca | gtatgccat | gcgctatttc | 540 |
| gccaccgttg | gtggctcggc | cagtgaaacc | aacatcgaag | agaaggtgct | ggcatccagt | 600 |
| cccatcatgg | aggccattgg | aaatgccaag | accaccgca | atgacaacag | cagccgtttt | 660 |
| ggcaagtaca | tccagattgg | cttgacaaa | aggtaccaca | tcatcggggc | caacatgagg | 720 |
| acttacctct | tggagaagtc | cagagtggtc | ttccaggcag | atgatgagag | gaattaccac | 780 |
| atcttttacc | agctctgtgc | tgctgccggt | cttccagaat | ttaaagagct | tgcactaaca | 840 |
| agtgcagagg | actttttcta | tacatcacag | ggaggagaca | cttccatcga | gggtgtggac | 900 |
| gatgctgagg | actttgagaa | gactcgacaa | gccttcacac | tcctcggagt | gaaagagtcc | 960 |
| catcagatga | gcattttaa | gataattgct | tctatcttgc | accttggaag | tgtggcgatt | 1020 |
| caggctgagc | gtgatggtga | ttcctgtagt | atatcacccc | aggatgtata | cctaagcaac | 1080 |
| ttctgccgac | tgctaggggt | ggagcacagt | cagatggagc | actggctgtg | tcatcgcaag | 1140 |
| ctggtcacca | cctcggagac | ctacgtcaag | accatgtccc | tgcagcaggt | gatcaatgcg | 1200 |
| cgcaacgccc | tggcgaagca | catctatgcc | cagttgttcg | gctggattgt | ggagcacatc | 1260 |
| aacaaggccc | tgcacacctc | cctcaagcag | cactccttca | tcgggtcct | ggacatctat | 1320 |
| gggtttgaga | catttgaggt | aaacagcttt | gagcagttct | gtatcaacta | tgcaaatgaa | 1380 |
| aagctccagc | agcagttcaa | ctcgcatgtt | ttcaaactgg | agcaagaaga | atacatgaag | 1440 |
| gaacagatcc | cttggaccct | gattgatttt | tatgataacc | aaccttgtat | cgacctcatt | 1500 |
| gaagccaagc | tgggtatctt | ggacctgttg | gatgaagaat | gtaaggtccc | caaaggaact | 1560 |
| gaccagaact | gggctcagaa | gctctatgac | cggcactcca | gcagccagca | cttccagaag | 1620 |
| ccccgcatgt | ccaacacggc | cttcatcatc | gtccactttg | cagacaaggt | ggagtacctc | 1680 |

```
tctgatggtt ttctggagaa aaacagagac acggtgtatg aagagcagat caatatcctg    1740
aaggccagca agttcccact agtggctgac ttgtttcatg atgacaagga ccctgttcct    1800
gccaccaccc ctgggaaggg gtcatcttcg aagatcagcg tccgttctgc cagaccccc    1860 atgaaagtct ccaacaagga gcacaagaaa accgttggcc accagttccg tacctccctg    1920
catctgctca tggagaccct gaatgccacg acacctcact atgtccgctg catcaagccc    1980
aacgatgaga agctccccct tcactttgac ccaaagagag cagtgcagca actcagagcc    2040
tgcggggtgt tggagacgat tcgaatcagt gcagctggct acccatccag gtgggcctac    2100
catgactttt tcaaccggta tcgggtgctg gtcaagaaga gagagctcgc caacacagac    2160
aaaaaggcca tctgcaggtc tgtcctggag aacctcatca aggaccccga caagttccag    2220
tttggccgca ccaagatctt ctttcgagca ggccaggtgg cctacctgga aagctgcgg    2280 gctgacaagt tccggacagc caccatcatg atccagaaaa ctgtccgggg atggctgcag    2340
aaggtgaaat atcacaggct gaaggggggct accttaaccc tgcagaggta ctgccgggga    2400
cacctggccc gcaggctggc tgagcacctg cggaggatca gagcggctgt ggtgctccag    2460
aaacattacc gcatgcagag ggcccgccag gcctaccaga gggtccgcag agctgccgtt    2520
gttatccagg ccttcacccg ggccatgttt gtgcggagaa cctaccgcca ggtcctcatg    2580
gagcacaagg ccaccaccat ccagaagcac gtgcggggct ggatggcacg caggcacttc    2640
cagcggctgc gggatgcagc cattgtcatc cagtgtgcct tccggatgct caaggccagg    2700
cgggagctga aggccctcag gattgaggcc cgctcagcag agcatctgaa acgtctcaac    2760
gtgggcatgg agaacaaggt ggtccagctg cagcggaaga tcgatgagca gaacaaagag    2820
ttcaagacac tttcagagca gttgtccgtg accacctcaa catacaccat ggaggtagag    2880
cggctgaaga aggagctggt gcactaccag cagagcccag gtgaggacac cagcctcagg    2940
ctgcaggagg aggtggagag cctgcgcaca gagctgcaga gggcccactc ggagcgcaag    3000
atcttggagg acgcccacag cagggagaaa gatgagctga ggaagcgagt tgcagacctg    3060
gagcaagaaa atgctctctt gaaagatgag aaagaacagc tcaacaacca aatcctgtgc    3120
cagtctaaag atgaatttgc ccagaactct gtgaaggaaa atctcatgaa gaaagaactg    3180
gaggaggagc gatcccggta ccagaacctt gtgaaggaat attcacagtt ggagcagaga    3240
tacgacaacc ttcgggatga aatgaccatc ataaagcaaa ctccaggtca taggcggaac    3300
ccatcaaacc aaagtagctt agaatctgac tccaattacc cctccatctc cacatctgag    3360
atcggagaca ctgaggatgc cctccagcag gtggaggaaa ttggcctgga aaggcagcc    3420 atggacatga cggtcttcct gaagctgcag aagagagtac gggagctgga gcaggagagg    3480
aaaaagctgc aagtgcagct ggagaagaga aacagcagg acagcaagaa agtccaggcg    3540
gaaccaccac agactgacat agatttggac ccgaatgcag atctggccta caatagtctg    3600
aagaggcaag agctggagtc agagaacaaa aagctgaaga atgacctgaa tgagctgagg    3660
aaagccgtgg ccgaccaagc cacgcagaat aactccagcc acggctcccc agatagctac    3720
agcctcctgc tgaaccagct caagctggcc cacgaggagc tcgaggtgcg caaggaggag    3780
gtgctcatcc tcaggaccca gatcgtgagc gccgaccagc ggcgactcgc cggcaggaac    3840
gcggagccga acattaatgc cagatcaagt tggcctaaca gtgaaaagca tgttgaccag    3900
gaggatgcca ttgaggccta tcacggggtc tgccagacaa acagcaagac tgaggattgg    3960
ggatatttaa atgaagatgg agaactcggc ttggcctacc aaggcctaaa gcaagttgcc    4020
aggctgctgg aggctcagct gcaggcccag agcctggagc atgaggagga ggtggagcat    4080
```

```
ctcaaggctc agctcgaggc cctgaaggag gagatggaca acagcagca gaccttctgc    4140 cagacgctac tgctctcccc agaggcccag gtggaattcg gcgttcagca ggaaatatcc    4200
cggctgacca acgagaatct ggaccttaaa gaactggtag aaaagctgga aagaatgag     4260 aggaagctca aaaagcaact gaagatttac atgaagaaag cccaggacct agaagctgcc    4320
caggcattgg cccagagtga gaggaagcgc catgagctca acaggcaggt cacggtccag    4380
cggaaagaga aggatttcca gggcatgctg gagtaccaca agaggacga ggccctcctc     4440 atccggaacc tggtgacaga cttgaagccc agatgctgt cgggcacagt gccctgtctc     4500
cccgcctaca tcctctacat gtgcatccgg cacgcggact acaccaacga cgatctcaag    4560
gtgcactccc tgctgaccct caccatcaac ggcattaaga aagtcctgaa aaagcacaat    4620
gatgactttg agatgacgtc attctggtta tccaacacct gccgccttct tcactgtctg    4680
aagcagtaca gcggggatga gggcttcatg actcagaaca ctgcaaagca gaatgaacac    4740
tgtcttaaga attttgaccct caccgaatac cgtcaggtgc tgagtgacct ttccattcag    4800
atctaccagc agctcattaa aattgccgag ggcgtgttac agccgatgat agtttctgcc    4860
atgttggaaa atgagagcat tcagggtcta tctggtgtga agcccaccgg ctaccggaag    4920
cgctcctcca gcatggcaga tggggataac tcatactgcc tggaagctat catccgccag    4980
atgaatgcct ttcatacagt catgtgtgac cagggcttgg accctgagat catcctgcag    5040
gtattcaaac agctcttcta catgatcaac gcagtgactc ttaacaaccct gctcttgcgg    5100 aaggacgtct gctcttggag cacaggcatg caactcaggt acaatataag tcagcttgag    5160
gagtggcttc ggggaagaaa ccttcaccag agtggagcag ttcagaccat ggaacctctg    5220
atccaagcag cccagctcct gcaattaaag aagaaaaccc aggaggacgc agaggctatc    5280
tgctccctgt gtacctccct cagcacccag cagattgtca aaattttaaa cctttatact    5340
cccctgaatg aatttgaaga acgggtaaca gtggccttta tacgaacaat ccaggcacaa    5400
ctacaagagc ggaatgaccc tcagcaactg ctattagatg ccaagcacat gtttcctgtt    5460
ttgtttccat ttaatccatc ttctctaacc atggactcaa tccacatccc agcgtgtctc    5520
aatctggaat tcctcaatga agtctga                                       5547
```

<210> SEQ ID NO 37
<211> LENGTH: 4608
<212> TYPE: DNA
<213> ORGANISM: Artificial
<220> FEATURE:
<223> OTHER INFORMATION: Chimeric myosin with Homo sapiens myosin Vb motor domain and Arabidopsis thaliana myosin XI-2 neck and tail domains

<400> SEQUENCE: 37

```
atgtcggtgg gcgagctcta cagccagtgc acaagggtct ggatccctga ccctgatgag     60
gtatggcgct cagctgagtt aaccaaggac tacaagaag gagacaagag cctacagctc    120
agactggagg atgaaacgat tctggaatac ccaattgatg tacaacgcaa ccagctgccc    180
ttcttacgga atccagatat cttggtggga gaaaatgacc tgactgccct tagctatctt    240
catgagcctg cagttttgca taatttgaag gtccgtttcc tggagtccaa ccatatctac    300
acttactgtg gtatcgtact tgttgccatt aatccttatg aacagttgcc aatctatgga    360
caagatgtca tctataccta cagtggccaa aacatgggag acatggaccc ccacatcttt    420
gctgtggcag aagaagccta caagcagatg gccagagatg agaagaatca gtccatcata    480
```

```
gtcagtgggg agtctggagc cgggaagacg gtatcagcca agtatgccat gcgctatttc    540
gccaccgttg gtggctcggc cagtgaaacc aacatcgaag agaaggtgct ggcatccagt    600
cccatcatgg aggccattgg aaatgccaag accacccgca atgacaacag cagccgtttt    660
ggcaagtaca tccagattgg ctttgacaaa aggtaccaca tcatcgggc  caacatgagg    720
acttacctct tggagaagtc cagagtggtc ttccaggcag atgatgagag gaattaccac    780
atcttttacc agctctgtgc tgctgccggt cttccagaat ttaaagagct tgcactaaca    840
agtgcagagg acttttttcta tacatcacag ggaggagaca cttccatcga gggtgtggac    900
gatgctgagg actttgagaa gactcgacaa gccttcacac tcctcggagt gaaagagtcc    960
catcagatga gcattttaa  gataattgct tctatcttgc accttggaag tgtggcgatt   1020
caggctgagc gtgatggtga ttcctgtagt atatcacccc aggatgtata cctaagcaac   1080
ttctgccgac tgctagggt  ggagcacagt cagatggagc actggctgtg tcatcgcaag   1140
ctggtcacca cctcggagac ctacgtcaag accatgtccc tgcagcaggt gatcaatgcg   1200
cgcaacgccc tggcgaagca catctatgcc cagttgttcg gctggattgt ggagcacatc   1260
aacaaggccc tgcacacctc cctcaagcag cactccttca tcggggtcct ggacatctat   1320
gggtttgaga catttgaggt aaacagcttt gagcagttct gtatcaacta tgcaaatgaa   1380
aagctccagc agcagttcaa ctcgcatgtt ttcaaactgg agcaagaaga atacatgaag   1440
gaacagatcc cttggaccct gattgatttt tatgataacc aaccttgtat cgacctcatt   1500
gaagccaagc tgggtatctt ggacctgttg gatgaagaat gtaaggtccc caaaggaact   1560
gaccagaact gggctcagaa gctctatgac cggcactcca gcagccagca cttccagaag   1620
ccccgcatgt ccaacacggc cttcatcatc gtccactttg cagacaaggt ggagtacctc   1680
tctgatggtt ttctggagaa aaacagagac acggtgtatg aagagcagat caatatcctg   1740
aaggccagca agttcccact agtggctgac ttgtttcatg atgacaagga ccctgttcct   1800
gccaccaccc tgggaagggg gtcatcttcg aagatcagcg tccgttctgc cagacccccc   1860
atgaaagtct ccaacaagga gcacaagaaa accgttggcc accagttccg tacctccctg   1920
catctgctca tggagaccct gaatgccacg acacctcact atgtccgctg catcaagccc   1980
aacgatgaga agctccccctt tcactttgac ccaaagagag cagtgcagca actcagagcc   2040
tgcggggtgt tggagacgat tcgaatcagt gcagctggct acccatccag gtgggcctac   2100
catgactttt tcaaccggta tcgggtgctg gtcaagaaga gagagctcgc caacacagac   2160
aaaaaggcca tctgcaggtc tgtcctggag aacctcatca aggaccccga caagttccag   2220
tttggccgca ccaagatctt ctttcgagca ggccaggtgg cctacctgga agctgcgg    2280
gctgacaagt tcgaagatc  agcaagcatt attcagagaa aagttcggtc atatctcgct   2340
aaaaagagtt tcatcgttct gcgtaattct gctaaacaga ttcagtcagt ttgcagaggt   2400
tatctcgcta aagtgtata  tgaaggcatg cgtagggaag ctgctgcttt aaaaatccag   2460
agagacttgc gtaggtttct ggctaggaag gcttacacag agctatattc tgctgctgtt   2520
tcggttcaag ctggtatgcg tggtatggtt gcccggaaag aactatgttt tagaagacaa   2580
accaaagctg caataataat tcagacttgg tgccgtggat acctggctcg cctgcattac   2640
agaaaactaa agaaagcagc tatcacgacc caatgtgcat ggagatcaaa agtggctcgt   2700
ggagaacttc gaaagcttaa gatggctgct agagaaactg gagcactcca agcagccaag   2760
aacaagctag agaagcaagt tgaagagctg acctggagat tgcagttaga gaaacggata   2820
aggactgacc tggaagaggc caaaaaacaa gaaagtgcaa aagcacagtc ttctttggag   2880
```

-continued

```
gaattgcaac tgaagtgcaa agaaacggag gcattgctta ttaaagaacg tgaagctgcc      2940
aagaagattg ctgagactgc cccgattatt aaggagattc tgtggttga tcaggaatta       3000 atggataaga tcacgaatga aaatgaaaag ctgaagagta tggtgagttc actggaaatg     3060
aaaatcggtg agacagagaa aaaacttcaa gagaccacca agattagcca ggatagacta     3120
aatcaagcat tggaggctga atctaaacta gtgaagttga agactgcaat gcagaggctt    3180
gaagagaaaa tattagatat ggaagctgag aagaaaatta tgcatcagca acaataagc    3240 actcctgtga ggacaaatct aggacatcct ccaactgcac ctgttaagaa tttggaaaat   3300
ggccaccaaa cgaacttgga aaggagttc aatgaagccg agtttacaac accagttgat   3360
ggcaaggctg ggaaatctgc tgcagaacgt caaattatga atgttgatgc tctcattgac   3420
tgtgtaaaag acaacatcgg tttcagtaat ggaaaacctg tggctgcatt tacaatttac  3480
aagtgtctac ttcactggaa gtgtttcgaa tctgagaaga ctaatgtgtt tgatcgtctg   3540
attcagatga ttggttccgc gattgagaat gaggatgaca atagtcactt ggcgtattgg   3600
ttgacaagca catcggcact actattttg cttcaaaaaa gtcttaaaac caatggcagc   3660
ggagcaacac aaagcaagaa gccacctgct tcaacttctt tatttggaag gatggccatg   3720
agcttccgct cttcacccgc ttcaggcaac cttgctgctg cagctgaagc tgctgctctt  3780
gcagtggtcc gcccagtgga ggcaaagtac ccggctctgc ttttcaagca acagcttgca   3840
gcctatgttg agaaaatgtt tgggatggtt agggataact tgaagagaga gttatcaact   3900
ttactttctc tatgcattca ggcacccaga tcttctaaag gagggatgct aagatctggc   3960
aggtcctttg gaaaagattc tcctgcagtt cactggcaaa gcattatcga cggtcttaat   4020
tcgcttcttg tcacactgaa agaaaatcat gttcctttag tactcatcca gaagatatac   4080
tctcaaactt tctcatacat taacgtacaa cttttcaaca gtctccttct gcgtaaagag  4140
tgctgtacat ttagcaatgg tgaatttgta aaatccgggc ttgcggagct agagctatgg  4200
tgttgtcaag ccaagaata ttctgggccg tcttgggaag aactgaaaca tattagacaa    4260
gccgttgggt tcttggttat ccaccagaaa tacagaatct catacgatga aatagcaaac   4320
gatctttgcc cggtcctcag tgtccagcag ctttaccgta tttgcaccct atactgggac   4380
gatagctata cacccgaag cgtctcacaa gaagtgatat cgagtatgcg gacactcatg   4440
acagaggaat ccaatgatgc agacagtgat tccttcttgt tggatgatga ttccagcatt   4500
cctttctcaa tcgatgatat ttcaagttcg atggaagaga aggattttgt aggaatcaaa   4560
ccagcagaag aacttcttga aaatccagca tttgtattct tgcactaa                4608
```

<210> SEQ ID NO 38
<211> LENGTH: 1535
<212> TYPE: PRT
<213> ORGANISM: Artificial
<220> FEATURE:
<223> OTHER INFORMATION: Chimeric myosin with Homo sapiens myosin Vb motor domain and Arabidopsis thaliana myosin XI-2 neck and tail domains

<400> SEQUENCE: 38

```
Met Ser Val Gly Glu Leu Tyr Ser Gln Cys Thr Arg Val Trp Ile Pro
 1               5                  10                  15

Asp Pro Asp Glu Val Trp Arg Ser Ala Glu Leu Thr Lys Asp Tyr Lys
            20                  25                  30

Glu Gly Asp Lys Ser Leu Gln Leu Arg Leu Glu Asp Glu Thr Ile Leu
        35                  40                  45
```

```
Glu Tyr Pro Ile Asp Val Gln Arg Asn Gln Leu Pro Phe Leu Arg Asn
     50                  55                  60

Pro Asp Ile Leu Val Gly Glu Asn Asp Leu Thr Ala Leu Ser Tyr Leu
 65                  70                  75                  80

His Glu Pro Ala Val Leu His Asn Leu Lys Val Arg Phe Leu Glu Ser
                     85                  90                  95

Asn His Ile Tyr Thr Tyr Cys Gly Ile Val Leu Val Ala Ile Asn Pro
                100                 105                 110

Tyr Glu Gln Leu Pro Ile Tyr Gly Gln Asp Val Ile Tyr Thr Tyr Ser
            115                 120                 125

Gly Gln Asn Met Gly Asp Met Asp Pro His Ile Phe Ala Val Ala Glu
        130                 135                 140

Glu Ala Tyr Lys Gln Met Ala Arg Asp Glu Lys Asn Gln Ser Ile Ile
145                 150                 155                 160

Val Ser Gly Glu Ser Gly Ala Gly Lys Thr Val Ser Ala Lys Tyr Ala
                165                 170                 175

Met Arg Tyr Phe Ala Thr Val Gly Gly Ser Ala Ser Glu Thr Asn Ile
                180                 185                 190

Glu Glu Lys Val Leu Ala Ser Ser Pro Ile Met Glu Ala Ile Gly Asn
            195                 200                 205

Ala Lys Thr Thr Arg Asn Asp Asn Ser Ser Arg Phe Gly Lys Tyr Ile
        210                 215                 220

Gln Ile Gly Phe Asp Lys Arg Tyr His Ile Ile Gly Ala Asn Met Arg
225                 230                 235                 240

Thr Tyr Leu Leu Glu Lys Ser Arg Val Val Phe Gln Ala Asp Asp Glu
                245                 250                 255

Arg Asn Tyr His Ile Phe Tyr Gln Leu Cys Ala Ala Ala Gly Leu Pro
                260                 265                 270

Glu Phe Lys Glu Leu Ala Leu Thr Ser Ala Glu Asp Phe Phe Tyr Thr
            275                 280                 285

Ser Gln Gly Gly Asp Thr Ser Ile Glu Gly Val Asp Asp Ala Glu Asp
        290                 295                 300

Phe Glu Lys Thr Arg Gln Ala Phe Thr Leu Leu Gly Val Lys Glu Ser
305                 310                 315                 320

His Gln Met Ser Ile Phe Lys Ile Ile Ala Ser Ile Leu His Leu Gly
                325                 330                 335

Ser Val Ala Ile Gln Ala Glu Arg Asp Gly Asp Ser Cys Ser Ile Ser
                340                 345                 350

Pro Gln Asp Val Tyr Leu Ser Asn Phe Cys Arg Leu Leu Gly Val Glu
            355                 360                 365

His Ser Gln Met Glu His Trp Leu Cys His Arg Lys Leu Val Thr Thr
        370                 375                 380

Ser Glu Thr Tyr Val Lys Thr Met Ser Leu Gln Gln Val Ile Asn Ala
385                 390                 395                 400

Arg Asn Ala Leu Ala Lys His Ile Tyr Ala Gln Leu Phe Gly Trp Ile
                405                 410                 415

Val Glu His Ile Asn Lys Ala Leu His Thr Ser Leu Lys Gln His Ser
                420                 425                 430

Phe Ile Gly Val Leu Asp Ile Tyr Gly Phe Glu Thr Phe Glu Val Asn
            435                 440                 445

Ser Phe Glu Gln Phe Cys Ile Asn Tyr Ala Asn Glu Lys Leu Gln Gln
        450                 455                 460
```

```
Gln Phe Asn Ser His Val Phe Lys Leu Glu Gln Glu Glu Tyr Met Lys
465                 470                 475                 480

Glu Gln Ile Pro Trp Thr Leu Ile Asp Phe Tyr Asp Asn Gln Pro Cys
        485                 490                 495

Ile Asp Leu Ile Glu Ala Lys Leu Gly Ile Leu Asp Leu Leu Asp Glu
            500                 505                 510

Glu Cys Lys Val Pro Lys Gly Thr Asp Gln Asn Trp Ala Gln Lys Leu
        515                 520                 525

Tyr Asp Arg His Ser Ser Gln His Phe Gln Lys Pro Arg Met Ser
    530                 535                 540

Asn Thr Ala Phe Ile Ile Val His Phe Ala Asp Lys Val Glu Tyr Leu
545                 550                 555                 560

Ser Asp Gly Phe Leu Glu Lys Asn Arg Asp Thr Val Tyr Glu Glu Gln
            565                 570                 575

Ile Asn Ile Leu Lys Ala Ser Lys Phe Pro Leu Val Ala Asp Leu Phe
            580                 585                 590

His Asp Asp Lys Asp Pro Val Pro Ala Thr Thr Pro Gly Lys Gly Ser
        595                 600                 605

Ser Ser Lys Ile Ser Val Arg Ser Ala Arg Pro Pro Met Lys Val Ser
        610                 615                 620

Asn Lys Glu His Lys Lys Thr Val Gly His Gln Phe Arg Thr Ser Leu
625                 630                 635                 640

His Leu Leu Met Glu Thr Leu Asn Ala Thr Thr Pro His Tyr Val Arg
                645                 650                 655

Cys Ile Lys Pro Asn Asp Glu Lys Leu Pro Phe His Phe Asp Pro Lys
            660                 665                 670

Arg Ala Val Gln Gln Leu Arg Ala Cys Gly Val Leu Glu Thr Ile Arg
        675                 680                 685

Ile Ser Ala Ala Gly Tyr Pro Ser Arg Trp Ala Tyr His Asp Phe Phe
690                 695                 700

Asn Arg Tyr Arg Val Leu Val Lys Lys Arg Glu Leu Ala Asn Thr Asp
705                 710                 715                 720

Lys Lys Ala Ile Cys Arg Ser Val Leu Glu Asn Leu Ile Lys Asp Pro
            725                 730                 735

Asp Lys Phe Gln Phe Gly Arg Thr Lys Ile Phe Phe Arg Ala Gly Gln
        740                 745                 750

Val Ala Tyr Leu Glu Lys Leu Arg Ala Asp Lys Phe Gly Arg Ser Ala
        755                 760                 765

Ser Ile Ile Gln Arg Lys Val Arg Ser Tyr Leu Ala Lys Lys Ser Phe
        770                 775                 780

Ile Val Leu Arg Asn Ser Ala Lys Gln Ile Gln Ser Val Cys Arg Gly
785                 790                 795                 800

Tyr Leu Ala Arg Ser Val Tyr Glu Gly Met Arg Arg Glu Ala Ala Ala
                805                 810                 815

Leu Lys Ile Gln Arg Asp Leu Arg Phe Leu Ala Arg Lys Ala Tyr
        820                 825                 830

Thr Glu Leu Tyr Ser Ala Ala Val Ser Val Gln Ala Gly Met Arg Gly
                835                 840                 845

Met Val Ala Arg Lys Glu Leu Cys Phe Arg Arg Gln Thr Lys Ala Ala
                850                 855                 860

Ile Ile Ile Gln Thr Trp Cys Arg Gly Tyr Leu Ala Arg Leu His Tyr
865                 870                 875                 880

Arg Lys Leu Lys Lys Ala Ala Ile Thr Thr Gln Cys Ala Trp Arg Ser
```

```
                885                 890                 895
Lys Val Ala Arg Gly Glu Leu Arg Lys Leu Lys Met Ala Ala Arg Glu
                    900                 905                 910

Thr Gly Ala Leu Gln Ala Ala Lys Asn Lys Leu Glu Lys Gln Val Glu
                    915                 920                 925

Glu Leu Thr Trp Arg Leu Gln Leu Glu Lys Arg Ile Arg Thr Asp Leu
                    930                 935                 940

Glu Glu Ala Lys Lys Gln Glu Ser Ala Lys Ala Gln Ser Ser Leu Glu
945                 950                 955                 960

Glu Leu Gln Leu Lys Cys Lys Glu Thr Glu Ala Leu Leu Ile Lys Glu
                    965                 970                 975

Arg Glu Ala Ala Lys Lys Ile Ala Glu Thr Ala Pro Ile Ile Lys Glu
                    980                 985                 990

Ile Pro Val Val Asp Gln Glu Leu  Met Asp Lys Ile Thr  Asn Glu Asn
                    995                 1000                1005

Glu Lys  Leu Lys Ser Met Val  Ser Ser Leu Glu Met  Lys Ile Gly
         1010                 1015                1020

Glu Thr  Glu Lys Lys Leu Gln  Glu Thr Thr Lys Ile  Ser Gln Asp
         1025                 1030                1035

Arg Leu  Asn Gln Ala Leu Glu  Ala Glu Ser Lys Leu  Val Lys Leu
         1040                 1045                1050

Lys Thr  Ala Met Gln Arg Leu  Glu Glu Lys Ile Leu  Asp Met Glu
         1055                 1060                1065

Ala Glu  Lys Lys Ile Met His  Gln Gln Thr Ile Ser  Thr Pro Val
         1070                 1075                1080

Arg Thr  Asn Leu Gly His Pro  Pro Thr Ala Pro Val  Lys Asn Leu
         1085                 1090                1095

Glu Asn  Gly His Gln Thr Asn  Leu Glu Lys Glu Phe  Asn Glu Ala
         1100                 1105                1110

Glu Phe  Thr Thr Pro Val Asp  Gly Lys Ala Gly Lys  Ser Ala Ala
         1115                 1120                1125

Glu Arg  Gln Ile Met Asn Val  Asp Ala Leu Ile Asp  Cys Val Lys
         1130                 1135                1140

Asp Asn  Ile Gly Phe Ser Asn  Gly Lys Pro Val Ala  Ala Phe Thr
         1145                 1150                1155

Ile Tyr  Lys Cys Leu Leu His  Trp Lys Cys Phe Glu  Ser Glu Lys
         1160                 1165                1170

Thr Asn  Val Phe Asp Arg Leu  Ile Gln Met Ile Gly  Ser Ala Ile
         1175                 1180                1185

Glu Asn  Glu Asp Asp Asn Ser  His Leu Ala Tyr Trp  Leu Thr Ser
         1190                 1195                1200

Thr Ser  Ala Leu Leu Phe Leu  Leu Gln Lys Ser Leu  Lys Thr Asn
         1205                 1210                1215

Gly Ser  Gly Ala Thr Gln Ser  Lys Lys Pro Pro Ala  Ser Thr Ser
         1220                 1225                1230

Leu Phe  Gly Arg Met Ala Met  Ser Phe Arg Ser Ser  Pro Ala Ser
         1235                 1240                1245

Gly Asn  Leu Ala Ala Ala Ala  Glu Ala Ala Ala Leu  Ala Val Val
         1250                 1255                1260

Arg Pro  Val Glu Ala Lys Tyr  Pro Ala Leu Leu Phe  Lys Gln Gln
         1265                 1270                1275

Leu Ala  Ala Tyr Val Glu Lys  Met Phe Gly Met Val  Arg Asp Asn
         1280                 1285                1290
```

```
Leu Lys Arg Glu Leu Ser Thr Leu Leu Ser Leu Cys Ile Gln Ala
    1295                1300            1305

Pro Arg Ser Ser Lys Gly Gly Met Leu Arg Ser Gly Arg Ser Phe
    1310                1315            1320

Gly Lys Asp Ser Pro Ala Val His Trp Gln Ser Ile Ile Asp Gly
    1325                1330            1335

Leu Asn Ser Leu Leu Val Thr Leu Lys Glu Asn His Val Pro Leu
    1340                1345            1350

Val Leu Ile Gln Lys Ile Tyr Ser Gln Thr Phe Ser Tyr Ile Asn
    1355                1360            1365

Val Gln Leu Phe Asn Ser Leu Leu Leu Arg Lys Glu Cys Cys Thr
    1370                1375            1380

Phe Ser Asn Gly Glu Phe Val Lys Ser Gly Leu Ala Glu Leu Glu
    1385                1390            1395

Leu Trp Cys Cys Gln Ala Lys Glu Tyr Ser Gly Pro Ser Trp Glu
    1400                1405            1410

Glu Leu Lys His Ile Arg Gln Ala Val Gly Phe Leu Val Ile His
    1415                1420            1425

Gln Lys Tyr Arg Ile Ser Tyr Asp Glu Ile Ala Asn Asp Leu Cys
    1430                1435            1440

Pro Val Leu Ser Val Gln Gln Leu Tyr Arg Ile Cys Thr Leu Tyr
    1445                1450            1455

Trp Asp Asp Ser Tyr Asn Thr Arg Ser Val Ser Gln Glu Val Ile
    1460                1465            1470

Ser Ser Met Arg Thr Leu Met Thr Glu Glu Ser Asn Asp Ala Asp
    1475                1480            1485

Ser Asp Ser Phe Leu Leu Asp Asp Ser Ser Ile Pro Phe Ser
    1490                1495            1500

Ile Asp Asp Ile Ser Ser Ser Met Glu Glu Lys Asp Phe Val Gly
    1505                1510            1515

Ile Lys Pro Ala Glu Glu Leu Leu Glu Asn Pro Ala Phe Val Phe
    1520                1525            1530

Leu His
    1535
```

PLANT WITH ENHANCED GROWTH AND METHOD FOR PRODUCING THE SAME

RELATED APPLICATIONS

This nonprovisional application claims priority under 35 U.S.C. § 119(e) to U.S. Patent Application No. 61/502,764 filed on Jun. 29, 2011.

TECHNICAL FIELD

The present invention relates to a plant with enhanced growth and a method for producing the same. Further, the present invention relates to a plant with suppressed growth and a method for producing the same.

BACKGROUND ART

Techniques for promoting plant growth enable early harvest of products and increase in plant biomass in a short period of time, and thus such techniques are very important for agriculture and forestry. Therefore, various attempts have been made to achieve the object, for example, by producing transgenic plants and knockout plants through optimization of cultivation conditions, treatment with plant hormones, modification of endogenous gene, and/or introduction of exogenous gene.

There have been inventions relating to enlargement of transgenic plant through introduction of exogenous gene. In most cases, the foreign genes conventionally introduced in techniques for enlarging plant were mainly genes encoding proteins involved in the photosynthesis pathway, for example, as described in Miyagawa et al., 2001, Nature Biotechnol, 19(10):965-969 and Chida et al., 2007, Plant Cell Physiol, 48(7): 948-957. Such method for enlarging plant through enhancement of the photosynthesis pathway is problematic. This is because even if the leaf photosynthetic capacity can be enhanced, only limited effects are exhibited in the whole plant. In addition, as a result of accumulation of photosynthetic products in leaves, the enhanced photosynthetic capacity becomes attenuated over time due to feedback effects.

SUMMARY OF THE INVENTION

Problems to be Solved by the Invention

An object of the present invention is to develop and provide a method for enhancing or suppressing the growth of a subject plant through introduction of a mutated gene in a way that differs from conventional methods for promoting plant growth based on the photosynthesis pathway.

Means for Solving the Problems

The present inventors presumed that the above problem is cause by a situation in which the velocity of cytoplasmic streaming for transport of a product obtained as a result of enhancement of photosynthetic capacity becomes a rate-determining factor in plant cells. Thus, the present inventors developed a system for increasing the velocity of cytoplasmic streaming in order to solve the problem. Specifically, the present inventors constructed a chimeric myosin XI protein by substituting the motor domain of a myosin XI protein of *Arabidopsis thaliana* with the motor domain of a myosin XI protein of *Chara corallina*, which is the fastest among organisms, and introduced the protein into *Arabidopsis thaliana*. The term "myosin" collectively refers to actin-dependent molecule motors that move along actin filaments by hydrolyzing ATP. Myosins classified into classes VIII, XI, and XIII according to the phylogenetic classification have been found in plants. It has been suggested that myosin XI proteins are involved in cytoplasmic streaming via transport of "cargoes" such as organelles. In addition, it has been reported that plant growth is inhibited through multiple knockout of the myosin genes involved in cytoplasmic streaming (Peremyslov, V. V. et al., Plant Cell, 2010, 22:1883-1897). However, functions of individual myosin XI proteins have not been elucidated. As a result of experiments conducted by the present inventors, it has been revealed that the growth of the above transgenic plant can be enhanced to a greater extent than that of a plant having wild-type myosin XI. To the contrary, it has been revealed that when a chimeric myosin Vb-XI protein obtained by substituting the motor domain of a myosin XI protein of *Arabidopsis thaliana* with the motor domain of a myosin Vb protein of a human (*Homo sapiens*), which is an animal, is introduced into *Arabidopsis thaliana*, the growth of the transgenic plant is suppressed. That is, the present inventors found that the growth of a plant can be enhanced or suppressed compared with a wild-type strain by substituting a motor domain of a myosin involved in cytoplasmic streaming of a host plant with a motor domain of which the sliding velocity is higher or lower than that of the endogenous motor domain. The present invention has been made based on the results of the above technological development. According to the present invention, the following are provided.

(1) A method for producing a plant with enhanced growth, which comprises a step of introducing a gene encoding a chimeric myosin protein into a host plant so as to transform the host plant, wherein
the chimeric myosin protein comprises:
a neck domain, a coiled-coil domain, and a globular tail domain from a myosin protein involved in cytoplasmic streaming of a donor plant; and
a motor domain from a myosin protein of a plant other than the host plant, which has sliding velocity that is higher than that of the myosin protein involved in cytoplasmic streaming of the donor plant.

(2) The method for producing a plant with enhanced growth according to (1), wherein the chimeric myosin XI protein is a chimeric myosin XI protein comprising:
a neck domain, a coiled-coil domain, and a globular tail domain from a myosin XI protein of a donor plant; and
a motor domain from a myosin XI protein of a plant belonging to the genus *Chara*.

(3) The method for producing a plant with enhanced growth according to (2), wherein the motor domain from a myosin XI protein of the plant belonging to the genus *Chara* has activity of imparting growth-enhancing action to a host plant and comprises an amino acid sequence specified in any one of the following (a) to (c):
(a) the amino acid sequence shown in SEQ ID NO: 1;
(b) an amino acid sequence that has a deletion, substitution, and/or addition of one or several amino acids with respect to the amino acid sequence shown in SEQ ID NO: 1; or
(c) an amino acid sequence having 70% or more identity with the amino acid sequence shown in SEQ ID NO: 1.

(4) The method for producing a plant with enhanced growth according to (2) or (3), wherein the neck domain, the coiled-coil domain, and the globular tail domain are from a single myosin XI protein of a donor plant.

(5) The method for producing a plant with enhanced growth according to (4), wherein the myosin XI protein is a myosin XI-1, XI-2, XI-B, or XI-K protein of *Arabidopsis thaliana*.
(6) The method for producing a plant with enhanced growth according to (5), wherein the neck domain has activity of imparting growth-enhancing action to a host plant and comprises any one of the following (a) to (c):

(a) an amino acid sequence comprising the 736th to 870th amino acid residues of the amino acid sequence shown in SEQ ID NO: 3;

(b) an acid sequence that has a deletion, substitution, and/or addition of one or several amino acids with respect to the amino acid sequence specified in (a); or (c) an amino acid sequence having 70% or more identity with the amino acid sequence specified in (a), wherein the coiled-coil domain has activity of imparting growth-enhancing action to a host plant and comprises any one of the following (d) to (f):

(d) an amino acid sequence comprising the 871st to 957th and the 967th to 1049th amino acid residues of the amino acid sequence shown in SEQ ID NO: 3;

(e) an amino acid sequence that has a deletion, substitution, and/or addition of one or several amino acids with respect to the amino acid sequence specified in (d); or (f) an amino acid sequence having 70% or more identity with the amino acid sequence specified in (d), and wherein the globular tail domain has activity of imparting growth-enhancing action to a host plant and comprises any one of the following (g) to (i):

(g) an amino acid sequence comprising the 1050th to 1505th amino acid residues of the amino acid sequence shown in SEQ ID NO: 3;

(h) an amino acid sequence that has a deletion, substitution, and/or addition of one or several amino acids with respect to the amino acid sequence specified in (g); or (i) an amino acid sequence having 70% or more identity with the amino acid sequence specified in (g).

(7) The method for producing a plant with enhanced growth according to any one of (1) to (6), wherein the donor plant is the host plant.

(8) A plant with enhanced growth, which contains a gene encoding the chimeric myosin protein defined in any one of (1) to (6) so that the gene can be expressed therein.

(9) The plant with enhanced growth according to (8), which is obtained by the method for producing a plant with enhanced growth according to any one of (1) to (8).

(10) A progeny of the plant with enhanced growth according to (8) or (9).

(11) A method for enhancing the growth of a subject plant, which comprises a step of introducing a gene encoding the chimeric myosin XI protein defined in (1) into the subject plant so that the gene can be expressed therein.

(12) A method for producing a plant with suppressed growth, which comprises a step of introducing a gene encoding a chimeric myosin protein into a host plant so as to transform the host plant, wherein the chimeric myosin protein comprises:

a neck domain, a coiled-coil domain, and a globular tail domain from a myosin protein involved in cytoplasmic streaming of a donor plant; and a motor domain from a myosin protein of a plant other than the host plant, which has sliding velocity that is lower than that of a myosin protein involved in cytoplasmic streaming of the donor plant.

(13) The method for producing a plant with suppressed growth according to (12), wherein the chimeric myosin protein is a chimeric myosin Vb-XI protein comprising:

a neck domain, a coiled-coil domain, and a globular tail domain from a myosin XI protein of a donor plant; and a motor domain from a myosin Vb protein of an animal.

(14) The method for producing a plant with suppressed growth according to (13), wherein the animal is an invertebrate or a vertebrate.

(15) The method for producing a plant with suppressed growth according to (14), wherein the vertebrate is a mammal.

(16) The method for producing a plant with suppressed growth according to (15), wherein the motor domain of a myosin Vb protein of a mammal has activity of imparting growth-suppressing action to a host plant and comprises an amino acid sequence specified in any one of the following (a) to (c):

(a) the amino acid sequence shown in SEQ ID NO: 35;

(b) an amino acid sequence that has a deletion, substitution, and/or addition of one or several amino acids with respect to the amino acid sequence shown in SEQ ID NO: 35; or (c) an amino acid sequence having 70% or more identity with the amino acid sequence shown in SEQ ID NO: 35.

Effects of the Invention

According to the method for producing a plant with enhanced growth of the present invention, a plant individual with enhanced growth compared with a wild-type strain of the host plant species used for the production of such plant can be obtained. Growth enhancement can not only cause increase in biomass of a plant itself but also promote faster blooming and fruiting of such plant. As a result, biomass resources can be increased and production efficiency in agriculture or forestry can be increased.

A transgenic plant, the growth rate of which is faster than that of a wild-type strain, can be provided for a desired plant using the plant with enhanced growth of the present invention.

In addition, according to the method for producing a plant with suppressed growth of the present invention, a plant individual with suppressed growth compared with a wild-type strain of the host plant used for the production of such plant can be obtained.

Therefore, growth of a plant can be controlled using the method for producing a plant with enhanced growth and the method for producing a plant with suppressed growth of the present invention.

BRIEF DESCRIPTION OF THE DRAWINGS

FIG. 4A shows the average main root length of T1 (MYA2) and that of T1 (chimera XI) on day 5 of culture.

FIG. 4B is a graph of the average main root length.

FIG. 4C shows enlarged views of the roots of T1 (MYA2) and that of T1 (chimera XI) shown in FIG. 4A.

FIG. 4D shows growth of the aerial portions of T1 (MYA2) and that of T1 (chimera XI).

FIG. 4E shows changes in shoot length during the period from day 20 to day 40 after sowing.

FIG. 5a shows root epithelial cells of T1 (MYA2) from the *A. thaliana* MYA2-KO strain. FIG. 5b shows root epithelial cells of T1 (chimera XI) from the *A. thaliana* MYA2-KO strain.

FIG. 6a shows the morphology of aerial portion of each plant. FIGS. 6b and 6c show the separated and arranged parts of the aerial portions of the Columbia strain and chimera XI, respectively.

FIG. 9 shows phenotypes of the aerial portions of the Columbia strain and the strain with introduced chimera Vb-XI on day 30 after sowing.

BEST MODE FOR CARRYING OUT THE INVENTION

Figure 1:
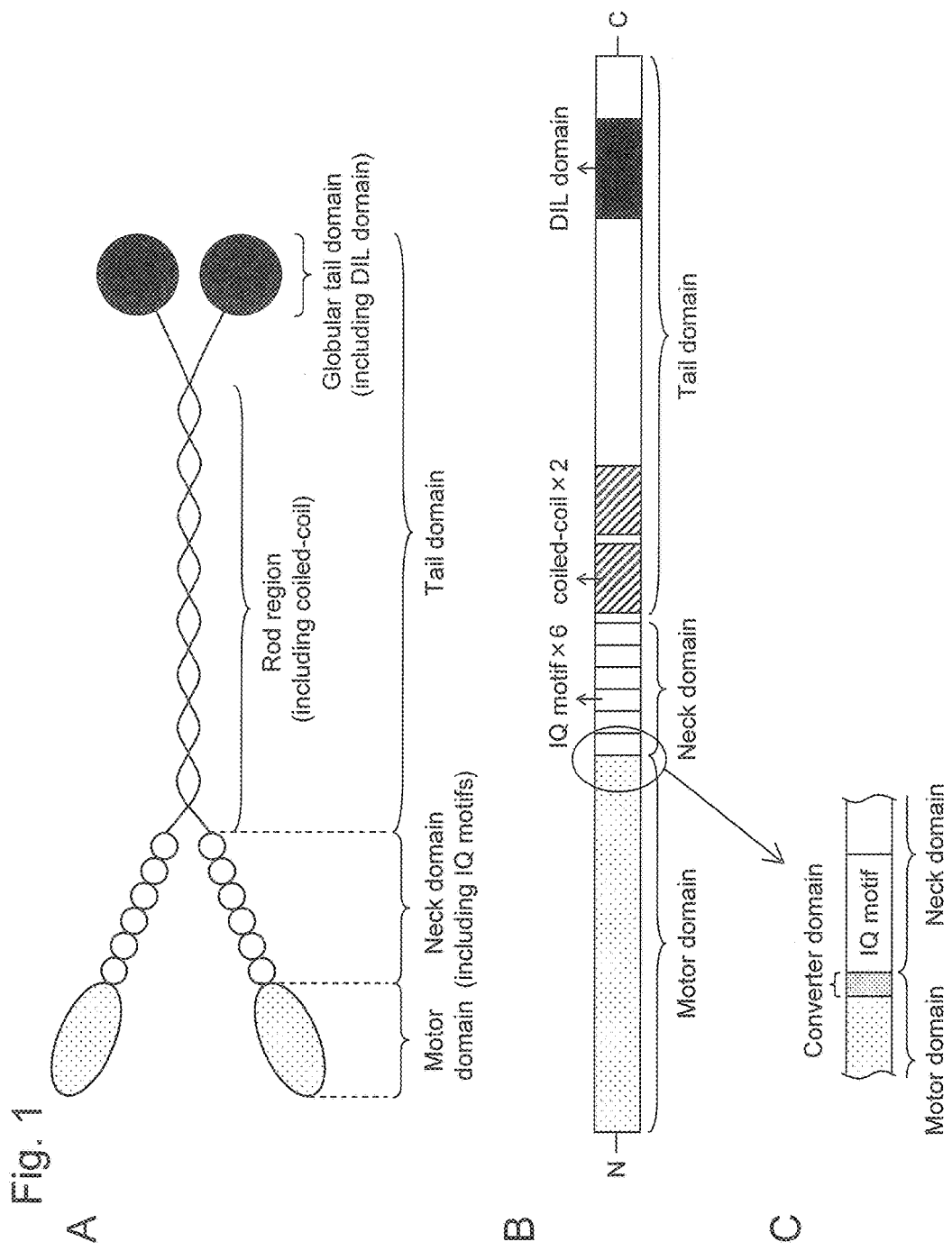
FIG. 1A shows the structure of a plant myosin XI molecule (a dimer).
FIG. 1B shows the structure of a plant myosin XI protein (a monomer polypeptide).
FIG. 1C is an enlarged view of the circled part in FIG. 1B. This region contains a converter domain which is important as a connection between the motor domain and the neck domain for construction of the chimeric myosin XI protein of the present invention.
Figure 2:
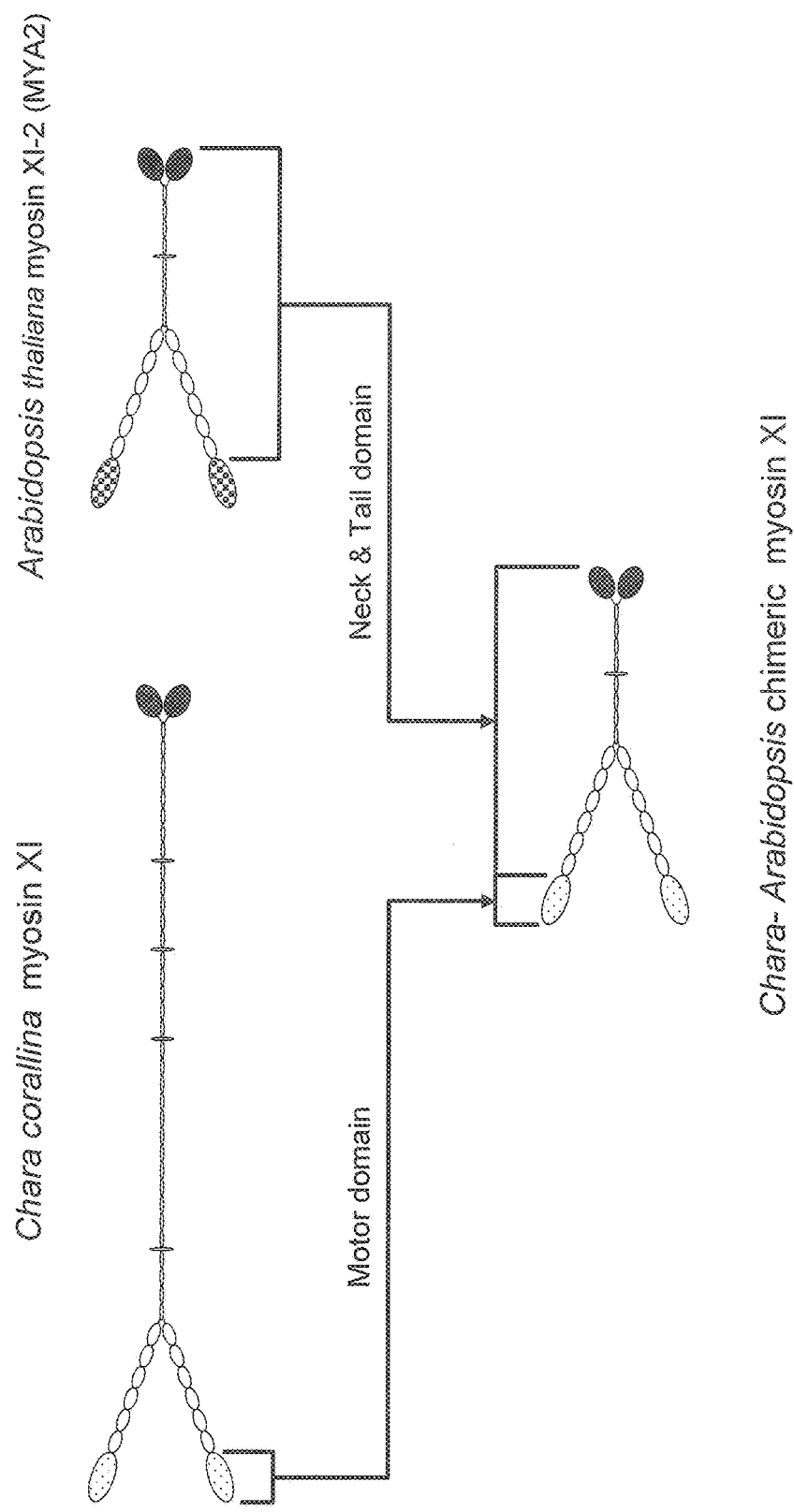
FIG. 2 shows the structure of the chimeric myosin XI molecule constructed in Example 1, and the structures of the *C. corallina* myosin XI molecule and the *A. thaliana* myosin XI-2 (MYA2) molecule used for construction of the chimeric myosin XI molecule.

1. A Method for Producing a Plant with Enhanced Growth
1-1. Outline and Definition The first embodiment of the present invention relates to a method for producing a plant with enhanced growth.

Specifically, the method for producing a plant with enhanced growth of the present invention comprises a step of introducing a gene encoding a chimeric myosin protein into a host plant so as to transform the host plant, wherein the chimeric myosin protein comprises: a neck domain, a coiled-coil domain, and a globular tail domain from a myosin protein involved in cytoplasmic streaming of a donor plant; and a motor domain from a myosin protein of a plant other then the host plant, which is not from, and has sliding velocity that is higher than that of, the myosin protein involved in cytoplasmic streaming of the donor plant.

Here, an example of a myosin protein involved in cytoplasmic streaming of a donor plant is a myosin XI protein. In addition, an example of a myosin protein having sliding velocity higher than that of the myosin protein involved in cytoplasmic streaming of the donor plant is a myosin XI protein from a plant belonging to the genus *Chara*. In such case, the host plant is a plant that is not a plant belonging to the genus *Chara*. Although the present invention is described below for such specific examples, the present invention is not limited thereto.

In the present invention, the term "plant with enhanced growth" refers to a transgenic plant whose growth is enhanced as compared with the wild-type strain of the host plant used for the production thereof. The phrase "with enhanced growth" used herein indicates an increase in plant size as a result of expansion of cell size. Specific examples thereof include elongation of stems (including petioles and pedicels) or roots (including root hairs), expansion of leaf size, and increase in the number of siliques. Therefore, the plant with enhanced growth can grow to a size larger than that of a wild-type strain in an identical growth environment. Enhancement of growth may be enhancement of growth of the whole plant or a portion thereof.

The production method of the present invention comprises a transformation step. In this embodiment, the term "transformation step" refers to a step of introducing a gene encoding a chimeric myosin XI protein (hereinafter sometimes referred to as the "chimeric myosin XI gene") into a host plant so as to transform the host plant.

The term "host plant" used herein refers to a plant species subjected to the method for producing a plant with enhanced growth of the present invention. Preferably, the host plant used herein is a plant that is not a plant belonging to the genus *Chara*. The host plant is not particularly limited as long as it is a plant that is not a plant belonging to the genus *Chara*. Examples thereof include bryophytes, pteridophytes, and seed plants. The "seed plants" used herein include angiosperms and gymnosperms. The term "angiosperms" used herein includes dicotyledons and monocotyledons. Preferable examples of a host plant include plants having agricultural or commercial use such as crop plants (e.g., cereals, vegetables, flowers, and fruits) and useful trees. Specific examples thereof include plants belonging to the family Brassicaceae (including *Lactuca sativa, Brassica oleracea, Raphanus sativus, Brassica rapa*, and *Arabidopsis thaliana*), plants belonging to the family Poaceae (including *Oryza sativa, Hordeum vulgare, Triticum aestivum, Zea mays, Brachypodium distachyon*, and *Sorgum bicolor*), plants belonging to the family Solanaceae (including *Solanum lycopersicum, Solanum melongena, Capsicum annuum*, and *Nicotiana tabacum*), plants belonging to the family Legminosae (including *Glycine max* and *Arachis hypogaea*), plants belonging to the family Vitaceae (including *Vitis vinifera*), plants belonging to the family Rosaceae (including *Fragaria, Rosa, Prunus, Pyrus, Malus pumila*, and *Amygdalus persica*), plants belonging to the family Cucurbitaceae (including *Cucurbita, Cucumis melo*, and *Citrullus lanatus*), plants belonging to the family Liliaceae (including *Allium fistulosum* and *Allium cepa*), plants belonging to the family Salicaceae (including *Populus*), and plants belonging to the family Myrtaceae (including *Eucalyptus*).

The term "plant belonging to the genus *Chara*" refers to algae belonging to the genus *Chara* of the family Characeae of the order Charales. Specific examples thereof include *C. corallina, C. braunii, C. australis, C. globularis, C. fibrosa*, and *C. zeylanica*. The myosin XI protein of *Chara corallina* has a sliding velocity of 50 μm/second, and thus it is known to be the fastest among organisms. Incidentally, both the myosin XI protein of tobacco (*Nicotiana tabacum*) and the myosin XI-2 protein of *A. thaliana* have a sliding velocity of 7 μm/second.

A "myosin XI protein" is one of polypeptides that constitute a myosin heavy chain, and is classified as belonging to the myosin XI class which is specific to plants and constitutes the myosin superfamily. A myosin XI protein forms a homodimer and functions as a myosin XI molecule in plant cells. It is known that a myosin XI molecule is a high-speed processive motor molecule that is capable of continuous long-distance movement in a plant cell at a step width of 35 nm on an actin filament which serves as a main rail. Specific examples of myosin proteins classified as belonging to the myosin XI class include XI-1, XI-2, XI-A, XI-B, XI-C, XI-D, XI-E, XI-F, XI-G, XI-H, XI-I, XI-J, and XI-K proteins. As shown in FIG. 1A, a myosin XI molecule is formed as a homodimer which is composed of two myosin proteins (polypeptides). As shown in FIG. 1B, each polypeptide comprises three functional regions; that is to say, a motor domain located in the N-terminal region, a neck domain located downstream of the motor domain, and a tail domain located downstream of the neck domain.

The motor domain is the velocity-determining region in a myosin molecule. The motor domain interacts with an actin filament and binds to ATP. The neck domain comprises six IQ motifs arranged in tandem, which function as binding sites for a calmodulin-like myosin light chain. The tail domain comprises a rod region and a globular tail domain (FIG. 1A). The rod region comprises two coiled-coil domains and contributes to the dimer formation of myosin XI protein. In addition, the globular tail domain comprises a DIL domain and binds to cargoes such as organelles.

The term "chimeric myosin XI protein" refers to a chimeric protein obtained by combining functional regions from two or more different plant species and artificially connecting the regions to form a single myosin XI protein.

1-2. Chimeric Myosin XI Protein
1-2-1. Structure

The "chimeric myosin XI protein" of the present invention is characterized in that it has a motor domain from a myosin XI protein of a plant belonging to the genus *Chara* and also has a neck domain, a coiled-coil domain, and a globular tail domain from a myosin XI protein of a donor plant.

The term "donor plant" used herein refers to a plant that is not a plant belonging to the genus *Chara*, which provides a polynucleotide region of an amino acid sequence comprising a neck domain, a coiled-coil domain, and a globular tail domain in a chimeric myosin XI protein. Two or more types of plants may be used as donor plants. In an exemplary case, a plant species providing a neck domain differs from a plant species providing a tail domain (which includes a coiled-coil domain and a globular tail domain). In such case, domains from the respective plant species may be from different types of myosin XI. For example, in a case in which a plant that provides a neck domain (designated as "plant A") and a plant that provides a tail domain (designated as "plant B") are used, and a neck domain is from a myosin XI-1 protein of plant A, a tail domain may be from a myosin XI-2 protein of plant B. When domains derived from different types of myosin XI are used in combination, it is preferable to select the types of myosin XI from among XI-1, XI-2, XI-B, and XI-K proteins, which are expressed in the whole plant, and thought to function to drive cytoplasmic streaming in plant cells. In addition, a neck domain functions as a lever arm upon myosin movement in both of plants and animals. Therefore, a neck domain may exceptionally be from animal myosin V. More preferably, the domains are from the same myosin XI type among donor plant species. For example, if a neck domain is from a myosin XI-1 protein of plant A, it is preferable that a tail domain is also from a myosin XI-1 protein of plant B. This is because it is highly probable that proteins of the same myosin XI type (i.e., ortholog proteins) will have similar functions even if they are from different species, and thus similar actions and effects can be exhibited. Preferably, a donor plant is a plant belonging to the same family as the host plant. More preferably, a donor plant is a plant belonging to the same genus as the host plant. Further preferably, a donor plant is the same plant as the host plant. Hence, it is most preferable for all of the neck domain, coiled-coil domain, and globular tail domain to be from a myosin XI protein of a host plant. The structure of each domain is specifically described below.

A. Structure of the Motor Domain

The motor domain of a chimeric myosin XI protein is not particularly limited as long as it is from a myosin XI protein of a plant belonging to the genus *Chara*. Examples thereof include myosin XI proteins of plant species belonging to the genus *Chara* (*C. corallina*, *C. braunii*, *C. australis*, *C. globularis*, *C. fibrosa*, and *C. zeylanica*) exemplified above. More specific examples thereof include a *C. corallina*-derived motor domain comprising the amino acid sequence shown in SEQ ID NO: 1 (GenBank: BAB03273.1).

In addition to the above, the motor domain of a chimeric myosin XI protein may be a motor domain from a myosin XI protein of a plant belonging to the genus *Chara* comprising an amino acid sequence that has a deletion, substitution, and/or addition of one or several amino acids with respect to the amino acid sequence shown in SEQ ID NO: 1, or a motor domain from a myosin XI protein of a plant belonging to the genus *Chara* comprising an amino acid sequence having 70% or more, preferably 80% or more, and more preferably 90% identity to the amino acid sequence shown in SEQ ID NO: 1, which maintains activity of imparting growth-enhancing action to a host plant. This is because it is highly probable that a myosin XI protein of a plant belonging to the genus *Chara* that comprises the motor domain comprising the above amino acid sequence is an ortholog of the *C. corallina* myosin XI protein and thus the motor domain is presumed to have actions and effects equivalent to the motor domain comprising the amino acid sequence shown in SEQ ID NO: 1. The term "several" used herein refers to an integer of 2 to 10, for example, an integer of 2 to 7, 2 to 5, 2 to 4, or 2 to 3. In addition, the term "identity" used herein refers to the percentage (%), in the total number of amino acids of one amino acid sequence (i.e., the amino acid sequence shown in SEQ ID NO: 1 in the above case), of the number of amino acids that match the amino acids in the other amino acid sequence, when the two amino acid sequences are aligned so that the number of matched amino acids is maximized, by introducing gap(s) into one or both of the sequences, if necessary.

B. Structures of the Neck Domain, the Coiled-Coil Domain, and the Globular Tail Domain The type of myosin XI protein of donor plant that provides the neck domain, the coiled-coil domain, and the globular tail domain of the above chimeric myosin XI protein is not particularly limited as long as it is a myosin XI protein belonging to the myosin XI class. For example, in the case of *A. thaliana*, any protein selected from among the group consisting of XI-1, XI-2, XI-A, XI-B, XI-C, XI-D, XI-E, XI-F, XI-G, XI-H, XI-I, XI-J, and XI-K proteins may be used. Preferable examples thereof include proteins that are thought to function to drive cytoplasmic streaming in plant cells, such as, XI-1, XI-2, XI-B, and XI-K proteins. It is possible to confirm whether or not a myosin XI protein of interest is involved in cytoplasmic streaming by observing the influence of the following upon cytoplasmic streaming: knockout of myosin (Peremyslov, V. V. et al., Plant Physiol., 2008, 146:1109-1116; Prokhnevsky, A. I. et al., Proc. Natl. Acad. Sci. USA, 2008, 105:19744-19749; Ueda, H. et al., Proc. Natl. Acad. Sci. USA, 2010, 107:6894-6899; Peremyslov, V. V. et al., Plant Cell, 2010, 22:1883-1897); functional inhibition of myosin by overexpression of tail domain (Sparkes, I. A. et al., J. Exp. Bot., 2008, 59:2499-2512;

Avisar, D. et al., Plant Physiol., 2008, 146:1098-1108); and functional inhibition of myosin by RNAi (Vidali, L. et al., Plant Cell, 2010, 22:1868-1882; Avisar, D. et al. (supra)). As described above, the neck domain, the coiled-coil domain, and the globular tail domain in a chimeric myosin XI protein may be from different plant species. However, it is desirable that the domains be obtained from myosin XI proteins of the same myosin XI class.

Specific examples of the donor plant from which the neck domain, the coiled-coil domain, and the globular tail domain in a chimeric myosin XI protein can be obtained, and the amino acid sequence of each domain are described below.

(1) *Arabidopsis thaliana*

If a donor plant is *Arabidopsis thaliana*, the neck domain, the coiled-coil domain, and/or the globular tail domain of a chimeric myosin XI protein may be from, for example, the myosin XI-2 protein shown in SEQ ID NO: 3 (GenBank: BAA98070.1) (designated herein for convenience as a "MYA2" protein according to the conventionally used name). In such case, the neck domain consists of the 736th to 870th amino acid residues of the amino acid sequence of SEQ ID NO: 3. The coiled-coil domain consists of the 871st to 957th and the 967th to 1049th amino acid residues of the amino acid sequence of SEQ ID NO: 3. The globular tail domain consists of the 1050th to 1505th amino acid residues of the amino acid sequence of SEQ ID NO: 3.

In addition, the neck domain, the coiled-coil domain, and/or the globular tail domain of the chimeric myosin XI protein may be from, for example, the *A. thaliana* myosin XI-1 protein shown in SEQ ID NO: 4 (GenBank: AEE29607.1). In such case, the neck domain consists of the 734th to 872nd amino acid residues of the amino acid sequence of SEQ ID NO: 4. The coiled-coil domain consists of the 873rd to 946th and the 968th to 1048th amino acid residues of the amino acid sequence of SEQ ID NO: 4. The globular tail domain consists of the 1049th to 1520th amino acid residues of the amino acid sequence of SEQ ID NO: 4.

Alternatively, the neck domain, the coiled-coil domain, and/or the globular tail domain of the chimeric myosin XI protein may be from, for example, the *A. thaliana* myosin XI-B protein shown in SEQ ID NO: 5 (GenBank: AEE27664.1). In such case, the neck domain consists of the 737th to 875th amino acid residues of the amino acid sequence of SEQ ID NO: 5. The coiled-coil domain consists of the 876th to 954th and 967th to 1050th amino acid residues of the amino acid sequence of SEQ ID NO: 5. The globular tail domain consists of the 1051st to 1500th amino acid residues of the amino acid sequence of SEQ ID NO: 5.

In another case, the neck domain, the coiled-coil domain, and/or the globular tail domain of the chimeric myosin XI protein may be from, for example, the *A. thaliana* myosin XI-K1 (XI-K Dolja) protein shown in SEQ ID NO: 6 (GenBank: ADV74830.1). In such case, the neck domain consists of 737th to 875th amino acid residues of the amino acid sequence of SEQ ID NO: 6. The coiled-coil domain consists of the 876th to 958th and the 967th to 1056th amino acid residues of the amino acid sequence of SEQ ID NO: 6. The globular tail domain consists of the 1057th to 1531st amino acid residues of the amino acid sequence of SEQ ID NO: 6.

Also, in another case, the neck domain, the coiled-coil domain, and/or the globular tail domain of the chimeric myosin XI protein may be from, for example, the *A. thaliana* myosin XI-K2 (XI-K Ojangu) protein shown in SEQ ID NO: (GenBank: AED92852.1). In such case, the neck domain consists of the 671st to 809th amino acid residues of the amino acid sequence of SEQ ID NO: 7. The coiled-coil domain consists of the 810th to 990th amino acid residues of the amino acid sequence of SEQ ID NO: 7. The globular tail domain consists of the 991st to 1523rd amino acid residues of the amino acid sequence of SEQ ID NO: 7.

In addition to the above, the neck domain, the coiled-coil domain, and/or the globular tail domain of a chimeric myosin XI protein may be a domain comprising an amino acid sequence that has a deletion, substitution, and/or addition of one or several amino acids with respect to the above amino acid sequence of the relevant domain or a domain comprising an amino acid sequence having 70% or more, preferably 80% or more, and more preferably 90% identity to the above amino acid sequence of the relevant domain, which maintains the activity of imparting growth-enhancing action to a host plant.

(2) *Oryza sativa*

If a donor plant is *Oryza sativa*, the neck domain, the coiled-coil domain, and/or the globular tail domain of a chimeric myosin XI protein may be from, for example, the myosin XI-I protein (NCBI: NP_921307.1) shown in SEQ ID NO: 8. In such case, the neck domain consists of the 735th to 874th amino acid residues of the amino acid sequence of SEQ ID NO: 8. The coiled-coil domain consists of the 875th to 1048th amino acid residues of the amino acid sequence of SEQ ID NO: 8. The globular tail domain consists of the 1049th to 1056th amino acid residues of the amino acid sequence of SEQ ID NO: 8.

In addition, the neck domain, the coiled-coil domain, and/or the globular tail domain of a chimeric myosin XI protein may be from, for example, the myosin XI-K protein (NCBI: NP_916622.1) shown in SEQ ID NO: 9. In such case, the neck domain consists of the 736th to 875th amino acid residues of the amino acid sequence of SEQ ID NO: 9. The coiled-coil domain consists of the 867th to 1018th amino acid residues of the amino acid sequence of SEQ ID NO: 9. The globular tail domain consists of the 1019th to 1553rd amino acid residues of the amino acid sequence of SEQ ID NO: 9.

Alternatively, the neck domain, the coiled-coil domain, and/or the globular tail domain of a chimeric myosin XI protein may be from, for example, the myosin XI-G protein (NCBI: XP_470510.1) shown in SEQ ID NO: 10. In such case, the neck domain consists of the 713th to 852nd amino acid residues of the amino acid sequence (Os50920299) of SEQ ID NO: 10. The coiled-coil domain consists of the 853rd to 887th and the 908th to 1047th amino acid residues of the amino acid sequence of SEQ ID NO: 10. The globular tail domain consists of the 1048th to 1478th amino acid residues of the amino acid sequence of SEQ ID NO: 10.

In another case, the neck domain, the coiled-coil domain, and/or the globular tail domain of a chimeric myosin XI protein may be from, for example, the myosin XI-J protein (GenBank: BAD37694.1) shown in SEQ ID NO: 11. In such case, the neck domain consists of the 736th to 875th amino acid residues of the amino acid sequence of SEQ ID NO: 11. The coiled-coil domain consists of the 876th to 1055th amino acid residues of the amino acid sequence of SEQ ID NO: 11. The globular tail domain consists of the 1056th to 1529th amino acid residues of the amino acid sequence of SEQ ID NO: 11.

In addition to the above, the neck domain, the coiled-coil domain, and/or the globular tail domain of a chimeric myosin XI protein may be a domain comprising an amino acid sequence that has a deletion, substitution, and/or addition of one or several amino acids with respect to the above amino acid sequence of the relevant domain or a domain comprising an amino acid sequence having 70% or more, preferably 80% or more, and more preferably 90% identity to the above amino acid sequence of the relevant domain, which maintains the activity of imparting growth-enhancing action to a host plant.

(3) *Brachypodium distachyon*

If a donor plant is *Brachypodium distachyon*, the neck domain, the coiled-coil domain, and/or the globular tail domain of a chimeric myosin XI protein may be from, for example, the myosin XI-I protein (*Brachypodium distachyon* GBrowse v1.0:Bradi3g57240.1) shown in SEQ ID NO: 12. In such case, the neck domain consists of the 734th to 873rd amino acid residues of the amino acid sequence of SEQ ID NO: 12. The coiled-coil domain consists of the 874th to 912th and the 971st to 1053rd amino acid residues of the amino acid sequence of SEQ ID NO: 12. The globular tail domain consists of the 1054th to 1501st amino acid residues of the amino acid sequence of SEQ ID NO: 12.

Alternatively, the neck domain, the coiled-coil domain, and/or the globular tail domain of a chimeric myosin XI protein may be from, for example, the myosin XI-F protein (*Brachypodium distachyon* GBrowse v1.0:Bradi1g08710.1) shown in SEQ ID NO: 13. In such case, the neck domain consists of the 735th to 874th amino acid residues of the amino acid sequence of SEQ ID NO: 13. The coiled-coil domain consists of the 875th to 957th and the 969th to 1092nd amino acid residues of the amino acid sequence of SEQ ID NO: 13. The globular tail domain consists of the 1093rd to 1556th amino acid residues of the amino acid sequence of SEQ ID NO: 13.

In addition, the neck domain, the coiled-coil domain, and/or the globular tail domain of a chimeric myosin XI protein may be from, for example, the myosin XI-G protein (*Brachypodium distachyon* GBrowse v1.0:Bradig29700.1) shown in SEQ ID NO: 14. In such case, the neck domain consists of the 740th to 879th amino acid residues of the amino acid sequence of SEQ ID NO: 14. The coiled-coil domain consists of the 880th to 1054th amino acid residues of the amino acid sequence of SEQ ID NO: 14. The globular tail domain consists of the 1055th to 1514th amino acid residues of the amino acid sequence of SEQ ID NO: 14.

In another case, the neck domain, the coiled-coil domain, and/or the globular tail domain of a chimeric myosin XI protein may be from, for example, the myosin XI-J protein (*Brachypodium distachyon* GBrowse v1.0:Bradi1g45120.1) shown in SEQ ID NO: 15. In such case, the neck domain consists of the 1058th to 1198th amino acid residues of the amino acid sequence of SEQ ID NO: 15. The coiled-coil domain consists of the 1199th to 1378th amino acid residues of the amino acid sequence of SEQ ID NO: 15. The globular tail domain consists of the 1379th to 1852nd amino acid residues of the amino acid sequence of SEQ ID NO: 15.

In addition to the above, the neck domain, the coiled-coil domain, and/or the globular tail domain of a chimeric myosin XI protein may be a domain comprising an amino acid sequence that has a deletion, substitution, and/or addition of one or several amino acids with respect to the above amino acid sequence of the relevant domain or a domain comprising an amino acid sequence having 70% or more, preferably 80% or more, and more preferably 90% identity to the above amino acid sequence of the relevant domain, which maintains the activity of imparting growth-enhancing action to a host plant.

(4) *Sorghum bicoler*

If a donor plant is *Sorghum bicoler*, the neck domain, the coiled-coil domain, and/or the globular tail domain of a chimeric myosin XI protein may be from the myosin XI-I protein (GenBank: EES05882.1) shown in SEQ ID NO: 16.

In such case, the neck domain consists of the 734th to 873rd amino acid residues of the amino acid sequence of SEQ ID NO: 16. The coiled-coil domain consists of the 874th to 914th and the 964th to 1054th amino acid residues of the amino acid sequence of SEQ ID NO: 16. The globular tail domain consists of the 1055th to 1520th amino acid residues of the amino acid sequence of SEQ ID NO: 16.

In addition, the neck domain, the coiled-coil domain, and/or the globular tail domain of a chimeric myosin XI protein may be from, for example, the myosin XI-K protein (GenBank: EES03166.1) shown in SEQ ID NO: 17. In such case, the neck domain consists of the 786th to 925th amino acid residues of the amino acid sequence of SEQ ID NO: 17. In addition, the coiled-coil domain consists of the 926th to 1003rd and the 1021st to 1106th amino acid residues of the amino acid sequence of SEQ ID NO: 17. The globular tail domain consists of the 1107th to 1529th amino acid residues of the amino acid sequence of SEQ ID NO: 17.

Alternatively, the neck domain, the coiled-coil domain, and/or the globular tail domain of a chimeric myosin XI protein may be from, for example, the myosin XI-F protein (GenBank: EER93462.1) shown in SEQ ID NO: 18. In such case, the neck domain consists of the 736th to 875th amino acid residues of the amino acid sequence of SEQ ID NO: 18. The coiled-coil domain consists of the 870th to 959th and the 967th to 1092nd amino acid residues of the amino acid sequence of SEQ ID NO: 18. The globular tail domain consists of the 1093rd to 1448th amino acid residues of the amino acid sequence of SEQ ID NO: 18.

In another case, the neck domain, the coiled-coil domain, and/or the globular tail domain of a chimeric myosin XI protein may be from, for example, the myosin XI-J protein (GenBank: EER88125.1) shown in SEQ ID NO: 19. In such case, the neck domain consists of the 746th to 885th amino acid residues of the amino acid sequence of SEQ ID NO: 19. In addition, the coiled-coil domain consists of the 886th to 1065th amino acid residues of the amino acid sequence of SEQ ID NO: 19. The globular tail domain consists of the 1066th to 1539th amino acid residues of the amino acid sequence of SEQ ID NO: 19.

In addition to the above, the neck domain, the coiled-coil domain, and/or the globular tail domain of a chimeric myosin XI protein may be a domain comprising an amino acid sequence that has a deletion, substitution, and/or addition of one or several amino acids with respect to the above amino acid sequence of the relevant domain or a domain comprising an amino acid sequence having 70% or more, preferably 80% or more, and more preferably 90% identity to the above amino acid sequence of the relevant domain, which maintains the activity of imparting growth-enhancing action to a host plant.

(5) *Populus trichocarpa*

If a donor plant is *Populus trichocarpa*, the neck domain, the coiled-coil domain, and/or the globular tail domain of a chimeric myosin XI protein may be from the myosin XI-M protein (GenBank: EEE92724.1) shown in SEQ ID NO: 20. In such case, the neck domain consists of the 746th to 864th amino acid residues of the amino acid sequence of SEQ ID NO: 20. The coiled-coil domain consists of the 865th to 1065th amino acid residues of the amino acid sequence of SEQ ID NO: 20. The globular tail domain consists of the 1066th to 1539th amino acid residues of the amino acid sequence of SEQ ID NO: 20.

In addition, the neck domain, the coiled-coil domain, and/or the globular tail domain of a chimeric myosin XI protein may be from, for example, the myosin XI-M protein (GenBank: EEE89075.1) shown in SEQ ID NO: 21. In such case, the neck domain consists of the 731st to 850th amino acid residues of the amino acid sequence of SEQ ID NO: 21. The coiled-coil domain consists of the 851st to 1045th amino acid residues of the amino acid sequence of SEQ ID NO: 21. The globular tail domain consists of the 1046th to 1509th amino acid residues of the amino acid sequence of SEQ ID NO: 21.

In another case, the neck domain, the coiled-coil domain, and/or the globular tail domain of a chimeric myosin XI protein may be from, for example, the myosin XI-M protein (GenBank: EEE82373.1) shown in SEQ ID NO: 22. In such case, the neck domain consists of the 737th to 875th amino acid residues of the amino acid sequence of SEQ ID NO: 22. The coiled-coil domain consists of the 876th to 1049th amino acid residues of the amino acid sequence of SEQ ID NO: 22. The globular tail domain consists of the 1050th to 1513th amino acid residues of the amino acid sequence of SEQ ID NO: 22.

In addition to the above, the neck domain, the coiled-coil domain, and/or the globular tail domain of a chimeric myosin XI protein may be a domain comprising an amino acid sequence that has a deletion, substitution, and/or addition of one or several amino acids with respect to the above amino acid sequence of the relevant domain or a domain comprising an amino acid sequence having 70% or more, preferably 80% or more, and more preferably 90% identity to the above amino acid sequence of the relevant domain, which maintains the activity of imparting growth-enhancing action to a host plant.

(6) Vitis vinifera

If a donor plant is Vitis vinifera, the neck domain, the coiled-coil domain, and/or the globular tail domain of a chimeric myosin XI protein may be from the myosin XI protein (GenBank: CBI37226.3) shown in SEQ ID NO: 30. In such case, the neck domain consists of the 765th to 903rd amino acid residues of the amino acid sequence of SEQ ID NO: 30. The coiled-coil domain consists of the 904th to 1079th amino acid residues of the amino acid sequence of SEQ ID NO: 30. The globular tail domain consists of the 1080th to 1540th amino acid residues of the amino acid sequence of SEQ ID NO: 30.

Alternatively, the neck domain, the coiled-coil domain, and/or the globular tail domain of a chimeric myosin XI protein may be from, for example, the myosin XI protein (GenBank: CBI27864.3) shown in SEQ ID NO: 31. In such case, the neck domain consists of the 755th to 893rd amino acid residues of the amino acid sequence of SEQ ID NO: 31. The coiled-coil domain consists of the 894th to 1074th amino acid residues of the amino acid sequence of SEQ ID NO: 31. The globular tail domain consists of the 1075th to 1547th amino acid residues of the amino acid sequence of SEQ ID NO: 31.

In addition, the neck domain, the coiled-coil domain, and/or the globular tail domain of a chimeric myosin XI protein may be from, for example, the myosin XI protein (GenBank: CBI35200.3) shown in SEQ ID NO: 32. In such case, the neck domain consists of the 765th to 903rd amino acid residues of the amino acid sequence of SEQ ID NO: 32. The coiled-coil domain consists of the 904th to 1070th amino acid residues of the amino acid sequence of SEQ ID NO: 32. The globular tail domain consists of the 1071st to 1630th amino acid residues of the amino acid sequence of SEQ ID NO: 32.

In another case, the neck domain, the coiled-coil domain, and/or the globular tail domain of a chimeric myosin XI protein may be from, for example, the myosin XI protein (GenBank: CBI18667.3) shown in SEQ ID NO: 33. In such case, the neck domain consists of the 769th to 907th amino acid residues of the amino acid sequence of SEQ ID NO: 33. In addition, the coiled-coil domain consists of the 908th to 1121st amino acid residues of the amino acid sequence of SEQ ID NO: 33. The globular tail domain consists of the 1122nd to 1587th amino acid residues of the amino acid sequence of SEQ ID NO: 33.

Also, in another case, the neck domain, the coiled-coil domain, and/or the globular tail domain of a chimeric myosin XI protein may be from, for example, the myosin XI protein (GenBank: CBI33312.3) shown in SEQ ID NO: 34. In such case, the neck domain consists of the 738th to 876th amino acid residues of the amino acid sequence of SEQ ID NO: 34. The coiled-coil domain consists of the 877 to 1140 amino acid residues of the amino acid sequence of SEQ ID NO: 34. The globular tail domain consists of the 1141st to 1669th amino acid residues of the amino acid sequence of SEQ ID NO: 34.

In addition to the above, the neck domain, the coiled-coil domain, and/or the globular tail domain of a chimeric myosin XI protein may be a domain comprising an amino acid sequence that has a deletion, substitution, and/or addition of one or several amino acids with respect to the above amino acid sequence of the relevant domain or a domain comprising an amino acid sequence having 70% or more, preferably 80% or more, and more preferably 90% identity to the above amino acid sequence of the relevant domain, which maintains the activity of imparting growth-enhancing action to a host plant.

C. Structure of the Tail Domain

The amino acid sequence of a region constituting a tail domain other than a coiled-coil domain and a globular tail domain in a chimeric myosin XI protein is not particularly limited as long as it is from a myosin XI protein. Preferably, it is an amino acid sequence from a myosin XI protein of a type identical to that of a myosin XI protein from which a coiled-coil domain and a globular tail domain are obtained. More preferably, the amino acid sequence is from a myosin XI protein from a plant belonging to the family of a host plant. Further preferably, it is from a myosin XI protein of a plant belonging to the genus of a host plant. Even further preferably, it is an amino acid sequence from a myosin XI protein of a host plant. Therefore, it is most preferable for the entire region of a tail domain to be from a myosin XI protein of a type identical to that of the host plant.

In addition, both of a neck domain and a tail domain (which includes a coiled-coil domain and a globular tail domain) are preferably from myosin XI proteins of the same type. More preferably, the donor plants are of the same species. Therefore, it is preferable for the entire region including a neck domain and the downstream region thereof in a chimeric myosin XI protein to be from a myosin XI protein of an identical type from an identical donor plant.

In a specific example, if a host plant is A. thaliana, it is preferable for a region including the neck domain and the downstream region thereof in a chimeric myosin XI protein to have a sequence of the 736th to 1505th amino acid residues of the myosin XI-2 protein shown in SEQ ID NO: 3, a sequence of the 734th to 1520th amino acid residues of the myosin XI-1 protein shown in SEQ ID NO: 4, a sequence of the 737th to 1500th amino acid residues of the myosin XI-B protein shown in SEQ ID NO: 5, a sequence of the 737th to 1531st amino acid residues of the myosin XI-K1 protein shown in SEQ ID NO: 6, or a sequence of the 671st to 1523rd amino acid residues of the myosin XI-K2 protein shown in SEQ ID NO: 7.

In addition, if the host plant is *O. sativa*, it is preferable for a region including the neck domain and the downstream region thereof in a chimeric myosin XI protein to have a sequence of the 735th to 1506th amino acid residues of the myosin XI-I protein shown in SEQ ID NO: 8, a sequence of the 736th to 1533rd amino acid residues of the myosin XI-K protein shown in SEQ ID NO: 9, a sequence of the 716th to 1478th amino acid residues of the myosin XI-G protein shown in SEQ ID NO: 10, or a sequence of the 736th to 1529th amino acid residues of the myosin XI-J protein shown in SEQ ID NO: 11.

Alternatively, if the host plant is *B. distachyon*, it is preferable for a region including the neck domain and the downstream region thereof in a chimeric myosin XI protein to have a sequence of the 734th to 1501st amino acid residues of the myosin XI-I protein shown in SEQ ID NO: 12, a sequence of the 735th to 1556th amino acid residues of the myosin XI-F protein shown in SEQ ID NO: 13, a sequence of the 740th to 1514th amino acid residues of the myosin XI-G protein shown in SEQ ID NO: 14, or a sequence of the 1058th to 1852nd amino acid residues of the myosin XI-J protein shown in SEQ ID NO: 15.

Further, if the host plant is *S. bicolor*, it is preferable for a region including the neck domain and the downstream region thereof in a chimeric myosin XI protein to have a sequence of the 734th to 1520th amino acid residues of the myosin XI-I protein shown in SEQ ID NO: 16, a sequence of the 786th to 1529th amino acid residues of the myosin XI-K protein shown in SEQ ID NO: 17, a sequence of the 736 to 1464 amino acid residues of the myosin XI-F protein shown in SEQ ID NO: 18, or a sequence of the 746th to 1539th amino acid residues of the myosin XI-J protein shown in SEQ ID NO: 19.

In another case, if the host plant is poplar, it is preferable for a region including the neck domain and the downstream region thereof in a chimeric myosin XI protein to have a sequence of the 746th to 1539th amino acid residues of the myosin XI-M protein shown in SEQ ID NO: 20, a sequence of the 731st to 1509th amino acid residues of the myosin XI-M protein shown in SEQ ID NO: 21, or a sequence of the 737th to 1513th amino acid residues of the myosin XI-M protein shown in SEQ ID NO: 22.

Also, in another case, if the host plant is *V. vinifera*, it is preferable for a region including the neck domain and the downstream region thereof in a chimeric myosin XI protein to have a sequence of the 765th to 1540th amino acid residues of the myosin XI protein shown in SEQ ID NO: 30, a sequence of the 755th to 1547th amino acid residues of the myosin XI protein shown in SEQ ID NO: 31, a sequence of the 765th to 1630th amino acid residues of the myosin XI protein shown in SEQ ID NO: 32, a sequence of the 769th to 1587th amino acid residues of the myosin XI protein shown in SEQ ID NO:, or a sequence of the 738th to 1669th amino acid residues of the myosin XI protein shown in SEQ ID NO: 34.

1-3. Chimeric Myosin XI Gene
1-3-1. Structure

The term "chimeric myosin XI gene" refers to a polynucleotide encoding the chimeric myosin XI protein as described above. Therefore, the chimeric myosin XI gene described herein has a nucleotide sequence that comprises a nucleic acid region encoding the motor domain of a myosin XI protein of a plant belonging to the genus *Chara* and nucleic acid regions encoding the neck domain, the coiled-coil domain, and the globular tail domain of a myosin XI protein of a host plant.

A nucleotide sequence that constitutes the chimeric myosin XI gene does not necessarily need to have a nucleotide sequence identical to the wild-type myosin XI gene sequence of the plant from which the sequence is derived as long as a chimeric myosin XI protein having the amino acid sequence as described in the above section "Structure" of "Chimeric myosin XI protein" is produced as a result of expression of the gene. For example, it may be a nucleotide sequence comprising a degenerate mutation.

1-3-2. Construction of the Chimeric Myosin XI Gene

A chimeric myosin XI gene is a chimeric gene obtained by connecting a region encoding the motor domain of a myosin XI protein of a plant belonging to the genus *Chara* and regions encoding the neck domain, the coiled-coil domain, and the globular tail domain of a myosin XI protein of a host plant by a gene recombination technique. It can be constructed using a method known in the art.

Specifically, first, myosin XI genes are cloned from cDNA library of a plant belonging to the genus *Chara* and that of a host plant. A cDNA library can be constructed by a known method. For instance, mRNA is extracted from each of a plant belonging to the genus *Chara* and a host plant by a known method. Subsequently, each prepared mRNA pool is used as a template to prepare a cDNA library via an RT (reverse transcription) reaction. Techniques known in the art can be employed for specific preparation method including mRNA extraction and RT reaction conditions, and specific method of isolating genes of interest. For example, the methods described in the following can be used: Sambrook, J. et. al., (1989) Molecular Cloning: a Laboratory Manual Second Ed., Cold Spring Harbor Laboratory Press, Cold Spring Harbor, N.Y. In addition, there are a variety of kits for preparing mRNA and cDNA commercially available from life-science-related manufacturers may be utilized. Alternatively, it is also possible to use cDNA libraries that are commercially available for certain types of host plant or the like.

Next, a myosin XI gene derived from each plant is isolated from the cDNA library by a nucleic acid amplification method using a set of adequate primers (e.g., PCR methods including inverse-PCR, anchor PCR, TAIL-PCR, and the like) or a hybridization method using an adequate probe (e.g., a plaque hybridization method). If the myosin XI gene is isolated by a nucleic acid amplification method, reactions conditions and the like can be determined, for example, according to the method described in Innis M. et al (Ed.), (1990) Academic Press, PCR Protocols: A Guide to Methods and Applications. Primers used in a nucleic acid amplification method and probes used in a hybridization method can be designed based on nucleotide sequence information of a desired myosin XI gene obtained from a generally available database such as the database of NCBI (www.ncbi.nlm.nih.gov), the database of RIKEN Plant Science Center (www.psc.riken.jp), the DNA sequence analysis information database of the Kazusa DNA Research Institute (www.kazusa.or.jp), NCBI or the like. Alternatively, such primers and probes may be designed based on nucleotide sequences predicted based on the herein described amino acid sequences shown in SEQ ID NO: 2 (*C. corallina* myosin XI protein), SEQ ID NO: 3 (*A. thaliana* MYA2 protein), SEQ ID NO: 4 (*A. thaliana* myosin XI-1 protein), SEQ ID NO: 5 (*A. thaliana* myosin XI-B protein), SEQ ID NO: 6 (*A. thaliana* myosin XI-K1 protein), SEQ ID NO: 7 (*A. thaliana* myosin XI-K2 protein), SEQ ID NO: 8 (*O. sativa* myosin XI-I protein), SEQ ID NO: 9 (*O. sativa* myosin XI-K protein), SEQ ID NO: 10 (*O. sativa* myosin XI-G protein), SEQ ID NO: 11 (*O. sativa* myosin XI-J protein), SEQ ID NO: 12 (*B. distachyon* myosin XI-I protein), SEQ ID NO: 13 (*B. distachyon* myosin XI-F protein), SEQ ID NO: 14 (*B. distachyon* myosin XI-G protein), SEQ ID NO: 15 (*B. distachyon* myosin XI-J protein), SEQ ID NO: 16 (*S. bicoler* myosin XI-I protein), SEQ ID NO: 17 (*S. bicoler* myosin XI-K protein), SEQ ID NO: 18 (*S. bicoler* myosin XI-F protein), SEQ ID NO: 19 (*S. bicoler* myosin XI-G protein), SEQ ID NO: 20 (*P. trichocarpa* myosin XI-M protein), SEQ ID NO: 21 (*P. trichocarpa* myosin XI-M protein), SEQ ID NO: 22 (*P. trichocarpa* myosin XI-M protein), SEQ ID NO: 30 (*V. vinifera* myosin XI protein), SEQ ID NO: 31 (*V. vinifera* myosin XI protein), SEQ ID NO: 32 (*V. vinifera* myosin XI protein), SEQ ID NO: 33 (*V. vinifera* myosin XI protein), and SEQ ID NO: 34 (*V. vinifera* myosin XI protein). Primers and probes can be prepared by chemical synthesis based on the designed nucleotide sequences.

As to the myosin XI gene of a plant belonging to the genus *Chara*, it is sufficient to isolate the 5'-end region encoding the motor domain, and it is not always necessary to isolate the downstream region thereof or the full-length gene. Similarly, as to the myosin XI gene of a host plant, it is sufficient to isolate regions encoding the neck domain, the coiled-coil domain, and the globular tail domain, and preferably the entire region including the 5' end of the region encoding the neck domain and the downstream region thereof, and it is not always necessary to isolate the 5'-end region including a region encoding the motor domain.

Next, a chimeric myosin XI gene is constructed employing the myosin XI gene of a plant belonging to the genus *Chara* or a gene fragment thereof comprising the 5'-end region including a region encoding the motor domain and the myosin XI gene of a host plant or a gene fragment thereof comprising the 3'-end region including regions encoding the neck domain, the coiled-coil domain, and the globular tail domain, which are isolated as described above. A chimeric myosin XI gene can be constructed by cloning gene fragments comprising regions each encoding the relevant domain by a nucleic acid amplification method using a set of adequately designed primers, and connecting regions each encoding the relevant domain in a desired combination. It should be noted that the domains are placed on the nucleotide sequence with an arrangement identical to that of wild-type myosin XI. Connection of regions each encoding the relevant domain can be achieved using enzymatic binding by ligase treatment via cohesive ends generated with restriction enzyme or single nucleotide overhangs or the like, or a nucleic acid amplification method such as PCR with the use of primers each comprising a sequence for connection, provided that there is no shift in the downstream reading frame.

It is desirable to connect the motor domain of a plant belonging to the genus *Chara* and the coiled-coil domain of a host plant within a lever arm cc helix. The "lever arm α helix" corresponds to a region composed of a neck domain and an α helix that starts at a position near the C terminus of a converter domain included in the motor domain (FIG. 1C). For instance, in the case of *C. corallina*, a region composed of the 730th to 881st amino acids corresponds to a lever arm α helix. In such case, a region composed of the 730th to 743rd amino acids corresponds to the converter domain and a region composed of the 744th to 881th amino acids corresponds to the neck domain. In addition, in the case of *A. thaliana* myosin XI-2, a region composed of the 722nd to 870th amino acids corresponds to a lever arm α helix. In such case, a region composed of the 722nd to 735th amino acids corresponds to the converter domain and a region composed of the 736th to 876th amino acids corresponds to the neck domain. Specifically, it is preferable to connect a position just downstream of the C terminus of the converter domain of myosin XI of a plant belonging to the genus *Chara* to the N terminus of IQ motif which is located on the most N-terminal side in the neck domain of a host plant. This is because it is necessary to include the entire converter region of myosin of the genus *Chara* in order that a motor domain derived from myosin XI of a plant belonging to the genus *Chara* has sufficient motor activity (Seki M et al., J. Mol. Biol., 2004, 344:311-315), and because a full IQ motif of a host plant is necessary for a myosin light chain of a host plant to bind to the IQ motif.

In a chimeric myosin XI protein produced in accordance with the above principles as described in Examples below, a region to the 742nd position from *C. corallina* myosin XI is connected to the 735th position of MYA2, which corresponds to the 743rd position of *C. corallina* myosin XI, and a downstream region thereof.

The constructed chimeric myosin XI gene may be inserted into an expression vector so that the gene can be expressed therein according to need. The term "expression vector" refers to a nucleic acid expression system that can transport a gene and the like comprised therein into target plant cells and allow the gene to be expressed therein under adequate conditions. Specific examples thereof include a plasmid expression vector which utilizes a plasmid and a virus expression vector which utilizes a virus.

Examples of a plasmid expression vector that can be used include pBI, pPZP, pSMA, pUC, pBR, pBluescript (stratagene) and pTriEXTM (TaKaRa), and pBI and pRI binary vectors.

In addition, in case of a virus expression vector, a cauliflower mosaic virus (CaMV), a bean golden mosaic virus (BGMV), a tobacco mosaic virus (TMV) or the like can be utilized.

An expression vector may contain a promoter, a terminator, an enhancer, a polyA addition signal, a 5'-UTR (untranslated region) sequence, a labeling or selection marker gene, a multicloning site, a replication origin, and the like. The type of each component is not particularly limited as long as the component can exhibit its function in plant cells. A component known in the art can be adequately selected depending on a plant into which the expression vector is introduced or the objective of the component in a plant (e.g., the expression pattern).

In addition to a promoter of the endogenous myosin XI gene of a host plant, an overexpression-type promoter, a constitutive promoter, a site-specific promoter, a stage-specific promoter, and/or an inducible promoter can be used as a promoter depending on a desired expression pattern. Specific examples of an overexpression-type constitutive promoter include a cauliflower mosaic virus (CaMV)-derived 35S promoter, a Ti plasmid-derived nopaline synthase gene promoter (Pnos), a maize-derived ubiquitin promoter, a rice-derived actin promoter, and a tobacco-derived PR protein promoter. Also, a ribulose bisphosphate carboxylase small subunit (Rubisco ssu) promoter or a histone promoter can be used. In addition, examples of a site-specific promoter include a promoter that induces root-specific expression described in JP Patent Publication (Kokai) No. 2007-77677. As described above, enhancement of growth may be enhancement of growth of the whole plant or enhancement of growth of a portion of a plant. In addition, according to the present invention, it is also possible to suppress growth of the whole plant or a portion thereof as described below. It is also possible by using site-specific promoters to enhance growth of one portion of a plant and suppress growth of another portion thereof. For instance, it is possible to enhance resistance to environmental stress by suppressing growth of the aerial portion of a plant and enhancing growth of the underground portion thereof.

Examples of a terminator include a nopaline synthase (NOS) gene terminator, an octopine synthase (OCS) gene terminator, a CaMV 35S terminator, a 3' terminator of *Escherichia coli* lipopolyprotein (lpp), a trp operon terminator, an amyB terminator, and an ADH1 gene terminator. A terminator used herein is not particularly limited as long as it has a sequence that can terminate transcription of a gene transcribed by the above promoter. Needless to say, a terminator inherent to an endogenous myosin XI gene of a host plant may be used.

Examples of an enhancer that can be used include an enhancer region which includes an upstream sequence in a CaMV 35S promoter and a CMV enhancer, in addition to an enhancer inherent to an endogenous myosin XI gene of a host plant. An enhancer used herein is not particularly limited as long as it can enhance efficiency of chimeric myosin XI expression.

Examples of a selection marker gene that can be used include drug-resistant genes (e.g., a tetracycline-resistant gene, an ampicillin-resistant gene, a kanamycin-resistant gene, a hygromycin-resistant gene, a spectinomycin-resistant gene, a chloramphenicol-resistant gene, and a neomycin-resistant gene), fluorescent or luminescent reporter genes (e.g., luciferase, β-galactosidase, β-glucuronidase (GUS), and a green fluorescent protein (GFP)), and genes for enzymes such as neomycin phosphotransferase II (NPT II) and dihydrofolate reductase. A labeling or selection marker gene may be inserted into an expression vector that comprises the chimeric myosin XI or another expression vector. In the latter case, by co-introducing the respective expression vectors into a desired plant, it is possible to obtain effects equivalent to those obtained with a single expression vector in which the above genes are connected.

A method known in the art can be used as a method for inserting the chimeric myosin XI gene into an expression vector at a specific site. An example of such method is described in Sambrook, J. et. al., (1989) Molecular Cloning: a Laboratory Manual Second Ed., Cold Spring Harbor Laboratory Press, Cold Spring Harbor, N.Y. According to a method usually used, a prepared chimeric myosin XI gene is cleaved with an adequate restriction enzyme, and inserted into and connected with a suitable expression vector at a corresponding restriction enzyme site or a multicloning site, or a 5'-T-protruding end in case of a PCR product having a 3'-A-protruding end which is obtained using Taq DNA polymerase or the like. Alternatively, if a commercially available system or kit is used, a method specific to such system or kit can be used for preparation. For example, a Gateway system (Invitrogen) can be used.

1-4. Transformation Method

A method known in the art can be used as a method for transforming a host plant. In general, transformation can be performed by introducing a chimeric myosin XI gene or a plasmid expression vector or virus expression vector containing such gene into host plant cells.

In a case in which a host plant is transformed using a chimeric myosin XI gene or a plasmid expression vector containing such gene, a protoplast method, a particle gun method or an *Agrobacterium* method, or the like can be used, for example.

The protoplast method is a method for introducing a desired chimeric myosin XI gene into plant cells, where protoplasts are obtained by removing cell walls from host plant cells via treatment with an enzyme such as cellulase, and the gene is introduced thereinto by means of a known technique such as an electroporation method, a microinjection method, or a polyethyleneglycol method. The electroporation method comprises applying electrical pulses to a mixture of protoplasts and a desired gene so as to introduce the gene into the protoplasts. The microinjection method comprises directly introducing a desired gene into protoplasts using a microneedle under a microscope. In addition, the polyethyleneglycol method comprises introducing a desired gene into protoplasts by allowing polyethyleneglycol to act thereon.

The particle gun method is a method in which a desired gene (a chimeric myosin XI gene in case of the present invention) is allowed to adhere to microparticles of gold, tungsten or the like, and the particles are shot into plant tissue cells using high-pressure gas so as to introduce the desired gene into cells. Accordingly, a transformant in which the desired gene is incorporated into the genomic DNA of the host cell can be obtained. In general, transformed cells can be screened for based on the presence of a marker gene product.

The *Agrobacterium* method is a transformation method comprising introducing a desired gene into host plant cells using a bacterium belonging to the genus *Agrobacterium* (e.g., *A. tumefaciens* or *A. rhizogenes*) as a transforming factor and Ti plasmid which is derived therefrom.

Any of the above transformation methods is known in the art. Specific examples of the methods are described in, for example, Bechtold et al., 1993, C. R. Acad. Sci. Paris, Life Sci.

In addition, in a case in which a virus expression vector (e.g., CaMV, BGMV, or TMV described above) containing a chimeric myosin XI gene is used, the chimeric myosin XI gene can be introduced into host plant cells by infecting the plant cells with the virus vector. Specifically, for example, a plant virus genome is inserted into a cloning vector such as an *Escherichia coli*-derived vector to prepare a recombinant, and a chimeric myosin XI gene is then inserted into the virus genome of the recombinant. Subsequently, the plant virus genome region is cut out from the recombinant using a restriction enzyme, and desired plant cells is infected with the obtained virus genome. Thus, a desired gene can be introduced into plant cells. Details of such gene transfer method using a virus vector are described in Hohn et al. (Molecular Biology of Plant Tumors (Academic Press, New York) 1982, p. 549), U.S. Pat. No. 4,407,956, and the like.

Further, a host plant transformed in this step may be a plant of a wild-type strain or a mutant strain. If a host plant is a plant of a mutant strain, it is preferably a knockout plant which is deficient in a gene for myosin XI of a type identical to that of a donor plant-derived coiled-coil domain in the chimeric myosin XI gene. For example, if the coiled-coil domain of a chimeric myosin XI gene to be introduced into a host plant is from the myosin XI-I gene of a donor plant, the host plant is preferably a plant of a myosin XI-1-deficient mutant strain.

1-5. Plant Regeneration Method

A method for regenerating a plant with enhanced growth from transformed host plant cells can be carried out based on a known method for regenerating a transgenic plant from transformed plant cells.

An example of such method is an in vitro regeneration method for regenerating a plant from transformed plant cells via formation of calluses which are composed of undifferentiated growing cells. Such method is known in the art. The method is specifically described in Bechtold et al., 1993, C. R. Acad. Sci. Paris, Life Sci described above or the like.

In addition, it is also possible to use an in planta method which comprises directly introducing a nucleic acid expression system into cells of a desired plant individual without the step of callus or cell culture. Plant hormones such as auxin, gibberellin and/or cytokinin may be used to promote growth and/or division of transformed cell.

A transgenic plant obtained by the above method is a first-generation transgenic plant, which is a plant with enhanced growth of interest. In addition, the term "first-generation transgenic plant" used herein also encompasses a clone of a first-generation transgenic plant having genetic information identical thereto. For example, a plant obtained via cutting, grafting, or layering of a portion of a plant obtained from a first-generation transgenic plant, a plant regenerated after cell culture and through callus formation, and a new autotroph generated from a vegetative propagation organ (e.g., a rhizome, tuberous nut, corm, or runner) obtained through asexual reproduction from a first-generation transgenic plant fall under the first-generation transgenic plant.

2. Method for Obtaining a Progeny of a Plant with Enhanced Growth

The second embodiment of the present invention relates to a method for obtaining a progeny of a plant with enhanced growth. The term "progeny of a plant with enhanced growth" used herein refers to a progeny which is obtained through sexual reproduction of a first-generation transgenic plant that is obtained by the production method of the first embodiment, and which retains a chimeric myosin XI gene so that the gene can be expressed therein. An example thereof is a seedling of a first-generation transgenic plant.

A progeny of the plant with enhanced growth of the present invention can be obtained by a known method. For instance, a plant with enhanced growth that is a first-generation transgenic plant is allowed to set seed to obtain a seed which is a first-generation progeny and a second-generation transgenic plant. In an example of a method for obtaining a second-generation progeny from the first-generation progeny of the present invention, the seeds are caused rooting on an adequate medium and the seedling is transplanted to a pot containing soil, and a second-generation progeny can then be obtained by cultivating under adequate cultivation conditions. The generation of a progeny obtained in this embodiment is not limited as long as the chimeric myosin XI gene described for the first embodiment is retained in the progeny. Therefore, a third- or later-generation progeny can be obtained by repeating a method similar to the method for obtaining a second-generation progeny.

3. Plant with Enhanced Growth

The third embodiment of the present invention relates to a plant with enhanced growth. Specific examples thereof include a transgenic plant with enhanced growth obtained by the production method of the first embodiment and a progeny obtained by the production method of the second embodiment. Thus, the plant with enhanced growth of the present invention includes any plant as long as it comprises at least one chimeric myosin XI gene described for the first embodiment so that the gene can be expressed therein, regardless of the generation after transformation.

The constitutions of the plant with enhanced growth are described in detail for the first and the second embodiments. Therefore, the details are omitted in this embodiment.

4. Method for Enhancing Growth of a Plant

The forth embodiment of the present invention relates to a method for enhancing growth of a desired target plant by introducing a chimeric myosin XI gene into the plant. The method of this embodiment is substantially the same as the method for producing a plant with enhanced growth of the first embodiment. Therefore, details of the method are omitted in this embodiment.

5. Method for Producing a Plant with Suppressed Growth 5-1. Outline and Definition The fifth embodiment of the present invention relates to a method for producing a plant with suppressed growth.

Specifically, the method for producing a plant with suppressed growth of the present invention comprises a step of introducing a gene encoding a chimeric myosin protein into a host plant so as to transform the host plant, wherein the chimeric myosin protein comprises a neck domain, a coiled-coil domain, and a globular tail domain from a myosin protein involved in cytoplasmic streaming of a donor plant, and a motor domain from a myosin protein of a plant other than the host plant, which has sliding velocity that is lower than that of the myosin protein involved in cytoplasmic streaming of the donor plant.

Here, examples of a myosin protein involved in a cytoplasmic streaming of a donor plant include a myosin XI protein. In addition, an example of a myosin protein which has sliding velocity that is lower than that of a myosin protein involved in cytoplasmic streaming of the donor plant is a myosin Vb protein and preferably an animal Vb protein. The present invention is described below with reference to the above specific examples; however, the present invention is not limited thereto. In addition, it is also possible to enhance growth of one portion of a plant and to suppress growth of another portion of the plant by combining the method for producing a plant with suppressed growth of the present invention and the method for producing a plant with enhanced growth of the present invention.

The term "plant with suppressed growth" used in the present invention refers to a transgenic plant whose growth is suppressed as compared with a wild-type strain used as the original host plant. Therefore, the plant size of such transgenic plant becomes smaller than that of a plant of a wild-type strain in an identical growth environment. Suppression of growth may be suppression of growth of a part or the whole of a plant.

Basically, the production method of the present invention conforms to the method of the first embodiment. However, this embodiment differs from the first embodiment in that a gene encoding a chimeric myosin Vb-XI protein (hereinafter sometimes referred to as "chimeric myosin Vb-XI gene") is introduced into a host plant in the "transformation step."

A host plant used in this embodiment is not particularly limited. Specifically, it may be the same as the one described in Example 1. It should be noted that the host plant used in this embodiment may be a plant belonging to the genus *Chara*, while the host plant used in the first to forth embodiments is a plant that is not a plant belonging to the genus *Chara*.

The term "chimeric myosin Vb-XI protein" refers to a chimeric protein formed with a myosin Vb protein and a plant myosin XI protein. The term "myosin XI protein" is as described for the first embodiment. A "myosin Vb protein" is one of polypeptides that constitute the myosin heavy chain like a plant myosin XI protein and classified as belonging to the myosin V class which constitutes the myosin superfamily. A myosin Vb protein forms a homodimer and functions as a myosin Vb molecule in cells. A myosin Vb molecule is formed as a homodimer which is composed of two myosin proteins (polypeptides), like a myosin XI molecule, and each polypeptide comprises three functional regions which are a motor domain located in the N-terminal region, a neck domain located downstream of the motor domain, and a tail domain located downstream of the neck domain. In humans, myosin Vb is expressed in a variety of tissues including lungs, kidneys, small intestine, testis, liver and heart (Rodriguez and Cheney, 2002, J. Cell Sci., 115: 991-1004). Results of analyses using human culture cells suggested that myosin Vb is involved in the cell membrane-recycling system that plays a fundamental role in the maintenance of the membrane composition (Lapierre et al., 2001, Mol. Biol. Cell, 12: 1843-1857; Fan et al., 2004, Mol. Biol. Cell 15: 2456-2469; Volpicelli et al., 2002, J. Neurosci., 22: 9776-9784; Provance et al., 2004, Proc. Natl. Acad. Sci. U.S.A., 101: 1868-1873). In addition, it is known from in vitro analysis that the sliding velocity of myosin Vb is approximately 0.2 μm/s (Watanabe et al., 2006, Biochemistry, 45: 2729-2738). In the present invention, a myosin Vb protein is preferably an animal-derived myosin Vb protein.

The "animal" in this embodiment is not particularly limited as long as it is an organism classified as belonging to the animal kingdom in terms of biotaxis. Such animal may be any of invertebrates including arthropods of the class *Insecta, Arachnida, Chilopoda* and *Crustacea*, notochords, echinoderms, mollusks and nematodes, and vertebrates including agnathonae, fish, amphibians, reptiles, birds, and mammals. The aminal used herein is preferably a vertebrate and more preferably a mammal. Examples thereof include humans, rats, mice, and rabbits.

5-2. Structure of Chimeric Myosin Vb-XI Protein

The "chimeric myosin Vb-XI protein" used in the present invention is characterized in that it comprises a motor domain from an animal myosin Vb protein, and a neck domain, a coiled-coil domain, and a globular tail domain from a donor plant myosin XI protein. The structure of such protein is basically identical to that of the chimeric myosin XI protein in the first embodiment except that it comprises a motor domain from an animal myosin Vb protein.

The motor domain of the chimeric myosin Vb-XI protein in this embodiment is not particularly limited as long as it is from an animal myosin Vb protein. An example thereof is a human (*Homo sapiens*) myosin Vb protein. More specifically, it is the motor domain comprising the amino acid sequence shown in SEQ ID NO: 35.

In addition, it may be the human myosin Vb protein motor domain comprising an amino acid sequence that has a deletion, substitution, and/or addition of one or several amino acids with respect to the amino acid sequence shown in SEQ ID NO: 35, or a myosin Vb protein motor domain from another animal that comprises an amino acid sequence having 70% or more, preferably 80% or more, and more preferably 90% identity to the amino acid sequence shown in SEQ ID NO: 35, which retains the activity of imparting growth-suppressing action to a host plant. This is because it is highly probable that a myosin Vb protein from an animal of a different species that comprises the motor domain comprising the above amino acid sequence will be an ortholog of a human myosin Vb protein, and thus such motor domain is presumed to have actions and effects equivalent to those of a motor domain comprising the amino acid sequence shown in SEQ ID NO: 35. In addition, the term "several" used herein refers to an integer of 2 to 10, for example, an integer of 2 to 7, 2 to 5, 2 to 4, or 2 to 3. In addition, the term "identity" used herein refers to the percentage (%), in the total number of amino acids of one amino acid sequence (i.e., the amino acid sequence shown in SEQ ID NO: 1 in the above case), of the number of amino acids that match the amino acids in the other amino acid sequence, when the two amino acid sequences are aligned so that the number of matched amino acids is maximized by introducing gap(s) into one or both of the sequences, if necessary.

5-3. Structure and Construction of a Chimeric Myosin Vb-XI Gene

The term "chimeric myosin Vb-XI gene" used herein refers to a polynucleotide encoding the chimeric myosin Vb-XI protein. Therefore, the chimeric myosin Vb-XI gene used herein has a nucleotide sequence including a nucleic acid region encoding the motor domain of an animal myosin Vb protein, and nucleic acid regions encoding the neck domain, the coiled-coil domain, and the globular tail domain of a host plant myosin XI protein.

A nucleotide sequence that constitutes the chimeric myosin Vb-XI gene does not necessarily need to have a nucleotide sequence identical to the wild-type myosin Vb-XI gene sequence of an animal and/or a plant used as the original animal and/or the original plant as long as a chimeric myosin Vb-XI protein having the amino acid sequence as described in the above section "Structure of chimeric myosin Vb-XI protein" is produced as a result of expression of the gene. For example, it may be a nucleotide sequence comprising a degenerate mutation.

A chimeric myosin Vb-XI gene is a chimeric gene obtained by connecting a region encoding the motor domain of an animal myosin Vb protein and regions encoding the neck domain, the coiled-coil domain, and the globular tail domain of a host plant myosin XI protein by a gene recombination technique. It can be constructed by a method known in the art. Such method is basically identical to the method described for the first embodiment and thus details of the method are omitted in this embodiment. In addition, a method for introducing a constructed chimeric myosin Vb-XI gene into a host plant and a method for regenerating a plant can be carried out according to the corresponding methods described for the first embodiment.

6. Method for Obtaining a Progeny of a Plant with Suppressed Growth

The sixth embodiment of the present invention relates to a method for obtaining a progeny of a plant with suppressed growth. The term "progeny of a plant with suppressed growth" used herein refers to a progeny which is obtained through sexual reproduction of a first-generation transgenic plant that is obtained by the production method of the fifth embodiment, and which retains a chimeric myosin Vb-XI gene so that the gene can be expressed therein. An example thereof is a seedling of a first-generation transgenic plant.

The method for obtaining a progeny from a plant with suppressed growth of the present invention can be carried out according to the method described in the second embodiment. Therefore, details of the method are omitted in this embodiment.

7. Plant with Suppressed Growth

The seventh embodiment of the present invention relates to a plant with suppressed growth. Specific examples thereof include a transgenic plant with suppressed growth obtained by the production method of the fifth embodiment or a progeny obtained by the obtainment method of the sixth embodiment. That is, the plant with suppressed growth of the present invention includes any plant regardless of the generation after transformation as long as it is a plant that comprises at least one chimeric myosin Vb-XI gene described for the fifth embodiment so that the gene can be expressed therein.

Details of the constitutions of the plant with suppressed growth are described for the fifth and six embodiments and thus are omitted in this embodiment.

8. Method for Suppressing Growth of a Plant

The eighth embodiment of the present invention relates to a method for suppressing growth of a desired target plant by introducing a chimeric myosin Vb-XI gene into the target plant. The method of this embodiment is substantially to the same as the method for producing a plant with suppressed growth of the fifth embodiment. Therefore, details of the method are omitted in this embodiment.

EXAMPLES

Example 1: Construction of the Chimeric Myosin XI Gene

The chimeric myosin XI gene used in the present invention was designed and constructed in the manner described below.

(Method)

1. Cloning of the *A. thaliana* XI-2 (MYA2) Gene

Total RNA was prepared from an *A. thaliana* plant on day 7 after sowing. Total RNA was prepared using an RNeasy Plant Mini Kit (QIAGEN) according to the manufacturer's protocol. First-strand cDNA was prepared using a Super-Script III First-Strand Synthesis System for RT-PCR (Invitrogen) according to the manufacturer's protocol. Next, the MYA2 gene was amplified by RT-PCR using total RNA prepared above. PCR was performed using the oligonucleotide shown in SEQ ID NO: 23 as a forward primer and the oligonucleotide shown in SEQ ID NO: 24 as a reverse primer under reaction conditions comprising 35 cycles of 98° C. for 10 seconds, 60° C. for 30 seconds, and 72° C. for 3.5 minutes. The amplified products were inserted into a pENTR-D-TOPO cloning vector included in a Directional TOPO Cloning Kit (Invitrogen, Carlsbad, Calif., U.S.A.) according to the manufacturer's protocol to clone the MYA2 gene.

2. Cloning of the *C. corallina* XI Gene

The *C. corallina* myosin XI (hereinafter referred to as "Chara XI") gene was prepared from total RNA according to the method of Kashiyama et al. (J. Biochem., 2000, 127: 1065-1070).

3. Construction of the Flag-Chimeric Myosin XI Gene

The chimera XI gene encoding chimeric myosin XI (hereinafter referred to as "chimera XI") which has a *Chara* XI motor domain on the MYA2 backbone was produced by connecting a nucleotide sequence (SEQ ID NO: 25) encoding the 1st to 742nd amino acid residues of *C. corallina* myosin XI and a nucleotide sequence (SEQ ID NO: 26) encoding the 735th to 1505th amino acid residues of *A. thaliana* MYA2 according to the amino acid positions reported by Ito et al. (J Biol Chem, 2007, 282: 19534-19545). Connection was carried out using EaqI sites added to the 3' end of the nucleotide sequence shown in SEQ ID NO: 25 and the 5' end of the nucleotide sequence shown in SEQ ID NO: 26. In addition, a FLAG tag sequence was fused to the 5' end of the chimera XI gene (hereinafter referred to as the "Flag-chimera XI" gene) in order to purify a chimera XI protein obtained as a result of gene expression.

4. Cloning of the MYA2 Gene Promoter

An MYA2 gene promoter was cloned in a manner similar to the case of cloning of the MYA2 gene. Specifically, the region of 3000-base length upstream of the initiation codon of MYA2 (hereinafter referred to as "ProXI-2"), which was predicted to comprise an MYA2 gene promoter, was amplified from the *A. thaliana* genome by PCR (35 cycles of 98° C. for 10 sec., 55° C. for 15 sec., and 72° C. for 2 min.) using a forward primer (SEQ ID NO: 27) in which a XmaI site had been added at the 5' end and a reverse primer (SEQ ID NO: 28) in which StuI and NcoI sites had been added at the 5' end. The obtained amplified product was inserted into a pENTR-D-TOPO cloning vector to clone ProXI-2.

5. Construction of the GFP-Chimeric Myosin XI Fusion Gene

Fusion genes of the sGFP gene (SEQ ID NO: 29) with MYA2 or chimeric myosin XI gene were constructed. Specifically, ProXI-2:sGFP: MYA2 connected downstream of the MYA2 gene promoter was constructed by Triple Template-PCR (TT-PCR), subcloned using a pENTR-D-TOPO cloning vector, and transferred to pGWB501 (Nakagawa et al., 2007, Biosci. Biotechnol. Biochem. 71: 2095-2100) via an LR reaction. The construct in pGWB501 was introduced into *Agrobacterium tumefaciens* GV3101::pMP90 strain using a Gene Pulser (Bio-Rad, Hercules, Calif., U.S.A.).

Example 2: In Vitro Motility Assay

The chimera XI gene constructed in Example 1 and the wild-type MYA2 gene were expressed in vitro for verification of the velocity of movement of each myosin molecule.

(Method)

The Flag-chimera XI gene and the Flag-MYA2 XI gene prepared in Example 1 were expressed by a known method using a baculovirus-insect cell system. Subsequently, a Flag-chimera XI protein was purified using an anti-FLAG M2 affinity resin (Sigma).

The velocity was determined for each myosin molecule by an antibody-based version of in vitro sliding filament assay using an anti-C-mic monoclonal antibody (Zymed Laboratories Inc.; Cat. No. 13-2500), except that, unlike conventional in vitro sliding filament assay, exogenous calmodulin (approximately 1 µM) was added to an assay buffer during the assay in this Example. The average sliding velocity of the myosin molecule was calculated by determining displacement of actin filament that smoothly moves over a distance more than 10 µm.

(Results)

Figure 3:
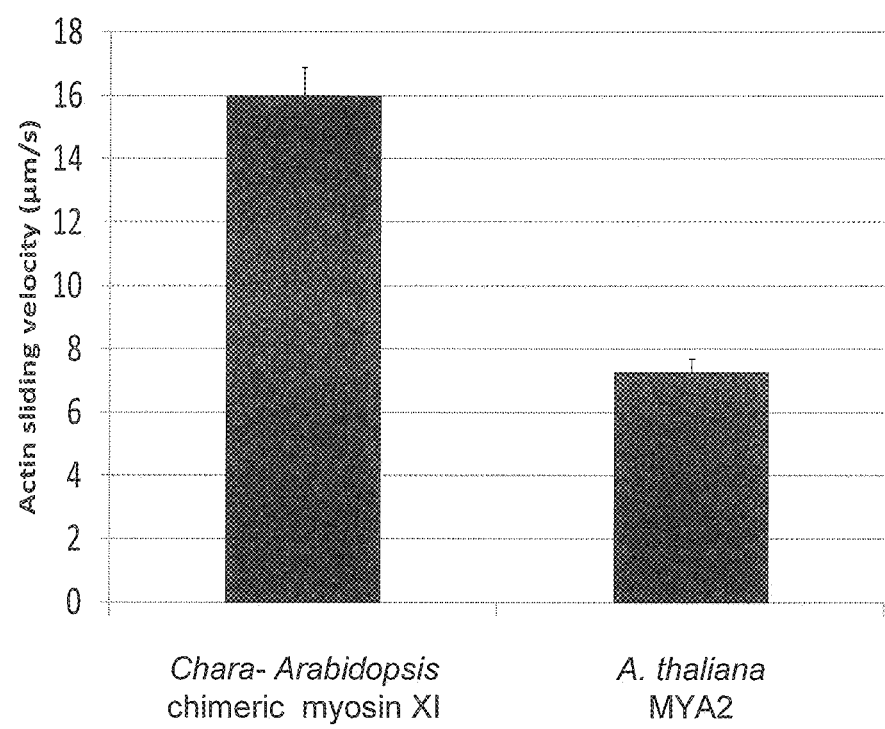
FIG. 3 shows results of in vitro motility assay for the chimeric myosin XI molecule and the MYA2 molecule.

FIG. 3 shows the results. The sliding velocity of the wild-type *A. thaliana* myosin XI-2 (MYA2) was 7.0±1.3 µm/sec at 25° C., while the sliding velocity of Flag-chimera XI was 16.2±0.84 µm/sec. This indicates that the sliding velocity of Flag-chimera XI becomes as high as almost two times that of the wild-type plant.

Example 3: Verification of the Phenotype of a Transgenic Plant (1)

The phenotype of *A. thaliana* transformed with the chimeric myosin XI gene constructed in Example 1 was compared with the phenotype of *A. thaliana* transformed with the wild-type MYA2 gene for verification.

1. Plant Transformation

The GFP-chimera XI gene constructed in Example 1 was introduced into a XI-2 gene-knockout *A. thaliana* (SALK 055785; At5g43900) strain (designated as the "MYA2-KO strain") (provided by Dr. Dolja of Oregon State University, USA) by a floral dipping method. As a control, the sGFP-MYA2 gene was constructed by connecting the sGFP gene to the 5' end of the wild-type MYA2 gene. Specifically, ProXI-2:sGFP:MYA-2 connected downstream of the MYA2 gene promoter was constructed by Triple Template-PCR (TT-PCR) and subcloned using a pENTR-D-TOPO cloning vector. Then, pGWB501 (Nakagawa et al., 2007, Biosci. Biotechnol. Biochem. 71: 2095-2100) was introduced into the MYA2-del strain via an LR reaction in a similar manner. First-generation (T1) transgenic plants of the transformed MYA2-KO strains were selected based on hygromycin resistance. Seeds of transformed plants were sown on a selective medium (MSO: 1 µL/mL Gamborg B5 vitamin, 2% sucrose, 100 mg/mL hygromycin, 250 mg/mL cefotaxime, 0.8% agarose) based on hygromycin resistance, and cultured at 23° C. under continuous light for 7 days.

2. Culture of Transgenic Plants

The obtained T1 strains were separately sown on a selective medium (MSO: 1 µL/mL Gamborg B5 vitamin, 2% sucrose, 100 mg/mL hygromycin, 250 mg/mL cefotaxime, and 0.8% agarose) prepared in a square culture dish in order to examine the state of growth, followed by cultivation at 23° C. under continuous light for 5 and 7 days. Then, growth of the main root and root hair was observed. Thereafter, each plant was transplanted to soil (Jiffy 7, 44 mm, Jiffy Products International AS, Norway) to examine the aerial portion thereof, followed by culture at 23° C. under sunlight for 12 hours/day for approximately 40 days.

(Results)

Figure 4A:
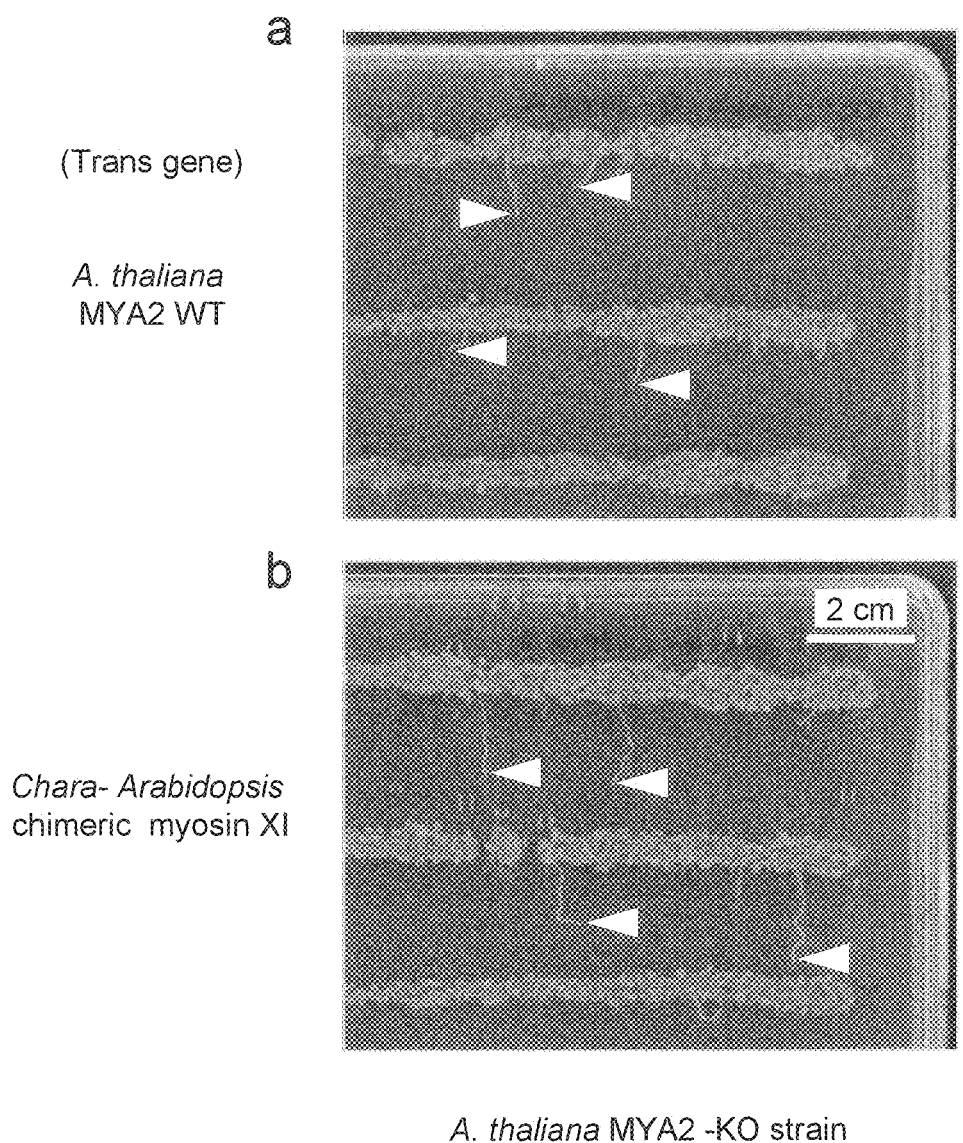
FIGS. 4A to 4E show phenotypes of first-generation (T1) transgenic plants obtained by introducing the chimeric myosin XI gene or the wild-type *A. thaliana* MYA2 gene into the *A. thaliana* MYA2-KO strain.
Figure 4B:
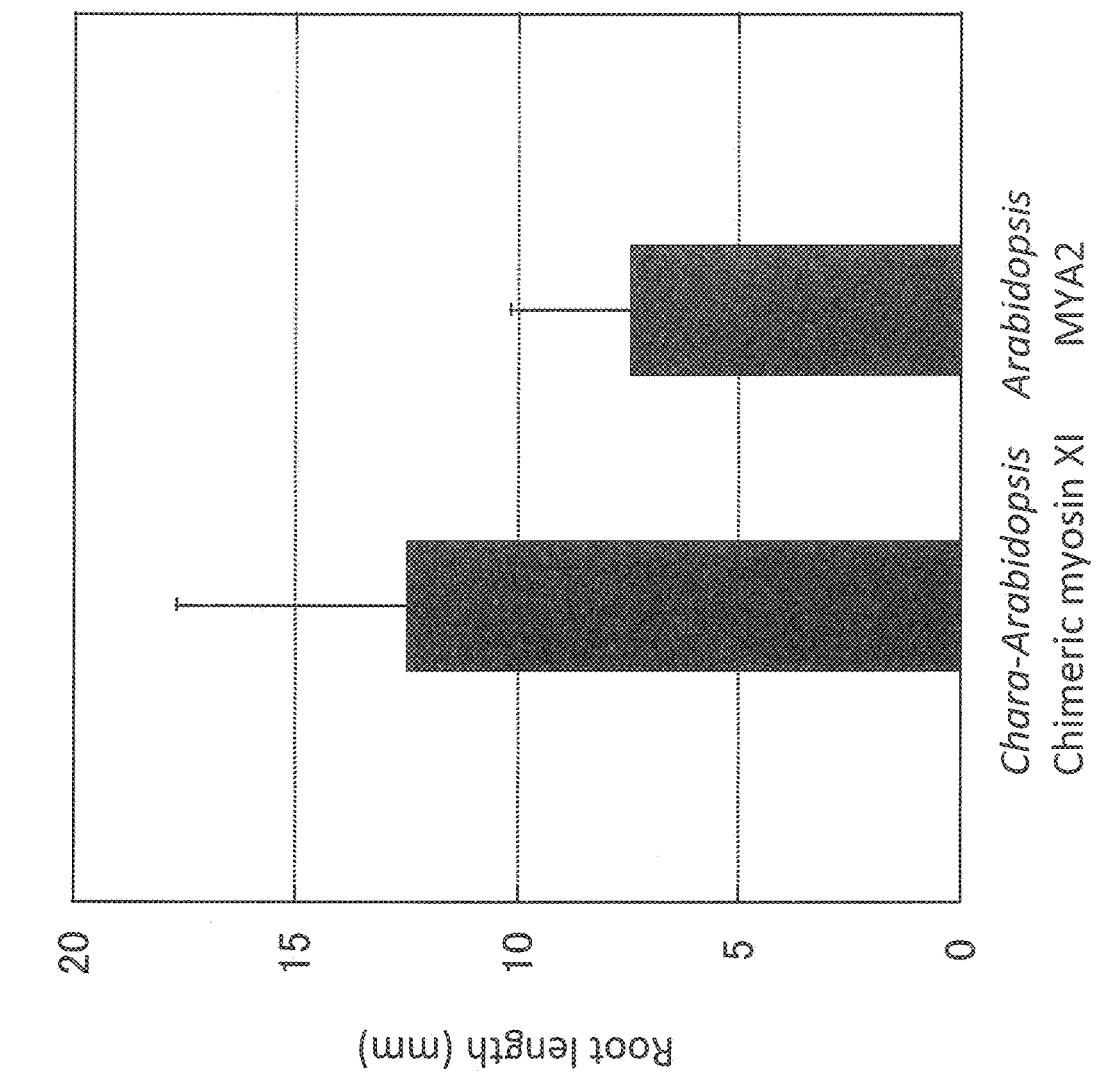
Figure 4C:
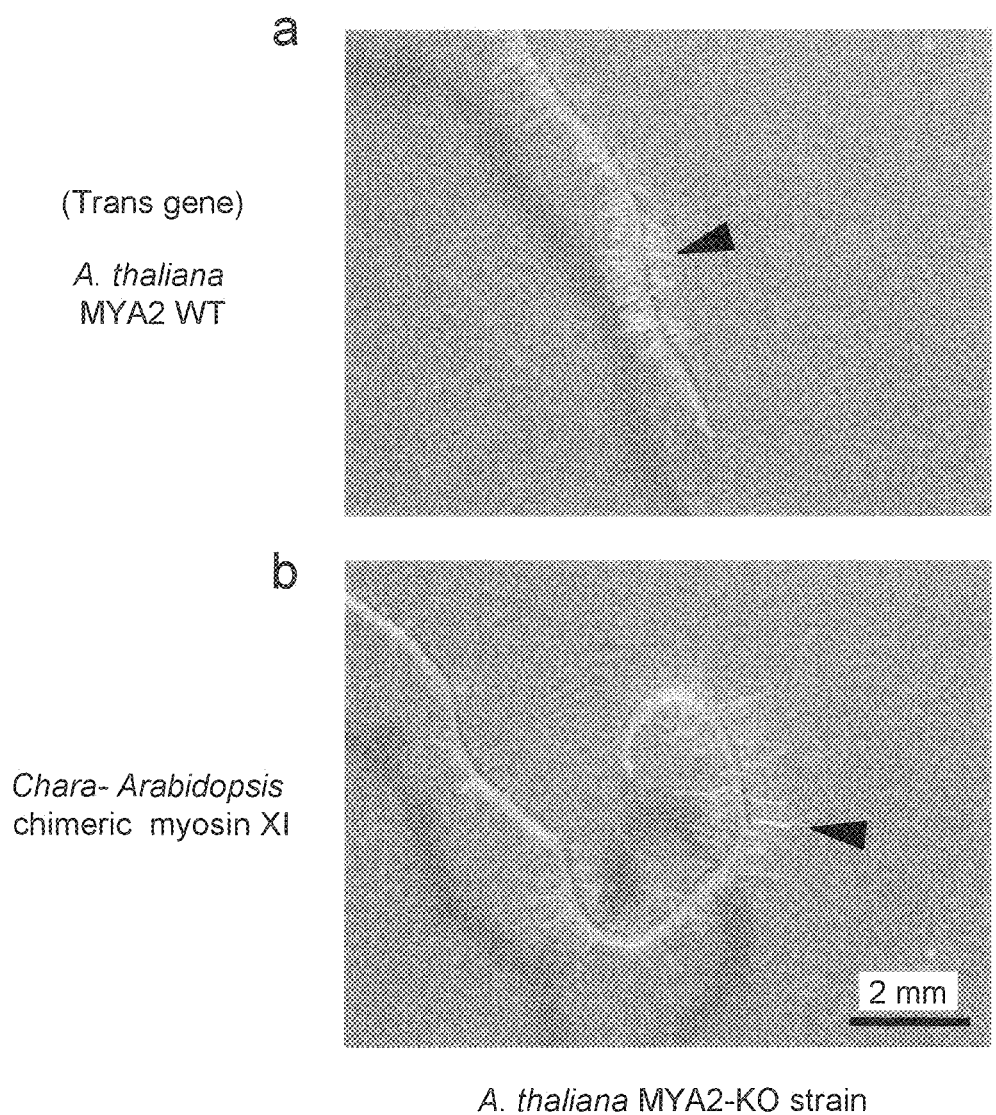
Figure 4D:
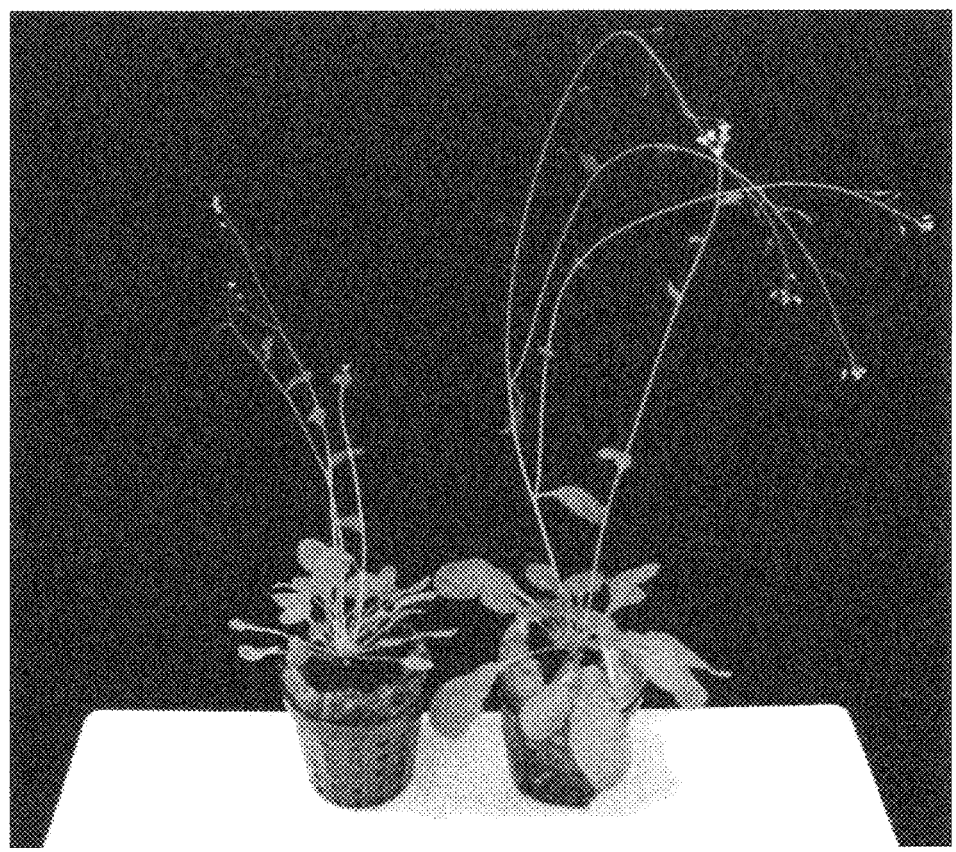
Figure 4E:
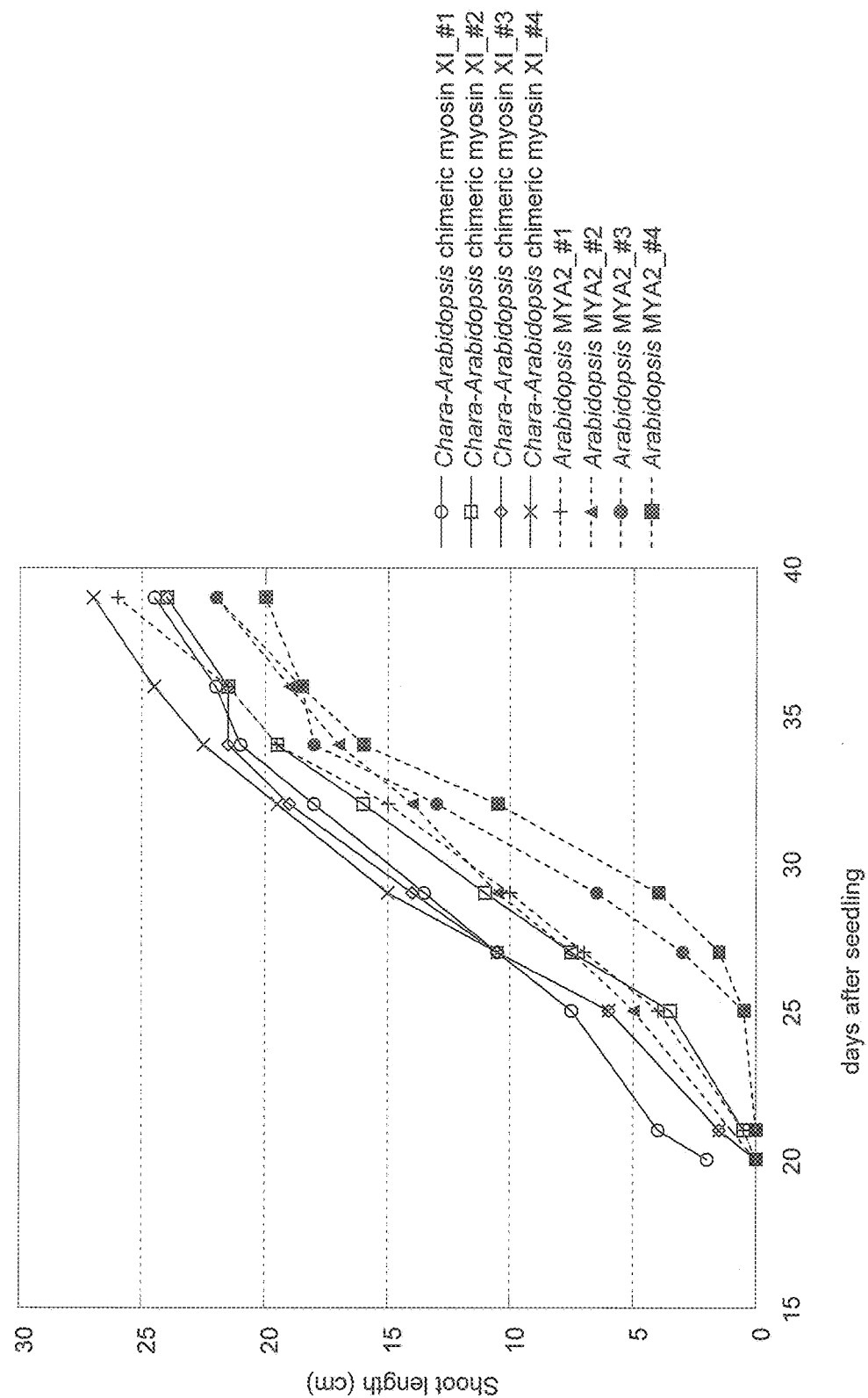

FIGS. 4A to 4E show the results. FIG. 4A shows main root lengths of T1 (MYA2) from the *A. thaliana* MYA2-KO strain and T1 (chimera XI) from the *A. thaliana* MYA2-KO strain on day 5 after sowing. FIG. 4B is a graph showing the average main root length. FIG. 4C shows enlarged views of the roots shown in FIG. 4A, showing the root hair length. FIG. 4D shows growth of the aerial portion of each T1 plant. FIG. 4E shows changes in the shoot length during the period from day 20 to day 40 after sowing.

Elongation of the main root and root hair, stem elongation, and leaf size enlargement were observed during a specific period of cultivation for T1 (chimera XI), into which the chimera XI gene had been introduced, to a greater extent than was observed for T1 (MYA2), into which the wild-type MYA2 gene had been introduced. That is, it was revealed that the growth of a transgenic plant transformed with the chimera XI gene is enhanced, compared with a plant having wild-type myosin XI.

Example 4: Verification of the Phenotype of a Transgenic Plant (2)

Other phenotypes of *A. thaliana* transformed with the chimeric myosin XI gene constructed in Example 1 were compared with those of the wild-type *A. thaliana* strain for verification.

1. Plant Transformation

The GFP-chimera XI gene constructed in Example 1 was introduced into a MYA2-KO strain by a floral dipping method. The specific introduction method is described in Example 3 above.

2. Culture of a Transgenic Plant

T3 seeds of the above transgenic plant were sown on rock wool (Yamamoto-Plastic Co., Ltd, Nara, Japan), followed by cultivation at 23° C. under continuous light at 50 µmoL/m$^2$/sec. Water was supplied daily as a 0.5 g/L Hyponex solution (Hyponex Japan, Osaka, Japan). After sowing, culture was carried out for 47 days, during which the plant was compared with the control in terms of phenotypes including leaf surface area, scape diameter, and the number of siliques for verification. In addition, since substantially no difference was confirmed between the phenotypes of T1 (MYA2) from the *A. thaliana* MYA2-KO strain and those of the Columbia strain (a wild-type strain) as a result of comparison in Example 3, a Columbia strain (a non-transgenic plant) was used as a control and cultured under the same conditions in this Example.

(Results)

Figure 6:
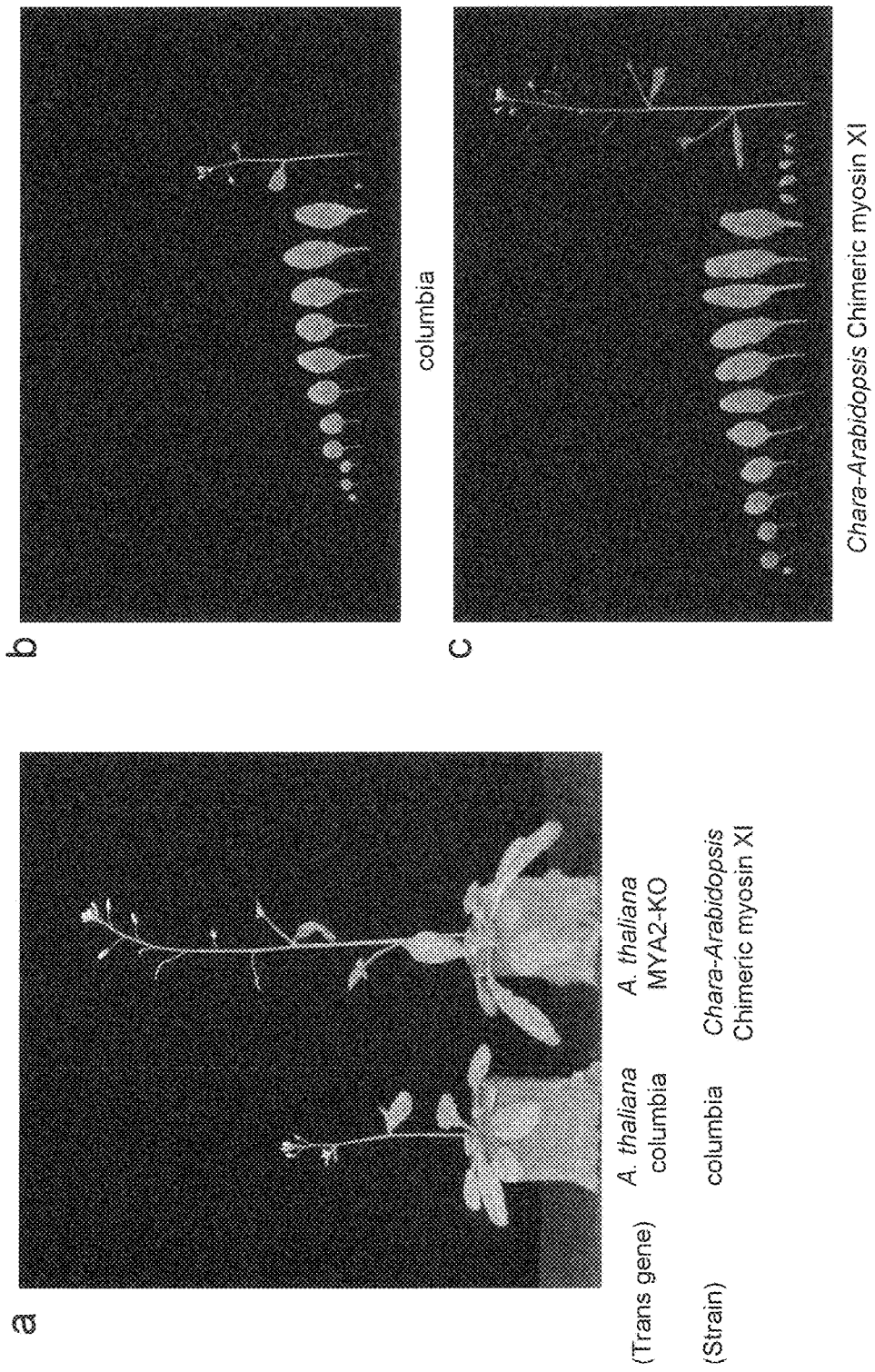
FIG. 6 shows phenotypes of the wild-type strain (the Columbia strain) and T1 (chimera XI) on day 35 after sowing.

FIG. 6 and table 1 show the results.

TABLE 1

|  | Chara-Arabidopsis Chimeric myosin XI | Columbia | Chimeric myosin XI/Columbia × 100 |
|---|---|---|---|
| Area of 1$^{st}$ leaf (25 Days) (mm$^2$) | 36.5 ± 4.7 | 25.8 ± 3.6 | 142 |
| Scape diameter (mm) | 0.96 ± 0.14 | 0.77 ± 0.12 | 125 |
| Number of siliques | 71.1 ± 15.5 | 64.6 ± 12.1 | 110 |

FIG. 6a shows growth of the aerial portion of the Columbia strain and that of T1 (chimera XI) into which the chimera XI gene had been introduced. FIGS. 6b and 6c show the parts, separated for comparison, of the aerial portions of the Columbia strain and those of chimera XI, respectively. Table 1 shows results of the first leaf surface area and scape elongation for the Columbia strain and chimera XI measured over time. Further, FIGS. 7 and 8 are graphs of the results for leaf surface area and scape elongation shown in Table 1, respectively.

Figure 7:
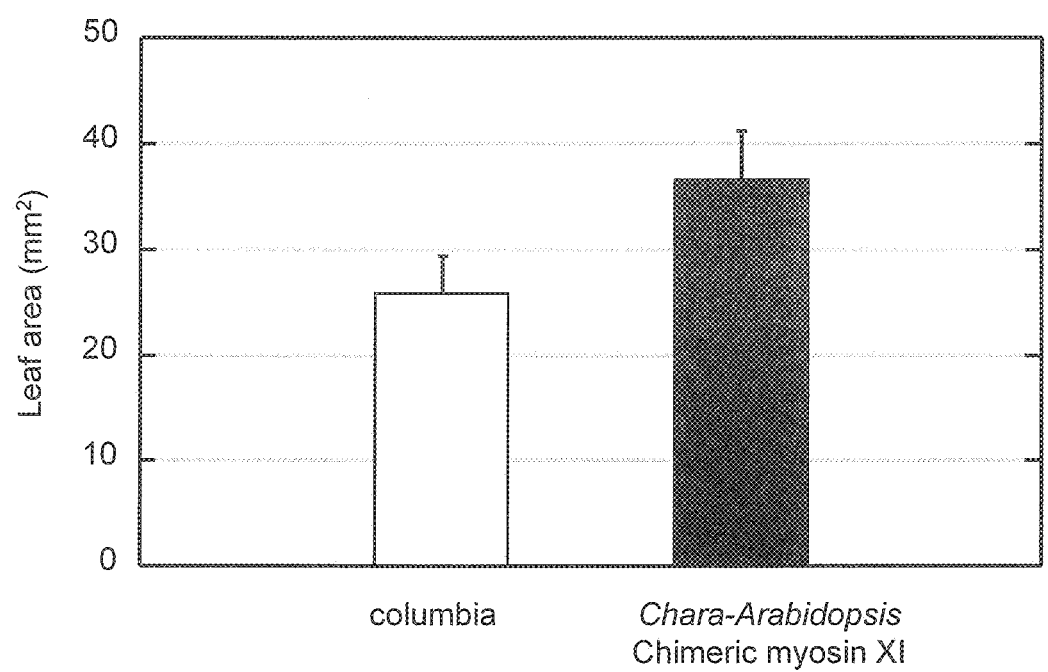
FIG. 7 shows a comparison of the Columbia strain and chimera XI in terms of the surface area of the first leaf.
Figure 8:
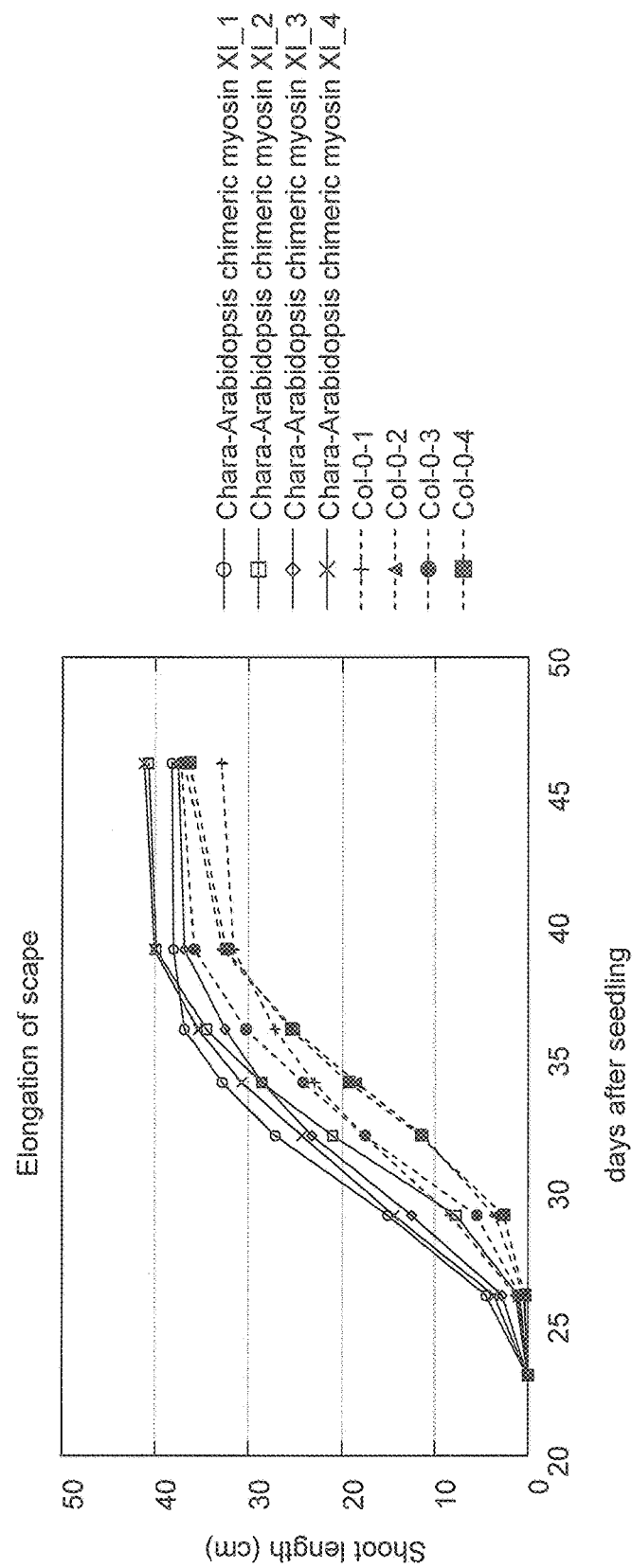
FIG. 8 shows results of scape elongation measured over time for the Columbia strain and chimera XI.

Based on the results shown in FIGS. 6 to 8 and Table 1, it was found that the leaf surface area was increased by 40% or more and the scape diameter was increased by 25% for chimera XI when compared with the Columbia strain (the wild-type strain). That is, it was revealed that growth of a transgenic plant subjected to transformation with the chimera XI gene is enhanced compared with a corresponding wild-type strain.

Example 5: Microscopic Observation of Transgenic Plants

It was verified whether the enhanced growth of a transgenic plant caused by the chimera XI gene confirmed in Example 3 was due to enlargement of cell size or increase in cell number.

(Method)

Root epithelial cells of T1 (chimera XI) from the *A. thaliana* MYA2-KO strain produced in Example 3 and T1 (MYA2) used as the control were microscopically observed in the following manner. For staining of cell walls, collected roots were immersed for approximately 1 minute in a solution obtained by dissolving 10 µg/mL propidium iodide in water. The stained roots were visualized using a spinning-disc confocal laser scanning microscope (CSU10, Yokogawa, Kanazawa, Japan) equipped with a high-resolution CCD camera (ORCA-AG, Hamamatsu Photonics, Hamamatsu, Japan), followed by imaging with the use of the iVision Mac software (BioVision Technologies, Exton, Pa., U.S.A.).

(Results)

Figure 5:
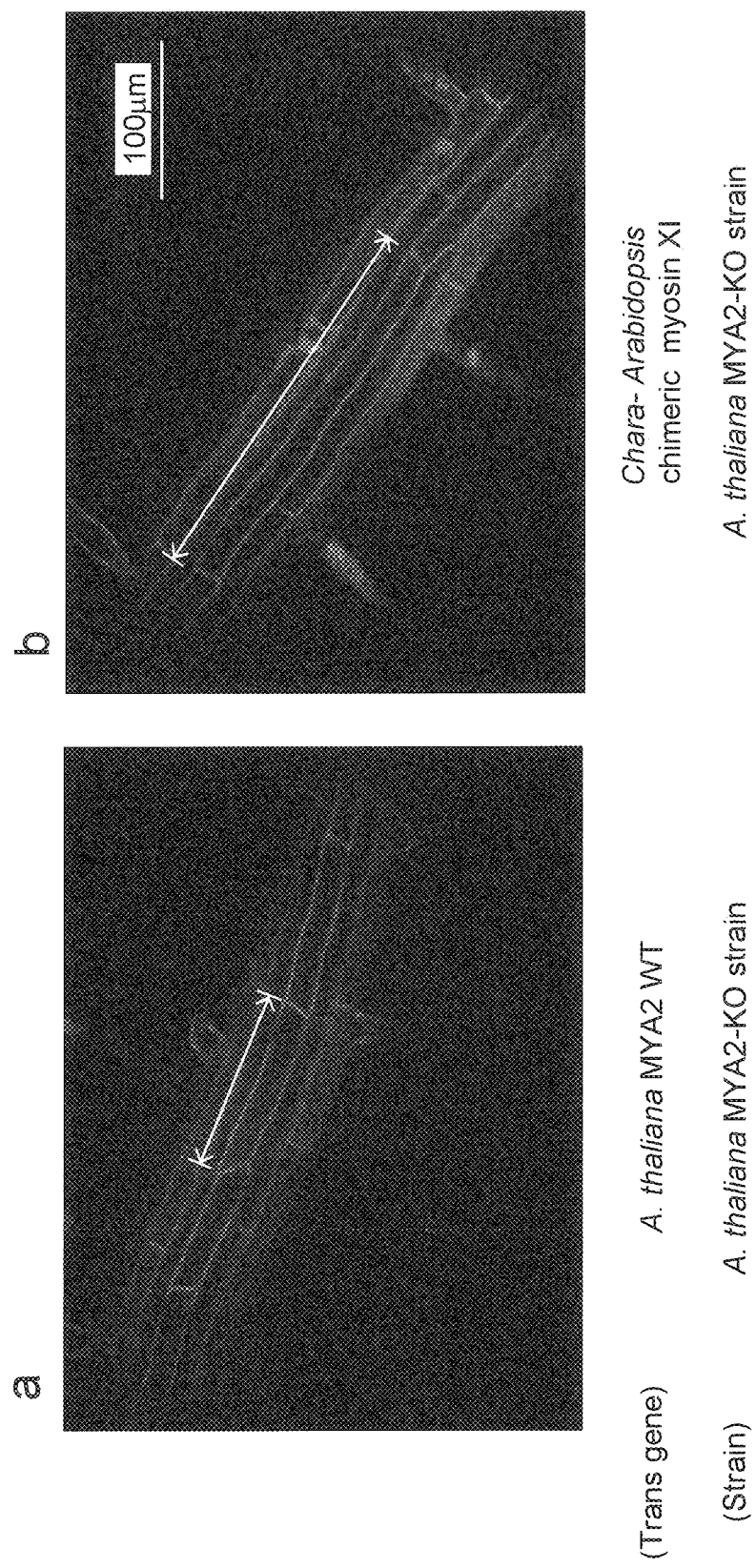
FIG. 5 shows propidium iodide (PI) staining images of root epithelial cells of first-generation (T1) transgenic plants obtained by introducing the chimeric myosin XI gene or the wild-type *A. thaliana* MYA2 gene into the *A. thaliana* MYA2-KO strain.

FIG. 5 shows the results. FIG. 5a shows a staining image of root epithelial cells of T1 (MYA2) from the *A. thaliana* MYA2-KO strain. FIG. 5b shows a staining image of root epithelial cells of T1 (chimera XI) from the *A. thaliana* MYA2-KO strain. The results revealed that the root epithelial cell size of T1 (chimera XI) was enlarged to become approximately 1.5 times that of T1 (MYA2). This suggested that the enhanced growth of a transgenic plant caused by the chimera XI gene is due to enlargement of cell size.

Example 6: Verification of the Phenotype of a Transgenic Plant with the Human-*A. thaliana* Chimeric Myosin Gene The chimeric myosin XI gene constructed in Example 1 was a chimeric gene between plants. Next, a chimeric myosin gene between an animal and a plant was constructed and the effects thereof were verified.

(Method)

1. Cloning of the Human Myosin Vb Gene

The human myosin Vb gene was used as an animal myosin gene. The human myosin Vb gene was obtained from the Kazusa DNA Research Institute (Chiba, Japan) (Product ID: ORK01152).

2. Method of Producing Human-*A. Thaliana* Chimeric Myosin

A chimeric myosin was prepared by substituting the motor domain of *A. thaliana* myosin XI-2 with the motor domain of human myosin Vb. Specifically, a chimeric myosin was prepared by connecting a nucleotide sequence encoding the 1st to 764th amino acid residues of the heavy chain of human myosin Vb (SEQ ID NO: 35) (i.e., a nucleotide sequence corresponding to the 1st to 2292nd positions of the gene for heavy chain of human myosin Vb shown in SEQ ID NO: 36) to a nucleotide sequence encoding the 735th to 1505th amino acid residues of the heavy chain of *A. thaliana* myosin XI-2 (SEQ ID NO: 26). More specifically, a gene obtained by adding a PacI site to the N terminus of the motor domain of human myosin Vb was subcloned into a pENTR-D-TOPO cloning vector and then the gene comprising the neck domain of myosin XI-2 and the downstream region thereof was connected thereto using an Infusion cloning system (Clontech). Basic procedures followed the manufacturer's protocols attached to the kits used. The amino acid sequence of the chimeric myosin obtained via the connection is shown in SEQ ID NO: 38. In addition, the GFP tag sequence was fused at the 5'-end of the chimera Vb-XI gene (hereinafter referred to as the "GFP-chimera Vb-XI" gene) for visualization and confirmation of expression of a chimera Vb-XI protein obtained as a result of gene expression.

3. Verification of the Phenotype of a Transgenic Plant

The phenotypes of *A. thaliana* transformed with the human-*A. thaliana* chimeric myosin (chimera Vb-XI) gene constructed above were compared with those of the wild-type strain (the Columbia strain) of *A. thaliana* for verification.

The chimera Vb-XI gene was introduced into *A. thaliana* according to the method as described in Example 4.

(Results)

FIG. 9 shows the results. FIG. 9 shows the growth of aerial portions of the Columbia strain and the strain into which chimera Vb-XI had been introduced on day 30 after sowing. As shown in the figure, a chimeric myosin (chimera Vb-XI) obtained by substituting the motor domain of plant myosin XI with the motor domain of an animal (i.e., a human) was found to exhibit a phenotype characterized by suppressed growth compared with a wild-type plant strain. This was in contrast to the transgenic plants transformed with the chimera XI gene obtained by substituting their motor domains with the motor domain from *C. corallina*, which were constructed and verified in Examples 1 to 4. That is, it was demonstrated that a plant with suppressed growth can be produced using a chimeric myosin which is a plant myosin XI comprising the motor domain from an animal.

All publications, patents, and patent applications cited herein are incorporated herein by reference in their entirety.

What is claimed is:

1. A method for producing a plant with enhanced growth, which comprises a step of introducing a gene encoding a chimeric myosin XI protein into a host plant so as to transform the host plant,
    wherein the chimeric myosin XI protein comprises
    a neck domain, a coiled-coil domain, and a globular tail domain from a single myosin XI protein of the host plant, said myosin XI being involved in cytoplasmic streaming of the host plant; and
    a motor domain from a myosin XI protein of *Chara corallina*, and
    wherein the host plant is selected from the family Brassicaceae or Poaceae.

2. The method for producing a plant with enhanced growth according to claim 1, wherein the single myosin XI protein of the host plant is a myosin XI-1, XI-2, XI-B, or XI-K protein of *Arabidopsis thaliana*, and wherein the host plant is *Arabidopsis thaliana*.

3. A plant with enhanced growth, which contains a gene encoding a chimeric myosin XI protein comprising:
    a neck domain, a coiled-coil domain, and a globular tail domain from a single myosin XI protein of the plant with enhanced growth, said single myosin XI being involved in cytoplasmic streaming of the plant with enhanced growth; and
    a motor domain from a myosin XI protein of *Chara corallina*,
    wherein the plant with enhanced growth belongs to the family Brassicaceae or Poaceae.

4. A plant with enhanced growth that is obtained by the method for producing a plant with enhanced growth according to claim 1.

5. A progeny of the plant with enhanced growth according to claim 3, wherein said progeny comprises said gene encoding the chimeric myosin XI protein.

6. The plant according to claim 3, wherein the motor domain from a myosin XI protein of *Chara* corallina comprises the amino acid shown in SEQ ID NO: 1.

7. A progeny of the plant according to claim 6, wherein said progeny comprises said gene encoding the chimeric myosin XI protein.

8. The method for producing a plant with enhanced growth according to claim 1, wherein the host plant is *Oryza sativa*.

\* \* \* \* \*